US012000003B2

(12) United States Patent
Yeh et al.

(10) Patent No.: US 12,000,003 B2
(45) Date of Patent: Jun. 4, 2024

(54) PLATFORM AND SAMPLE TYPE INDEPENDENT SINGLE SAMPLE CLASSIFIER FOR TREATMENT DECISION MAKING IN PANCREATIC DUCTAL ADENOCARCINOMA CANCER

(71) Applicant: The University of North Carolina at Chapel Hill, Chapel Hill, NC (US)

(72) Inventors: Jen Jen Yeh, Chapel Hill, NC (US); Richard Moffitt, Stony Brook, NY (US); Naim Ur Rashid, Raleigh, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 17/601,002

(22) PCT Filed: Apr. 1, 2020

(86) PCT No.: PCT/US2020/026209

§ 371 (c)(1),
(2) Date: Oct. 1, 2021

(87) PCT Pub. No.: WO2020/205993

PCT Pub. Date: Oct. 8, 2020

(65) Prior Publication Data

US 2022/0170109 A1 Jun. 2, 2022

Related U.S. Application Data

(60) Provisional application No. 62/827,473, filed on Apr. 1, 2019.

(51) Int. Cl.

*C12Q 1/6886* (2018.01)
*G16B 25/00* (2019.01)
*G16B 25/10* (2019.01)

(52) U.S. Cl.

CPC ........... *C12Q 1/6886* (2013.01); *G16B 25/00* (2019.02); *G16B 25/10* (2019.02); *C12Q 2600/106* (2013.01); *C12Q 2600/112* (2013.01); *C12Q 2600/158* (2013.01)

(58) Field of Classification Search

None

See application file for complete search history.

(56) References Cited

U.S. PATENT DOCUMENTS

| | | | |
|---|---|---|---|
| 5,974,164 | A | 10/1999 | Chee |
| 6,185,561 | B1 | 2/2001 | Balaban et al. |
| 6,229,911 | B1 | 5/2001 | Balaban et al. |
| 11,053,550 | B2 | 7/2021 | Moffitt et al. |
| 2007/0023179 | A1 | 2/2007 | Mita et al. |
| 2008/0050726 | A1 | 2/2008 | Wang et al. |
| 2009/0203547 | A1 | 8/2009 | Banes et al. |
| 2015/0260721 | A1 | 9/2015 | Eisen et al. |
| 2016/0090638 | A1 | 3/2016 | Tsai et al. |
| 2017/0233827 | A1 | 8/2017 | Moffitt et al. |
| 2017/0260593 | A1 | 9/2017 | Trumpp et al. |
| 2022/0127676 | A1 | 4/2022 | Moffitt et al. |

FOREIGN PATENT DOCUMENTS

| | | |
|---|---|---|
| WO | WO 2004/046098 | 3/2004 |
| WO | WO 2007/001324 | 1/2007 |
| WO | WO 2007/056332 | 5/2007 |
| WO | WO 2007/070252 | 6/2007 |
| WO | WO 2014/056626 A1 | 4/2014 |
| WO | WO 2020/191413 A1 | 9/2020 |

OTHER PUBLICATIONS

Newhook et al. A Thirteen-Gene Expression Signature Predicts Survival of Patients with Pancreatic Cancer and Identifies New Genes of Interest, PLOS One, Sep. 2014 | vol. 9 | Issue 9 | e105631.*

Shinkawa et al. Subtypes in pancreatic ductal adenocarcinoma based on niche factor dependency show distinct drug treatment responses J Exp Clin Cancer Res (2022) 41:89 https://doi.org/10.1186/s13046-022-02301-9.*

Aung et al Genomics-Driven Precision Medicine for Advanced Pancreatic Cancer: Early Results from the COMPASS Trial Clin Cancer Res; 24(6) Mar. 15, 2018 doi: 10.1158/1078-0432.CCR-17-2994.*

Rashid et al. (2019) Purity Independent Subtyping of Tumors (PurIST), A Clinically Robust, Single-sample Classifier for Tumor Subtyping in Pancreatic Cancer. Clinical Cancer Research 26(1):82-92.

Afsari et al. (2014) Rank Discriminants for Predicting Phenotypes from RNA Expression. Ann Appl Stat 8:1469-1491.

Afsari et al. (2015) Switch Box: an R package for k-Top Scoring Pairs classifier development. Bioinformatics, 31(2):273-274.

(Continued)

*Primary Examiner* — Joseph Woitach

(74) *Attorney, Agent, or Firm* — Jenkins, Taylor & Hunt, P.A.

(57) ABSTRACT

Provided are methods for identifying pancreatic cancer subtypes in a subject and treating the same. In some embodiments, the method comprise obtaining gene expression levels for each of the following genes in the biological sample: GPR87, KRT6A, BCAR3, PTGES, 1TGA3, C16orf74, S100A2, KRT5, REG4, ANXA10, GATA6, CLDN18, LGALS4, DDC, SLC40A1, CLRN3; performing pair-wise comparisons of gene expression levels for combinations of these genes, and calculating a Raw Score for the biological sample, wherein the Raw Score is indicative of the pancreatic cancer subtype in the subject. Also provided are methods for identifying differential treatment strategies for subjects diagnosed with PDAC, methods for treating PDAC patients based on the subtype of PD AC the patients have; and methods for classifying subjects diagnosed with PDAC as having a basal-like subtype or a classical subtype of PDAC.

6 Claims, 7 Drawing Sheets

Specification includes a Sequence Listing.

(56) References Cited

OTHER PUBLICATIONS

Aguirre et al. (2018) Real-time genomic characterization of advanced pancreatic cancer to enable precision medicine. Cancer Discovery 8(9):1096-1111.
Ahn et al. (2013) DeMix: deconvolution for mixed cancer transcriptomes using raw measured data. Bioinformatics 29, 1865-1871.
Alexandrov et al. Signatures of mutational processes in human cancer. Nature, vol. 500, pp. 415-421 (2013).
Alexandrov et al. Deciphering Signatures of Mutational Processes Operative in Human Cancer. Cell Reports, vol. 3, No. 1, pp. 246-259 (2013).
Biankin et al. Pancreatic cancer genomes reveal aberrations in axon guidance pathway genes Nature, vol. 491, pp. 399-405(2012).
Biton et al. Independent component analysis uncovers the landscape of the bladder tumor transcriptome and reveals insights into luminal and basal subtypes Cell Rep, vol. 9, pp. 1235-1245(2014).
Bolker, BM. Ecological models and data in R. Princeton University Press, pp. 215 (2008).
Breheny & Huang Coordinate descent algorithms for nonconvex penalized regression, with applications to biological feature selection Ann Appl Stat, vol. 5, pp. 232-253(2011).
Cancer Genome Atlas Research Network, Integrated Genomic Analyses of Ovarian Carcinoma. Nature, 474, pp. 609-615 (2011).
Cancer Genome Atlas Research Network, Comprehensive molecular characterization of human colon and rectal cancer. Nature, vol. 487, pp. 330-337(2012a).
Cancer Genome Atlas Research Network, Comprehensive genomic characterization of squamous cell lung cancers Nature, vol. 489, pp. 519-525 (2012b).
Cancer Genome Atlas Research Network, Comprehensive molecular portraits of human breast tumours. Nature, vol. 490, pp. 61-70(2012c).
Cancer Genome Atlas Network (2012d) Comprehensive molecular portraits of human breast tumours. Nature 490:61-70.
Cancer Genome Atlas Research Network, Integrated genomic characterization of endometrial carcinoma. Nature, vol. 497, pp. 67-73(2013a).
Cancer Genome Atlas Research Network, Comprehensive molecular characterization of clear cell renal cell carcinoma. Nature, vol. 499, pp. 43-49(2013b).
Cancer Genome Atlas Research Network, Genomic and epigenomic landscapes of adult de novo acute myeloid leukemia. New Eng J Med, vol. 368, pp. 2059 (2013c).
Cancer Genome Atlas Research Network, Comprehensive molecular characterization of urothelial bladder carcinoma. Nature, vol. 507, pp. 315-322 (2014a).
Cancer Genome Atlas Research Network, Comprehensive molecular profiling of lung adenocarcinoma. Nature, vol. 511, pp. 543-550(2014b).
Cancer Genome Atlas Research Network (2017) Integrated genomic characterization of pancreatic ductal adenocarcinoma. Cancer Cell 32:185-203.
Cheng (2014) A signature of epithelial-mesenchymal plasticity and stromal activation in primary tumor modulates late recurrence in breast cancer independent of disease subtype Breast Cancer Research 16: Article 407.
Cohen et al. (2008) Fibroblast activation protein and its relationship to clinical outcome in pancreatic adenocarcinoma. Pancreas, 37:154-158.
Collisson et al. Subtypes of Pancreatic Ductal Adenocarcinoma and Their Differing Responses to Therapy Nat Med, vol. 17, pp. 500-503 (2011).
Connor et al. (2017) Association of Distinct Mutational Signatures With Correlates of Increased Immune Activity in Pancreatic Ductal Adenocarcinoma. JAMA Oncol 3(6):774-783.
Connor et al. (2019) Integration of genomic and transcriptional features in pancreatic cancer reveals increased cell cycle progression in metastases. Cancer Cell 35:267-282.
Corces et al. (2018) The chromatin accessibility landscape of primary human cancers. Science 362:eaav1898.
Crnogorac-Jurcevic et al. Expression profiling of microdissected pancreatic adenocarcinomas. Oncogene, vol. 21, pp. 4587-4594 (2002).
Dal Molin et al. Very Long-term Survival Following Resection for Pancreatic Cancer Is Not Explained by Commonly Mutated Genes: Results of Whole-Exome Sequencing Analysis. Clin Cancer Res, vol. 21, pp. 1944-1950 (2015).
Damrauer et al. Intrinsic subtypes of high-grade bladder cancer reflect the hallmarks of breast cancer biology Proc Nat Acad Sci U S A, vol. 111, No. 8 pp. 3110-3115 (2014).
Erkan et al. (2008) The activated stroma index is a novel and independent prognostic marker in pancreatic ductal adenocarcinoma. Clin Gastroenterol Hepatol 6:1155-1161.
Froeling et al. (2011) Retinoic acid-induced pancreatic stellate cell quiescence reduces paracrine Wnt-β-catenin signaling to slow tumor progression. Gastroenterol 141:1486-1497.
Garrido-Laguna et al. Tumor engraftment in nude mice and enrichment in stroma- related gene pathways predict poor survival and resistance to gemcitabine in patients with pancreatic cancer. Clin Cancer Res, vol. 17, pp. 5793-5800 (2011).
Geman et al. (2004) Classifying gene expression profiles from pairwise mRNA comparisons. Statistical applications in genetics molecular biology 3(1):1-19.
Gong & Szustakowski (2013) DeconRNASeq: a statistical framework for deconvolution of heterogeneous tissue samples based on mRNA-Seq data. Bioinformatics 29:1083-1085.
Haeger et al. Smad4 loss promotes lung cancer formation but increases sensitivity to DNA topoisomerase inhibitors. Oncogene, vol. 35, No. 5, pp. 577-586 (2015).
Haque et al. (2017) A practical guide to single-cell RNA-sequencing for biomedical research and clinical applications. Genome Med. 9:75.
Herrera et al. Functional heterogeneity of cancer-associated fibroblasts from human colon tumors shows specific prognostic gene expression signature. Clin Cancer Res, vol. 19, pp. 5914-5926 (2013).
Hoadley et al. (2018) cell-of-origin patterns dominate the molecular classification of 10,000 tumors from 33 types of cancer. Cell 173:291-304.
Hoadley et al. Multiplatform analysis of 12 cancer types reveals molecular classification within and across tissues of origin. Cell, vol. 158, pp. 929-944(2014).
Hwang et al. Cancer-associated stromal fibroblasts promote pancreatic tumor progression. Cancer Res, vol. 68, pp. 918-926 (2008).
Iacobuzio-Donahue et al. DPC4 gene status of the primary carcinoma correlates with patterns of failure in patients with pancreatic cancer. J Clin Oncol, vol. 27, pp. 1806-1813 (2009).
Iacobuzio-Donahue et al. Exploration of global gene expression patterns in pancreatic adenocarcinoma using cDNA microarrays. Am J Pathol, vol. 162, pp. 1151-1162 (2003).
Ihle et al. Effect of KRAS oncogene substitutions on protein behavior: implications for signaling and clinical outcome. J Natl Cancer Inst, vol. 104, pp. 228-239 (2012).
Isella et al. (2015) Stromal contribution to the colorectal cancer transcriptome. Nat Genet 47:312-319.
Ji et al. LKB1 modulates lung cancer differentiation and metastasis. Nature, vol. 448, pp. 807-810 (2007).
Jones et al. Core signaling pathways in human pancreatic cancers revealed by global genomic analyses. Science, vol. 321, pp. 1801-1806 (2008).
Kindler et al. (2019) Olaparib as maintenance treatment following first-line platinum-based chemotherapy (PBC) in patients (pts) with a germline BRCA mutation metastatic pancreatic cancer (mPC): Phase III POLO trial. J Clin Oncol 37:18_suppl.
Liu et al. (2018) An integrated TCGA pan-cancer clinical data resource to drive high-quality survival outcome analytics. Cell 173:400-416.
Logsdon et al. Molecular profiling of pancreatic adenocarcinoma and chronic pancreatitis identifies multiple genes differentially regulated in pancreatic cancer. Cancer Res, vol. 63, pp. 2649-2657(2003).

(56) References Cited

OTHER PUBLICATIONS

Martens et al. (2019) Different shades of pancreatic ductal adenocarcinoma, different paths towards precision therapeutic applications. Ann. Oncol. 30:1428-1436.
Maurer et al. (2019) Experimental microdissection enables functional harmonisation of pancreatic cancer subtypes. Gut 68:1034-1043.
McLendon et al. Comprehensive genomic characterization defines human glioblastoma genes and core pathways. Nature, vol. 455, pp. 1061-1068 (2008).
Moffitt et al. (2015) Virtual microdissection identifies distinct tumor- and stroma-specific subtypes of pancreatic ductal adenocarcinoma. Nat. Genet. 47:1168-1178.
Newman et al. (2015) Robust enumeration of cell subsets from tissue expression profiles. Nat. Methods 12:453-457.
Nones et al. (2014) Genome-wide DNA methylation patterns in pancreatic ductal adenocarcinoma reveal epigenetic deregulation of SLIT-ROBO, ITGA2 and MET signaling. Int J Cancer 135:1110-1118.
Paquet & Hallett (2015) Absolute assignment of breast cancer intrinsic molecular subtype. J Natl Cancer Inst 107(1):dju357.
Parker et al. Supervised risk predictor of breast cancer based on intrinsic subtypes. J Clin Oncol, vol. 27, pp. 1160-1167(2009).
Patil et al. (2015) Test set bias affects reproducibility of gene signatures. Bioinformatics 31(14):2318-2323.
Prat et al. Phenotypic and molecular characterization of the claudin-low intrinsic subtype of breast cancer. Breast Cancer Res, vol. 12, pp. R68(2010).
Puleo et al. (2018) Stratification of pancreatic ductal adenocarcinomas based on tumor and microenvironment features. Gastroenterology 155:1999-2013.
Rhim et al. (2014) Stromal elements act to restrain, rather than support, pancreatic ductal adenocarcinoma. Cancer Cell 16:735-747.
Rubio-Viqueira et al. An in vivo platform for translational drug development in pancreatic cancer. Clin Cancer Res, vol. 12, pp. 4652-4661 (2006).
Search Report corresponding to European Patent Application Serial No. 20781829.5 dated Nov. 4, 2022.
Stolze et al. (2015) Comparative analysis of KRAS codon 12, 13, 18, 61, and 117 mutations using human MCF10A isogenic cell lines. Sci Rep 5:8535.
Stuart et al. In silico dissection of cell-type-associated patterns of gene expression in prostate cancer. Proc Nat Acad Sci U S A, vol. 101, pp. 615-620(2004).
Tan et al. (2005) Simple decision rules for classifying human cancers from gene expression profiles. Bioinformatics 21(20):3896-3904.
Tibshirani et al. Diagnosis of multiple cancer types by shrunken centroids of gene expression. Proc Nat Acad Sci U S A, vol. 99, pp. 6567-6572(2002).
Veldman-Jones et al. (2015) Reproducible, Quantitative, Flexible Molecular Subtyping of Clinical DLBCL Samples Using the NanoString nCounter System. Clin Cancer Res 21(10):2367-2378.
Waddell et al. (2015) Whole genomes redefine the mutational landscape of pancreatic cancer. Nature 518:495-501.
Wamunyokoli et al. Expression profiling of mucinous tumors of the ovary identifies genes of clinicopathologic importance. Clin Cancer Res, vol. 12, pp. 690-700(2006).
Wang et al. (2015) UNDO: a bioconductor R package for unsupervised deconvolution of mixed gene expressions in tumor samples. Bioinformatics 31:137-139.
Wang et al. In silico estimates of tissue components in surgical samples based on expression profiling data. Cancer Res, vol. 70, pp. 6448-6455(2010).
Weber et al. (2018a) Characterization of the olfactory receptor OR10H1 in human urinary bladder cancer. Front. Physiol. 9:456.
Weber et al. (2018b) Olfactory receptors as biomarkers in human breast carcinoma tissues. Front. Oncol. 8:33.
Wei et al. (2012) Insights into pancreatic cancer etiology from pathway analysis of genome-wide association study data. PLoS One 7:e46887.
Witkiewicz et al. (2015) Whole-exome sequencing of pancreatic cancer defines genetic diversity and therapeutic targets. Nature Commun 6:6744.
Yabushita et al. Metabolomic and Transcriptomic Profiling of Human K-Ras Oncogene Transgenic Rats With Pancreatic Ductal Adenocarcinomas. Carcinogenesis, vol. 34, No. 6, pp. 1251-1259(2013).
Yadav & De (2015) An assessment of computational methods for estimating purity and clonality using genomic data derived from heterogeneous tumor tissue samples. Brief. Bioinform. 16:232-241.
Yoshihara et al. Inferring tumour purity and stromal and immune cell admixture from expression data. Nat Commun, vol. 4, pp. 2612(2013).
Zhang et al. A Gata6-Wnt pathway required for epithelial stem cell development and airway regeneration. Nat Genet, vol. 40, pp. 862-870(2008).
Zheng et al. (2017) Estimating and accounting for tumor purity in the analysis of DNA methylation data from cancer studies. Genome Biol. 18:17.
Zhong et al. (2011) GATA6 Activates Wnt Signaling in Pancreatic Cancer by Negatively Regulating the Wnt Antagonist Dickkopf-1. PLoS One 6:e22129.

* cited by examiner

PLATFORM AND SAMPLE TYPE INDEPENDENT SINGLE SAMPLE CLASSIFIER FOR TREATMENT DECISION MAKING IN PANCREATIC DUCTAL ADENOCARCINOMA CANCER

CROSS-REFERENCE TO RELATED APPLICATIONS

This application is a U.S. National Phase Application of PCT International Patent Application No. PCT/US2020/026209, filed Apr. 1, 2020, incorporated herein by reference in its entirety and which claims the benefit of U.S. Provisional Patent Application Ser. No. 62/827,473, filed Apr. 1, 2019, the disclosure of which incorporated herein by reference in its entirety.

GOVERNMENT INTEREST

This invention was made with government support under grant numbers CA199064 and CA211000 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 421_454_PCT_US_ST25.txt. The text file is 444,494 bytes, was created on Oct. 1, 2021, and is being submitted electronically via EFS-Web.

BACKGROUND

Recent treatment advances, including FOLFIRINOX (Conroy et al., 2011), gemcitabine plus nab-paclitaxel (Von Hoff et al., 2013), and olaparib for BRCA-mutant patients (Kindler et al., 2019), have provided patients and providers with better options. With the substantial progress in molecular subtyping for pancreatic cancer (Collisson et al., 2011; Moffitt et al., 2015; Bailey et al., 2016; Cancer Genome Atlas Research Network, 2017; Puleo et al., 2018; Maurer et al., 2019), there is now an opportunity to determine the optimal choice of therapy given a patient's molecular subtype and other biomarker information, enabling "precision medicine" approaches in pancreatic cancer (Aguirre et al., 2018; Aung et al., 2018).

Transcriptomic molecular subtyping in pancreatic cancer is currently an area of active development, where multiple subtyping schemas for pancreatic cancer have been proposed. For example, three molecular subtypes with potential clinical and therapeutic relevance were first described by Collisson and colleagues (Collisson et al., 2011), leveraging a combination of cell line, bulk, and laser capture microdissected (LCM) patient samples: Collisson (i) quasi-mesenchymal (QM-PDA), (ii) classical, and (iii) exocrine-like. A subsequent study of patients with pancreatic cancer (Bailey et al., 2016), based on more diverse pancreatic cancer histologies in addition to the most common pancreatic ductal adenocarcinoma (PDAC), found four molecular subtypes: Bailey (i) squamous, (ii) pancreatic progenitor, (iii) immunogenic, and (iv) aberrantly differentiated endocrine exocrine (ADEX). More recently, Puleo and colleagues describe five subtypes that are based on features specific to tumor cells and the local microenvironment (Puleo et al., 2018). Maurer and colleagues performed LCM of both tumor and stroma and showed the contribution of each to the three schemas above (Maurer et al., 2019). Finally, we have previously shown two tumor-intrinsic subtypes of PDAC (Moffitt et al., 2015), which we called Moffitt (i) basal-like, given the similarities with basal breast and basal bladder cancer, and (ii) classical, given the overlap with the Collisson classical subtype.

However, consensus regarding proposed subtypes for clinical decision making in PDAC has been elusive. In addition, each proposed schema utilized independent cohorts of patients to demonstrate clinical relevance. As a result, the generalizability, robustness, and relative clinical utility of each proposed subtyping schema remains unclear. Comparative evaluations of these proposed subtyping systems have been limited, partially due to the difficulty in curating and applying these diverse subtyping approaches in new datasets.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides in some embodiments methods for determining a subtype of a pancreatic tumor in a biological sample comprising, consisting essentially of, or consisting of pancreatic tumor cells obtained from a subject. In some embodiments, the methods comprise obtaining gene expression levels for each of the following genes in the biological sample: GPR87, KRT6A, BCAR3, PTGES, ITGA3, C16orf74, S100A2, KRT5, REG4, ANXA10, GATA6, CLDN18, LGALS4, DDC, SLC40A1, CLRN3; performing a pair-wise comparison of the gene expression levels for each of Gene Pairs 1-8 or for each of Gene Pairs A-H, wherein Gene Pairs 1-8 and Gene Pairs A-H are presented in Table 1, and calculating a Raw Score for the biological sample, wherein the calculating comprises assigning a value of 1 for each Gene Pair for which Gene A of the Gene Pair has a higher expression level than Gene B of the Gene Pair, and a value of 0 for each Gene Pair for which Gene A of the Gene Pair has a lower expression level than Gene B of the Gene Pair; multiplying each assigned value by the coefficient listed above for the corresponding Gene Pair to calculate eight individual Gene Pair scores; and adding the eight individual Gene Pair scores together along with a baseline effect to calculate a Raw Score for the biological sample, wherein the baseline effect is −6.815 for Gene Pairs 1-8 and −12.414 for Gene Pairs A-H, wherein if the calculated Raw Score is greater than or equal to 0, the tumor subtype is determined to be a basal-like subtype, and if the calculated Raw Score if less than 0, the tumor subtype is determined to be a classical subtype. In some embodiments, the method further comprises converting the Raw Score to a predicted basal-like probability (PBP) using the inverse-logit transformation $$PBP=e^{Raw\ score}/(1+e^{Raw\ Score}),$$

wherein if the PBP is greater than 0.5, the tumor subtype is determined to be a basal-like subtype and if the PBP if less than or equal to 0.5, the tumor subtype is determined to be a classical subtype. In some embodiments, the pancreatic tumor is a pancreatic ductal adenocarcinoma (PDAC). In some embodiments, the biological sample comprises a biopsy sample, optionally a fine needle biopsy aspiration or a percutaneous core needle biopsy, or comprises a frozen or archival sample derived therefrom. In some embodiments, the obtaining employs a technique selected from the group consisting of microarray analysis, RNAseq, quantitative RT-PCR, NanoString, or any combination thereof. In some embodiments, the technique comprises NanoString and employs probes comprising the SEQ ID NOs. as set forth in Table 2. In some embodiments, the subject is a human.

The presently disclosed subject matter also provides in some embodiments methods for identifying a differential treatment strategy for a subject diagnosed with pancreatic ductal adenocarcinoma (PDAC). In some embodiments, the methods comprise obtaining gene expression levels for each of the following genes in a biological sample comprising PDAC cells isolated from the subject: GPR87, KRT6A, BCAR3, PTGES, ITGA3, C16orf74, S100A2, KRT5, REG4, ANXA10, GATA6, CLDN18, LGALS4, DDC, SLC40A1, CLRN3; performing a pair-wise comparison of the gene expression levels for each of Gene Pairs 1-8 or for each of Gene Pairs A-H, wherein Gene Pairs 1-8 and Gene Pairs A-H are as defined herein above, calculating a Raw Score for the biological sample, wherein the calculating comprises assigning a value of 1 for each Gene Pair for which Gene A of the Gene Pair has a higher expression level than Gene B of the Gene Pair, and a value of 0 for each Gene Pair for which Gene A of the Gene Pair has a lower expression level than Gene B of the Gene Pair; multiplying each assigned value by the coefficient listed above for the corresponding Gene Pair to calculate eight individual Gene Pair scores; and adding the eight individual Gene Pair scores together along with a baseline effect to calculate a Raw Score for the biological sample, wherein the baseline effect is −6.815 for Gene Pairs 1-8 and −12.414 for Gene Pairs A-H, wherein if the calculated Raw Score is greater than or equal to 0, the tumor subtype is determined to be a basal-like subtype, and if the calculated Raw Score if less than 0, the tumor subtype is determined to be a classical subtype; identifying a differential treatment strategy for the subject based on the subtype assigned, wherein if the assigned subtype is a basal-like subtype, the differential treatment strategy comprises treatment with gemcitabine, optionally in combination with nab-paclitaxel; and if the assigned subtype is a classical subtype, the different treatment strategy comprises treatment with FOLFIRINOX. In some embodiments, the biological sample comprises a biopsy sample, optionally a fine needle biopsy aspiration or a percutaneous core needle biopsy, or comprises a frozen or archival sample derived therefrom. In some embodiments, the obtaining employs a technique selected from the group consisting of microarray analysis, RNAseq, quantitative RT-PCR, NanoString, or any combination thereof. In some embodiments, the technique comprises NanoString and employs probes comprising the SEQ ID NOs: identified herein above. In some embodiments, the subject is a human.

The presently disclosed subject matter also provides in some embodiments methods for treating patients diagnosed with pancreatic ductal adenocarcinoma (PDAC). In some embodiments, the methods comprise identifying a subtype of the patient's PDAC via any method disclosed herein; and treating the patient with gemcitabine, optionally in combination with nab-paclitaxel, if the assigned subtype is a basal-like subtype and treating the patient with FOLFIRINOX if the assigned subtype is classical. In some embodiments, the treating comprises at least one additional anti-PDAC treatment. In some embodiments, the at least one additional anti-PDAC treatment is surgery, radiation, administration of an additional chemotherapeutic agent, and any combination thereof. In some embodiments, the additional chemotherapeutic agent is a CCR2 inhibitor, a checkpoint inhibitor, or any combination thereof. In some embodiments, the patient is a human.

The presently disclosed subject matter also provides in some embodiments methods for classifying a subject diagnosed with pancreatic ductal adenocarcinoma (PDAC) as having a basal-like subtype or a classical subtype of PDAC. In some embodiments, the methods comprise performing a pair-wise comparison of gene expression levels for each of Gene Pairs 1-8 or for each of Gene Pairs A-H in a sample comprising PDAC cells isolated from the subject, wherein Gene Pairs 1-8 and Gene Pairs A-H are as defined herein above; and calculating a Raw Score for the sample, wherein the calculating comprises assigning a value of 1 for each Gene Pair for which Gene A of the Gene Pair has a higher expression level than Gene B of the Gene Pair, and a value of 0 for each Gene Pair for which Gene A of the Gene Pair has a lower expression level than Gene B of the Gene Pair; multiplying each assigned value by the coefficient listed above for the corresponding Gene Pair to calculate eight individual Gene Pair scores; and adding the eight individual Gene Pair scores together along with a baseline effect to calculate a Raw Score for the biological sample, wherein the baseline effect is −6.815 for Gene Pairs 1-8 and −12.414 for Gene Pairs A-H, wherein if the calculated Raw Score is greater than or equal to 0, the PDAC subtype is determined to be a basal-like subtype, and if the calculated Raw Score if less than 0, the PDAC subtype is determined to be a classical subtype. In some embodiments, the methods further comprise converting the Raw Score to a predicted basal-like probability (PBP) using the inverse-logit transformation $$PBP=e^{Raw\ score}/(1+e^{Raw\ Score})$$

wherein if the PBP is greater than 0.5, the PDAC subtype is determined to be a basal-like subtype and if the PBP if less than or equal to 0.5, the PDAC subtype is determined to be a classical subtype. In some embodiments, the sample comprises a biopsy sample, optionally a fine needle biopsy aspiration or a percutaneous core needle biopsy, or comprises a frozen or archival sample derived therefrom. In some embodiments, the gene expression levels for each of Gene Pairs 1-8 or for each of Gene Pairs A-H in a sample are determined using a technique selected from the group consisting of microarray analysis, RNAseq, quantitative RT-PCR, NanoString, or any combination thereof. In some embodiments, the technique comprises NanoString and employs probes comprising the SEQ ID NOs: identified herein above. In some embodiments, the subject is a human.

Thus, it is an object of the presently disclosed subject matter to provide methods for classifying PDAC cancers into basal-like or classical subtypes, which in some embodiments can be used to differentially treat the PDAC cancers based on the subtype identified. An object of the presently disclosed subject matter having been stated hereinabove, and which is achieved in whole or in part by the presently disclosed subject matter, other objects will become evident as the description proceeds when taken in connection with the accompanying EXAMPLES and Figures as best described herein below.

BRIEF DESCRIPTION OF THE FIGURES

FIGS. 3A and 3B are Kaplan-Meier plots of OS in pooled datasets (FIG. 3A) belonging to the survival group minus datasets belonging to the training group and Yeh Seq FNA samples (FIG. 3B). P value and HRs for overall association were estimated by stratified Cox proportional hazards model in FIG. 3A, where dataset of origin was used as a stratification factor. FIGS. 3C and 3D are waterfall plots showing the percent change (% change) in size of tumor target lesions from baseline in the context of PurIST subtypes in the COMPASS (FIG. 3C) and Linehan trials (FIG. 3D). +20% and −30% of size change are marked by dashed lines. In FIG. 3C, gray vs. black bars denote PurIST subtype calls of the patient tumors. Patients marked with * were treated with gemcitabine/nab-paclitaxel (GP)-based therapy, and the rest were treated with modified FOLFIRINOX (m-FOLFIRINOX). In FIG. 3D, gray vs. black bars denote PurIST subtype calls of pretreatment samples. Colored tracks below to compare subtype calls for samples pre- and posttreatment of PurIST subtyping and the Moffitt schema. Patients marked with * were treated with FOLFIRINOX, and the rest were treated with FOLFIRINOX+PF-04133309. FIG. 3E is a plot of correlation between the PurIST score (basal-like probability) for patient samples pre- and posttreatment in the Linehan trial. Basal-like samples are denoted with light gray triangles and classical samples are denoted with black triangles. FIGS. 3F and 3G are plots showing correlation between the percentage of change (% change) of tumors and the PurIST score (basal-like probability) derived from PurIST in basal-like (FIG. 3F) and classical samples (FIG. 3G), excluding a basal-like sample with an unstable DNA subtype.

BRIEF DESCRIPTION OF THE SEQUENCE LISTING

Figure 1A:
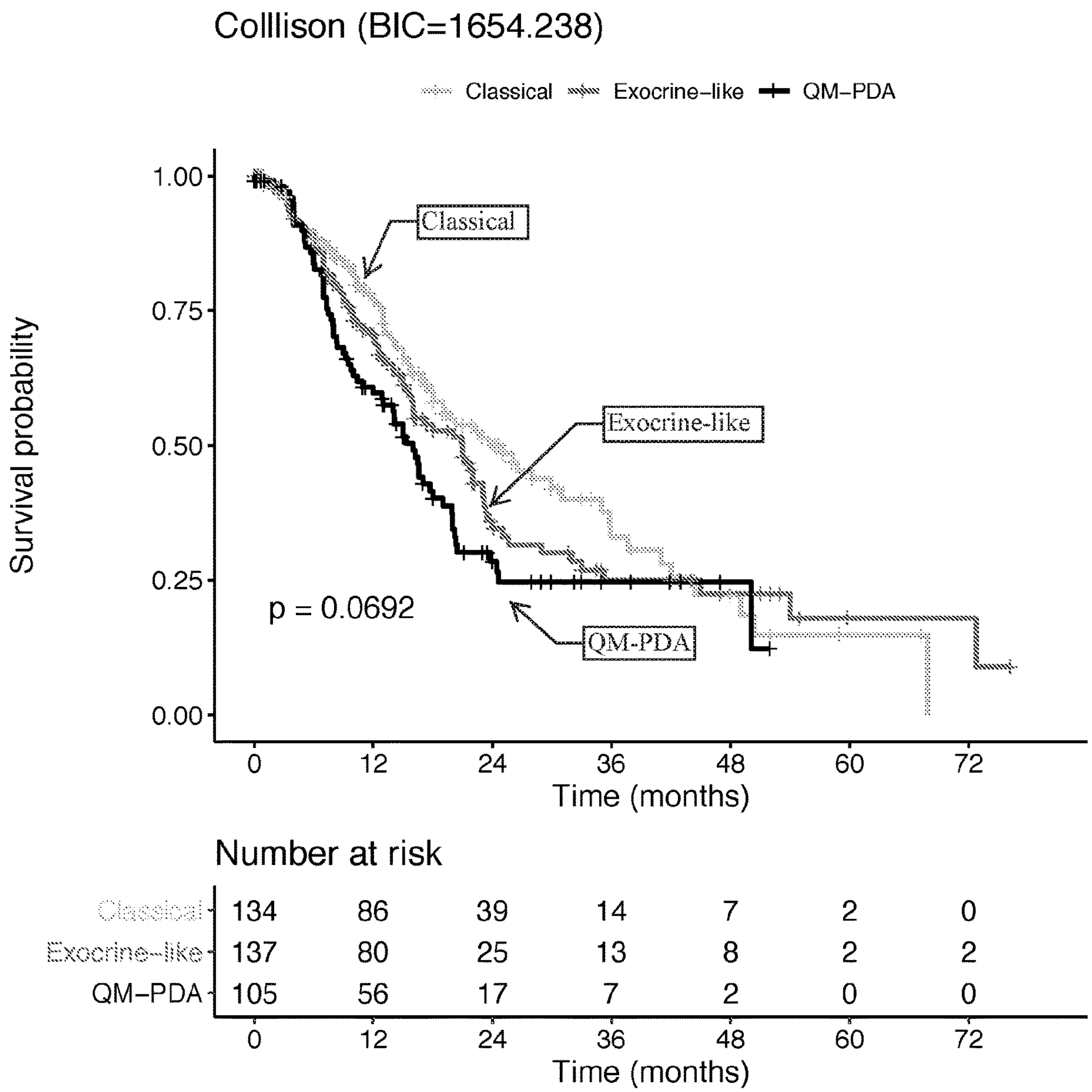
FIGS. 1A-1C are Kaplan-Meier plots showing subtype performance in predicting patient prognosis in pooled datasets from the survival group (see Table 7). Kaplan-Meier plots of OS in the context of the subtyping schemas of Collisson (FIG. 1A), Bailey (FIG. 1B), and Moffitt (FIG. 1C). Log-rank P values for overall association were determined from stratified Cox proportional hazards models, where dataset was used as a stratification factor to account for variation in baseline hazard across studies. BIC was calculated to compare the three subtyping schemas.

SEQ ID NOs: 1-58 are exemplary biosequences corresponding to certain human gene products as disclosed herein and summarized herein below. For each of SEQ ID NOs: 1-58, the odd numbered SEQ ID NO: encodes the immediately following even numbered SEQ ID NO. as set forth in Table 3.

SEQ ID NOs: 59-102 are exemplary NanoString probes for certain gene products disclosed herein, which are as follows: ANXA10 (SEQ ID NO: 59), C16orf74 (SEQ ID NO: 60), CDH17 (SEQ ID NO: 61), DCBLD2 (SEQ ID NO: 62), DDC (SEQ ID NO: 63), GPR87 (SEQ ID NO: 64), KRT6A (SEQ ID NO: 65), KRT15 (SEQ ID NO: 66), KRT17 (SEQ ID NO: 67), LGALS4 (SEQ ID NO: 68), PLA2G10 (SEQ ID NO: 69), PTGES (SEQ ID NO: 70), REG4 (SEQ ID NO: 71), S100A2 (SEQ ID NO: 72), TFF1 (SEQ ID NO: 73), TSPAN8 (SEQ ID NO: 74), CTSE (SEQ ID NO: 75), LYZ (SEQ ID NO: 76), MUC17 (SEQ ID NO: 77), MYOIA (SEQ ID NO: 78), NR1I2 (SEQ ID NO: 79), PIP5K1B (SEQ ID NO: 80), BCAR3 (SEQ ID NO: 81), GATA6 (SEQ ID NO: 82), CLRN3 (SEQ ID NO: 83), CLDN18 (SEQ ID NO: 84), ITGA3 (SEQ ID NO: 85), SLC40A1 (SEQ ID NO: 86), KRT5 (SEQ ID NO: 87), RPLP0 (SEQ ID NO: 88), B2M (SEQ ID NO: 89), ACTB (SEQ ID NO: 90), RPL19 (SEQ ID NO: 91), GAPDH (SEQ ID NO: 92), LDHA (SEQ ID NO: 93), PGK1 (SEQ ID NO: 94), TUBB (SEQ ID NO: 95), SDHA (SEQ ID NO: 96), CLTC (SEQ ID NO: 97), HPRT1 (SEQ ID NO: 98), ABCF1 (SEQ ID NO: 99), GUSB (SEQ ID NO: 100), TBP (SEQ ID NO: 101), and ALAS1 (SEQ ID NO: 102).

Genes listed among SEQ ID NOs: 59-102 that are not included in those among SEQ ID NOs: 1-59 (e.g., those corresponding to SEQ ID NOs: 75-80 and 88-102) can be employed in some embodiments as internal controls for any of the gene expression techniques disclosed herein.

DETAILED DESCRIPTION

I. General Considerations

Molecular subtyping for pancreatic cancer has made substantial progress in recent years, facilitating the optimization of existing therapeutic approaches to improve clinical outcomes in pancreatic cancer. Disclosed herein are assessments of three major subtype classification schemas in the context of results from two clinical trials and by meta-analysis of publicly available expression data to assess statistical criteria of subtype robustness and overall clinical relevance. We then developed a single-sample classifier (SSC) using penalized logistic regression based on the most robust and replicable schema.

Demonstrated herein is that a tumor-intrinsic two-subtype schema is most robust, replicable, and clinically relevant. We developed Purity Independent Subtyping of Tumors (PurIST), a SSC with robust and highly replicable performance on a wide range of platforms and sample types. We show that PurIST subtypes have meaningful associations with patient prognosis and have significant implications for treatment response to FOLIFIRNOX.

We show that a tumor-intrinsic two-subtype schema is the most replicable and clinically robust across different subtype schemas, with basal-like subtype tumors showing resistance to FOLFIRINOX-based regimens in two independent clinical trials. Our results strongly support the need to evaluate molecular subtyping in treatment decision-making for patients with PDAC in the context of future clinical trials. We present PurIST, a clinically usable single-sample classifier that is robust and highly replicable across different gene expression platforms and sample collection types, and may be utilized in future clinical trials.

As such, present herein is a clinically usable SSC that may be used on any type of gene expression data including RNAseq, microarray, and NanoString, and on diverse sample types including FFPE, core biopsies, FNAs, and bulk frozen tumors. Although results of the association of FOLFIRINOX resistance in patients with basal-like subtype tumors is compelling, future prospective clinical trials in patients with PDAC will be needed to evaluate the utility of PurIST in treatment decision making, and in the context of different therapies. The flexibility and utility of PurIST on low-input samples such as tumor biopsies allows it to be used at the time of diagnosis to facilitate the choice of effective therapies for patients with pancreatic ductal adenocarcinoma and should be considered in the context of future clinical trials.

II. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a," "an," and "the" mean "one or more" when used in this application, including the claims. Thus, the phrase "a cell" refers to one or more cells, unless the context clearly indicates otherwise.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising," "consisting essentially of," and "consisting of," where one of these three terms is used herein, the presently disclosed and claimed subject matter can include the use of either of the other two terms. For example, it is understood that the methods of the presently disclosed subject matter in some embodiments comprise the steps that are disclosed herein and/or that are recited in the claims, in some embodiments consist essentially of the steps that are disclosed herein and/or that are recited in the claims, and in some embodiments consist of the steps that are disclosed herein and/or that are recited in the claim.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Aves (birds), and Mammalia (mammals)), and all Orders and Families encompassed therein. In some embodiments, the presently disclosed subject matter relates to human subjects.

Similarly, all genes, gene names, and gene products disclosed herein are intended to correspond to orthologs from any species for which the compositions and methods disclosed herein are applicable. Thus, the terms include, but are not limited to genes and gene products from humans. It is understood that when a gene or gene product from a particular species is disclosed, this disclosure is intended to be exemplary only, and is not to be interpreted as a limitation unless the context in which it appears clearly indicates. Thus, for example, the genes and/or gene products disclosed herein are also intended to encompass homologous genes and gene products from other animals including, but not limited to other mammals, fish, amphibians, reptiles, and birds.

The methods and compositions of the presently disclosed subject matter are particularly useful for warm-blooded vertebrates. Thus, the presently disclosed subject matter concerns mammals and birds. More particularly provided is the use of the methods and compositions of the presently disclosed subject matter on mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the application of the methods and compositions of the presently disclosed subject matter to livestock, including but not limited to domesticated swine (pigs and hogs), ruminants, horses, poultry, and the like.

The term "about," as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods and/or to employ the presently disclosed arrays.

As used herein the term "gene" refers to a hereditary unit including a sequence of DNA that occupies a specific location on a chromosome and that contains the genetic instruction for a particular characteristic or trait in an organism. Similarly, the phrase "gene product" refers to biological molecules that are the transcription and/or translation products of genes. Exemplary gene products include, but are not limited to mRNAs and polypeptides that result from translation of mRNAs. Any of these naturally occurring gene products can also be manipulated in vivo or in vitro using well known techniques, and the manipulated derivatives can also be gene products. For example, a cDNA is an enzymatically produced derivative of an RNA molecule (e.g., an mRNA), and a cDNA is considered a gene product. Additionally, polypeptide translation products of mRNAs can be enzymatically fragmented using techniques well known to those of skill in the art, and these peptide fragments are also considered gene products.

As used herein, the term "ANXA10" refers to the annexin A10 (ANXA10) gene and its transcription and translation products. Exemplary ANXA 10 nucleic acid and amino acid sequences are presented in Accession Nos. NM_007193.5 and NP_009124.2 of the GENBANK® biosequence database, respectively, and are also set forth in SEQ ID NOs: 1 and 2, respectively.

As used herein, the term "BCAR3" refers to the BCAR3 adaptor protein, NSP family member (BCAR3), gene and its transcription and translation products. Exemplary BCAR3 nucleic acid and amino acid sequences are presented in Accession Nos. NM_001261408.2 and NP_001248337.1 of the GENBANK® biosequence database, and are also set forth in SEQ ID NOs: 3 and 4, respectively.

As used herein, the term "C16orf74" refers to the *Homo sapiens* chromosome 16 open reading frame 74 (C16orf14) gene and its transcription and translation products. Exemplary C16orf74 nucleic acid and amino acid sequences are presented in Accession Nos. NM_206967.3 and NP_996850.1 of the GENBANK® biosequence database, and are also set forth in SEQ ID NOs: 5 and 6, respectively.

As used herein, the term "CDH17" refers to the cadherin 17 (CDH17) gene and its transcription and translation products. Exemplary CDH17 nucleic acid and amino acid sequences are presented in Accession Nos. NM_004063.4 and NP_004054.3 of the GENBANK® biosequence database, and are also set forth in SEQ ID NOs: 7 and 8, respectively.

As used herein, the term "CLDN18" refers to the claudin 18 (CLDN18) gene and its transcription and translation products. Exemplary CLDN18 nucleic acid and amino acid sequences are presented in Accession Nos. NM_016369.4 and NP_057453.1 of the GENBANK@ biosequence database, and are also set forth in SEQ ID NOs: 9 and 10, respectively.

As used herein, the term "CLRN3" refers to the clarin 3 (CLRN3) gene and its transcription and translation products. Exemplary CLRN3 nucleic acid and amino acid sequences are presented in Accession Nos. NM_152311.5 and NP_689524.1 of the GENBANK@ biosequence database, and are also set forth in SEQ ID NOs: amino acid and 12, respectively.

As used herein, the term "CTSE" refers to the cathepsin E (CTSE) gene and its transcription and translation products. Exemplary CTSE nucleic acid and amino acid sequences are presented in Accession Nos. NM_001910.4 and NP_001901.1 of the GENBANK® biosequence database, and are also set forth in SEQ ID NOs: 13 and 14, respectively.

As used herein, the term "DCBLD2" refers to the discoidin, CUB and LCCL domain containing 2 (DCBLD2) gene and its transcription and translation products. Exemplary DCBLD2 nucleic acid and amino acid sequences are presented in Accession Nos. NM_080927.4 and NP_563615.3 of the GENBANK® biosequence database, and are also set forth in SEQ ID NOs: 15 and 16, respectively.

As used herein, the term "DDC" refers to the dopa decarboxylase (DDC) gene and its transcription and translation products. Exemplary DDC nucleic acid and amino acid sequences are presented in Accession Nos. NM_000790.4 and NP_000781.2 of the GENBANK® biosequence database, and are also set forth in SEQ ID NOs: 17 and 18, respectively.

As used herein, the term "GATA6" refers to the GATA binding protein 6 (GATA6) gene and its transcription and translation products. Exemplary GATA6 nucleic acid and amino acid sequences are presented in Accession Nos. NM_005257.6 and NP_005248.2 of the GENBANK® biosequence database, and are also set forth in SEQ ID NOs: 19 and 20, respectively.

As used herein, the term "GPR87" refers to the G protein-coupled receptor 87 (GPR87) gene and its transcription and translation products. Exemplary GPR87 nucleic acid and amino acid sequences are presented in Accession Nos. NM_023915.4 and NP_076404.3 of the GENBANK® biosequence database, and are also set forth in SEQ ID NOs: 21 and 22, respectively.

As used herein, the term "ITGA3" refers to the integrin subunit alpha 3 (ITGA3) gene and its transcription and translation products. Exemplary ITGA3 nucleic acid and amino acid sequences are presented in Accession Nos. NM_002204.4 and NP_002195.1 of the GENBANK® biosequence database, and are also set forth in SEQ ID NOs: 23 and 24, respectively.

As used herein, the term "KRT5" refers to the keratin 5 (KRT5) gene and its transcription and translation products. Exemplary KRT5 nucleic acid and amino acid sequences are presented in Accession Nos. NM_000424.4 and NP_000415.2 of the GENBANK® biosequence database, and are also set forth in SEQ ID NOs: 25 and 26, respectively.

As used herein, the term "KRT6A" refers to the keratin 6A (KRT6A) gene and its transcription and translation products. Exemplary KRT6A nucleic acid and amino acid sequences are presented in Accession Nos. NM_005554.4 and NP_005545.1 of the GENBANK® biosequence database, and are also set forth in SEQ ID NOs: 27 and 28, respectively.

As used herein, the term "KRT15" refers to the keratin 15 (KRT15) gene and its transcription and translation products. Exemplary KRT15 nucleic acid and amino acid sequences are presented in Accession Nos. NM_002275.4 and NP_002266.3 of the GENBANK® biosequence database, and are also set forth in SEQ ID NOs: 29 and 30, respectively.

As used herein, the term "KRT17" refers to the keratin 17 (KRT17) gene and its transcription and translation products. Exemplary KRT17 nucleic acid and amino acid sequences are presented in Accession Nos. NM_000422.3 and NP_000413.1 of the GENBANK® biosequence database, and are also set forth in SEQ ID NOs: 31 and 32, respectively.

As used herein, the term "LGALS4" refers to the galectin 4 (LGALS4) gene and its transcription and translation products. Exemplary LGALS4 nucleic acid and amino acid sequences are presented in Accession Nos. NM_006149.4 and NP_006140.1 of the GENBANK® biosequence database, and are also set forth in SEQ ID NOs: 33 and 34, respectively.

As used herein, the term "LYZ" refers to the lysozome (LYZ) gene and its transcription and translation products. Exemplary LYZ nucleic acid and amino acid sequences are presented in Accession Nos. NM_000239.3 and NP_000230.1 of the GENBANK® biosequence database, and are also set forth in SEQ ID NOs: 35 and 36, respectively.

As used herein, the term "MUC17" refers to the mucin 17, cell surface associated (MUC17) gene and its transcription and translation products. Exemplary MUC17 nucleic acid and amino acid sequences are presented in Accession Nos. NM_001040105.2 and NP_001035194.1 of the GENBANK@ biosequence database, and are also set forth in SEQ ID NOs: 37 and 38, respectively.

As used herein, the term "MYOIA" refers to the myosin 1A (MYOIA) gene and its transcription and translation products. Exemplary MYOIA nucleic acid and amino acid sequences are presented in Accession Nos. NM_005379.4 and NP_005370.1 of the GENBANK@ biosequence database, and are also set forth in SEQ ID NOs: 39 and 40, respectively.

As used herein, the term "NR1I2" refers to the nuclear receptor subfamily 1 group I member 2 (NR1I2) gene and its transcription and translation products. Exemplary NR1I2 nucleic acid and amino acid sequences are presented in Accession Nos. NM_022002.2 and NP_071285.1 of the GENBANK@ biosequence database, and are also set forth in SEQ ID NOs: 41 and 42, respectively.

As used herein, the term "PIP5K1B" refers to the phosphatidylinositol-4-phosphate 5-kinase, type I, beta (PIP5K1B) gene and its transcription and translation products. Exemplary PIP5K1B nucleic acid and amino acid sequences are presented in Accession Nos. NM_003558.4 and NP_003549.1 of the GENBANK® biosequence database, and are also set forth in SEQ ID NOs: 43 and 44, respectively.

As used herein, the term "PLA2G10" refers to the phospholipase A2 group X (PLA2G10) gene and its transcription and translation products. Exemplary PLA2G10 nucleic acid and amino acid sequences are presented in Accession Nos. NM_003561.3 and NP_003552.1 of the GENBANK® biosequence database, and are also set forth in SEQ ID NOs: 45 and 46, respectively.

As used herein, the term "PTGES" refers to the prostaglandin E synthase (PTGES) gene and its transcription and translation products. Exemplary PTGES nucleic acid and amino acid sequences are presented in Accession Nos. NM_004878.5 and NP_004869.1 of the GENBANK® biosequence database, and are also set forth in SEQ ID NOs: 47 and 48, respectively.

As used herein, the term "REG4" refers to the regenerating family member 4 (REG4) gene and its transcription and translation products. Exemplary REG4 nucleic acid and amino acid sequences are presented in Accession Nos. NM_032044.4 and NP_114433.1 of the GENBANK® biosequence database, and are also set forth in SEQ ID NOs: 49 and 50, respectively.

As used herein, the term "S100A2" refers to the S100 calcium binding protein A2 (S100A2) gene and its transcription and translation products. Exemplary S100A2 nucleic acid and amino acid sequences are presented in Accession Nos. NM_005978.4 and NP_005969.2 of the GENBANK® biosequence database, and are also set forth in SEQ ID NOs: 51 and 52, respectively.

As used herein, the term "SLC40A1" refers to the solute carrier family 40 member 1 (SLC40A1) gene and its transcription and translation products. Exemplary SLC40A1 nucleic acid and amino acid sequences are presented in Accession Nos. NM_014585.6 and NP_055400.1 of the GENBANK® biosequence database, and are also set forth in SEQ ID NOs: 53 and 54, respectively.

As used herein, the term "TFF1" refers to the trefoil factor 1 (TFF1) gene and its transcription and translation products. Exemplary TFF1 nucleic acid and amino acid sequences are presented in Accession Nos. NM_003225.3 and NP_003216.1 of the GENBANK® biosequence database, and are also set forth in SEQ ID NOs: 55 and 56, respectively.

As used herein, the term "TSPAN8" refers to the tetraspanin 8 (TSPAN8) gene and its transcription and translation products. Exemplary TSPAN8 nucleic acid and amino acid sequences are presented in Accession Nos. NM_004616.3 and NP_004607.1 of the GENBANK® biosequence database, and are also set forth in SEQ ID NOs: 57 and 58, respectively.

The term "isolated," as used in the context of a nucleic acid or polypeptide (including, for example, a nucleotide sequence, a polypeptide, and/or a peptide), indicates that the nucleic acid or polypeptide exists apart from its native environment. An isolated nucleic acid or polypeptide can exist in a purified form or can exist in a non-native environment.

Further, as used for example in the context of a cell, nucleic acid, polypeptide, or peptide, the term "isolated" indicates that the cell, nucleic acid, polypeptide, or peptide exists apart from its native environment. In some embodiments, "isolated" refers to a physical isolation, meaning that the cell, nucleic acid, polypeptide, or peptide has been removed from its native environment (e.g., from a subject).

The terms "nucleic acid molecule" and "nucleic acid" refer to deoxyribonucleotides, ribonucleotides, and polymers thereof, in single-stranded or double-stranded form. Unless specifically limited, the term encompasses nucleic acids containing known analogues of natural nucleotides that have similar properties as the reference natural nucleic acid. The terms "nucleic acid molecule" and "nucleic acid" can also be used in place of "gene," "cDNA," and "mRNA." Nucleic acids can be synthesized, or can be derived from any biological source, including any organism.

As used herein, the terms "peptide" and "polypeptide" refer to polymers of at least two amino acids linked by peptide bonds. Typically, "peptides" are shorter than "polypeptides," but unless the context specifically requires, these terms are used interchangeably herein.

As used herein, a cell, nucleic acid, or peptide exists in a "purified form" when it has been isolated away from some, most, or all components that are present in its native environment, but also when the proportion of that cell, nucleic acid, or peptide in a preparation is greater than would be found in its native environment. As such, "purified" can refer to cells, nucleic acids, and peptides that are free of all components with which they are naturally found in a subject, or are free from just a proportion thereof.

II. Methods

In some embodiments, the presently disclosed subject matter relates to methods for determining a subtype of a pancreatic tumor in a biological sample comprising, consisting essentially of, or consisting of pancreatic tumor cells obtained from a subject. As used herein, the phrase "subtype of a pancreatic tumor" refers to classifications wherein the underlying nature of the pancreatic tumor and/or cells thereof are classified differentially with respect to gene expression, prognosis, treatment decisions, etc. Various subtypes for pancreatic tumors and cells thereof have been described in the literature, including those set forth in, for example, U.S. Patent Application Publication No. 2017/

0233827; Moffitt et al., 2015; Bailey et al., 2016; Nywening et al., 2016; Aung et al., 2017; Cancer Genome Atlas Research Network, 2017; Connor et al., 2017; and Aguirre et al., 2018; each of which is incorporated herein by reference in its entirety.

In some embodiments, the pancreatic tumor is classified as being of the basal-like subtype or of the classical subtype. The classification with respect to basal-like vs. classical can be made on the basis of the methods disclosed herein. By way of example and not limitation, a method for classifying a pancreatic tumor as being of the classical vs. the basal-like subtype can comprise obtaining gene expression levels for each of the following genes in the biological sample: GPR87, KRT6A, BCAR3, PTGES, ITGA3, C16orf74, S100A2, KRT5, REG4, ANXA10, GATA6, CLDN18, LGALS4, DDC, GENE SLC40A1, CLRN3; performing a pair-wise comparison of the gene expression levels for each of Gene Pairs 1-8 or for each of Gene Pairs A-H, wherein Gene Pairs 1-8 and Gene Pairs A-H are as shown in Table 1; and calculating a Raw Score for the biological sample. In some embodiments, the calculating comprises assigning a value of 1 for each Gene Pair for which Gene A of the Gene Pair has a higher expression level than Gene B of the Gene Pair, and a value of 0 for each Gene Pair for which Gene A of the Gene Pair has a lower expression level than Gene B of the Gene Pair; multiplying each assigned value by the coefficient listed in Table 1 for the corresponding Gene Pair to calculate eight individual Gene Pair scores; and adding the eight individual Gene Pair scores together along with a baseline effect to calculate a Raw Score for the biological sample, wherein the baseline effect is −6.815 for Gene Pairs 1-8 and −12.414 for Gene Pairs A-H (i.e., the intercepts identified in Tables 25 and 26). To assign a subtype to the biological sample, if the calculated Raw Score is greater than or equal to 0, the tumor subtype is determined to be a basal-like subtype, and if the calculated Raw Score if less than 0, the tumor subtype is determined to be a classical subtype.

In some embodiments, the Raw Score that is calculated is further converted to a predicted basal-like probability (PBP) using the inverse-logit transformation $$PBP=e^{Raw\ Score}/(1+e^{Raw\ score}.$$

The PBP is another way to classify pancreatic tumor subtypes as being basal-like or classical. When a PBP is calculated, the threshold value for classifying basal-like vs. classical is slightly modified. In these cases, if the PBP is greater than 0.5, the tumor subtype is determined to be a basal-like subtype, and if the PBP if less than or equal to 0.5, the tumor subtype is determined to be a classical subtype.

As used herein, the terms "biological sample" and "sample" refer to a biopsy sample, optionally a fine needle biopsy aspiration or a percutaneous core needle biopsy, or a frozen or archival sample derived therefrom, that comprises pancreatic tumor (in some embodiments, pancreatic ductal adenocarcinoma (PDAC)) cells that have been isolated from a patient with a pancreatic tumor and/or nucleic acids and/or proteins that have been isolated from such a sample. Depending on the type of gene expression analysis to be employed (discussed in more detail herein below), the sample should comprise DNA, RNA (in some embodiments messenger RNA; mRNA), or protein.

Given that the methods disclosed herein relate to pairwise comparisons of multiple genes with respect to expression levels of the corresponding gene products in the biological samples, comparisons of nucleic acid gene products or protein gene products can be employed. As would be understood by one of ordinary skill in the art, quantitative assays can be desirable to determine relative expression levels. With respect to nucleic acids, particularly mRNA gene products, a technique selected from the group consisting of microarray analysis, RNAseq, quantitative RT-PCR, NanoString, or any combination thereof can be employed. Non-limiting examples of such techniques include whole transcriptome RNAseq, targeted RNAseq, SAGE, RT-PCR (particularly QRT-PCR), cDNA microarray analyses, and NanoString analysis. Techniques for assaying gene expression levels using RT-PCR, nucleic acid and/or protein microarray hybridization, and RNA-Seq are known in the art (see e.g., U.S. Pat. Nos. 5,800,992; 6,004,755; 6,013,449; 6,020,135; 6,033,860; 6,040,138; 6,177,248; 6,251,601; 6,309,822, 7,824,856; 9,920,367; 10,227,584; each of which is incorporated by reference in its entirety. See also U.S. Patent Application Publication Nos. 2010/0120097; 2011/0189679; 2014/0113333; 2015/0307874; each of which is incorporated by reference in its entirety.

In some embodiments, the assay involves use of NanoString. The basic NanoString technology is described in PCT International Patent Application Publication No. WO 2019/226514 and U.S. Pat. No. 9,181,588, each of which is incorporated herein by reference in its entirety. For use with Gene Pairs 1-8 and A-H, one of ordinary skill in the art can design appropriate NanoString probes based on the sequences of the corresponding gene products. Exemplary NanoString probes are identified in Table 6. In some embodiments, and particularly wherein different assay techniques are employed with different samples, an internal control can be employed to normalize and/or harmonize gene expression data. In some embodiments, an internal control comprises a housekeeping gene. Exemplary housekeeping genes include the CTSE, LYZ, MUC17, MYO1A, NR1I2, PIP5K1B, RPLP0, B2M, ACTB, RPL19, GAPDH, LDHA, PGK1, TUBB, SDHA, CLTC, HPRT1, ABCF1, GUSB, TBP, and ALAS1, and exemplary NanoString probes that can be employed with these genes are disclosed in SEQ ID NOs: 75-102, respectively.

In some embodiments, a gene product is a protein gene product, and gene expression is determined by quantifying an amount of protein present in a sample. Methods for quantifying gene expression at the protein level are known, and include but are not limited to enzyme-linked immunosorbent assay (ELISA), immunoprecipitation (IP), radioimmunoassay (RIA), mass spectroscopy (MS), quantitative western blotting, protein and/or peptide microarrays, etc. See e.g., U.S. Pat. Nos. 7,595,159; 8,008,025; 8,293,489; and 10,060,912; each of which is incorporated by reference herein in its entirety. For those assays that require the use of antibodies, various commercial sources of antibodies, including monoclonal antibodies, exist, including but not limited to ProMab Biotechnologies, Inc. (Richmond, Calif., United States of America), abcam plc (Cambridge, United Kingdom), Santa Cruz Biotechnology, Inc. (California, United States of America), etc.

In some embodiments, the determination of subtype of a pancreatic tumor sample, optionally a PDAC sample, can be employed in making a differential treatment decision with respect to the subject since basal-like and classical subtypes respond differently to different treatments. By way of example and not limitation, if the assigned subtype is a basal-like subtype, a differential treatment strategy for that subject/patient could be with gemcitabine (i.e., 4-amino-1-[(2R,4R,5R)-3,3-difluoro-4-hydroxy-5-(hydroxymethyl) oxolan-2-yl]pyrimidin-2-one, which is often administered as a hydrochloride; see U.S. Patent Application Publication No.

2008/0262215 and U.S. Pat. No. 8,299,239), optionally in combination with paclitaxel (i.e., [(1S,2S,3R,4S,7R,9S,10S,12R,15S)-4,12-diacetyloxy-15-[(2R,3S)-3-benzamido-2-hydroxy-3-phenylpropanoyl]oxy-1,9-dihydroxy-10,14,17,17-tetramethyl-11-oxo-6-oxatetracyclo[11.3.1.03,10.04,7]heptadec-13-en-2-yl] benzoate; see U.S. Pat. No. 6,753,006) or nab-paclitaxel (i.e., ABRAXANE® brand nanoparticle albumin-bound paclitaxel; see U.S. Pat. No. 7,758,891). Methods for treating pancreatic cancer with gemcitabine and/or paclitaxel/nab-paclitaxel are known (see e.g., U.S. Patent Application Publication No. 2017/0020824, which is incorporated herein by reference in its entirety).

If the subtype of the pancreatic tumor sample is classical, then in some embodiments the subject/patient is treated with FOLFIRINOX (composed of folinic acid (leucovorin), fluorouracil, irinotecan, and oxaliplatin; Conroy et al., 2011). In some embodiments, FOLFIRINOX can be combined with other treatments, including but not limited to the CCR2 inhibitor PF-04136309 (see Nywening et al., 2016).

In some embodiments, additional anti-pancreatic cancer/tumor strategies can be employed, including but not limited to surgery, radiation, or administration of other chemotherapeutics. Exemplary chemotherapeutics that can be employed in the methods of the presently disclosed subject matter include, but are not limited to protein kinase inhibitors (PKIs). A listing of exemplary PKIs, their targets, and their associations with basal-like and classical tumor subtypes is presented in Table 28. In some embodiments, a PKI that is associated with overexpression in basal-like subtypes tumors is employed in a combination therapy for samples that are of a basal-like subtype. In some embodiments, a PKI that is associated with overexpression in classical subtype tumors is employed in a combination therapy for samples that are of the classical subtype.

In some embodiments, the presently disclosed subject matter also provides methods for treating patients diagnosed with PDAC. In some embodiments, the methods comprise determining a subtype of the patient's PDAC as being basal-like or classical, and treating the subject as disclosed herein. In some embodiments, basal-like subtype patients are treated with gemcitabine, optionally in combination with nab-paclitaxel, and classical subtype patients are treated with FOLFIRINOX, optionally in combination with a CCR2 inhibitor. The combination therapies discussed herein above can also be employed in the treatment methods of the presently disclosed subject matter.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the Examples

Public datasets. Archival data were obtained from public sources (see Moffitt et al., 2015; Aung et al., 2017; Aguirre et al., 2018; Bailey et al., 2016; Nywening et al., 2016; Connor et al., 2017; and Cancer Genome Atlas Research Network, 2017) and are summarized in Table 4. For the public datasets, expression was used "as-is" with respect to the original publication; that is, RNAseq data were not realigned and gene-level expression estimates were provided in terms of fragments per kilobase per million reads (FPKM) or transcripts per million (TPM), depending on the study.

Sample collection. Deidentified bulk and FNA samples (see Table 5) were collected from the Institutional Review Board (IRB)-approved University of North Carolina Lineberger Comprehensive Cancer Center Tissue Procurement Core Facility after IRB exemption in accordance with the U.S. Common Rule and were flash frozen in liquid nitrogen. FNA samples were collected ex vivo at the time of resection. The FNA technique used mirrors standard cytopathology procedures, where three passes were performed using a 22-gauge needle. Palpation was used to localize the tumor. Samples were frozen in either PBS or RNALATER@ brand stabilizing reagent (Sigma-Aldrich Corp., St. Louis, Mo., United States of America). FFPE samples were prepared, hematoxylin and eosin stained, and reviewed by a single pathologist who was blinded to the results as described herein. See below for data processing and analysis of Yeh_Seq samples. RNAseq (GSE131050) and NanoString (GSE131051) data generated from these samples are deposited in Gene Expression Omnibus (GEO).

RNAseq. Samples for Yeh_Seq were sequenced on a NEXTSEQ® 500 brand sequencing system (Illumina, inc., San Diego, Calif., United States of America). We converted BCL files to FASTQ using bcl2fastq2 Conversion Software 2.20.0 (Illumina, Inc.). Individual lane files were combined into one FASTQ for each sample. FASTQ of PDX samples were split into human and mouse reads using bbmap v37.90 (Bushnell, 2014). The total expected read counts per gene were quantified by Salmon 0.9.1 (Patro et al., 2017) using arguments "—gcBias—seqBias". For human samples, Genome Reference Consortium Human Build 38 (GRCh38) was used. For PDX samples, GRCh38 was involved in quantification for human reads, while the mouse reference genome GRCm38/mm10 (December 2011) available at the website of the University of California Santa Cruz (UCSC) Genomics Institute was used to quantify mouse reads. The expression of each gene was measured by the Transcripts per Million (TPM), which was subjected to downstream analysis.

Customized quality control guidelines were used for low-input (FNA) and degraded (FFPE) samples (Adiconis et al., 2013). Bulk or FNA samples were flagged if the proportion of bases mapped to coding regions fell below 30%. For FFPE samples, samples were flagged if the proportion fell below 10%. We also checked the total number of unique reads after deduplication. Bulk and FFPE samples were flagged if the total number of unique reads were below 1 million. FNA samples were flagged if the total number of unique reads were below half a million. We also checked the uniformity of transcript coverage by assessing 5'-to-3' bias using gene body plots, and insert size distribution, so that any sample that clearly distinguished itself as an outlier was flagged.

For the Linehan dataset, total RNA was isolated from matched patient tumor biopsies collected at baseline and post-treatment cycle two as part of clinical study NCT01413022 testing the efficacy of PF-04136309 in combination with FOLFIRINOX as previously described (Nywening et al., 2016). RNA expression libraries were generated with TruSeq Stranded mRNA kits according to the manufacturer's instructions and sequencing was performed on the HiSeq 2500 Sequencing System (Illumina, Inc.). BCL files were converted to FASTQ with bcltofastq software v2.19.0 (Illumina, Inc.). The total expected read counts per gene were quantified by Salmon 0.9.1 using arguments "—gcBias—seqBias" and reference genome GRCh38, which were normalized to TPM as described above.

CC based subtype calling. Unsupervised CC was applied for each of the subtyping schemas (Collisson, Bailey, and Moffitt) on all public datasets included in our study as previously described using the ConsensusClusterPlus package in R (Aguirre et al., 2018), subsequent to sample filtering. In brief, 62 genes identified by Collisson (Collisson et al., 2011), 613 differentially expressed genes from the multiclass SAM analysis by Bailey (Bailey et al., 2016), and 50 tumor specific genes from Moffitt (Moffitt et al., 2015) were utilized for subtyping analysis, seeking the presence of 3, 4, and 2 clusters respectively. For the Bailey and Collisson schemas and using published calls as the gold standard (Bailey subtypes in the PACA_AU_array and PACA_AU_seq datasets, and Bailey and Collisson subtypes in the TCGA_PAAD dataset), we found a better concordance of the subtype calls by applying row-scaling than without row-scaling prior to consensus clustering (CC). Therefore, for the Bailey and Collisson schemas, each dataset was subjected to gene-wise (row) scaling across samples so that expressions were normalized to z-scores for each gene as the input for CC. Row-scaling was not applied to the Moffitt schema. For the COMPASS and Connor datasets, the 10 least variable signature genes were dropped in subtype calling for the Bailey schema since, in these two datasets, the CC found subsamples with 0 variance which led to termination of the function in R.

PurIST Single Sample Classifier.

Data pre-processing. For each RNAseq dataset, we first removed genes in the bottom 20% percentile in expression on average in that dataset. This is to remove consistently low expressing genes that may be unhelpful for prediction later. For microarray data, due to probe-specific effects, it is more difficult to assume that measured expression is correlated with actual biological expression, so we do not apply this filtering here. We then further reduced the list of remaining genes in each dataset to those belonging to a list of 500 Moffitt tumor-specific genes determined previously (Moffitt et al., 2015). Finally, we retained only those genes that were in common across all nine datasets after these filtering steps. At the end of this process, we had 412 genes out of 500 tumor-specific genes remaining that were in common across all 9 data datasets.

Training Datasets and candidate gene ranking. Training labels and expression values from the genes in our tumor-specific gene list served as the basis for our building the PurIST model. Training labels for PurIST were a subset of the Moffitt CC in the Training Group datasets (Aguirre, Moffitt_GEO_array and TCGA_PAAD; Table 7) were utilized. These samples were further filtered to provide final training labels for the PurIST algorithm by dropping poorly clustered samples on the clustered dendrogram in each dataset based on visual inspection. We considered these filtered calls as "training labels". Because not all genes may be consistent in their relationship with tumor subtype across training datasets or may be strongly discriminatory between subtypes, we ranked candidate genes in based on the consistency of their Differential Expression (DE) between subtypes in each individual Training Group dataset, as well as the consistency in the direction of their DE for utilization in subsequent steps (Lusa et al., 2007; Paquet & Hallett, 2015). We applied the Wilcoxon Rank Sum test to each gene in a given study to test for differences in mean expression between basal-like and classical subjects. We then obtained a cross-study DE consistency score by summing the $-\log_{10}$ p-values for differential expression across studies. In general, genes that were consistently differentially expressed were most likely to have higher scores. Then, we ranked genes based on this score from largest to smallest. We then considered the top 10% of this list for model training. Lastly, we removed genes where the sign of the difference in mean subtype expression was not the same in all Training Group datasets. The remaining genes then formed our final candidate gene list for downstream steps in PurIST model training.

kTSP selection for prediction: overview. Let us define a gene pair ($g_{dis}$, $g_{dit}$), where $g_{dis}$ is the raw expression of gene s for subject i in study d, and $g_{dit}$ is defined similarly with respect to some gene t. A TSP is an indicator variable based on this gene pair, $I(g_{dis}>g_{dit})-1/2$, where its value represents which gene in the pair has higher expression in subject i from study d (1/2 if $g_{dis}>g_{dit}$, and $-1/2$ otherwise). In traditional applications (k=1), a single TSP is selected out of the set of all possible gene pairs such that if $I(g_{dis}>g_{dit})-1/2>0$, this implies subtype A with high probability in the training data, otherwise implying subtype B (Geman et al., 2004). Therefore, in a new subject, binary class prediction is performed by checking whether $I(g_{dis,1}>g_{dit,1})-1/2>0$ vs otherwise. We view such binary variables as "biological switches" indicating how pairs of genes are expressed relative to some clinical outcome. TSPs were originally proposed in the context of binary classification (Geman et al., 2004; Tan et al., 2005; Afsari et al., 2014). In the kTSP setting, class prediction reduces to verifying whether the sum across k selected TSPs is greater than 0:

$$\sum_{l=1}^{k} I(g_{dis,l} > g_{dit,l}) - \frac{1}{2} > 0$$

This reduces to a majority vote across the selected k TSPs, where the contribution of each of the k TSPs are equally weighted to select subtype A if the above sum is greater than 0, and subtype B otherwise.

We describe this approach to select TSPs in the next section. However, several studies have found that equal weighting of TSPs in majority voting may be suboptimal, as some TSPs may be more informative than others (Shi et al., 2011). Therefore, we utilized penalized logistic regression (Breheny & Huang, 2011) to jointly estimate the effect of each of the k selected TSPs in predicting binary subtype, and to further remove TSPs with weak or redundant effects. Predicted probabilities of basal-like subtype membership may then be obtained from the fitted model logistic regression model on our training samples, where values greater than 0.5 indicate predicted membership to the basal-like subtype and classical otherwise.

Horizontal data integration and kTSP selection via switchbox. To apply the top scoring pairs transformation, we utilized the switchBox R package (Afsari et al., 2015) to enumerate all possible gene pairs based on our final candidate gene list and training samples (function SWAP.KTSP.Train, with optimal parameters featureNo=1000, krange=50, FilterFunc=NULL). Given the large number of potential gene pairs based on this list, in addition to the strong correlation between gene pairs sharing the same gene, the switchBox package utilized a greedy algorithm to select from this list a subset of gene pairs that were helpful for prediction, given the set of training labels. We merged data from each Training Group dataset without normalization prior to applying switchBox, as the method only looked at the relative gene expression ranking within each sample from each study. The method then selected a subset of k TSPs, where k is determined through a greedy optimization procedure.

Model training based on selected kTSP list. To remove redundant TSPs and to jointly estimate their contribution in predicting subtype in our training samples, we utilized the ncvreg R package (Breheny & Huang, 20111) to fit a penalized logistic regression model based upon the selected TSPs from switchBox. Our design matrix was an N× (k+1) matrix, where the first column pertained to the intercept and the remaining k columns pertained to the k selected TSPs from switchBox. Here N was the total number of training samples from each dataset employed for training. Each TSP in the design matrix was represented as a binary vector, taking on the value of 1 if gene A's expression was greater than gene B's expression. Our outcome variable here was binary subtype (1=Basal, 0 otherwise). We utilized optional parameters alpha=0.5 and nfolds=N. We allowed for correlation between TSPs by setting the ncvreg alpha parameter to 0.5 in order to shrink the coefficients of highly correlated TSPs and also remove correlated uninformative TSPs from the model. We set nfolds=N to apply leave one out cross validation in order to choose the optimal MCP penalty tuning parameter for variable selection, where the optimal tuning parameter was the one that minimized the cross-validation error of the fitted model. Our final model then reported the set of coefficients estimated for each of the kTSPs, where each coefficient may be interpreted as the change in log odds of a patient being part of the basal-like subtype when the $1^{th}$ TSP is equal to 1, given the others in the model. TSPs with coefficient of 0 were those that have been removed from the model for either weak effect or redundancy with other TSPs. Predicted probabilities of Basal subtype membership may be obtained by computing the inverse logit of the linear predictor $X_{i,new}\hat{\beta}$(the Raw Score), where $X_{i,new}$ was a 1×(k+1) TSP predictor vector from a new sample, and P was our estimated set of coefficients from the fitted penalized logistic regression model. Then, predicted probabilities of basal-like subtype membership for this new sample can be computed through the inverse logit function:

$$\hat{p}_{i,new}=\exp(X_{i,new}\hat{\beta})(1+\exp(X_{i,new}\hat{\beta}))$$

$\hat{p}_{i,new}$ values greater than 0.5 indicated predicted membership basal-like subtype, and those less than 0.5 were those that were predicted those be of the classical subtype. This was equivalent to determining whether $X_{i,new}\hat{\beta}>0$ (basal-like subtype) vs $X_{i,new}\hat{\beta}<0$ (classical subtype), where $X_{i,new}\hat{\beta}$ may also be utilized as a continuous score for classification ("PurIST Score"). Therefore, prediction in new samples, such as from our validation datasets, reduced to simply checking the relative expression of each gene within the set of TSPs. Those TSPs with selected 0 coefficient can be ignored in this setting.

For all discussions regarding classifier performance, we obtained the predicted subtypes in the manner described above. The level of confidence in the prediction can be determined based upon the distance of $\hat{p}_{i,new}$ from 0.5, where values closer to $\hat{p}_{i,new}$ indicated lower confidence in the predicted subtype and higher confidence otherwise. Specifically, values of $\hat{p}_{i,new}$ between 0.5 and 0.6 indicated the lean basal-like prediction category, 0.6 and 0.9 represented the likely basal-like prediction category, and values greater than 0.9 indicated the strong basal-like prediction category. Values of $\hat{p}_{i,new}$ between 0.5 and 0.4 indicated the lean classical prediction category, 0.6 and 0.1 represented the likely classical prediction category, and values less than 0.1 indicated the strong classical prediction category.

NanoString and PurIST-n. We repeated the above procedure with a subset of genes using NanoString probes (PurIST-n; see Table 6). We then retrained our model in given our training datasets limiting to these genes, rebuilding candidate TSPs and applying our penalized logistic regression model to obtain our PurIST-n classifier. Matched samples from RNAseq were run on the NanoString nCounter platform as per manufacturers instruction. In brief, for each sample, RNA was combined with the NanoString master mix and the Capture Probe set. Hybridization of the RNA with the Capture Probe set took place overnight while incubating at 65° C. After hybridization completed, the samples were added to the NanoString nCounter cartridge and placed in the nCounter Prep Station using the high sensitivity setting. After the Prep Station run was complete, the cartridge was removed and placed in the NanoString Digital Analyzer for scanning.

Sample inclusion for consensus clustering analysis and PurIST training. For treatment response and survival analysis, samples with available clinical and RNAseq data were used. Specifically, for the pooled survival analysis, samples from the following datasets with RNAseq data and CC calls were utilized: Linehan, Moffitt_GEO_array, PACA_AU_seq, PACA_AU_array, and TCGA_PAAD (survival group; Table 7). Duplicated samples in PACA_AU_seq and PACA_AU_array datasets were only used once, with the subtypes called in PACA_AU_array used when mismatches of subtype calls were found between the two datasets. To train PurIST, Moffitt schema CC calls from the datasets in the training group (Aguirre, Moffitt_GEO_array, and TCGA_PAAD; Table 7) were utilized. These samples were further filtered to provide final training labels for the PurIST algorithm by dropping poorly clustered samples on the clustered dendrogram in each dataset based on visual inspection. We considered these filtered calls as "training labels." Model training for PurIST is described herein above.

Statistical Analysis. Overall survival estimates were calculated using the Kaplan-Meier method. Association between overall survival and individual covariates such as subtype were evaluated via the cox proportional hazards (coxph) models using the coxph function from the 'survival' R package, where a given subtyping schema was considered as a multi-level categorical predictor. The logrank p-value was utilized to evaluate overall association of a subtyping system with overall survival. In the pooled analyses, a stratified coxph model was utilized, where dataset of origin was used as a stratification factor to account for variation in baseline hazard across studies. To test for differences in survival between individual subtypes within a schema, linear contrasts were utilized in conjunction with the fitted stratified coxph model to construct a general linear hypothesis test. BIC pertaining to each fitted stratified coxph model was calculated for each schema using the "BIC" function in R, where smaller BIC values indicate better model fit.

Agreement between subtype calls in patients within matched samples were performed using Cohen's Kappa via the "kappa2" function from the irr package in R. Hypothesis tests evaluating the null hypothesis that Kappa=0, indicating random agreement, was also performed using the kappa2 function. Kappa values of 1 indicate perfect agreement. Association between categorical response, defined by RECIST 1.1 criteria (PD, SD, PR, CR), and called subtypes from in a given clinical trial with treatment response was evaluated using the Generalized Cochran-Mantel-Haenszel test, with trial arm utilized as the stratification factor and assuming categorical treatment response as an ordinal variable. This is to correct for potential confounding due to differences between arms. This test was carried out using the "cmh_test" function from the coin R package. We determined an empirical null distribution for this test using permutation testing, assuming 5 million permutations to ensure robustness against any deviations from test assumptions. In modeling response as a continuous variable (% change in tumor volume from baseline) with respect to a given schema, two-way ANOVA was utilized, where schema subtype and arm were utilized as categorical factors, and BIC was calculated similar to before. When categorical response was utilized, a multinomial regression model utilizing schema subtypes as a categorical prediction was fit using the "polr" from the MASS R package, and BIC was calculated as mentioned previously. For the permutation test to compare correlation among various gene sets, we first evaluated the Spearman correlations between each of the PurIST TSP genes in FFPE vs. bulk, FFPE vs. FNA, and also bulk vs. FNA. This was also repeated for each of the Bailey ADEX genes and Bailey immunogenic genes. We then calculated paired Wilcoxon signed-rank statistic of to test if the 18 correlations among TSP genes was significantly higher than that of ADEX genes (or immunogenic genes). Since the 18 correlations were not independent observations, the null distribution was approximated using permutations. The permutation of the FFPE and FNA matches for the 6 bulk samples was done 10,000 times and the paired Wilcoxon statistic was likewise computed for each permutation. This generated the distribution of the statistic under the null hypothesis that the paired difference between correlations among TSP genes versus those among ADEX genes (or immunogenic genes) are centered around zero, which allowed us to derive a p-value for the observed statistic before permutation.

Example 1

The Moffitt Tumor-intrinsic Two-subtype Schema has Important Implications for Treatment Response To evaluate the potential impact of molecular subtypes on treatment response, we utilized transcriptomic and treatment response data from two independent clinical trials, and performed a systematic analysis of treatment response with respect to CC calls from each of the three different subtyping schemas (described herein above)) for PDAC: Collisson, Bailey, and Moffitt (Collisson et al., 2011; Bailey et al., 2016; Moffitt et al., 2015). We first examined the association of the subtypes from each schema with treatment response using patient samples from a promising phase Ib trial by Nywening and colleagues ("Linehan," Linehan_seq dataset; Tables 8-17) of FOLFIRINOX in combination with a CCR2 inhibitor (PF-04136309) in patients with locally advanced PDAC, where an objective response was seen in 49% of patients (Nywening et al., 2016). Enrolled patients had no prior treatment, and underwent core biopsies prior to the start of therapy. Twenty-eight patients with RNAseq and treatment data were available for analysis.

We found a significant overall association between categorical treatment response (based on RECIST 1.1 criteria) and pretreatment subtype classifications from the Moffitt schema (p=0.0117; Tables 18-21), where basal-like tumors showed no response to FOLFIRINOX alone or FOLFIRINOX plus PF-04136309 after stratifying by arm [overall response rate (ORR)=0%; disease control rate (DCR)=33%; Tables 18-21, generalized Cochran-Mantel-Haenszel test], whereas classical tumors showed a much stronger response overall (ORR=40%; DCR=100%). In contrast, we were unable to identify a relationship between subtype and treatment response under the Collisson (p=0.428) and Bailey (p=0.113) schemas (Tables 18-21). As the sample size in this phase Ib trial (n=28 patients) was small, we similarly reanalyzed the COMPASS trial results (n=40 patients) in the context of the three subtyping schemas.

Patients enrolled in COMPASS underwent core-needle biopsies and were treated with one of two standard first-line therapies, modified-FOLFIRINOX or gemcitabine plus nanoparticle albumin-bound paclitaxel (nab-paclitaxel). Collected patient samples in COMPASS underwent laser capture microdissection (LCM) followed by whole genome sequencing and RNAseq. Subtypes for each schema were determined as mentioned previously. Similar to our findings in the Linehan phase Ib trial, we found a significant association between the Moffitt two subtype schema with categorical treatment response stratifying by arm (P=0.00098, generalized Cochran-Mantel-Haenszel test), where the basal-like subtype had much lower response to either treatment (ORR=10%; DCR=50%) relative to the classical subtype (ORR=36.7%; DCR=100%). We also found significant associations between treatment response and the subtypes from the Collisson (p=0.0024) and Bailey (p=0.0067) schemas. However, we notably observe that the Bailey squamous subtype strongly overlaps with the Moffitt basal-like subtype, and the remaining nonsquamous Bailey subtypes appear to overlap strongly with the Moffitt classical subtype (Cohen Kappa=1.0, $p=2.54\times10^{-10}$). We similarly found that the Collisson QM-PDA and the remaining non-QM-PDA subtypes correspond strongly with the Moffitt basal-like and classical subtypes, respectively (Cohen Kappa=0.875, $p=2.44\times10^{-8}$), a fact also mirrored in the Linehan trial.

Given these observations, we formally evaluated the relative clinical utility of each subtyping system using non-nested model selection criteria such as Bayesian information criterion (BIC; Schwarz, 1978). Briefly, such criteria evaluate model fit relative to the complexity of the model, as models with more predictors (subtypes) may simply have better fit due to overfitting, and also may contain excess predictors (additional subtypes) that do not contribute meaningfully in differentiating clinical outcomes. The model with the lowest BIC in a series of competing candidate models is preferred in statistical applications, and is agnostic to the magnitude of the difference (Kass et al., 1995). Considering response as a continuous outcome (% change in tumor volume), we find that the Moffitt schema had the best (lowest) BIC score in both datasets (Linehan BIC=247.37, COMPASS BIC=378.75, two-way ANOVA model; Tables 18-21), compared with the Collisson (Linehan BIC=254.63, COMPASS BIC=382.8) and Bailey (Linehan BIC=250.75, COMPASS BIC=385.66) schemas. This result similarly held if we considered response as a categorical variable (ordinal regression model; Tables 18-21). This finding was also reflected among the non-QM-PDA and nonsquamous subtypes (Tables 18-21), where little difference in response can be seen between these subtypes. Our results using BIC suggested that the additional subtypes found in the Collisson and Bailey schemas do not demonstrate additional benefit in differentiating treatment response over the Moffitt two-subtype schema. Taken together, these results suggest that the Moffitt basal-like and classical subtypes strongly and parsimoniously explained treatment response relative to other schemas in both clinical trials.

The Linehan phase Ib trial captured both pre- and post-treatment biopsies, providing a unique opportunity to evaluate the stability of molecular subtypes after treatment. As pre- and post-treatment biopsies were unlikely to be obtained from the same location, these samples may also provide an opportunity to evaluate intrapatient tumor heterogeneity. Interestingly, we found strong stability in the Moffitt schema subtypes in pre- and post-treatment biopsies (Cohen Kappa=1.0; p=2.54 $10^{-10}$), suggesting that not only may there be less tumor-intrinsic subtype heterogeneity within a tumor, but also that the Moffitt schema subtypes are not affected by treatment, either with FOLFIRINOX or with the addition of the CCR2 inhibitor. In contrast, we found higher rates of switching in Collisson subtypes pre- to posttreatment (Tables 23 and 24), where changes in the exocrine-like and classical subtypes were more common. Similarly, the nonsquamous Bailey subtypes appeared to show the highest rate of subtype switching pre- and post-treatment, with the ADEX subtype demonstrating the highest rate of switching among these subtypes (Tables 23 and 24).

It was unclear whether there is any clinical significance to such subtype transitions. Prior studies had suggested that the Bailey ADEX, Bailey immunogenic, and Collisson exocrine-like subtypes are confounded by tumor purity in contrast to the Moffitt subtypes (Cancer Genome Atlas Research Network, 2017; Puleo et al., 2018; Maurer et al., 2019), which may explain some of the increased heterogeneity in subtypes pre- and posttreatment in these schemas. In contrast, the Collisson QM-PDA and Bailey squamous subtypes, which were shown to overlap strongly with the Moffitt basal-like subtype, were observed to be much more stable between the two time points.

Example 2

The Tumor-intrinsic Two-subtype Schema Strongly and Replicably Differentiates Patient Survival Across Multiple Studies Given the paucity of available genomic data in the context of treatment response in PDAC, we also performed a meta-analysis of five independent patient cohorts with OS data available: Linehan_seq, Moffitt GEO array (GSE71729), ICGC PACA_AU array, ICGC PACA_AU seq, and TCGA PAAD (survival group; Table 7). To determine the potential replicability of the different subtyping schemas (Collisson, Bailey, Moffitt) in differentiating clinical outcomes, we utilized CC subtype calls from each schema.

Figure 1B:
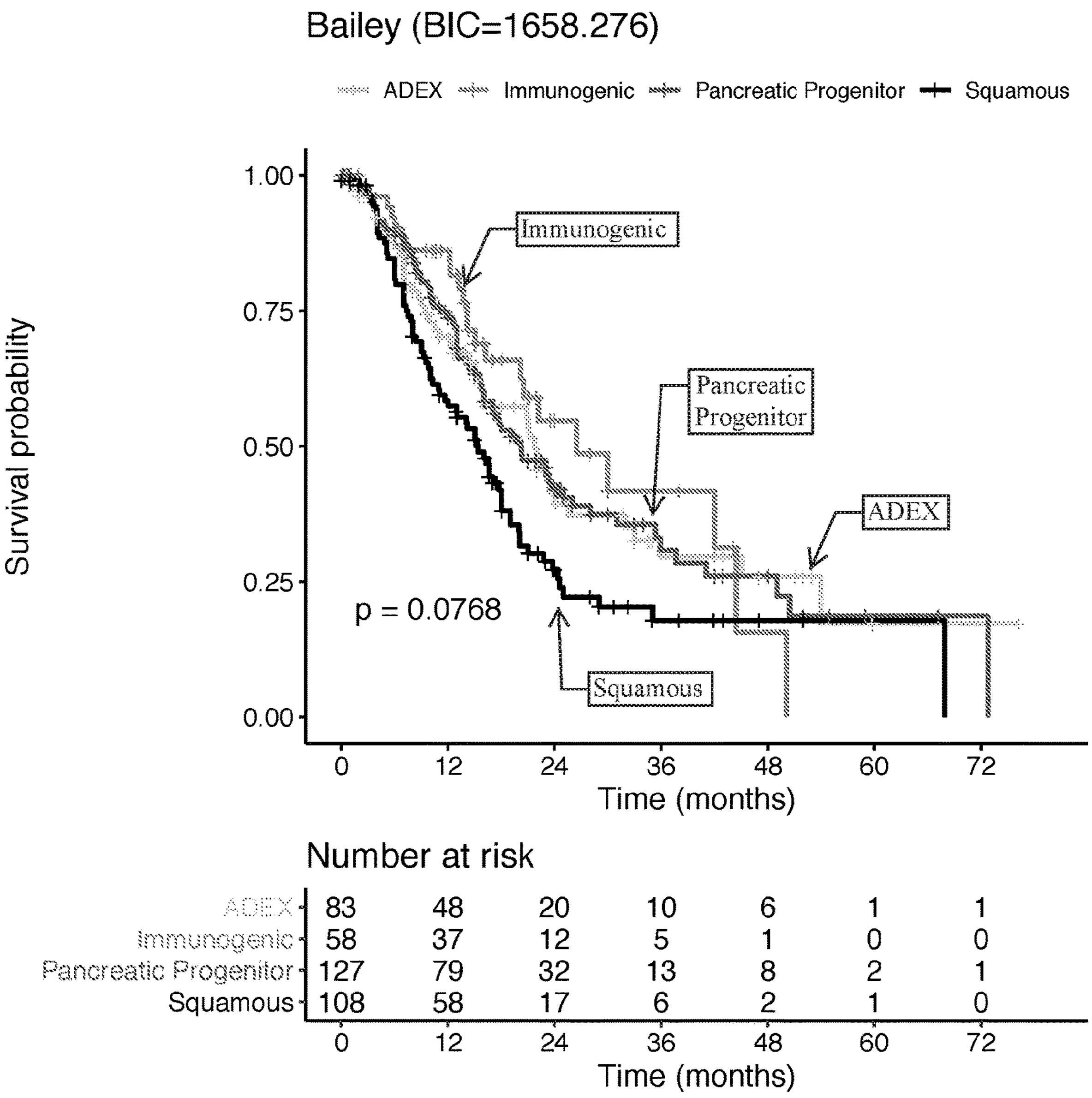
Figure 1C:
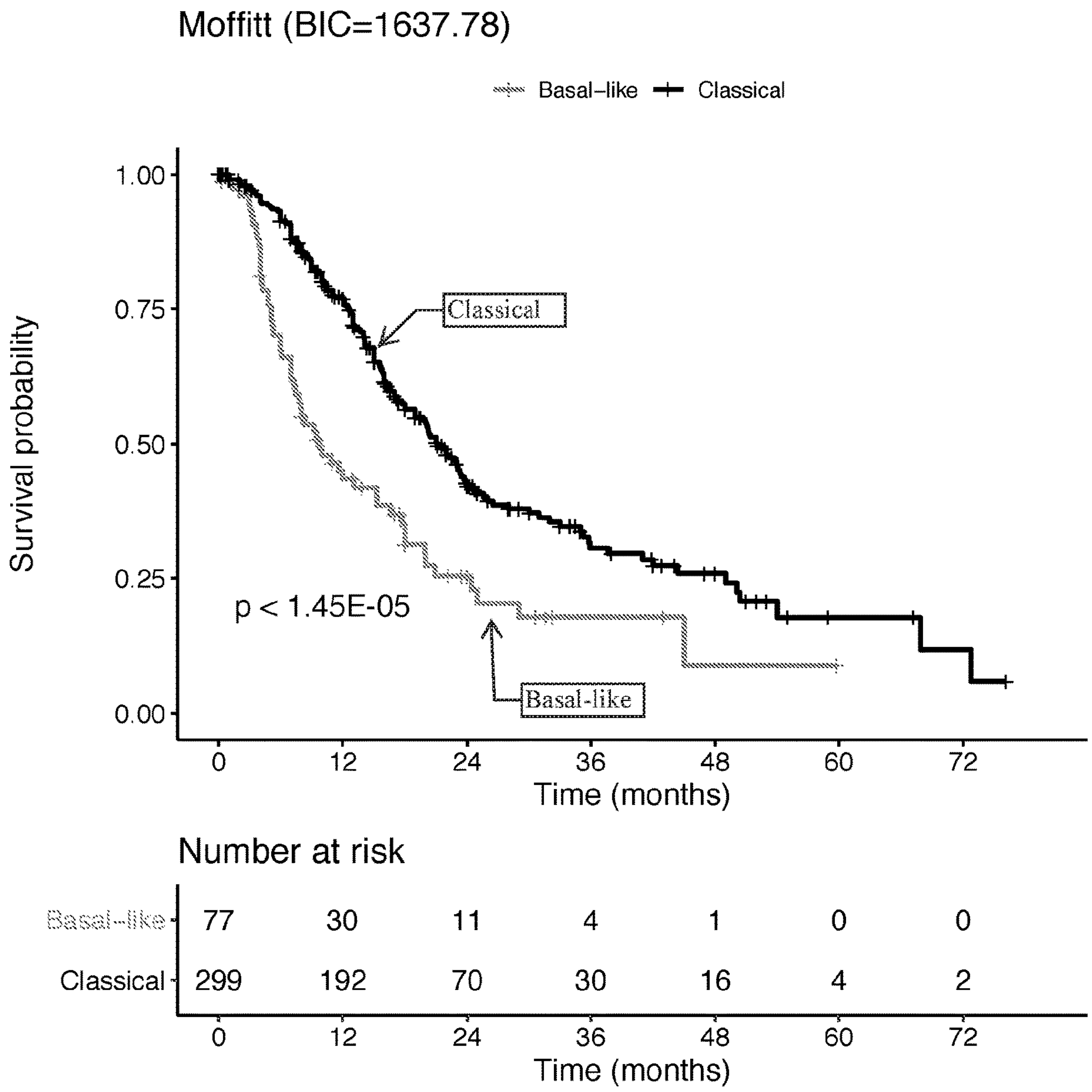
Figure 2:
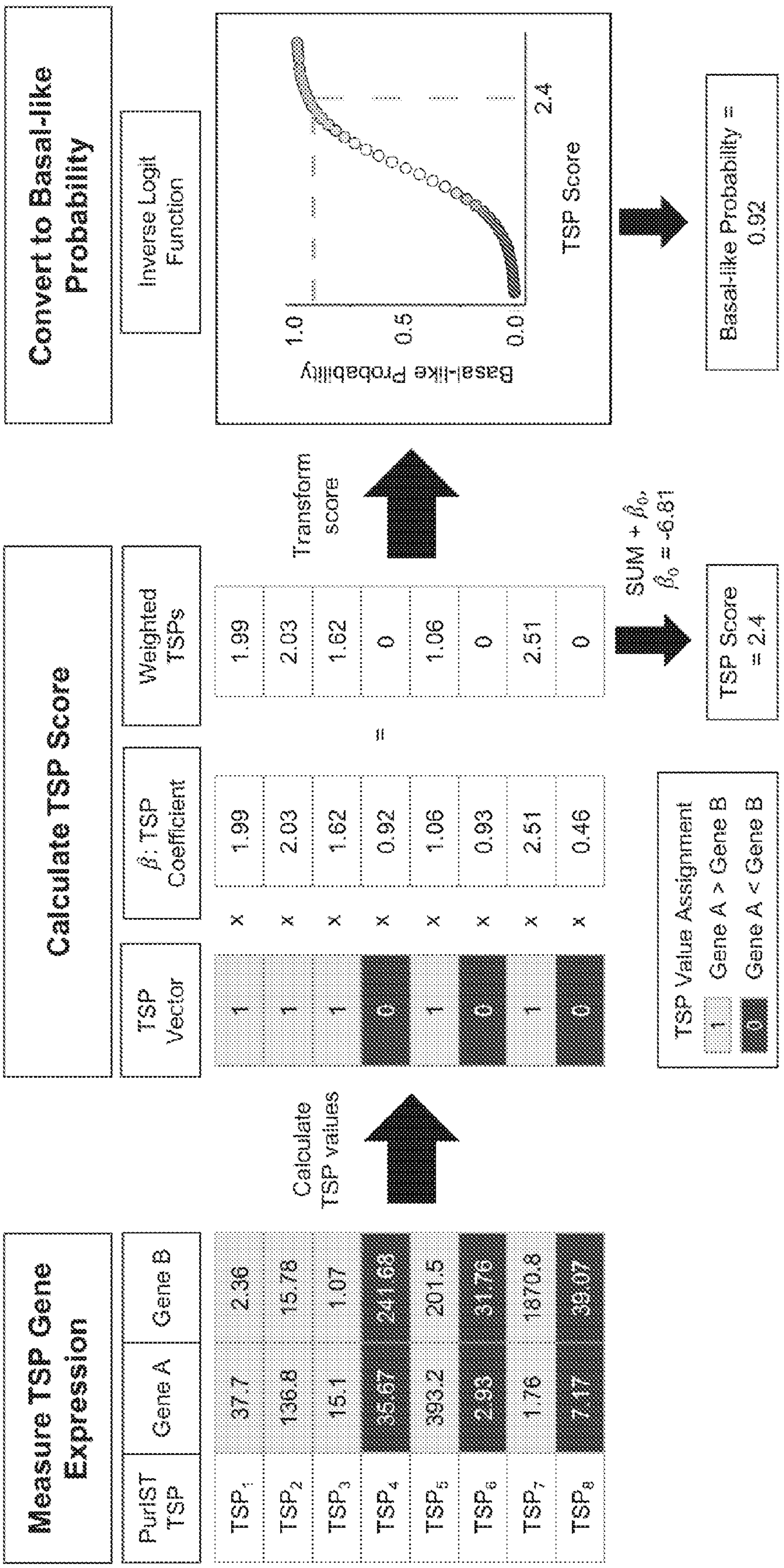
FIG. 2 shows the results of development and validation of the PurIST SSC classifier. It provides an overview of the PurIST prediction procedure. Gene expression for genes pertaining to each PurIST TSP is first measured in a new sample. Values are assigned for each TSP given the relative expression of each gene in the TSP (1 if gene A>gene B expression in the pair, 0 otherwise). Given the set of estimated PurIST TSP coefficients, a TSP score is calculated by summing the product of each TSP and its corresponding TSP coefficient, adjusting for the model intercept. This value is finally transformed into a predicted probability of belonging to the basal-like subtype for classification (inverse logit function).

We found that the Moffitt tumor-intrinsic two-subtype schema reliably differentiated survival across individual datasets (Table 22), showing significant associations with OS in the majority of individual studies in contrast to other schemas. After pooling datasets, we found that patients with Moffitt basal-like subtype tumors had significantly worse prognosis compared with the Moffitt classical subtype (FIG. 1C, stratified HR=1.98, p<0.0001, stratified Cox proportional hazards model). We also observed similar trends in the Bailey squamous and Collisson QM-PDA subtypes relative to other subtypes in the same schemas (FIGS. 1A and 1B), mirroring our treatment response results described herein above. However, overall subtype-specific survival differences were most pronounced within the two-subtype schema across studies (Table 22), compared with the Collisson (p=0.069) and Bailey (p=0.076) schemas.

Moreover, we found that nonsquamous subtypes in the Bailey schema had very similar OS to one another (FIG. 1B), where a direct overall comparison of these subtypes showed no statistically significant differences in survival in our pooled dataset (immunogenic vs. ADEX stratified HR=1.07, pancreatic progenitor vs. ADEX HR=1.01, overall p=0.82). We found a similar result when comparing survival among patients from the non-QM-PDA subtypes in the Collisson schema in the pooled data (FIG. 1A; exocrine-like vs. classical stratified HR=1.17; p=0.344).

In our pooled dataset, strong correspondence was again found between the Bailey squamous, Collisson QM-PDA, and Moffitt basal-like subtypes, and between the Moffitt classical subtype and the remaining subtypes in the Bailey (Cohen Kappa=0.56, p=0) and Collisson (Cohen Kappa=0.4, p=0) schemas. In TCGA PAAD, where estimates of tumor purity were available, Moffitt classical patients that were also classified as QM-PDA in the Collisson schema had much lower tumor purity than other samples (p=0.0016). The Bailey ADEX and immunogenic samples also had lower tumor purity, regardless of whether they were called Moffitt classical or basal-like. These findings were similar to other studies (Cancer Genome Atlas Research Network, 2017; Puleo et al., 2018; Maurer et al., 2019), and suggested that the discordance in subtype assignment between schemas may be driven by tumor purity.

To determine the best fitting model for OS, we calculated BIC with respect to the stratified Cox proportional hazards model pertaining to each schema. Similar to our analysis of treatment response, we found that the Moffitt two-subtype schema had the best (lowest) BIC and therefore had the best and most parsimonious fit to the pooled survival data (FIGS. 1A-1C; Table 22). We also found this to be the case in the majority of individual studies, replicated across each of our validation datasets (Table 22). These results reflected our finding that no difference in OS can be observed among the Collisson non-QM-PDA and Bailey nonsquamous subtypes in our pooled analysis.

Taken together, these findings supported the conclusion that the Moffitt two-subtype schema strongly and parsimoniously explained differences in OS as compared to alternate subtyping schemas. Our results further suggested that the additional subtypes found in the Collisson and Bailey schemas did not demonstrate additional clinical benefit in terms of predicting OS relative to the simpler Moffitt two-subtype schema, based on BIC and direct statistical comparison of the Collisson non-QM-PDA and Bailey nonsquamous subtypes. Given the robustness and highly replicable clinical utility of the Moffitt schema, we next developed a SSC based on this tumor-intrinsic two-subtype schema to avoid reliance on CC-based analysis.

Example 3

PurIST SSC

The ability to resolve and assign subtypes via clustering is limited when applied to individual patients. Reclustering new samples with existing training samples may also change existing subtype assignments. Thus, we developed a robust SSC, PurIST, to predict subtype in individual patients, based on our three largest bulk gene expression datasets (TCGA PAAD, Aguirre Biopsies, and Moffitt GSE71729, training group). A key element of our method includes the utilization of tumor-intrinsic genes previously identified (Moffitt et al., 2015) to avoid the possible confounding of tumor gene expression with those from other tissue types. For model training, we designated training labels as described herein above. We used rank-derived quantities as predictors in our final SSC model instead of the raw expression values, utilizing the k Top Scoring Pair (kTSP) approach to generate these predictors (described herein above). The motivation of this approach was that while the raw values of gene expression may be on different scales in different studies, their relative magnitudes can be preserved by ranks.

We found that this type of rank transformation of the raw expression data had several advantages. First, a single predictor (TSP) only depends on the ranks of raw gene expression of a gene pair in a sample. Hence, its value is robust to overall technical shifts in raw expression values (i.e., due to variation in sequencing depth), and, as a result, is less sensitive to common between-sample normalization procedures of data preprocessing (Leek, 2009; Afsari et al., 2014; Patil et al., 2015). Second, it simplifies data integration over different training studies as data are on the same scale. Finally, prediction in new patients is also simplified, as normalizing new patient data to the training set is no longer necessary, which may further affect the accuracy of model predictions (Patil et al., 2015).

Example 4

Development and External Validation of PurIST Classifier

We applied the systematic procedure described herein implementing the above approach to derive our PurIST model for prediction in the tumor-intrinsic two-subtype schema given the training labels and ranked transformed predictors for each training samples. The selected eight gene pairs (TSP), fitted model, and model coefficients are given in Tables 25 and 26. The validation that is performed in a hypothetical new patient comprises computing the values of each of the eight selected TSPs in that patient, where a value of 1 is assigned if the first gene in a TSP—gene A—has greater expression than the second gene—gene B—in that patient (and assigned 0 value otherwise). These values are then multiplied by the corresponding set of estimated TSP model coefficients, summing these values to get the patient "TSP Score" after correction for estimated baseline effects. This score is then converted to a predicted probability of belonging to the basal-like subtype, where values greater than 0.5 suggest basal-like subtype membership and the classical subtype otherwise.

To assess the quality of our prediction model, we evaluated the cross-validation error of the final model in our training group. We found that the internal leave-one-out cross-validation error for PurIST on the training group was low (3.1%).

To validate this model, we applied it to the validation group datasets and determined whether PurIST predictions recapitulated the CC subtypes in each study. We found that pooled validation samples strongly segregated by CC subtype when sorted by their predicted basal-like probability, despite diverse studies of origin. These suggested that our methodology avoided potential study-level batch effects. The relative expression of classifier genes within each classifier TSP (paired rows) strongly discriminated between subtypes in each sample, forming the basis of our robust TSP-oriented approach for subtype prediction. We also found that, visually, predicted subtypes from PurIST had strong correspondence with independently determined CC subtypes.

Overall, the PurIST classifier predicted subtypes with high levels of confidence with most basal-like subtype predictions having predicted basal-like probabilities >0.9 (strong basal-like) and most classical subtype predictions with predicted basal probabilities of <0.1 (strong classical). Among these high confidence predictions, the majority of these calls corresponded with subtypes obtained independently via CC. Lower confidence calls (likely/lean basal-like/classical categories of prediction) had higher rates of misclassification, although these less confident calls were more rare in our validation datasets.

To evaluate the overall classification performance of PurIST across studies, we applied a nonparametric meta-analysis approach to obtain a consensus ROC curve based on the individual ROC curves from each validation study (Martinez-Camblor, 2017). We found that the overall consensus AUC was high, with a value of 0.993. ROC curves from individual studies were also consistent. In addition, we found that the estimated interstudy variability of these ROC curves with respect to predicted basal-like probability threshold t was low overall, with relatively higher variance at low thresholds and almost no variability at our standard threshold of 0.5 or greater. These reflected the similarity of individual ROC curves that were observed.

We found that within our validation datasets, the prediction accuracy rates were in general 90% or higher, and individual study AUCs were 0.95 or greater (see Table 27). Furthermore, sensitivities and specificities were often high and in some cases equal to 1, reflecting near perfect classification accuracy. These results suggested that PurIST was robust across multiple datasets and platforms and recapitulated the subtypes independently obtained via CC, which we have shown to have high clinical utility.

Example 5

Replicability of PurIST in Archival Formalin-fixed and Paraffin-embedded and FNA Samples Because frozen bulk tumor samples are not commonly available in routine clinical practice, we next looked at the replicability of PurIST predictions across sample types that are more widely collected in clinical practice. Notably, nearly all preoperative and metastatic biopsies are obtained using either FNA or core biopsy techniques. Prior studies have shown the feasibility of performing RNAseq on core biopsies (Aguirre et al., 2018) and endoscopic ultrasound guided FNAs, both of which are commonly utilized in the diagnosis of pancreatic cancer (Rodriguez et al., 2016). We therefore evaluated the performance of PurIST in both formalin-fixed and paraffin embedded (FFPE) and FNA samples.

Among 47 pairs of matched FNA and bulk samples that passed quality control (Yeh_Seq dataset), we found significant agreement between the PurIST subtype calls of the matched FNA and bulk samples (Cohen Kappa=0.544; $p=2.8\times10^{5}$). Only three pairs of samples (6.4%) show disagreement in subtype calling results using PurIST. CC calls of the bulk samples are also shown as a comparison.

We performed a similar evaluation with tumors that we had matched FFPE, FNA, and bulk samples available. We found complete agreement among PurIST subtype predictions among FFPE, FNA, and bulk samples in patients that had all three sample types available (five sets total), further supporting that PurIST was robust across different sample preparations.

We also found that the genes pertaining to PurIST TSPs are comparatively less variable than genes not designated as tumor-intrinsic. For example, PurIST TSP genes, originally selected from our tumor-intrinsic gene list, had significantly higher Spearman correlation between sample types than Bailey immunogenic (p=0.0149) or ADEX genes (p=0.0083) using a permutation test described herein above. The stability of TSP genes across sample types supported their robustness and their ability to identify tumor-intrinsic signals in samples that may be confounded by low-input or degradation.

Example 6

Replicability of PurIST Predictions on a NanoString Platform

RNAseq assays in Clinical Laboratory Improvement Amendments (CLIA)-certified laboratories are still in their infancy. Thus, we evaluated the performance of PurIST on samples using NCOUNTER@ brand detection technology (NanoString Technologies, Inc., Seattle, Wash., United States of America), a gene expression quantification system that directly quantifies molecular barcodes. This platform has been widely used in cancer molecular subtyping (Veldman-Jones et al., 2015), and is more widely available in CLIA-certified laboratories.

In samples with both RNAseq and NanoString platform expression data available, we evaluated the consistency between subtype calls based on their RNAseq and NanoString expression data using PurIST-n. This updated classifier was trained in a manner similar to PurIST, with the exception that genes were limited to those in common between the two platforms, as a more limited set of genes were available for our NanoString probeset. We found that there was strong agreement between PurIST-n calls in 51 patients with matched RNAseq/NanoString samples (Cohen Kappa=0.879; $p=2.25\times10^{-11}$), where only one sample showed disagreement in its PurIST-n call. This discrepancy may have been due to the relatively lower read count in the RNAseq sample for this patient. In addition, it is noteworthy that the PurIST-n call for this sample was a low confidence call ("lean classical"). These results supported the replicability of PurIST on the NanoString platform and suggested that NanoString may be more robust at overcoming the hurdles of low input or degraded samples.

Example 7

Applicability of PurIST to Treatment Decision Making

Figure 3A:
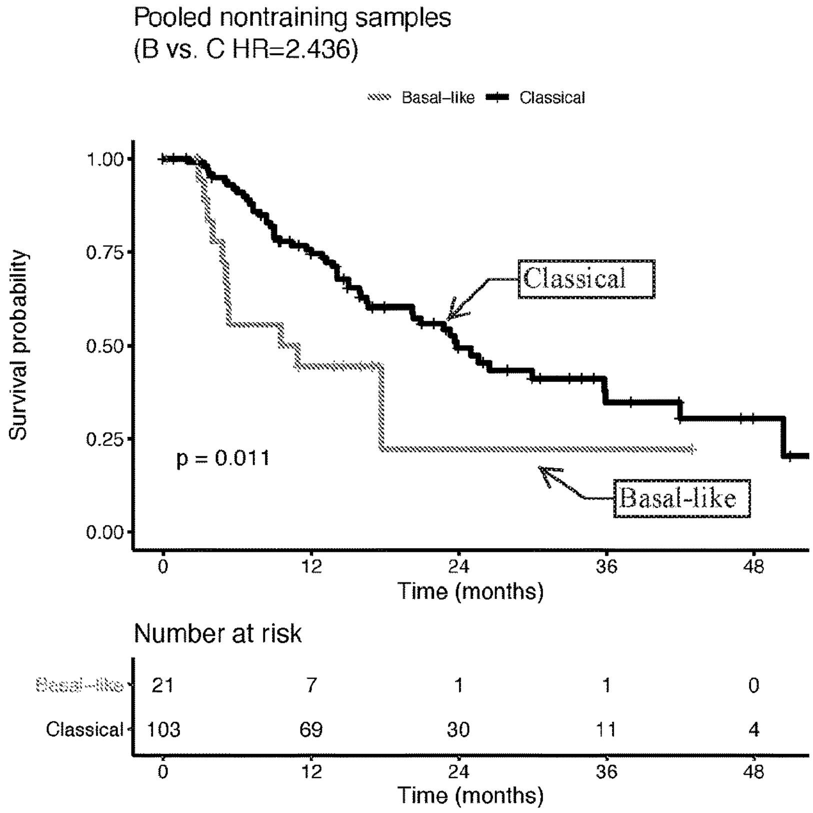
FIGS. 3A-3G show clinical relevance of PurIST SSC in datasets belonging to the treatment group.
Figure 3B:
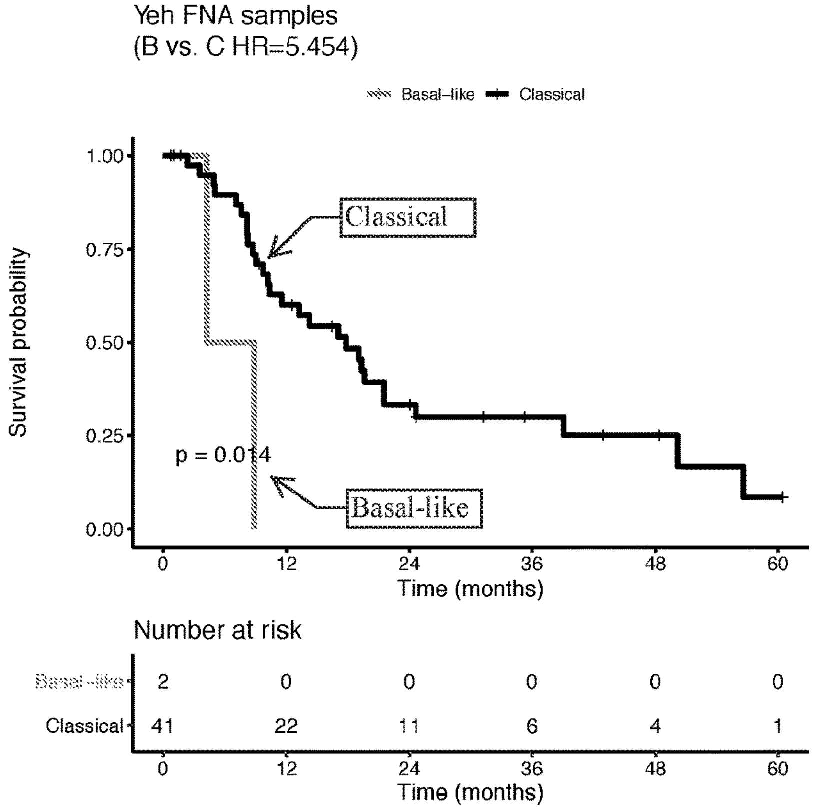

We next evaluated the potential utility of using PurIST for clinical decision making. In basal-like and classical samples that were classified by PurIST, we found significant survival differences in both the pooled public (with all training group samples removed) and the Yeh_Seq FNA datasets, with basal-like samples showing shorter OS (FIGS. 3A and 3B; Table 22).

Figure 3C:
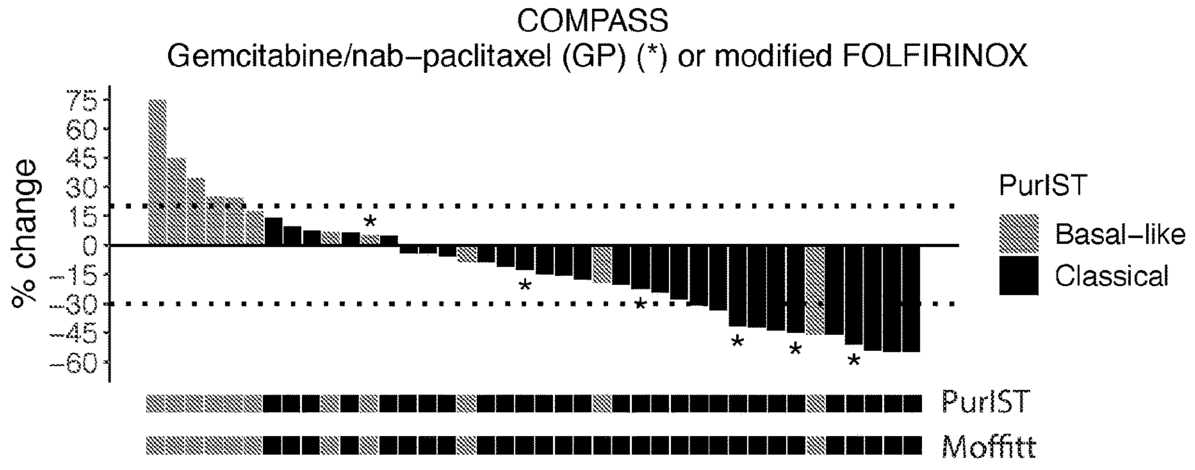
Figure 3D:
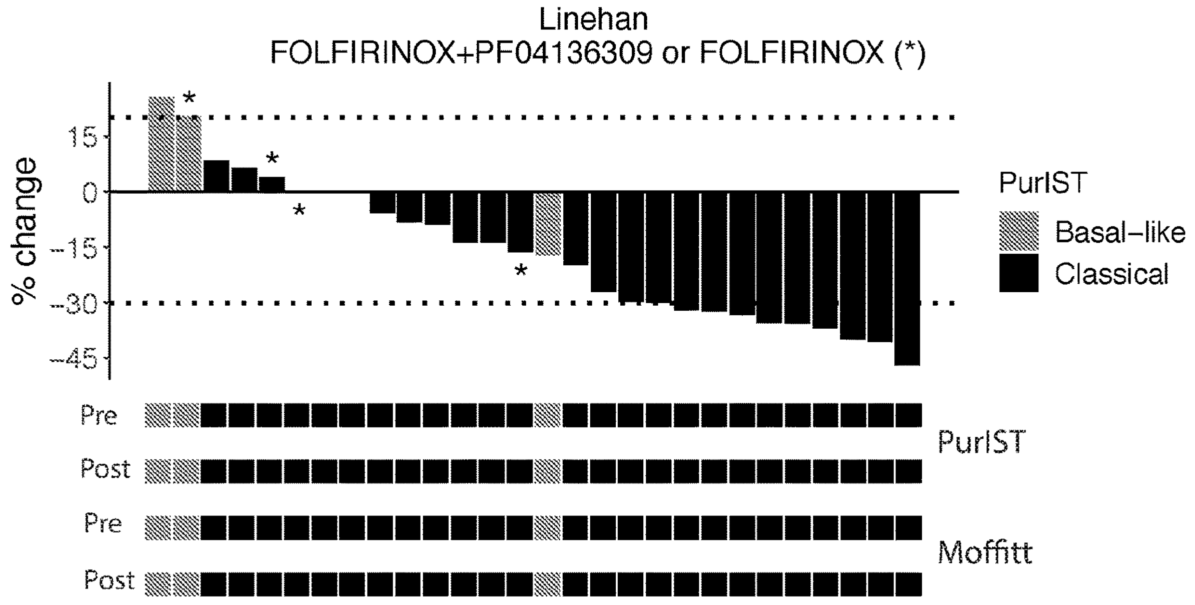

We then looked at the relevance of PurIST to treatment response in the COMPASS and Linehan trials (FIGS. 3C and 3D). PurIST recapitulated 48 of 49 PDAC subtype calls compared with the previous CC-based calls in the COMPASS dataset, and 66 of 66 subtype calls in the Linehan dataset. Only one patient with a CC classical tumor was called basal-like by PurIST and had stable disease (SD, % change >−30% and <20%) in the COMPASS trial. Notably, the only PR seen in a PurIST basal-like tumor was in a patient with an unstable DNA subtype (Aung et al., 2018).

Figure 3E:
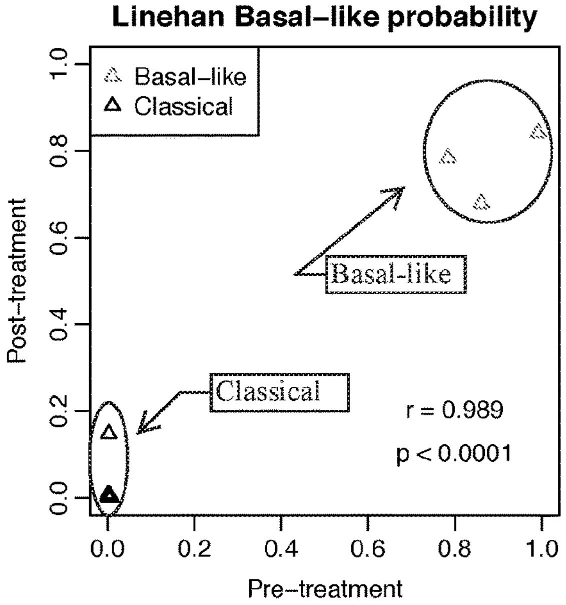
Figure 3F:
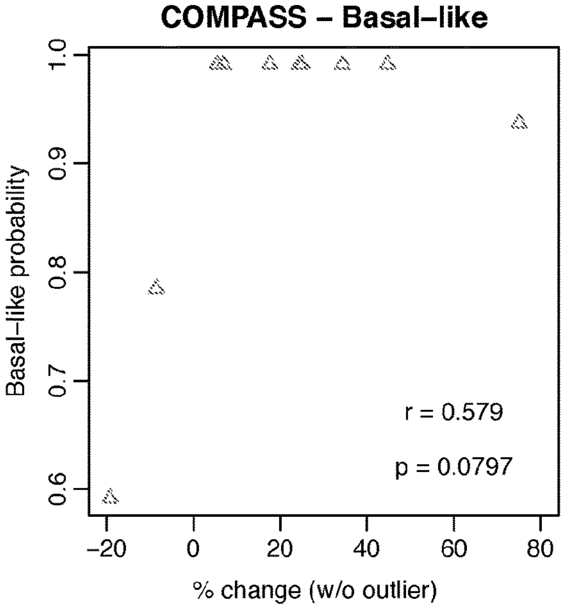
Figure 3G:
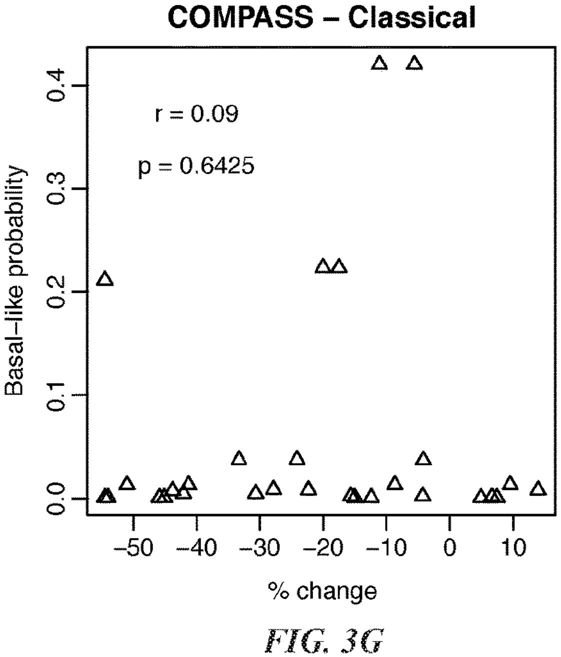

In agreement with our CC analysis, we found that PurIST-predicted subtype tumors had similar associations with treatment response (FIGS. 3C and 3D; Tables 18-21). We also found no change in PurIST subtype or the confidence of the call after treatment, suggesting that PurIST tumor subtypes were unchanged after treatment with FOLFIRINOX and PF-04136300 (FIGS. 3D and 3E). Finally, after excluding the sample with an unstable-DNA-subtype, we showed a positive correlation between PurIST basal-like predicted class probabilities and worse treatment response in basal-like tumors (FIG. 3F). No association of PurIST classical confidence and treatment response was seen (FIG. 3G).

Discussion of the Examples

The availability of next-generation sequencing has facilitated a wealth of genomic studies in pancreatic cancer (Collisson et al., 2011; Moffitt et al., 2015; Bailey et al., 2016; Cancer Genome Atlas Research Network, 2017; Puleo et al., 2018; Maurer et al., 2019). Paired with the increasing availability of promising treatment options for patients with pancreatic ductal adenocarcinomas (PDAC), the ability to predict optimal treatment regimens for patients is becoming ever more critical. Treatments such as FOLFIRINOX have nearly doubled median overall survival (OS) from 6.8 to 11.1 months (Conroy et al., 2011), and gemcitabine plus nab-paclitaxel has increased median OS to 8.5 months (Von Hoff et al., 2013) in patients with metastatic disease. Determining the optimal choice of therapy given a patient's individual clinical or molecular characteristics, thereby enabling "precision medicine" approaches (Ashley, 2016) in PDAC, may improve these outcomes further.

The ongoing multi-center study of changes and characteristics of genes in patients with pancreatic cancer for better treatment selection (COMPASS) was the first study to show treatment ramifications with two molecular subtypes (Aung et al., 2018) first introduced by Moffitt and co-workers in 2015 (Moffitt et al., 2015). Patients enrolled in COMPASS underwent percutaneous core needle biopsies and were treated with one of two standard first-line therapies, modified-FOLFIRINOX or gemcitabine plus nab-paclitaxel according to physician choice. Collected patient samples in COMPASS underwent laser capture microdissection (LCM) followed by whole genome and RNA sequencing, providing an essential opportunity to evaluate genomic associations with treatment response. The findings from COMPASS demonstrated strong associations of molecular subtypes derived from consensus clustering (CC) with treatment response, and further support the need for a clinically usable subtyping system that can be integrated into future clinical studies.

While the development of subtype-based precision medicine approaches is advanced for some cancers (Parker, 2009; Hood, 2011; Vargas, 2016; Dienstmann, 2017), consensus regarding such molecular subtypes for clinical decision-making in pancreatic ductal adenocarcinoma (PDAC) has been elusive. Multiple molecular subtyping systems for pancreatic cancer have been recently proposed in the literature with some studies isolated to PDAC and others that include additional histologies that fall under pancreatic cancer. For example, three molecular subtypes with potential clinical and therapeutic relevance (Collisson classical, quasi-mesenchymal and exocrine-like) were first described in Collisson et al., 2011, leveraging a combination of cell line, bulk, and microdissected patient samples. In contrast, a subsequent study of pancreatic cancer patients later found four molecular subtypes (Bailey et al., 2016) based upon the more diverse pancreatic cancer types: PDAC, adenosquamous, colloid, IPMN with invasive cancer, acinar cell and undifferentiated cancers (Bailey pancreatic progenitor, squamous, immunogenic, and aberrantly differentiated endocrine exocrine (ADEX)). More recently, Puleo et al., described five subtypes which are based on features specific to tumor cells and the local microenvironment (Puleo et al., 2018). Maurer et al. experimentally demonstrated the epithelial and stromal origin of many these transcripts with a cohort of microdissected samples (Maurer et al., 2019). Using non-negative matrix factorization to virtually microdissect tumor samples, we previously have shown two tumor-specific subtypes of PDAC (Moffitt et al., 2015) that we called basal-like, given the similarities with basal breast and basal bladder cancer, and classical, given the overlap with Collisson classical.

Comparative evaluations of these proposed subtyping systems have been limited, partially due to the difficulty in curating and applying these diverse subtyping approaches in new datasets. In one study, The Cancer Genome Atlas (TCGA) pancreatic cancer (PAAD) working group showed that the Collisson quasi-mesenchymal, Bailey immunogenic, and Bailey ADEX subtypes are enriched in low molecular purity PDAC samples (Cancer Genome Atlas Research Network, 2017). In samples of sufficient purity, Collisson classical/Moffitt classical/Bailey pancreatic progenitor and Collisson quasi-mesenchymal/Moffitt basal-like/Bailey squamous were most closely aligned. However, no other independent molecular or clinical evaluations of alternate subtyping systems have been proposed.

Through the careful curation of a large number of publicly available PDAC gene expression datasets, we perform, for the first time, a systematic interrogation of the aforementioned subtyping systems based upon their molecular fidelity and clinical utility across multiple validation datasets. We describe herein that the two-tumor subtype model developed by Moffitt et al. (Moffitt et al., 2015) is robust to confounders such as purity and best explains clinical outcomes across multiple validation datasets. Given the performance of this two-tumor subtype model, we have developed a single sample classifier that we call Purity Independent Subtyping of Tumors (PurIST) to perform subtype calling for clinical use. We showed that PurIST performs well on multiple gene expression platforms including microarray, RNA sequencing, and NanoString. In addition, we demonstrated its potential utility for small sample volumes such as fine needle aspirations (FNAs), given the preponderance of non-surgical biopsies in the neoadjuvant and metastatic settings. Lastly, we confirmed the stability of PurIST subtypes after treatment, and augmented the prior findings in COMPASS that subtypes are associated with treatment response. Particularly, we showed that PurIST basal-like subtype tumors were associated with treatment resistance to FOLFIRINOX, strongly supporting the need to incorporate subtyping into clinical trials of patients with PDAC.

Several subtyping systems for pancreatic cancer have now been proposed. Despite this, several limitations remain before they can be clinically usable. Here we leverage the wealth of transcriptomic studies that have been performed in pancreatic cancer to determine the molecular subtypes that may be most clinically useful and replicable across studies. Our results show that while multiple molecular subtypes may be used to characterize patient samples, the two tumor-intrinsic subtypes from the Moffitt schema: basal-like (overlaps with Bailey squamous/Collisson QM-PDA) and classical (overlaps with non-Bailey squamous/non-Collisson QMPDA) are the most concordant and clinically robust. The compelling findings of basal-like tumors showing resistance to FOLFIRINOX and the lack of objective studies comparing current first-line therapies FOLFIRINOX versus gemcitabine plus nab-paclitaxel strongly support the need to evaluate the role of molecular subtyping in treatment decision making for patients with PDAC. Therefore, we have developed a SSC based on the two tumor-intrinsic subtypes that avoids the instability associated with current strategies of clustering multiple samples and the low tumor purity issues in PDAC samples.

Prior studies have shown that merging samples from multiple studies (horizontal data integration) can improve the performance of prediction models, relative to training on individual studies (Richardson et al., 2016). However, systematic differences in the scales of the expression values in each dataset are often observed, as some may have been separately normalized prior to their publication or were generated from a variety of expression platforms. Complicated cross-platform normalizations are often employed in such situations prior to model training. Furthermore, new samples must be normalized to the training dataset prior to prediction to obtain relevant predicted values. This often results in a "test-set bias" (Patil et al., 2015), where predictions may change due to the samples in the test set or the normalization approach used. In addition, prediction models may change with the addition of new training samples, as renormalizations may be warranted among training samples. In all, this leads to potential complications for data merging, stability of prediction, and model accuracy (Lusa et al., 2007; Paquet & Hallett, 2015).

These drawbacks are largely addressed by the presently disclosed PurIST approach, which is not dependent on cross-study normalization, and is robust to platform type and sample collection differences. We showed that the sensitivity and specificity of PurIST calls are high across multiple independent studies, demonstrating that the PurIST classifier recapitulated the tumor-intrinsic subtype calling obtained initially by CC. Given the significant clinical relevance of the two tumor-intrinsic subtypes for both prognosis and treatment response and the high accuracy of predicted subtype calls in our validation datasets, PurIST would appear to have tremendous clinical value. Specifically, PurIST worked for gene expression data assayed across multiple platforms, including microarrays, RNAseq, and NanoString. Furthermore, the algorithm provided replicable classification for matched samples from snap-frozen bulk tissue as well as FNA, core biopsies, and archival tissues.

Thus, PurIST may be flexibly used on low input and more degraded samples and may be performed with targeted gene expression platforms such as NanoString, avoiding the need for a CLIA RNAseq assay. Our enduring findings that basal-like subtype tumors were significantly less likely to respond to FOLFIRINOX-based regimens strongly supported the need for the incorporation of molecular subtyping in treatment decision making to determine the association of molecular subtypes with this and other therapies. In addition, the stability of PurIST subtypes after treatment is a noteworthy finding and may point to fundamental biological differences in the tumor subtypes. Our ability to subtype based on either core or FNA biopsies considerably increases the flexibility and practicality of integrating PDAC molecular subtypes into future clinical trials in the metastatic and neoadjuvant setting where bulk specimens are rarely available.

Summarily, several genomic studies in pancreatic cancer suggest clinically relevant expression-based subtypes. However, consensus subtypes remain unclear. Using the explosion of publicly available data, the relationships of the different subtypes were examined and it has been demonstrated that a two-tumor subtype schema was most robust and clinically relevant. A single-sample classifier (SSC) that is referred to herein as Purity Independent Subtyping of Tumors (PurIST) with robust and highly replicable performance on a wide range of platforms and sample types has been produced and is described herein. That PurIST subtypes have meaningful associations with patient prognosis and have significant implications for treatment response has been demonstrated. The flexibility and utility of PurIST on low-input samples such as tumor biopsies allows it to be used at the time of diagnosis to facilitate the choice of effective therapies for PDAC patients and should be considered in the context of future clinical trials.

REFERENCES

All references cited in the instant disclosure, including but not limited to all patents, patent applications and publications thereof, scientific journal articles, and database entries (including but not limited to GENBANK® biosequence database entries and all annotations available therein) are incorporated herein by reference in their entireties to the extent that they supplement, explain, provide a background for, or teach methodology, techniques, and/or compositions employed herein.

Adiconis et al. (2013) Comparative analysis of RNA sequencing methods for degraded or low-input samples. Nat Methods 10(7):623-629.

Afsari et al. (2014) Rank Discriminants for Predicting Phenotypes from RNA Expression. Annals of Applied Statistics 8(3):1469-1491.

Afsari et al. (2015) switchBox: an R package for k-Top Scoring Pairs classifier development. Bioinformatics 31(2):273-274.

Aguirre et al. (2018) Real-time genomic characterization of advanced pancreatic cancer to enable precision medicine. Cancer Discovery 8(9):1096-1111.

Aung et al. (2018) Genomics-Driven Precision Medicine for Advanced Pancreatic Cancer—Early Results from the COMPASS Trial. Clin Cancer Res 24(6):1344-1354.

Bailey et al. (2016) Genomic analyses identify molecular subtypes of pancreatic cancer. Nature 531(7592):47-52.

Breheny & Huang (2011) Coordinate Descent Algorithms for Nonconvex Penalized Regression, with Applications to Biological Feature Selection. Ann Appl Stat 5(1):232-253.

Bushnell (2014) BBMap:A Fast, Accurate, Splice-Aware Aligner. United States:N. p., 2014. Web.

Cancer Genome Atlas Research Network. (2017) Integrated Genomic Characterization of Pancreatic Ductal Adenocarcinoma. Cancer Cell 32(2):185-203 el 13.

Carter et al. (2012) Absolute quantification of somatic DNA alterations in human cancer. Nat Biotechnol 30(5):413-421.

Collisson et al. (2011) Subtypes of pancreatic ductal adenocarcinoma and their differing responses to therapy. Nat Med 17(4):500-503.

Connor et al. (2017) Association of Distinct Mutational Signatures With Correlates of Increased Immune Activity in Pancreatic Ductal Adenocarcinoma. JAMA Oncol 3(6):774-783.

Conroy et al. (2011) FOLFIRINOX versus gemcitabine for metastatic pancreatic cancer. New England Journal of Medicine 364(19):1817-1825.

Geman et al. (2004) Classifying gene expression profiles from pairwise mRNA comparisons. Statistical applications in genetics and molecular biology 3(1):1-19.

Kass et al. (1995) Bayes factors. J Am Statist Assoc 90:773-795.

Kindler et al. (2019) Olaparib as maintenance treatment following first-line platinum-based chemotherapy (PBC) in patients (pts) with a germline BRCA mutation and metastatic pancreatic cancer (mPC): Phase III POLO trial. J Clin Oncol 37:18_suppl.

Leek (2009) The tspair package for finding top scoring pair classifiers in R. Bioinformatics 25(9):1203-1204.

Lusa et al. (2007) Challenges in projecting clustering results across gene expression-profiling datasets. J Natl Cancer Inst 99(22):1715-1723.

Martinez-Camblor (2017) Fully non-parametric receiver operating characteristic curve estimation for random-effects meta-analysis. Stat Methods Med Res 26:5-20.

Maurer et al. (2019) Experimental microdissection enables functional harmonisation of pancreatic cancer subtypes. Gut 68:1034-1043.

Moffitt et al. (2015) Virtual microdissection identifies distinct tumor- and stroma-specific subtypes of pancreatic ductal adenocarcinoma. Nat Genet 47(10):1168-1178.

Nywening et al. (2016) Targeting tumour-associated macrophages with CCR2 inhibition in combination with FOLFIRINOX in patients with borderline resectable and locally advanced pancreatic cancer:a single-centre, open-label, dose-finding, non-randomised, phase 1b trial. Lancet Oncol 17(5):651-662.

Paquet & Hallett (2015) Absolute assignment of breast cancer intrinsic molecular subtype. J Natl Cancer Inst 107(1):dju357.

Patil et al. (2015) Test set bias affects reproducibility of gene signatures. Bioinformatics 31(14):2318-2323.

Patro et al. (2017) Salmon provides fast and bias-aware quantification of transcript expression. Nat Methods 14(4):417-419.

PCT International Patent Application Publication No. WO 2019/226514.

Puleo et al. (2018) Stratification of Pancreatic Ductal Adenocarcinomas Based on Tumor and Microenvironment Features. Gastroenterology 155(6):1999-2013.e1993.

Rashid et al. (2020) Purity Independent Subtyping of Tumors (PurIST), A Clinically Robust, Single-sample Classifier for Tumor Subtyping in Pancreatic Cancer. Clinical Cancer Research 26(1):82-92.

Richardson et al. (2016) Statistical Methods in Integrative Genomics. Annual Review of Statistics and Its Application. 3:181-209.

Rodriguez et al. (2016) RNA sequencing distinguishes benign from malignant pancreatic lesions sampled by EUS-guided FNA. Gastrointest Endosc 84(2):252-258.

Schwarz (1978) Estimating Dimension of a Model. Annals of Statistics 6(2):461-464.

Shi et al. (2011) Top scoring pairs for feature selection in machine learning and applications to cancer outcome prediction. BMC Bioinformatics 12: Article 375.

Tan et al. (2005) Simple decision rules for classifying human cancers from gene expression profiles. Bioinformatics 21(20):3896-3904.

U.S. Patent Application Publication Nos. 2008/0262215, 2010/0120097, 2011/0189679, 2014/0113333, 2015/0307874, 2017/0020824, 2017/0233827.

U.S. Pat. Nos. 5,800,992; 6,004,755; 6,013,449; 6,020,135; 6,033,860; 6,040,138; 6,177,248; 6,251,601; 6,309,822; 7,595,159; 7,824,856; 8,008,025; 8,293,489; 8,299,239; 9,181,588; 9,920,367; 10,060,912; 10,227,584.

Veldman-Jones et al. (2015) Reproducible, Quantitative, and Flexible Molecular Subtyping of Clinical DLBCL Samples Using the NanoString nCounter System. Clin Cancer Res 21(10):2367-2378.

Von Hoff et al. (2013) Increased survival in pancreatic cancer with nab-paclitaxel plus gemcitabine. N Engl J Med 369(18):1691-1703.

Zhao et al. (2014) Comparison of RNA-Seq by poly (A) capture, ribosomal RNA depletion, and DNA microarray for expression profiling. BMC Genomics 15: Article 419.

It will be understood that various details of the presently disclosed subject matter can be changed without departing from the scope of the presently disclosed subject matter. Furthermore, the foregoing description is for the purpose of illustration only, and not for the purpose of limitation.

TABLE 1

Gene Pairs and Related Coefficients for PurIST and PurIST-n

| GENE PAIR | GENE A | GENE B | Coefficient |
|---|---|---|---|
| 1 | GPR87 | REG4 | 1.994 |
| 2 | KRT6A | ANXA10 | 2.031 |
| 3 | BCAR3 | GATA6 | 1.618 |
| 4 | PTGES | CLDN18 | 0.922 |
| 5 | ITGA3 | LGALS4 | 1.059 |
| 6 | C16orf74 | DDC | 0.929 |
| 7 | S100A2 | SLC40A1 | 2.505 |
| 8 | KRT5 | CLRN3 | 0.485 |
| A | GPR87 | REG4 | 3.413 |
| B | KRT6A | ANXA10 | 3.437 |
| C | KRT17 | LGALS4 | 2.078 |
| D | S100A2 | TFF1 | 2.651 |
| E | C16orf74 | DDC | 0.901 |
| F | KRT15 | PLA2G10 | 2.677 |
| G | PTGES | CDH17 | 2.911 |
| H | DCBLD2 | TSPAN8 | 1.903 |

TABLE 2

Exemplary NanoString Probes and SEQ ID NOs.

| GENE PAIR | GENE A | SEQ ID NO: | GENE B | SEQ ID NO: |
|---|---|---|---|---|
| 1 | GPR87 | 64 | REG4 | 71 |
| 2 | KRT6A | 65 | ANXA10 | 59 |
| 3 | BCAR3 | 81 | GATA6 | 82 |
| 4 | PTGES | 70 | CLDN18 | 84 |
| 5 | ITGA3 | 85 | LGALS4 | 68 |
| 6 | C16orf74 | 60 | DDC | 63 |
| 7 | S100A2 | 72 | SLC40A1 | 86 |
| 8 | KRT5 | 87 | CLRN3 | 83 |
| A | GPR87 | 64 | REG4 | 71 |
| B | KRT6A | 65 | ANXA10 | 59 |
| C | KRT17 | 67 | LGALS4 | 68 |

TABLE 2-continued

Exemplary NanoString Probes and SEQ ID NOs.

| GENE PAIR | GENE A | SEQ ID NO: | GENE B | SEQ ID NO: |
|---|---|---|---|---|
| D | S100A2 | 72 | TFF1 | 73 |
| E | C16orf74 | 60 | DDC | 63 |
| F | KRT15 | 66 | PLA2G10 | 69 |
| G | PTGES | 70 | CDH17 | 61 |
| H | DCBLD2 | 62 | TSPAN8 | 74 |

TABLE 3

Listing of Exemplary Nucleic acid and Amino acid Sequences with GENBANK ® Accession Nos.

| Gene Name (Coding Nucleotides*) | Nucleic Acid and Amino Acid Accession Nos.** (SEQ ID NO:) |
|---|---|
| ANXA10 (165-1139) | NM_007193.5 (1); NP_009124.2 (2) |
| BCAR3 (359-2836) | NM_001261408.2 (3); NP_001248337.1 (4) |
| C16orf74 (190-420) | NM_206967.3 (5); NP_996850.1 (6) |
| CDH17 (94-2592) | NM_004063.4 (7); NP_004054.3 (8) |
| CLDNI8 (62-847) | NM_016369.4 (9); NP_057453.1 (10) |
| CLRN3 (158-838) | NM_152311.5 (11); NP_689524.1 (12) |
| CTSE (105-1295) | NM_001910.4 (13); NP_001901.1(14) |
| DCBLD2 (370-2697) | NM_080927.4 (15); NP_563615.3 (16) |
| DDC (87-1529) | NM_000790.4 (17); NP_000781.2 (18) |
| GATA6 (132-1919) | NM_005257.6 (19); NP_005248.2 (20) |
| GPR87 (334-1410) | NM_023915.4 (21); NP_076404.3 (22) |
| ITGA3 (331-3486) | NM_002204.4 (23); NP_002195.1 (24) |
| KRT5 (99-1871) | NM_000424.4 (25); NP_000415.2 (26) |
| KRT6A (70-1764) | NM_005554.4 (27); NP_005545.1 (28) |
| KRT15 (64-1434) | NM_002275.4 (29); NP_002266.3 (30) |
| KRT17 (67-1365) | NM_000422.3 (31); NP_000413.1 (32) |
| LGALS4 (60-1031) | NM_006149.4 (33); NP_006140.1 (34) |
| LYZ (29-475) | NM_000239.3 (35); NP_000230.1 (36) |
| MUC17 (56-13537) | NM_001040105.2 (37); NP_001035194.1 (38) |
| MYO1A (264-3395) | NM_005379.4 (39); NP_005370.1 (40) |
| NR1I2 (49-1470) | NM_022002.2 (41); NP_071285.1 (42) |
| PIP5K1B (766-2388) | NM_003558.4 (43); NP_003549.1 (44) |
| PLA2G10 (80-577) | NM_003561.3 (45); NP_003552.1 (46) |
| PTGES (31-489) | NM_004878.5 (47); NP_004869.1 (48) |
| REG4 (147-623) | NM_032044.4 (49); NP_114433.1 (50) |
| S100A2 (350-646) | NM_005978.4 (51); NP_005969.2 (52) |
| SLC40A1 (327-2042) | NM_014585.6 (53); NP_055400.1 (54) |
| TFF1 (41-295) | NM_003225.3 (55); NP_003216.1 (56) |
| TSPAN8 (180-893) | NM_004616.3 (57); NP_004607.1 (58) |

*nucleotide positions in the corresponding an Accession No.

**Accession Nos. in the GENBANK ® biosequence database.

TABLE 4

| Summary of Public Datasets | | | | | |
|---|---|---|---|---|---|
| Dataset | Platform | Sample Collection | Sample Types | Samples | Reference |
| MoffittGEO (G5E71729) | microarray | Bulk | Primary PDAC, PDAC metastases, normal tissues | 357 | Moffitt et al., 2015 |
| COMPASS | RNAseq | Core biopsies, LCM | Primary PDAC, PDAC metastases | 50 | Auna et al., 2017 |
| Aguirre Biopsies | RNAseq | Core biopsies, FNA | Primary PDAC, PDAC metastases, acinar cell carcinoma | 73 | Aguirre et al., 2018 |
| ICGC PACA-AU seq | RNAseq | Bulk, >12% celluarity | Primary pancreatic cancers: PDAC, adenosquamous, colloid, IPMN with invasive cancer, acinar cell and undifferentiated | 92 | Bailey et al., 2016 |
| ICGC PACA-AU array | microarray | Bulk, >12% celluarity | Primary pancreatic cancers: PDAC, adenosquamous, colloid, IPMN with invasive cancer, acinar cell and undifferentiated, mucinous non-cystic carcinoma, and signet ring | 131 | Bailey et al., 2016 |
| Moffitt | RNAseq | Bulk | PDX, PDAC cell lines, CAFS | 61 | Moffitt et al., 2015 |
| Linehan seq | RNAseq | Core biopsies, bulk | Primary PDAC | 66 | Nywening et al., 2016 |
| Connor | RNAseq | LCM | Primary PDAC, PDAC metastases | 74 | Connor et al., 2017 |
| TCGA PAAD | RNAseq | Bulk | Primary PDAC | 181 | CGARN, 2017 |

*Cancer Genome Atlas Research Network

TABLE 5

| Yeh_Seq Samples | | | | | |
|---|---|---|---|---|---|
| | | Platform | | | |
| | | RNA-seq | | NanoString | |
| Sample type | | Primary | PDX | Primary | PDX |
| Bulk | FF* | 47 | 18 | 16 | 18 |
| | FFPE | 5 | 7 | 1 | 7 |
| FNA | | 45 | 3 | 16 | 0 |

*FF: flash frozen

TABLE 6

| Genes and Probes Analyzed by NanoString | | | | |
|---|---|---|---|---|
| GENE PAIR | GENE A | SEQ ID NO: | GENE B | SEQ ID NO: |
| A | GPR87 | 64 | REG4 | 71 |
| B | KRT6A | 65 | ANXA10 | 59 |
| C | KRT17 | 67 | LGALS4 | 68 |
| D | S100A2 | 77 | TFF1 | 73 |
| E | C16orf74 | 60 | DDC | 63 |
| F | KRT15 | 66 | PLA2G10 | 69 |
| G | PTGES | 70 | CDH17 | 61 |
| H | DCRLD2 | 62 | TSPAN8 | 74 |

TABLE 7

| Group Membership | | | | |
|---|---|---|---|---|
| Public Dataset and Citation | Treatment Group (#) | Survival Group (#) | Training Group (#) | Validation Group (#) |
| Moffitt GEO (GSE71729); Moffitt et al. 2015 | N | Y (125) | Y (139) | N |
| COMPASS Aung et al., 2017 | Y (40) | N | N | Y (49) |
| Aguirre Biopsies; Aguirre et al., 2018 | N | N | Y (46) | N |
| ICGC PACA-AU seq; Bailey et al., 2016 | N | Y (57) | N | Y (65) |
| ICGC PACA-AU array; Bailey et al., 2016 | N | Y (71) | N | Y (97) |
| Moffitt; Moffitt et al., 2015 | N | N | N | Y (37) |
| Linehan seq; Nywening et al., 2016 | Y (28) | Y (28) | N | Y (66) |
| Connor; Connor et al., 2017 | N | N | N | Y (66) |
| TCGA PAAD; CGARN*, 2017 | N | Y (146) | Y (136) | N |
| Pooled | | 376 | 321 | 378 |
| Group Notes (see below) | A | B | C | D |

#: number of samples in Group

*: CGARN: Cancer Genome Atlas Research Network

A: Only samples with RNA-seq AND treatment response were considered.

B: duplicated samples between ICGC PACA-AU seq and ICGC PACA-AU array were removed when pooling.

C: Training Samples used here are a subset of the CC subtypes derived on each dataset.

D: Samples with CC labels were considered for validation.

TABLE 8

| Aguirre_seq | | | | | | |
|---|---|---|---|---|---|---|
| ID and Method | Collisson | Bailey | Moffitt | PurIST.training | PurIST | PurIST.basal.prob |
| 0400001_T1; resection | | | | FALSE | Classical | 0.032063 |
| 0400003_T1; resection | | | | FALSE | Basal | 0.991223 |
| 0400005_T1; resection | | | | FALSE | Classical | 0.0055 |
| 0400008_T1; biopsy | classical | Pancreatic Progenitor | classical | TRUE | Classical | 0.001779 |
| 0400009_T1; resection | exocrine-like | Immunogenic | classical | TRUE | Classical | 0.002749 |
| 0400010_T1; biopsy | classical | Immunogenic | classical | TRUE | Classical | 0.013709 |
| 0400017_T1; resection | | | | FALSE | Classical | 0.146883 |
| 0400025_T1; resection | | | | FALSE | Classical | 0.001096 |
| 0400027_T1; biopsy | | | | FALSE | Classical | 0.012753 |
| 0400040_T1; resection | | | | FALSE | Classical | 0.023545 |
| 0400047_T1; biopsy | classical | Pancreatic Progenitor | classical | TRUE | Classical | 0.001096 |
| 0400047_T2; resection | | | | FALSE | Classical | 0.001779 |
| 0400049_T1; resection | | | | FALSE | Basal | 0.785925 |
| 0400050_T1; resection | | | | FALSE | Classical | 0.008293 |
| 0400055_T1; biopsy | exocrine-like | Immunogenic | classical | TRUE | Classical | 0.019979 |
| 0400062_T1; biopsy | classical | Immunogenic | classical | TRUE | Classical | 0.001096 |
| 0400067_T1; biopsy | exocrine-like | Immunogenic | classical | TRUE | Classical | 0.001096 |
| 0400068_T1; biopsy | QM | Squamous | basal | TRUE | Basal | 0.991223 |
| 0400069_T1; biopsy | classical | Pancreatic Progenitor | classical | TRUE | Classical | 0.001096 |
| 0400070_T1; resection | | | | FALSE | Classical | 0.001096 |
| 0400071_T1; resection | | | | FALSE | Classical | 0.019979 |
| 0400075_T1; biopsy | classical | Pancreatic Progenitor | classical | TRUE | Classical | 0.001096 |
| 0400078_T1; biopsy | QM | Squamous | basal | TRUE | Basal | 0.991223 |
| 0400081_T1; resection | | | | FALSE | Classical | 0.013709 |
| 0400083_T1; biopsy | | | | FALSE | Classical | 0.013709 |
| 0400087_T1; biopsy | classical | Pancreatic Progenitor | classical | TRUE | Classical | 0.00799 |
| 0400088_T1; resection | | | | FALSE | Classical | 0.003153 |
| 0400089_T1; biopsy | exocrine-like | Squamous | classical | TRUE | Classical | 0.00693 |
| 0400091_T1; biopsy | exocrine-like | Squamous | basal | TRUE | Basal | 0.902224 |
| 0400096_T1; biopsy | classical | Immunogenic | classical | TRUE | Classical | 0.002749 |
| 0400097_T1; biopsy | classical | Immunogenic | classical | TRUE | Classical | 0.001096 |
| 0400098_T1; biopsy | classical | Pancreatic Progenitor | classical | TRUE | Classical | 0.002769 |
| 0400123_T1; biopsy | classical | Pancreatic Progenitor | classical | TRUE | Classical | 0.001096 |
| 0400124_T1; biopsy | classical | Squamous | basal | TRUE | Basal | 0.784733 |
| 0400127_T1; biopsy | classical | Pancreatic Progenitor | classical | TRUE | Classical | 0.280897 |
| 0400127_T2; resection | | | | FALSE | Classical | 0.020585 |
| 0400129_T1; biopsy | QM | Squamous | basal | TRUE | Basal | 0.991223 |
| 0400136_T1; biopsy | QM | Squamous | basal | TRUE | Basal | 0.991223 |
| 0400137_T1; biopsy | exocrine-like | ADEX | classical | TRUE | Classical | 0.236376 |
| 0400142_T1; biopsy | QM | Squamous | basal | TRUE | Basal | 0.991223 |
| 0400148_T1; biopsy | exocrine-like | ADEX | classical | TRUE | Classical | 0.001096 |
| 0400151_T2; biopsy | classical | Pancreatic Progenitor | classical | TRUE | Classical | 0.002769 |
| 0400164_T1; biopsy | classical | ADEX | classical | TRUE | Classical | 0.001096 |
| 0400165_T1; biopsy | exocrine-like | ADEX | classical | TRUE | Classical | 0.001096 |
| 0400167_T1; biopsy | exocrine-like | ADEX | basal | TRUE | Basal | 0.784733 |
| 0400171_T1; biopsy | QM | Squamous | basal | TRUE | Basal | 0.991223 |
| 0400172_T1; biopsy | exocrine-like | ADEX | classical | TRUE | Classical | 0.426918 |
| 0400174_T1; biopsy | classical | Pancreatic Progenitor | classical | TRUE | Classical | 0.001096 |
| 0400177_T1; biopsy | classical | Pancreatic Progenitor | classical | TRUE | Classical | 0.032865 |
| 0400179_T1; biopsy | classical | Immunogenic | classical | TRUE | Classical | 0.001096 |
| 0400192_T1; biopsy | QM | ADEX | basal | TRUE | Basal | 0.975101 |
| 0400193_T1; biopsy | | | | FALSE | Classical | 0.001096 |
| 0400195_T1; biopsy | QM | Squamous | basal | TRUE | Basal | 0.985816 |
| 0400198_T1; biopsy | | | | FALSE | Classical | 0.002749 |
| 0400202_T1; biopsy | | | | FALSE | Classical | 0.280897 |
| 0400203_T1; biopsy | | | | FALSE | Classical | 0.002749 |
| 0400208_T1; biopsy | QM | Squamous | classical | TRUE | Classical | 0.032865 |
| 0400214_T1; biopsy | exocrine-like | ADEX | classical | TRUE | Classical | 0.001779 |
| 0400215_T1; biopsy | classical | Pancreatic Progenitor | classical | TRUE | Classical | 0.002749 |
| 0400220_T1; biopsy | QM | Squamous | basal | TRUE | Basal | 0.850276 |
| 0400231_T1; biopsy | QM | Squamous | classical | FALSE | Classical | 0.211492 |
| 0400233_T1; biopsy | QM | Squamous | basal | TRUE | Basal | 0.991223 |
| 0400235_T1; biopsy | exocrine-like | ADEX | basal | FALSE | Basal | 0.96486 |
| 0400237_T1; biopsy | exocrine-like | ADEX | classical | TRUE | Classical | 0.001096 |

TABLE 8-continued

| Aguirre_seq | | | | | | |
|---|---|---|---|---|---|---|
| ID and Method | Collisson | Bailey | Moffitt | PurIST.training | PurIST | PurIST.basal.prob |
| 0400242_T1; biopsy | classical | Immunogenic | classical | TRUE | Classical | 0.437577 |
| 0400243_T1; biopsy | QM | ADEX | basal | TRUE | Basal | 0.991223 |
| 0400245_T1; biopsy | | | | FALSE | Classical | 0.092608 |
| 0400251_T1; biopsy | classical | Pancreatic Progenitor | classical | TRUE | Classical | 0.002769 |
| 0400253_T1; biopsy | | | | FALSE | Classical | 0.193605 |
| 0400267_T1; biopsy | | | | FALSE | Classical | 0.002749 |
| 0400268_T1; biopsy | | | | FALSE | Classical | 0.092608 |
| 0400270_T1; biopsy | classical | Immunogenic | classical | TRUE | Classical | 0.00799 |
| 0400278_T1; biopsy | | | | FALSE | Classical | 0.205302 |

TABLE 9

| COMPASS | | | | | | | | | | |
|---|---|---|---|---|---|---|---|---|---|---|
| ID | Histology | Change | RECIST | Treatment | Collisson | Bailey | Moffitt | PurIST.training | PurIST | PurIST.basal.prob |
| COMP0014 | | −8.7 | SD | FFX | Classical | Pancreatic Progenitor | Classical | FALSE | Classical | 0.013405 |
| COMP0001 | Adenoca. | −30.6 | PR | FFX | Classical | Immunogenic | Classical | FALSE | Classical | 0.005113 |
| COMP0002 | Adenoca. | −45.1 | PR | GP | Exocrine-like | ADEX | Classical | FALSE | Classical | 0.001096 |
| COMP0004 | Adenoca. | −15.6 | SD | FFX | Classical | Pancreatic Progenitor | Classical | FALSE | Classical | 0.002749 |
| COMP0005 | Adenoca. | −4.2 | SD | FFX | Classical | Immunogenic | Classical | FALSE | Classical | 0.037269 |
| COMP0006 | Adenoca. | −54 | PR | FFX | Classical | Pancreatic Progenitor | Classical | FALSE | Classical | 0.001096 |
| COMP0007 | Adenoca. | | | GP | QM-PDA | Squamous | Basal-like | FALSE | Basal-like | 0.691693 |
| COMP0008 | | −22.3 | SD | GP | Classical | Immunogenic | Classical | FALSE | Classical | 0.008293 |
| COMP0010 | Adenoca. | 5.4 | SD | GP | QM-PDA | Squamous | Basal-like | FALSE | Basal-like | 0.991223 |
| COMP0009 | | −27.8 | SD | FFX | Classical | ADEX | Classical | FALSE | Classical | 0.008906 |
| COMP0011 | Adenoca. | | | FFX | QM-PDA | Squamous | Basal-like | FALSE | Basal-like | 0.902224 |
| COMP0012 | Adenoca. | | | GP | Exocrine-like | Pancreatic Progenitor | Classical | FALSE | Classical | 0.001096 |
| COMP0013 | Adenosq. | 75 | PD | FFX | QM-PDA | Squamous | Basal-like | FALSE | Basal-like | 0.936765 |
| COMP0015 | Adenoca. | 25 | PD | FFX | QM-PDA | Squamous | Basal-like | FALSE | Basal-like | 0.991223 |
| COMP0017 | Adenoca. | 9.5 | SD | FFX | Classical | Immunogenic | Classical | FALSE | Classical | 0.013405 |
| COMP0018 | | 44.7 | PD | FFX | QM-PDA | Squamous | Basal-like | FALSE | Basal-like | 0.991223 |
| COMP0019 | Adenoca. | −45.9 | PR | FFX | Classical | Immunogenic | Classical | FALSE | Classical | 0.001096 |
| COMP0020 | Adenoca. | 17.5 | SD | FFX | QM-PDA | Squamous | Basal-like | FALSE | Basal-like | 0.991223 |
| COMP0021 | Adenosq. | −45.8 | PR | FFX | QM-PDA | Squamous | Basal-like | FALSE | Basal-like | 0.854066 |
| COMP0023 | | −42.1 | PR | FFX | Classical | Immunogenic | Classical | FALSE | Classical | 0.005113 |
| COMP0025 | Adenoca. | | | FFX | Classical | Pancreatic Progenitor | Classical | FALSE | Classical | 0.001096 |
| COMP0026 | Adenoca. | −8.6 | SD | FFX | QM-PDA | Squamous | Basal-like | FALSE | Basal-like | 0.784733 |
| COMP0028 | | 14 | SD | FFX | Exocrine-like | Pancreatic Progenitor | Classical | FALSE | Classical | 0.008293 |
| COMP0030 | Adenoca. | −4.3 | SD | FFX | Classical | Immunogenic | Classical | FALSE | Classical | 0.002749 |
| COMP0029 | Adenoca. | −15 | SD | FFX | Classical | Pancreatic Progenitor | Classical | FALSE | Classical | 0.001096 |
| COMP0032 | Adenoca. | 6.6 | SD | FFX | Classical | ADEX | Classical | FALSE | Classical | 0.001779 |
| COMP0033 | | | | GP | Classical | Pancreatic Progenitor | Classical | FALSE | Classical | 0.008293 |
| COMP0034 | | 24.5 | PD | FFX | QM-PDA | Squamous | Basal-like | FALSE | Basal-like | 0.991223 |
| COMP0035 | | −33.3 | PR | FFX | Classical | Immunogenic | Classical | FALSE | Classical | 0.037703 |
| COMP0036 | Adenoca. | 4.9 | SD | FFX | Classical | Pancreatic Progenitor | Classical | FALSE | Classical | 0.001096 |
| COMP0037 | | −43.8 | PR | FFX | Classical | Immunogenic | Classical | FALSE | Classical | 0.007887 |
| COMP0038 | Adenoca. | 7.4 | SD | FFX | Classical | Pancreatic Progenitor | Classical | FALSE | Classical | 0.001096 |
| COMP0039 | Adenoca. | | | FFX | QM-PDA | Squamous | Basal-like | FALSE | Basal-like | 0.991223 |
| COMP0041 | | | | FFX | Exocrine-like | Pancreatic Progenitor | Classical | FALSE | Classical | Classical |
| COMP0042 | Adenoca. | −17.5 | SD | FFX | Classical | Immunogenic | Classical | FALSE | Classical | 0.223407 |
| COMP0043 | | −20 | SD | FFX | Exocrine-like | ADEX | Classical | FALSE | Classical | 0.223407 |
| COMP0044 | Adenoca. | −24.1 | SD | FFX | Exocrine-like | Immunogenic | Classical | FALSE | Classical | 0.037703 |
| COMP0045 | | 34.4 | PD | FFX | QM-PDA | Squamous | Basal-like | FALSE | Basal-like | 0.991223 |
| COMP0046 | Adenoca. | −11.1 | SD | FFX | QM-PDA | ADEX | Classical | FALSE | Classical | 0.419634 |
| COMP0047 | | −54.5 | PR | FFX | Exocrine-like | Pancreatic Progenitor | Classical | FALSE | Classical | 0.001096 |
| COMP0048 | | 6.9 | SD | FFX | QM-PDA | Squamous | Basal-like | FALSE | Basal-like | 0.991223 |
| COMP0050 | | −12.4 | SD | GP | Classical | Immunogenic | Classical | FALSE | Classical | 0.001096 |
| COMP0049 | Adenoca. | −19.2 | SD | FFX | Classical | ADEX | Classical | FALSE | Basal-like | 0.591897 |
| COMP0052 | Adenoca. | | | Classical | Immunogenic | Classical | FALSE | Classical | 0.00446 | 0.001096 |

TABLE 9-continued

| COMPASS | | | | | | | | | | |
|---|---|---|---|---|---|---|---|---|---|---|
| ID | Histology | Change | RECIST | Treatment | Collisson | Bailey | Moffitt | PurIST.training | PurIST | PurIST.basal.prob |
| COMP0055 | Acinar | −8.1 | SD | FFX | Exocrine-like | ADEX | | FALSE | Classical | 0.005113 |
| COMP0056 | Adenoca. | −54.5 | PR | FFX | Exocrine-like | ADEX | Classical | FALSE | Classical | 0.211492 |
| COMP0057 | | −5.6 | SD | FFX | QM-PDA | ADEX | Classical | FALSE | Classical | 0.419634 |
| COMP0058 | Adenoca. | −51 | PR | GP | Exocrine-like | Immunogenic | Classical | FALSE | Classical | 0.013405 |
| COMP0059 | Adenoca. | −41.3 | PR | GP | Classical | Immunogenic | Classical | FALSE | Classical | 0.013405 |
| COMP0060 | Adenoca. | | GP + Medi + Tremi | Classical | Immunogenic | Classical | FALSE | Classical | 0.001096 | |

TABLE 10

| Connor | | | | | | | |
|---|---|---|---|---|---|---|---|
| ID | SampleType | Collisson | Bailey | Moffitt | PurIST.training | PurIST | PurIST.basal.prob |
| PCSI_0083 | Primary | Exocrine-like | Squamous | Basal-like | FALSE | Basal-like | 0.936765 |
| PCSI_0103 | Primary | Classical | Pancreatic Progenitor | Classical | FALSE | Classical | 0.001096 |
| PCSI_0132 | Primary | QM-PDA | Pancreatic Progenitor | Classical | FALSE | Classical | 0.005113 |
| PCSI_0142 | Primary | QM-PDA | Pancreatic Progenitor | Classical | FALSE | Classical | 0.001096 |
| PCSI_0145 | Primary | Exocrine-like | Squamous | Basal-like | FALSE | Classical | 0.150416 |
| PCSI_0173 | Primary | QM-PDA | Squamous | Classical | FALSE | Classical | 0.325049 |
| PCSI_0226 | Primary | Exocrine-like | Squamous | Basal-like | FALSE | Basal-like | 0.978228 |
| PCSI_0233 | Primary | Exocrine-like | Squamous | Classical | FALSE | Classical | 0.005113 |
| PCSI_0235 | Primary | Exocrine-like | ADEX | Classical | FALSE | Classical | 0.001779 |
| PCSI_0240 | Primary | Exocrine-like | Squamous | Basal-like | FALSE | Basal-like | 0.978077 |
| PCSI_0261 | Primary | QM-PDA | Immunogenic | Classical | FALSE | Classical | 0.001096 |
| PCSI_0263 | Primary | QM-PDA | Immunogenic | Classical | FALSE | Classical | 0.020585 |
| PCSI_0264 | Primary | QM-PDA | Pancreatic Progenitor | Classical | FALSE | Classical | 0.001096 |
| PCSI_0268 | Primary | Classical | Pancreatic Progenitor | Classical | FALSE | Classical | 0.008293 |
| PCSI_0269 | Primary | QM-PDA | Immunogenic | Classical | FALSE | Classical | 0.001779 |
| PCSI_0274 | Primary | Classical | Pancreatic Progenitor | Classical | FALSE | Classical | 0.001096 |
| PCSI_0279 | Primary | Classical | Pancreatic Progenitor | Classical | FALSE | Classical | 0.001096 |
| PCSI_0280 | Primary | Classical | ADEX | Classical | FALSE | Classical | 0.001779 |
| PCSI_0283 | Primary | Classical | Immunogenic | Classical | FALSE | Classical | 0.001779 |
| PCSI_0284 | Primary | Exocrine-like | Squamous | Basal-like | FALSE | Classical | 0.089648 |
| PCSI_0285 | Primary | Classical | Immunogenic | Classical | FALSE | Classical | 0.001779 |
| PCSI_0286 | Primary | Exocrine-like | ADEX | Classical | FALSE | Classical | 0.001779 |
| PCSI_0287 | Primary | Classical | Pancreatic Progenitor | Classical | FALSE | Classical | 0.001096 |
| PCSI_0290 | Primary | QM-PDA | Pancreatic Progenitor | Classical | FALSE | Classical | 0.001096 |
| PCSI_0292 | Primary | Exocrine-like | Squamous | Basal-like | FALSE | Basal-like | 0.946668 |
| PCSI_0302 | Primary | QM-PDA | Pancreatic Progenitor | Classical | FALSE | Classical | 0.005113 |
| PCSI_0303 | Primary | Classical | Pancreatic Progenitor | Classical | FALSE | Classical | 0.001096 |
| PCSI_0305 | Primary | Classical | Pancreatic Progenitor | Classical | FALSE | Classical | 0.001096 |
| PCSI_0307 | Primary | QM-PDA | Squamous | Classical | FALSE | Basal-like | 0.556881 |
| PCSI_0309 | Primary | QM-PDA | Immunogenic | Classical | FALSE | Classical | 0.001096 |
| PCSI_0310 | Primary | QM-PDA | Squamous | Classical | FALSE | Classical | 0.001096 |
| PCSI_0311 | Primary | Classical | Pancreatic Progenitor | Classical | FALSE | Classical | 0.001096 |
| PCSI_0312 | Primary | QM-PDA | Immunogenic | Classical | FALSE | Classical | 0.001096 |
| PCSI_0324 | Primary | Classical | Pancreatic Progenitor | Classical | FALSE | Classical | 0.001096 |
| PCSI_0325 | Primary | Classical | Pancreatic Progenitor | Classical | FALSE | Classical | 0.001096 |
| PCSI_0326 | Primary | Classical | Pancreatic Progenitor | Classical | FALSE | Classical | 0.001779 |
| PCSI_0328 | Primary | Classical | Immunogenic | Classical | FALSE | Classical | 0.001096 |
| PCSI_0329 | Primary | Classical | Pancreatic Progenitor | Classical | FALSE | Classical | 0.001096 |
| PCSI_0330 | Primary | QM-PDA | Immunogenic | Classical | FALSE | Classical | 0.001096 |
| PCSI_0334 | Primary | Classical | Immunogenic | Classical | FALSE | Classical | 0.001096 |
| PCSI_0337 | Primary | Classical | ADEX | Classical | FALSE | Classical | 0.06411 |

TABLE 10-continued

| Connor | | | | | | | |
|---|---|---|---|---|---|---|---|
| ID | SampleType | Collisson | Bailey | Moffitt | PurIST.training | PurIST | PurIST.basal.prob |
| PCSI_0338 | Primary | Classical | Pancreatic Progenitor | Classical | FALSE | Classical | 0.001096 |
| PCSI_0340 | Primary | Classical | Pancreatic Progenitor | Classical | FALSE | Classical | 0.001096 |
| PCSI_0341 | Primary | Classical | Pancreatic Progenitor | Classical | FALSE | Classical | 0.00799 |
| PCSI_0345 | Primary | Exocrine-like | ADEX | Classical | FALSE | Classical | 0.013405 |
| PCSI_0350 | Primary | Classical | Pancreatic Progenitor | Classical | FALSE | Classical | 0.001096 |
| PCSI_0353 | Primary | QM-PDA | Immunogenic | Classical | FALSE | Classical | 0.023545 |
| PCSI_0355 | Primary | QM-PDA | Pancreatic Progenitor | Classical | FALSE | Classical | 0.001096 |
| PCSI_0403 | Primary | Classical | Pancreatic Progenitor | Classical | FALSE | Classical | 0.001096 |
| PCSI_0453 | Primary | QM-PDA | Immunogenic | Classical | FALSE | Classical | 0.012753 |
| PCSI_0456 | Primary | Classical | Pancreatic Progenitor | Classical | FALSE | Classical | 0.001779 |
| PCSI_0457 | Primary | Classical | Pancreatic Progenitor | Classical | FALSE | Classical | 0.001779 |
| PCSI_0458 | Primary | Classical | ADEX | Classical | FALSE | Classical | 0.033022 |
| PCSI_0477 | Primary | Exocrine-like | Squamous | Basal-like | FALSE | Classical | 0.090712 |
| PCSI_0489 | Liver Metastasis | | | | FALSE | Classical | 0.001096 |
| PCSI_0506 | Primary | Classical | Immunogenic | Classical | FALSE | Classical | 0.019841 |
| PCSI_0508 | Primary | QM-PDA | ADEX | Classical | FALSE | Classical | 0.001779 |
| PCSI_0509 | Primary | Exocrine-like | ADEX | Classical | FALSE | Classical | 0.001779 |
| PCSI_0511 | Primary | QM-PDA | Pancreatic Progenitor | Classical | FALSE | Classical | 0.013405 |
| PCSI_0528 | Primary | QM-PDA | Immunogenic | Classical | FALSE | Classical | 0.00799 |
| PCSI_0531 | Primary | Classical | Pancreatic Progenitor | Classical | FALSE | Classical | 0.001096 |
| PCSI_0537 | Primary | Classical | Pancreatic Progenitor | Classical | FALSE | Classical | 0.001096 |
| PCSI_0572 | Primary | Exocrine-like | Squamous | Basal-like | FALSE | Classical | 0.309466 |
| RAMP_0002 | Lymph Node Metastasis | | | | FALSE | Classical | 0.146883 |
| RAMP_0002 | Liver Metastasis | | | | FALSE | Classical | 0.001096 |
| RAMP_0004 | Lymph Node Metastasis | | | | FALSE | Basal-like | 0.991223 |
| RAMP_0004 | Liver Metastasis | | | | FALSE | Basal-like | 0.978077 |
| RAMP_0004 | Primary | Exocrine-hike | Squamous | Basal-like | FALSE | Basal-like | 0.991223 |
| RAMP_0006 | Liver Metastasis | | | | FALSE | Classical | 0.037703 |
| RAMP_0006 | Primary | Exocrine-like | Squamous | Basal-like | FALSE | Classical | 0.419634 |
| RAMP_0007 | Primary | QM-PDA | ADEX | Basal-like | FALSE | Basal-like | 0.556881 |
| RAMP_0008 | Lymph Node Metastasis | | | | FALSE | Classical | 0.013405 |
| RAMP_0008 | Liver Metastasis | | | | FALSE | Classical | 0.001096 |
| RAMP_0008 | Primary | QM-PDA | Immunogenic | Classical | FALSE | Classical | 0.037703 |

TABLE 11

| Linehan_seq | | | | | | | | | | |
|---|---|---|---|---|---|---|---|---|---|---|
| ID | Treatment | Pre.Post | Change | RECIST | Collisson | Bailey | Moffitt | PurIST.training | PurIST | PurIST.basal.prob |
| S1124.02.01 | FOLF | Pre | | | Classical | Immunogenic | Classical | FALSE | Classical | 0.001096 |
| S1124.02.02 | FOLF | Post | | | Exocrine-like | ADEX | Classical | FALSE | Classical | 0.001096 |
| S1124.03.01 | FOLF | Pre | 4 | SD | Classical | Immunogenic | Classical | FALSE | Classical | 0.001096 |
| S1124.03.02 | FOLF | Post | 4 | SD | Exocrine-like | Immunogenic | Classical | FALSE | Classical | 0.00799 |
| S1124.04.01 | FOLF | Pre | | | Exocrine-like | Squamous | Classical | FALSE | Classical | 0.054078 |
| S1124.07.01 | FOLF | Pre | 20.40816 | PD | QM-PDA | Squamous | Basal-like | FALSE | Basal-like | 0.860249 |
| S1124.07.02 | FOLF | Post | 20.40816 | PD | QM-PDA | Squamous | Basal-like | FALSE | Basal-like | 0.679704 |
| S1124.08.01 | FOLF | Pre | 0 | SD | Classical | Immunogenic | Classical | FALSE | Classical | 0.00693 |
| S1124.08.02 | FOLF | Post | 0 | SD | Classical | Pancreatic Progenitor | Classical | FALSE | Classical | 0.001096 |
| S1124.09.01 | FOLF | Pre | | | Exocrine-like | Squamous | Classical | FALSE | Classical | 0.052325 |
| S1124.11.01 | FOLF | Pre | | | Exocrine-like | Pancreatic Progenitor | Classical | FALSE | Classical | 0.0055 |
| S1124.12.01 | FOLF | Pre | | | QM-PDA | Squamous | Classical | FALSE | Classical | 0.001779 |

TABLE 11-continued

| Linehan_seq | | | | | | | | | | |
|---|---|---|---|---|---|---|---|---|---|---|
| ID | Treatment | Pre.Post | Change | RECIST | Collisson | Bailey | Moffitt | PurIST.training | PurIST | PurIST.basal.prob |
| S1124.13.01 | FOLF | Pre | −16.2791 | SD | Classical | Immunogenic | Classical | FALSE | Classical | 0.001096 |
| S1124.13.02 | FOLF | Post | −16.2791 | SD | Exocrine-like | Pancreatic Progenitor | Classical | FALSE | Classical | 0.001096 |
| S1124.14.01 | FOLF + PF | Pre | −31.8182 | PR | Exocrine-like | ADEX | Classical | FALSE | Classical | 0.0055 |
| S1124.14.02 | FOLF + PF | Post | −31.8182 | PR | Exocrine-like | ADEX | Classical | FALSE | Classical | 0.0055 |
| S1124.15.01 | FOLF + PF | Pre | −32.1429 | PR | Exocrine-like | Pancreatic Progenitor | Classical | FALSE | Classical | 0.0055 |
| S1124.15.02 | FOLF + PF | Post | −32.1429 | PR | Classical | Pancreatic Progenitor | Classical | FALSE | Classical | 0.0055 |
| S1124.16.01 | FOLF + PF | Pre | −8.82353 | SD | Exocrine-like | ADEX | Classical | FALSE | Classical | 0.001096 |
| S1124.16.02 | FOLF + PF | Post | −8.82353 | SD | Classical | Pancreatic Progenitor | Classical | FALSE | Classical | 0.001096 |
| S1124.17.01 | FOLF + PF | Pre | 0 | SD | Exocrine-like | ADEX | Classical | FALSE | Classical | 0.001096 |
| S1124.17.02 | FOLF + PF | Post | 0 | SD | Classical | Immunogenic | Classical | FALSE | Classical | 0.001096 |
| S1124.21.01 | FOLF + PF | Pre | | | Exocrine-like | ADEX | Classical | FALSE | Classical | 0.001096 |
| S1124.23.01 | FOLF + PF | Pre | | | Classical | Immunogenic | Classical | FALSE | Classical | 0.002769 |
| S1124.24.01 | FOLF + PF | Pre | −40.625 | PR | Classical | Pancreatic Progenitor | Classical | FALSE | Classical | 0.001096 |
| S1124.24.02 | FOLF + PF | Post | −40.625 | PR | Classical | Immunogenic | Classical | FALSE | Classical | 0.001096 |
| S1124.25.01 | FOLF + PF | Pre | −19.697 | SD | Classical | Immunogenic | Classical | FALSE | Classical | 0.001096 |
| S1124.25.02 | FOLF + PF | Post | −19.697 | SD | QM-PDA | Squamous | Classical | FALSE | Classical | 0.001096 |
| S1124.28.01 | FOLF + PF | Pre | −37.037 | PR | QM-PDA | Immunogenic | Classical | FALSE | Classical | 0.0055 |
| S1124.28.02 | FOLF + PF | Post | −37.037 | PR | QM-PDA | Immunogenic | Classical | FALSE | Classical | 0.002769 |
| S1124.30.01 | FOLF + PF | Pre | −46.875 | PR | QM-PDA | Squamous | Classical | FALSE | Classical | 0.002749 |
| S1124.30.02 | FOLF + PF | Post | −46.875 | PR | QM-PDA | Squamous | Classical | FALSE | Classical | 0.147772 |
| S1124.31.01 | FOLF + PF | Pre | 25.64103 | PD | QM-PDA | Squamous | Basal-like | FALSE | Basal-like | 0.783895 |
| S1124.31.02 | FOLF + PF | Post | 25.64103 | PD | QM-PDA | Squamous | Basal-like | FALSE | Basal-like | 0.783895 |
| S1124.32.01 | FOLF + PF | Pre | −17.1429 | SD | QM-PDA | Squamous | Basal-like | FALSE | Basal-like | 0.991223 |
| S1124.32.02 | FOLF + PF | Post | −17.1429 | SD | QM-PDA | Squamous | Basal-like | FALSE | Basal-like | 0.842116 |
| S1124.33.01 | FOLF + PF | Pre | −8.16327 | SD | Classical | Pancreatic Progenitor | Classical | FALSE | Classical | 0.0055 |
| S1124.33.02 | FOLF + PF | Post | −8.16327 | SD | QM-PDA | Squamous | Classical | FALSE | Classical | 0.0055 |
| S1124.34.01 | FOLF + PF | Pre | −40 | PR | Classical | Immunogenic | Classical | FALSE | Classical | 0.001096 |
| S1124.34.02 | FOLF + PF | Post | −40 | PR | Classical | Immunogenic | Classical | FALSE | Classical | 0.002769 |
| S1124.35.01 | FOLF + PF | Pre | −26.9841 | SD | QM-PDA | Immunogenic | Classical | FALSE | Classical | 0.002769 |
| S1124.35.02 | FOLF + PF | Post | −26.9841 | SD | QM-PDA | Immunogenic | Classical | FALSE | Classical | 0.002769 |
| S1124.37.01 | FOLF + PF | Pre | −30 | PR | Classical | Immunogenic | Classical | FALSE | Classical | 0.002769 |
| S1124.37.02 | FOLF + PF | Post | −30 | PR | Classical | Immunogenic | Classical | FALSE | Classical | 0.004491 |
| S1124.38.01 | FOLF + PF | Pre | 8.571429 | SD | Exocrine-like | Pancreatic Progenitor | Classical | FALSE | Classical | 0.0055 |
| S1124.38.02 | FOLF + PF | Post | 8.571429 | SD | Classical | Immunogenic | Classical | FALSE | Classical | 0.001096 |
| S1124.40.01 | FOLF + PF | Pre | | | Classical | Pancreatic Progenitor | Classical | FALSE | Classical | 0.001096 |
| S1124.41.01 | FOLF + PF | Pre | 6.451613 | SD | Exocrine-like | Pancreatic Progenitor | Classical | FALSE | Classical | 0.0055 |
| S1124.41.02 | FOLF + PF | Post | 6.451613 | SD | Exocrine-like | ADEX | Classical | FALSE | Classical | 0.001096 |
| S1124.42.01 | FOLF + PF | Pre | −29.6296 | SD | QM-PDA | Immunogenic | Classical | FALSE | Classical | 0.001096 |

TABLE 11-continued

| Linehan_seq | | | | | | | | | | |
|---|---|---|---|---|---|---|---|---|---|---|
| ID | Treatment | Pre.Post | Change | RECIST | Collisson | Bailey | Moffitt | PurIST.training | PurIST | PurIST.basal.prob |
| S1124.42.02 | FOLF + PF | Post | −29.6296 | SD | QM-PDA | Immunogenic | Classical | FALSE | Classical | 0.001096 |
| S1124.43.01 | FOLF + PF | Pre | −35.7143 | PR | Classical | Immunogenic | Classical | FALSE | Classical | 0.001096 |
| S1124.43.02 | FOLF + PF | Post | −35.7143 | PR | QM-PDA | Squamous | Classical | FALSE | Classical | 0.0055 |
| S1124.46.01 | FOLF + PF | Pre | −35.5556 | PR | QM-PDA | Immunogenic | Classical | FALSE | Classical | 0.001096 |
| S1124.46.02 | FOLF + PF | Post | −35.5556 | PR | Classical | Immunogenic | Classical | FALSE | Classical | 0.001096 |
| S1124.48.01 | FOLF + PF | Pre | 0 | SD | Classical | Pancreatic Progenitor | Classical | FALSE | Classical | 0.0055 |
| S1124.48.02 | FOLF + PF | Post | 0 | SD | Classical | Immunogenic | Classical | FALSE | Classical | 0.0055 |
| S1124.51.01 | FOLF + PF | Pre | −13.5135 | SD | Classical | Pancreatic Progenitor | Classical | FALSE | Classical | 0.0055 |
| S1124.51.02 | FOLF + PF | Post | −13.5135 | SD | Exocrine-like | Pancreatic Progenitor | Classical | FALSE | Classical | 0.001096 |
| S1124.52.01 | FOLF + PF | Pre | | | QM-PDA | Squamous | Classical | FALSE | Classical | 0.002769 |
| S1124.53.01 | FOLF + PF | Pre | −13.5135 | SD | Exocrine-like | Pancreatic Progenitor | Classical | FALSE | Classical | 0.0055 |
| S1124.53.02 | FOLF + PF | Post | −13.5135 | SD | Exocrine-like | ADEX | Classical | FALSE | Classical | 0.001096 |
| S1124.54.01 | FOLF + PF | Pre | −5.71429 | SD | QM-PDA | Squamous | Classical | FALSE | Classical | 0.002769 |
| S1124.54.02 | FOLF + PF | Post | −5.71429 | SD | Classical | Immunogenic | Classical | FALSE | Classical | 0.001779 |
| S1124.57.01 | FOLF + PF | Pre | −33.3333 | PR | Exocrine-like | ADEX | Classical | FALSE | Classical | 0.001096 |
| S1124.57.02 | FOLF + PF | Post | −33.3333 | PR | Exocrine-like | ADEX | Classical | FALSE | Classical | 0.001096 |

TABLE 12

| Moffitt_GEO_array | | | | | | | |
|---|---|---|---|---|---|---|---|
| ID | SampleType | Collisson | Bailey | Moffitt | PurIST.training | PurIST | PurIST.basal.prob |
| 53862-Primary-Pancreas | Primary | Exocrine-like | Squamous | Classical | TRUE | Classical | 0.007943 |
| 49360-Primary-Pancreas | Primary | QM-PDA | Squamous | Basal-like | TRUE | Basal-like | 0.766498 |
| 54249-Primary-Pancreas | Primary | QM-PDA | Pancreatic Progenitor | Classical | TRUE | Classical | 0.013247 |
| 48661-Primary-Pancreas | Primary | Exocrine-like | Pancreatic Progenitor | Classical | TRUE | Classical | 0.001096 |
| 49071-Primary-Pancreas | Primary | Exocrine-like | ADEX | Classical | TRUE | Classical | 0.001779 |
| 53838-Primary-Pancreas | Primary | Exocrine-like | ADEX | Classical | TRUE | Classical | 0.002749 |
| 49073-Primary-Pancreas | Primary | QM-PDA | Squamous | Classical | TRUE | Classical | 0.050513 |
| 48556-Primary-Pancreas | Primary | QM-PDA | Squamous | Basal-like | TRUE | Basal-like | 0.936765 |
| 48558-Primary-Pancreas | Primary | Classical | Squamous | Classical | TRUE | Classical | 0.146264 |
| 52042-Primary-Pancreas | Primary | QM-PDA | Squamous | Classical | TRUE | Classical | 0.002769 |
| 52043-Primary-Pancreas | Primary | Classical | Pancreatic Progenitor | Classical | TRUE | Classical | 0.001096 |
| 48562-Primary-Pancreas | Primary | Classical | Pancreatic Progenitor | Classical | TRUE | Classical | 0.001096 |
| 48564-Primary-Pancreas | Primary | QM-PDA | Squamous | Basal-like | FALSE | Classical | 0.429034 |
| 48567-Primary-Pancreas | Primary | Classical | Immunogenic | Classical | TRUE | Classical | 0.019979 |
| 48568-Primary-Pancreas | Primary | Exocrine-like | Squamous | Classical | TRUE | Basal-like | 0.755533 |
| 49388-Primary-Pancreas | Primary | Exocrine-like | ADEX | Classical | TRUE | Classical | 0.001096 |
| 46648-Primary-Pancreas | Primary | Classical | Pancreatic Progenitor | Classical | TRUE | Classical | 0.001096 |
| 46649-Primary-Pancreas | Primary | QM-PDA | Squamous | Classical | TRUE | Classical | 0.001096 |
| 46650-Primary-Pancreas | Primary | Exocrine-like | Pancreatic Progenitor | Classical | TRUE | Classical | 0.001096 |
| 46651-Primary-Pancreas | Primary | Exocrine-like | Pancreatic Progenitor | Classical | TRUE | Classical | 0.019841 |
| 47702-Primary-Pancreas | Primary | Classical | Squamous | Classical | TRUE | Classical | 0.001096 |
| 46652-Primary-Pancreas | Primary | Classical | Pancreatic Progenitor | Classical | TRUE | Classical | 0.001096 |
| 46987-Primary-Pancreas | Primary | Exocrine-like | Immunogenic | Classical | TRUE | Classical | 0.002769 |
| 46653-Primary-Pancreas | Primary | Classical | Squamous | Basal-like | TRUE | Basal-like | 0.827009 |
| 46832-Primary-Pancreas | Primary | Exocrine-like | Squamous | Basal-like | TRUE | Basal-like | 0.975101 |
| 46831-Primary-Pancreas | Primary | QM-PDA | Squamous | Basal-like | TRUE | Basal-like | 0.991223 |
| 46985-Primary-Pancreas | Primary | Classical | Squamous | Classical | TRUE | Classical | 0.013247 |
| 46828-Primary-Pancreas | Primary | Classical | Pancreatic Progenitor | Classical | TRUE | Classical | 0.089725 |
| 47692-Primary-Pancreas | Primary | QM-PDA | Squamous | Basal-like | TRUE | Basal-like | 0.991223 |
| 46986-Primary-Pancreas | Primary | Classical | Squamous | Classical | TRUE | Classical | 0.001096 |
| 47590-Primary-Pancreas | Primary | Exocrine-like | Pancreatic Progenitor | Classical | TRUE | Classical | 0.001096 |
| 47969-Primary-Pancreas | Primary | Exocrine-like | ADEX | Classical | TRUE | Classical | 0.002769 |
| 47989-Primary-Pancreas | Primary | Classical | Pancreatic Progenitor | Classical | TRUE | Classical | 0.013247 |
| 46581-Primary-Pancreas | Primary | Exocrine-like | ADEX | Classical | TRUE | Classical | 0.001779 |

TABLE 12-continued

| Moffitt_GEO_array | | | | | | | |
|---|---|---|---|---|---|---|---|
| ID | SampleType | Collisson | Bailey | Moffitt | PurIST.training | PurIST | PurIST.basal.prob |
| 46582-Primary-Pancreas | Primary | Classical | Pancreatic Progenitor | Classical | TRUE | Classical | 0.001096 |
| 46830-Primary-Pancreas | Primary | QM-PDA | Squamous | Classical | TRUE | Classical | 0.001096 |
| 46584-Primary-Pancreas | Primary | Classical | Pancreatic Progenitor | Classical | TRUE | Classical | 0.001096 |
| 47703-Primary-Pancreas | Primary | QM-PDA | Squamous | Basal-like | TRUE | Basal-like | 0.991223 |
| 47708-Primary-Pancreas | Primary | Exocrine-like | ADEX | Classical | TRUE | Classical | 0.001096 |
| 46450-Primary-Pancreas | Primary | Classical | Pancreatic Progenitor | Classical | TRUE | Classical | 0.001096 |
| 47695-Primary-Pancreas | Primary | Classical | Pancreatic Progenitor | Classical | TRUE | Classical | 0.001096 |
| 48550-Primary-Pancreas | Primary | Exocrine-like | Immunogenic | Classical | TRUE | Classical | 0.001096 |
| 46339-Primary-Pancreas | Primary | Classical | Squamous | Basal-like | TRUE | Basal-like | 0.975101 |
| 46578-Primary-Pancreas | Primary | Classical | Pancreatic Progenitor | Classical | TRUE | Classical | 0.001096 |
| 46585-Primary-Pancreas | Primary | Exocrine-like | Squamous | Classical | TRUE | Classical | 0.052325 |
| 46337-Primary-Pancreas | Primary | QM-PDA | Squamous | Classical | TRUE | Classical | 0.048743 |
| 46587-Primary-Pancreas | Primary | Classical | Pancreatic Progenitor | Classical | TRUE | Classical | 0.013247 |
| 47700-Primary-Pancreas | Primary | Exocrine-like | Squamous | Classical | TRUE | Classical | 0.002749 |
| 46826-Primary-Pancreas | Primary | Classical | Pancreatic Progenitor | Classical | TRUE | Classical | 0.001096 |
| 46592-Primary-Pancreas | Primary | Classical | Pancreatic Progenitor | Classical | TRUE | Classical | 0.001096 |
| 46452-Primary-Pancreas | Primary | Exocrine-like | ADEX | Classical | TRUE | Classical | 0.001096 |
| 46460-Primary-Pancreas | Primary | QM-PDA | Squamous | Basal-like | FALSE | Classical | 0.288464 |
| 47983-Primary-Pancreas | Primary | Classical | Pancreatic Progenitor | Classical | TRUE | Classical | 0.00799 |
| 46642-Primary-Pancreas | Primary | Classical | Pancreatic Progenitor | Classical | TRUE | Classical | 0.001096 |
| 47701-Primary-Pancreas | Primary | QM-PDA | Squamous | Classical | TRUE | Classical | 0.199683 |
| 46643-Primary-Pancreas | Primary | Classical | Pancreatic Progenitor | Classical | TRUE | Classical | 0.013247 |
| 47965-Primary-Pancreas | Primary | Exocrine-like | Squamous | Classical | TRUE | Classical | 0.00693 |
| 46644-Primary-Pancreas | Primary | Classical | Pancreatic Progenitor | Classical | TRUE | Classical | 0.002769 |
| 46645-Primary-Pancreas | Primary | Exocrine-like | Pancreatic Progenitor | Classical | TRUE | Classical | 0.019841 |
| 46646-Primary-Pancreas | Primary | Classical | Pancreatic Progenitor | Classical | TRUE | Classical | 0.001096 |
| 49390-Primary-Pancreas | Primary | Exocrine-like | ADEX | Classical | TRUE | Classical | 0.001096 |
| 49392-Primary-Pancreas | Primary | QM-PDA | Squamous | Basal-like | TRUE | Basal-like | 0.837062 |
| 64482-Primary-Pancreas | Primary | Exocrine-like | ADEX | Classical | TRUE | Classical | 0.00799 |
| 64500-Primary-Pancreas | Primary | Exocrine-like | ADEX | Classical | TRUE | Classical | 0.001096 |
| 72613-Primary-Pancreas | Primary | Classical | Pancreatic Progenitor | Classical | TRUE | Classical | 0.001096 |
| 64501-Primary-Pancreas | Primary | Classical | Pancreatic Progenitor | Classical | TRUE | Classical | 0.001096 |
| 72616-Primary-Pancreas | Primary | Exocrine-like | ADEX | Classical | TRUE | Classical | 0.002749 |
| 64502-Primary-Pancreas | Primary | Exocrine-like | ADEX | Classical | TRUE | Classical | 0.13805 |
| 64503-Primary-Pancreas | Primary | Exocrine-like | Pancreatic Progenitor | Classical | TRUE | Classical | 0.021347 |
| 64504-Primary-Pancreas | Primary | Exocrine-like | ADEX | Classical | TRUE | Classical | 0.001096 |
| 64505-Primary-Pancreas | Pdmary | Exocrine-like | ADEX | Classical | TRUE | Classical | 0.001096 |
| 64507-Primary-Pancreas | Pdmary | Exocrine-like | ADEX | Classical | TRUE | Classical | 0.204595 |
| 64508-Primary-Pancreas | Primary | Exocrine-like | ADEX | Classical | TRUE | Classical | 0.001096 |
| 64509-Primary-Pancreas | Primary | Exocrine-like | ADEX | Basal-like | TRUE | Basal-like | 0.898468 |
| 64510-Primary-Pancreas | Primary | Exocrine-like | Pancreatic Progenitor | Classical | TRUE | Classical | 0.013247 |
| 46647-Primary-Pancreas | Primary | QM-PDA | Squamous | Basal-like | TRUE | Basal-like | 0.991223 |
| 48569-Primary-Pancreas | Primary | Classical | Pancreatic Progenitor | Classical | TRUE | Classical | 0.013247 |
| 64498-Primary-Pancreas | Primary | QM-PDA | Squamous | Basal-like | TRUE | Basal-like | 0.957264 |
| 64490-Primary-Pancreas | Primary | QM-PDA | Squamous | Classical | FALSE | Classical | 0.020585 |
| 64491-Primary-Pancreas | Primary | Exocrine-like | ADEX | Classical | TRUE | Classical | 0.001779 |
| 64492-Primary-Pancreas | Primary | Exocrine-like | ADEX | Classical | TRUE | Classical | 0.001096 |
| 64494-Primary-Pancreas | Primary | QM-PDA | Squamous | Basal-like | TRUE | Basal-like | 0.957264 |
| 64495-Primary-Pancreas | Primary | QM-PDA | Squamous | Classical | TRUE | Classical | 0.001096 |
| 56525-Primary-Pancreas | Primary | QM-PDA | Squamous | Basal-like | TRUE | Basal-like | 0.671478 |
| 56527-Primary-Pancreas | Primary | Exocrine-like | Pancreatic Progenitor | Classical | TRUE | Classical | 0.013247 |
| 56536-Primary-Pancreas | Primary | QM-PDA | Squamous | Basal-like | TRUE | Basal-like | 0.978228 |
| 56537-Primary-Pancreas | Primary | Exocrine-like | ADEX | Classical | TRUE | Classical | 0.001096 |
| 56538-Primary-Pancreas | Primary | Classical | Pancreatic Progenitor | Classical | TRUE | Classical | 0.001096 |
| 56539-Primary-Pancreas | Primary | Classical | Pancreatic Progenitor | Classical | TRUE | Classical | 0.013247 |
| 56367-Primary-Pancreas | Primary | QM-PDA | Pancreatic Progenitor | Classical | TRUE | Classical | 0.019841 |
| 56369-Primary-Pancreas | Primary | Classical | Pancreatic Progenitor | Classical | TRUE | Classical | 0.001096 |
| 56528-Primary-Pancreas | Primary | Classical | Pancreatic Progenitor | Classical | TRUE | Classical | 0.001096 |
| 56529-Primary-Pancreas | Primary | Exocrine-like | Squamous | Classical | TRUE | Classical | 0.001096 |
| 56530-Primary-Pancreas | Primary | Exocrine-like | Squamous | Classical | TRUE | Classical | 0.001096 |
| 56540-Primary-Pancreas | Primary | Exocrine-like | Squamous | Classical | TRUE | Classical | 0.001779 |
| 56377-Primary-Pancreas | Primary | Exocrine-like | ADEX | Basal-like | FALSE | Classical | 0.012917 |
| 56373-Primary-Pancreas | Primary | Exocrine-like | Pancreatic Progenitor | Classical | TRUE | Classical | 0.001096 |
| 56374-Primary-Pancreas | Primary | Exocrine-like | ADEX | Classical | TRUE | Classical | 0.00799 |
| 56541-Primary-Pancreas | Primary | Exocrine-like | Squamous | Basal-like | FALSE | Classical | 0.005113 |
| 56542-Primary-Pancreas | Primary | Classical | Pancreatic Progenitor | Classical | TRUE | Classical | 0.013247 |
| 56375-Primary-Pancreas | Primary | Exocrine-like | ADEX | Classical | TRUE | Classical | 0.001096 |
| 56535-Primary-Pancreas | Primary | Classical | Pancreatic Progenitor | Classical | TRUE | Classical | 0.013247 |
| 54175-Primary-Pancreas | Primary | QM-PDA | Squamous | Classical | TRUE | Classical | 0.001096 |
| 54301-Primary-Pancreas | Primary | Exocrine-like | ADEX | Classical | TRUE | Classical | 0.001779 |
| 54291-Primary-Pancreas | Primary | QM-PDA | Squamous | Classical | TRUE | Classical | 0.089725 |
| 54302-Primary-Pancreas | Primary | QM-PDA | Squamous | Basal-like | TRUE | Basal-like | 0.991223 |
| 54303-Primary-Pancreas | Primary | Classical | Pancreatic Progenitor | Classical | TRUE | Classical | 0.001096 |
| 54172-Primary-Pancreas | Primary | QM-PDA | Squamous | Classical | TRUE | Classical | 0.001096 |
| 54304-Primary-Pancreas | Primary | Classical | Pancreatic Progenitor | Classical | TRUE | Classical | 0.001096 |
| 54305-Primary-Pancreas | Primary | QM-PDA | Squamous | Classical | TRUE | Classical | 0.013247 |

TABLE 12-continued

| Moffitt_GEO_array | | | | | | | |
|---|---|---|---|---|---|---|---|
| ID | SampleType | Collisson | Bailey | Moffitt | PurIST.training | PurIST | PurIST.basal.prob |
| 54309-Primary-Pancreas | Primary | Exocrine-like | ADEX | Classical | TRUE | Classical | 0.001096 |
| 54306-Primary-Pancreas | Primary | Exocrine-like | Squamous | Basal-like | TRUE | Basal-like | 0.754774 |
| 54307-Primary-Pancreas | Primary | QM-PDA | Squamous | Classical | TRUE | Classical | 0.00799 |
| 54292-Primary-Pancreas | Primary | Exocrine-like | ADEX | Classical | TRUE | Classical | 0.001096 |
| 54243-Primary-Pancreas | Primary | Classical | Pancreatic Progenitor | Classical | TRUE | Classical | 0.001096 |
| 54308-Primary-Pancreas | Primary | QM-PDA | Squamous | Classical | TRUE | Classical | 0.019979 |
| 54293-Primary-Pancreas | Primary | QM-PDA | Squamous | Classical | TRUE | Classical | 0.002769 |
| 54310-Primary-Pancreas | Primary | QM-PDA | Squamous | Classical | TRUE | Classical | 0.001096 |
| 54315-Primary-Pancreas | Primary | QM-PDA | Squamous | Basal-like | TRUE | Basal-like | 0.936765 |
| 54311-Primary-Pancreas | Primary | Classical | Pancreatic Progenitor | Classical | TRUE | Classical | 0.0055 |
| 54312-Primary-Pancreas | Primary | Exocrine-like | Pancreatic Progenitor | Classical | TRUE | Classical | 0.001096 |
| 54299-Primary-Pancreas | Primary | Exocrine-like | ADEX | Classical | TRUE | Classical | 0.001096 |
| 54313-Primary-Pancreas | Primary | Exocrine-like | Squamous | Basal-like | TRUE | Basal-like | 0.978077 |
| 54314-Primary-Pancreas | Primary | QM-PDA | Pancreatic Progenitor | Classical | TRUE | Classical | 0.013247 |
| 54294-Primary-Pancreas | Primary | Exocrine-like | ADEX | Classical | TRUE | Classical | 0.001096 |
| 54295-Primary-Pancreas | Primary | Classical | Pancreatic Progenitor | Classical | TRUE | Classical | 0.013247 |
| 54173-Primary-Pancreas | Primary | Exocrine-like | Pancreatic Progenitor | Classical | TRUE | Classical | 0.001096 |
| 54316-Primary-Pancreas | Primary | QM-PDA | Squamous | Basal-like | TRUE | Basal-like | 0.859538 |
| 54317-Primary-Pancreas | Primary | Classical | Pancreatic Progenitor | Classical | TRUE | Classical | 0.001096 |
| 54297-Primary-Pancreas | Primary | Exocrine-like | ADEX | Classical | TRUE | Classical | 0.001096 |
| 54300-Primary-Pancreas | Primary | QM-PDA | Squamous | Classical | TRUE | Classical | 0.089725 |
| 54318-Primary-Pancreas | Primary | Classical | Immunogenic | Classical | TRUE | Classical | 0.013247 |
| 54296-Primary-Pancreas | Primary | Classical | Pancreatic Progenitor | Classical | TRUE | Classical | 0.001096 |
| 54174-Primary-Pancreas | Primary | Classical | Pancreatic Progenitor | Classical | TRUE | Classical | 0.001096 |
| 54298-Primary-Pancreas | Primary | Exocrine-like | ADEX | Classical | TRUE | Classical | 0.00446 |
| 54171-Primary-Pancreas | Primary | QM-PDA | Squamous | Classical | TRUE | Classical | 0.004491 |
| 64496-Primary-Pancreas | Primary | QM-PDA | Squamous | Basal-like | FALSE | Classical | 0.031663 |
| 56322-Primary-Pancreas | Primary | Exocrine-like | Immunogenic | Classical | TRUE | Classical | 0.013247 |
| 56326-Primary-Pancreas | Primary | QM-PDA | Squamous | Basal-like | TRUE | Basal-like | 0.790185 |
| 56534-Primary-Pancreas | Primary | QM-PDA | Pancreatic Progenitor | Classical | TRUE | Classical | 0.013247 |
| 56531-Primary-Pancreas | Primary | QM-PDA | Squamous | Classical | TRUE | Classical | 0.001096 |
| 56523-Primary-Pancreas | Primary | QM-PDA | Squamous | Classical | TRUE | Classical | 0.001096 |
| 56316-Primmy-Pancreas | Primary | QM-PDA | ADEX | Classical | TRUE | Classical | 0.001096 |
| 56320-Primary-Pancreas | Primary | QM-PDA | Squamous | Classical | TRUE | Classical | 0.052325 |
| 64497-Primary-Pancreas | Primary | Exocrine-like | ADEX | Classical | TRUE | Classical | 0.002749 |

TABLE 13

| Moffitt_S2 | | | | | | | |
|---|---|---|---|---|---|---|---|
| ID | SampleType | Collisson | Bailey | Moffitt | PurIST.training | PurIST | PurIST.basal.prob |
| PDX-1 | PDX | | | Classical | FALSE | Classical | 0.001096 |
| PDX-2 | PDX | | | Classical | FALSE | Classical | 0.001096 |
| PDX-3 | PDX | | | Classical | FALSE | Basal-like | 0.514077 |
| PDX-4 | PDX | | | Classical | FALSE | Classical | 0.001096 |
| PDX-5 | PDX | | | Basal-like | FALSE | Basal-like | 0.991223 |
| PDX-6 | PDX | | | Classical | FALSE | Classical | 0.078689 |
| PDX-7 | PDX | | | Classical | FALSE | Classical | 0.001096 |
| PDX-8 | PDX | | | Classical | FALSE | Classical | 0.001096 |
| PDX-9 | PDX | | | Classical | FALSE | Classical | 0.001096 |
| PDX-10 | PDX | | | Classical | FALSE | Classical | 0.001096 |
| PDX-11 | PDX | | | Classical | FALSE | Classical | 0.002769 |
| PDX-12 | PDX | | | Classical | FALSE | Classical | 0.001096 |
| PDX-13 | PDX | | | Classical | FALSE | Classical | 0.001096 |
| PDX-14 | PDX | | | Classical | FALSE | Classical | 0.001096 |
| PDX-15 | PDX | | | Classical | FALSE | Classical | 0.020585 |
| PDX-16 | PDX | | | Classical | FALSE | Classical | 0.001096 |
| PDX-17 | PDX | | | Classical | FALSE | Classical | 0.001096 |
| PDX-18 | PDX | | | Classical | FALSE | Classical | 0.013805 |
| PDX-19 | PDX | | | Classical | FALSE | Classical | 0.013247 |
| PDX-20 | PDX | | | Classical | FALSE | Classical | 0.013805 |
| PDX-21 | PDX | | | Classical | FALSE | Classical | 0.001096 |
| PDX-22 | PDX | | | Classical | FALSE | Classical | 0.0055 |
| PDX-23 | PDX | | | Classical | FALSE | Classical | 0.02224 |
| PDX-24 | PDX | | | Classical | FALSE | Classical | 0.001096 |
| PDX-25 | PDX | | | Classical | FALSE | Classical | 0.002749 |
| PDX-26 | PDX | | | Basal-like | FALSE | Basal-like | 0.691693 |
| PDX-27 | PDX | | | Classical | FALSE | Classical | 0.001096 |
| PDX-28 | PDX | | | Classical | FALSE | Classical | 0.001096 |
| PDX-29 | PDX | | | Classical | FALSE | Classical | 0.013247 |
| PDX-30 | PDX | | | Basal-like | FALSE | Basal-like | 0.960163 |

TABLE 13-continued

| Moffitt_S2 | | | | | | | |
|---|---|---|---|---|---|---|---|
| ID | SampleType | Collisson | Bailey | Moffitt | PurIST.training | PurIST | PurIST.basal.prob |
| PDX-31 | PDX | | | Classical | FALSE | Classical | 0.001096 |
| PDX-32 | PDX | | | Classical | FALSE | Classical | 0.001096 |
| PDX-33 | PDX | | | Classical | FALSE | Classical | 0.001096 |
| PDX-34 | PDX | | | Basal-like | FALSE | Basal-like | 0.991223 |
| PDX-35 | PDX | | | Classical | FALSE | Classical | 0.001096 |
| PDX-36 | PDX | | | Classical | FALSE | Classical | 0.001096 |
| PDX-37 | PDX | | | Basal-like | FALSE | Basal-like | 0.991223 |

TABLE 14

| PACA_AU_array | | | | | | | | |
|---|---|---|---|---|---|---|---|---|
| ID | SampleType | Collisson | Bailey_original | Bailey | Moffitt | PurIST.training | PurIST | PurIST.basal.prob |
| SA407779 | Primary tumour | Exocrine-like | | ADEX | | FALSE | Classical | 0.014 |
| SA407918 | Primary tumour | Exocrine-like | Immunogenic | ADEX | Classical | FALSE | Classical | 0.014 |
| SA407946 | Cell line | Exocrine-like | | ADEX | | FALSE | Classical | 0.005 |
| SA408003 | Primary tumour | Exocrine-like | Squamous | Squamous | | FALSE | Classical | 0.427 |
| SA408106 | Primary tumour | Classical | | Pancreatic Progenitor | Classical | FALSE | Classical | 0.005 |
| SA408266 | Cell line | Exocrine-like | | ADEX | | FALSE | Classical | 0.014 |
| SA408314 | Primary tumour | Exocrine-like | | ADEX | Classical | FALSE | Classical | 0.005 |
| SA408414 | Primary tumour | QM-PDA | Squamous | ADEX | Classical | FALSE | Classical | 0.005 |
| SA408530 | Primary tumour | Exocrine-like | Squamous | Squamous | Basal-like | FALSE | Classical | 0.211 |
| SA408570 | Primary tumour | Exocrine-like | ADEX | ADEX | Classical | FALSE | Classical | 0.014 |
| SA408650 | Metastatic tumour | QM-PDA | | ADEX | | FALSE | Classical | 0.014 |
| SA408706 | Primary tumour | Classical | Pancreatic Progenitor | Pancreatic Progenitor | Classical | FALSE | Classical | 0.014 |
| SA408726 | Cell line | QM-PDA | | Immunogenic | | FALSE | Classical | 0.014 |
| SA408758 | Primary tumour | Exocrine-like | ADEX | ADEX | Classical | FALSE | Classical | 0.014 |
| SA408774 | Cell line | QM-PDA | | ADEX | | FALSE | Classical | 0.014 |
| SA408806 | Primary tumour | QM-PDA | | Immunogenic | | FALSE | Classical | 0.005 |
| SA408843 | Primary tumour | QM-PDA | | Immunogenic | Classical | FALSE | Classical | 0.093 |
| SA408867 | Primary tumour | QM-PDA | Squamous | Squamous | Basal-like | FALSE | Classical | 0.427 |
| SA408891 | Primary tumour | QM-PDA | Squamous | Squamous | Basal-like | FALSE | Basal-like | 0.975 |
| SA408946 | Primary tumour | Exocrine-like | | Squamous | Classical | FALSE | Classical | 0.412 |
| SA408963 | Cell line | Classical | | Pancreatic Progenitor | | FALSE | Classical | 0.005 |
| SA409186 | Primary tumour | Exocrine-like | ADEX | ADEX | Classical | FALSE | Classical | 0.005 |
| SA409258 | Primary tumour | QM-PDA | Pancreatic Progenitor | Pancreatic Progenitor | Classical | FALSE | Classical | 0.005 |
| SA409310 | Primary tumour | Exocrine-like | Squamous | Squamous | Basal-like | FALSE | Basal-like | 0.975 |
| SA409342 | Primary tumour | QM-PDA | Pancreatic Progenitor | ADEX | | FALSE | Classical | 0.034 |
| SA409398 | Primary tumour | Exocrine-like | | ADEX | Classical | FALSE | Classical | 0.022 |
| SA409446 | Primary tumour | Classical | Pancreatic Progenitor | Pancreatic Progenitor | Classical | FALSE | Classical | 0.005 |
| SA409498 | Primary tumour | QM-PDA | Immunogenic | ADEX | | FALSE | Classical | 0.034 |
| SA409527 | Cell line | Exocrine-like | | ADEX | | FALSE | Classical | 0.022 |
| SA409543 | Primary tumour | Classical | Immunogenic | Pancreatic Progenitor | | FALSE | Classical | 0.014 |
| SA409590 | Primary tumour | Exocrine-like | | Squamous | Classical | FALSE | Classical | 0.014 |
| SA409622 | Primary tumour | QM-PDA | Pancreatic Progenitor | Immunogenic | Classical | FALSE | Classical | 0.014 |
| SA409662 | Primary tumour | QM-PDA | Squamous | Immunogenic | Classical | FALSE | Classical | 0.005 |
| SA409678 | Cell line | Exocrine-like | | Squamous | | FALSE | Classical | 0.054 |
| SA409711 | Primary tumour | Exocrine-like | ADEX | Squamous | Classical | FALSE | Classical | 0.438 |
| SA409775 | Primary tumour | QM-PDA | Squamous | Immunogenic | Classical | FALSE | Classical | 0.034 |
| SA409818 | Cell line | Exocrine-like | | ADEX | | FALSE | Classical | 0.005 |
| SA409838 | Primary tumour | Classical | | Pancreatic Progenitor | Classical | FALSE | Classical | 0.005 |
| SA409891 | Primary tumour | Exocrine-like | ADEX | ADEX | Classical | FALSE | Classical | 0.005 |
| SA409923 | Primary tumour | Classical | Pancreatic Progenitor | Pancreatic Progenitor | | FALSE | Classical | 0.014 |
| SA410030 | Primary tumour | QM-PDA | | Immunogenic | Classical | FALSE | Classical | 0.005 |
| SA410054 | Primary tumour | QM-PDA | | ADEX | Classical | FALSE | Classical | 0.205 |
| SA410103 | Primary tumour | QM-PDA | Immunogenic | ADEX | Classical | FALSE | Classical | 0.039 |
| SA410118 | Primary tumour | Exocrine-like | Immunogenic | Immunogenic | Classical | FALSE | Classical | 0.014 |
| SA410207 | Primary tumour | Classical | ADEX | Pancreatic Progenitor | Classical | FALSE | Classical | 0.005 |
| SA410234 | Primary tumour | Exocrine-like | Pancreatic Progenitor | Pancreatic Progenitor | | FALSE | Classical | 0.005 |
| SA410263 | Primary tumour | QM-PDA | Immunogenic | Squamous | Classical | FALSE | Basal-like | 0.548 |
| SA410286 | Primary tumour | QM-PDA | | Immunogenic | Classical | FALSE | Classical | 0.014 |
| SA410310 | Primary tumour | Classical | Immunogenic | Pancreatic Progenitor | Classical | FALSE | Classical | 0.005 |
| SA410382 | Primary tumour | Exocrine-like | | Pancreatic Progenitor | Classical | FALSE | Classical | 0.005 |
| SA410383 | Primary tumour | QM-PDA | Squamous | Squamous | Basal-like | FALSE | Basal-like | 0.986 |
| SA410410 | Primary tumour | Exocrine-like | ADEX | ADEX | Classical | FALSE | Classical | 0.009 |
| SA410503 | Primary tumour | Exocrine-like | Pancreatic Progenitor | ADEX | Classical | FALSE | Classical | 0.014 |
| SA410535 | Primary tumour | Classical | Immunogenic | Pancreatic Progenitor | Classical | FALSE | Classical | 0.005 |
| SA410559 | Cell line | Exocrine-like | | ADEX | | FALSE | Classical | 0.005 |
| SA410566 | Primary tumour | Classical | | Pancreatic Progenitor | Classical | FALSE | Classical | 0.005 |
| SA410582 | Primary tumour | QM-PDA | Immunogenic | Pancreatic Progenitor | Classical | FALSE | Classical | 0.005 |
| SA410606 | | QM-PDA | | Squamous | | FALSE | Classical | 0.205 |
| SA410687 | Primary tumour | QM-PDA | Pancreatic Progenitor | Immunogenic | | FALSE | Classical | 0.211 |

TABLE 14-continued

| PACA_AU_array | | | | | | | | |
|---|---|---|---|---|---|---|---|---|
| ID | SampleType | Collisson | Bailey_original | Bailey | Moffitt | PurIST.training | PurIST | PurIST.basal.prob |
| SA410742 | Primary tumour | Classical | Pancreatic Progenitor | Pancreatic Progenitor | Classical | FALSE | Classical | 0.014 |
| SA410750 | Primary tumour | Classical | Immunogenic | Pancreatic Progenitor | Classical | FALSE | Classical | 0.005 |
| SA410758 | Primary tumour | Classical | Pancreatic Progenitor | Pancreatic Progenitor | Classical | FALSE | Classical | 0.005 |
| SA410763 | Primary tumour | Classical | Immunogenic | Pancreatic Progenitor | Classical | FALSE | Classical | 0.005 |
| SA410859 | Primary tumour | QM-PDA | Squamous | Squamous | Basal-like | FALSE | Basal-like | 0.837 |
| SA410883 | Primary tumour | Exocrine-like | ADEX | ADEX | Classical | FALSE | Classical | 0.014 |
| SA410899 | Primary tumour | Classical | Pancreatic Progenitor | Pancreatic Progenitor | Classical | FALSE | Classical | 0.005 |
| SA410911 | Primary tumour | Exocrine-like | Squamous | Squamous | Basal-like | FALSE | Basal-like | 0.991 |
| SA410933 | Primary tumour | Classical | Pancreatic Progenitor | Pancreatic Progenitor | | FALSE | Classical | 0.005 |
| SA411001 | Primary tumour | Classical | Pancreatic Progenitor | Pancreatic Progenitor | | FALSE | Classical | 0.205 |
| SA411029 | Primary tumour | Classical | Pancreatic Progenitor | Pancreatic Progenitor | | FALSE | Classical | 0.005 |
| SA411042 | Primary tumour | QM-PDA | | Immunogenic | Classical | FALSE | Classical | 0.211 |
| SA411189 | Primary tumour | QM-PDA | Squamous | Immunogenic | Classical | FALSE | Classical | 0.054 |
| SA411209 | Primary tumour | Exocrine-like | ADEX | ADEX | Classical | FALSE | Classical | 0.093 |
| SA411241 | Primary tumour | Classical | Pancreatic Progenitor | Pancreatic Progenitor | Classical | FALSE | Classical | 0.014 |
| SA411261 | Primary tumour | QM-PDA | | Immunogenic | Classical | FALSE | Classical | 0.205 |
| SA411305 | Primary tumour | QM-PDA | Squamous | Immunogenic | Classical | FALSE | Classical | 0.034 |
| SA411360 | Cell line | QM-PDA | | Immunogenic | | FALSE | Classical | 0.014 |
| SA411397 | Primary tumour | Classical | Squamous | Immunogenic | Classical | FALSE | Classical | 0.014 |
| SA411406 | Primary tumour | Classical | Immunogenic | Pancreatic Progenitor | Classical | FALSE | Classical | 0.005 |
| SA411430 | Primary tumour | Classical | Immunogenic | Pancreatic Progenitor | | FALSE | Classical | 0.005 |
| SA411454 | Primary tumour | Exocrine-like | | Pancreatic Progenitor | Classical | FALSE | Classical | 0.005 |
| SA411557 | Primary tumour | Classical | Immunogenic | Pancreatic Progenitor | | FALSE | Classical | 0.005 |
| SA411578 | Primary tumour | QM-PDA | Squamous | Immunogenic | Classical | FALSE | Classical | 0.296 |
| SA411721 | Primary tumour | Classical | Pancreatic Progenitor | Pancreatic Progenitor | Classical | FALSE | Classical | 0.005 |
| SA411745 | Primary tumour | Classical | Immunogenic | Pancreatic Progenitor | Classical | FALSE | Classical | 0.014 |
| SA411769 | Primary tumour | Classical | Pancreatic Progenitor | Pancreatic Progenitor | Classical | FALSE | Classical | 0.005 |
| SA411797 | Primary tumour | Classical | Pancreatic Progenitor | Pancreatic Progenitor | | FALSE | Classical | 0.005 |
| SA411833 | Primary tumour | Classical | Immunogenic | Pancreatic Progenitor | Classical | FALSE | Classical | 0.005 |
| SA411907 | Cell line | QM-PDA | | Pancreatic Progenitor | | FALSE | Classical | 0.014 |
| SA411923 | Primary tumour | Exocrine-like | Squamous | Immunogenic | Classical | FALSE | Classical | 0.301 |
| SA412003 | Primary tumour | QM-PDA | | Immunogenic | Classical | FALSE | Classical | 0.034 |
| SA412076 | Primary tumour | QM-PDA | Squamous | Immunogenic | Classical | FALSE | Classical | 0.093 |
| SA412212 | Primary tumour | QM-PDA | Pancreatic Progenitor | Immunogenic | Classical | FALSE | Classical | 0.014 |
| SA412299 | Primary tumour | Exocrine-like | ADEX | ADEX | | FALSE | Classical | 0.039 |
| SA412367 | Primary tumour | Exocrine-like | | ADEX | Classical | FALSE | Classical | 0.034 |
| SA412455 | Primary tumour | Exocrine-like | | Squamous | Classical | FALSE | Classical | 0.412 |
| SA518603 | Primary tumour | Classical | Pancreatic Progenitor | Pancreatic Progenitor | Classical | FALSE | Classical | 0.014 |
| SA518614 | Primary tumour | Classical | Immunogenic | Pancreatic Progenitor | | FALSE | Classical | 0.014 |
| SA518615 | Primary tumour | Classical | Immunogenic | Pancreatic Progenitor | Classical | FALSE | Classical | 0.005 |
| SA518624 | | Classical | | Pancreatic Progenitor | | FALSE | Classical | 0.005 |
| SA518630 | Primary tumour | Exocrine-like | ADEX | ADEX | | FALSE | Classical | 0.005 |
| SA518633 | Primary tumour | QM-PDA | Squamous | Squamous | Basal-like | FALSE | Basal-like | 0.991 |
| SA518637 | Primary tumour | QM-PDA | Squamous | Squamous | Basal-like | FALSE | Basal-like | 0.975 |
| SA518665 | Primary tumour | Exocrine-like | ADEX | Pancreatic Progenitor | Classical | FALSE | Classical | 0.005 |
| SA518689 | Primary tumour | Classical | Immunogenic | Pancreatic Progenitor | Classical | FALSE | Classical | 0.005 |
| SA518695 | Primary tumour | Classical | Pancreatic Progenitor | Pancreatic Progenitor | Classical | FALSE | Classical | 0.005 |
| SA518701 | Primary tumour | Classical | Pancreatic Progenitor | Pancreatic Progenitor | | FALSE | Classical | 0.005 |
| SA518704 | Primary tumour | Exocrine-like | ADEX | Immunogenic | Classical | FALSE | Classical | 0.014 |
| SA518709 | Primary tumour | Exocrine-like | | Immunogenic | Classical | FALSE | Classical | 0.034 |
| SA518712 | Primary tumour | Exocrine-like | | Immunogenic | Classical | FALSE | Classical | 0.014 |
| SA518716 | Primary tumour | Exocrinc-like | Immunogenic | Pancreatic Progenitor | Classical | FALSE | Classical | 0.005 |
| SA518724 | Primary tumour | Classical | Pancreatic Progenitor | Pancreatic Progenitor | Classical | FALSE | Classical | 0.005 |
| SA518765 | Primary tumour | Classical | Pancreatic Progenitor | Pancreatic Progenitor | Classical | FALSE | Classical | 0.014 |
| SA518806 | Primary tumour | QM-PDA | Squamous | Immunogenic | Classical | FALSE | Classical | 0.205 |
| SA518817 | Primary tumour | Classical | Immunogenic | Pancreatic Progenitor | Classical | FALSE | Classical | 0.005 |
| SA518851 | Primary tumour | QM-PDA | Squamous | Squamous | Basal-like | FALSE | Basal-like | 0.991 |
| SA518854 | Primary tumour | Exocrine-like | | Squamous | Classical | FALSE | Classical | 0.034 |
| SA518868 | Primary tumour | QM-PDA | Immunogenic | Immunogenic | Classical | FALSE | Classical | 0.093 |
| SA518878 | Primary tumour | QM-PDA | Squamous | Immunogenic | Classical | FALSE | Classical | 0.039 |
| SA528670 | Primary tumour | Exocrine-like | | Squamous | Basal-like | FALSE | Basal-like | 0.975 |
| SA528675 | Primary tumour | Classical | Immunogenic | Pancreatic Progenitor | | FALSE | Classical | 0.014 |
| SA528676 | Primary tumour | QM-PDA | | Immunogenic | Classical | FALSE | Classical | 0.034 |
| SA528687 | Primary tumour | Classical | Immunogenic | Pancreatic Progenitor | Classical | FALSE | Classical | 0.005 |
| SA528693 | Primary tumour | QM-PDA | ADEX | Squamous | Basal-like | FALSE | Basal-like | 0.991 |
| SA528695 | Primary tumour | Classical | Pancreatic Progenitor | Pancreatic Progenitor | Classical | FALSE | Classical | 0.005 |
| SA528697 | Primary tumour | Exocrine-like | | Immunogenic | Classical | FALSE | Classical | 0.014 |
| SA528709 | Primary tumour | QM-PDA | Squamous | Squamous | Basal-like | FALSE | Basal-like | 0.991 |
| SA528712 | Cell line | QM-PDA | | Immunogenic | | FALSE | Classical | 0.022 |
| SA528713 | Metastatic tumour | Exocrine-like | | Squamous | | FALSE | Classical | 0.034 |
| SA528755 | Primary tumour | Classical | Immunogenic | Pancreatic Progenitor | Classical | FALSE | Classical | 0.005 |
| SA528761 | Primary tumour | QM-PDA | Squamous | Squamous | Basal-like | FALSE | Basal-like | 0.558 |

TABLE 15

PACA_AU_seq

| ID | SampleType | Collisson | Balley_original | Bailey | Moffitt | PurIST.training | PurIST | PurIST.basal.prob |
|---|---|---|---|---|---|---|---|---|
| SA407858 | Primary tumour | Classical | | Pancreatic Progenitor | | FALSE | Classical | 0.001 |
| SA408414 | Primary tumour | QM-PDA | Squamous | Immunogenic | Classical | FALSE | Classical | 0.002 |
| SA408530 | Primary tumour | Exocrine-like | Squamous | Squamous | Basal-like | FALSE | Basal-like | 0.991 |
| SA408570 | Primary tumour | Exocrine-like | ADEX | ADEX | Classical | FALSE | Classical | 0.096 |
| SA408758 | Primary tumour | Exocrine-like | ADEX | Immunogenic | Classical | FALSE | Classical | 0.001 |
| SA408867 | Primary tumour | QM-PDA | Squamous | Squamous | Basal-like | FALSE | Classical | 0.427 |
| SA409775 | Primary tumour | QM-PDA | Squamous | ADEX | Classical | FALSE | Basal-like | 0.850 |
| SA409923 | Primary tumour | Classical | Pancreatic Progenitor | Pancreatic Progenitor | | FALSE | Classical | 0.005 |
| SA409990 | Cell line | QM-PDA | | Squamous | | FALSE | Basal-like | 0.991 |
| SA410103 | Primary tumour | QM-PDA | Immunogenic | Immunogenic | Classical | FALSE | Classical | 0.138 |
| SA410118 | Primary tumour | Exocrine-like | Immunogenic | ADEX | Classical | FALSE | Classical | 0.014 |
| SA410263 | Primary tumour | QM-PDA | Immunogenic | Squamous | Basal-like | FALSE | Basal-like | 0.991 |
| SA410311 | Primary tumour | Classical | Pancreatic Progenitor | Pancreatic Progenitor | Classical | FALSE | Classical | 0.001 |
| SA410566 | Primary tumour | Classical | | Pancreatic Progenitor | Classical | FALSE | Classical | 0.005 |
| SA410742 | Primary tumour | Classical | Pancreatic Progenitor | Immunogenic | Classical | FALSE | Classical | 0.008 |
| SA410750 | Primary tumour | Classical | Immunogenic | Pancreatic Progenitor | Classical | FALSE | Classical | 0.005 |
| SA410758 | Primary tumour | Classical | Pancreatic Progenitor | Pancreatic Progenitor | Classical | FALSE | Classical | 0.001 |
| SA410763 | Primary tumour | Classical | Immunogenic | Pancreatic Progenitor | Classical | FALSE | Classical | 0.001 |
| SA410859 | Primary tumour | QM-PDA | Squamous | Squamous | Basal-like | FALSE | Basal-like | 0.991 |
| SA410883 | Primary tumour | Exocrine-like | ADEX | ADEX | Classical | FALSE | Classical | 0.014 |
| SA410899 | Primary tumour | Classical | Pancreatic Progenitor | Pancreatic Progenitor | Classical | FALSE | Classical | 0.008 |
| SA410911 | Primary tumour | QM-PDA | Squamous | Squamous | Basal-like | FALSE | Basal-like | 0.991 |
| SA410933 | Primary tumour | Classical | Pancreatic Progenitor | Pancreatic Progenitor | | FALSE | Classical | 0.001 |
| SA410977 | Cell line | QM-PDA | | Squamous | | FALSE | Basal-like | 0.937 |
| SA411001 | Primary tumour | Classical | Pancreatic Progenitor | Pancreatic Progenitor | | FALSE | Classical | 0.014 |
| SA411025 | Cell line | QM-PDA | | Squamous | | FALSE | Basal-like | 0.991 |
| SA411029 | Primary tumour | Classical | Pancreatic Progenitor | Pancreatic Progenitor | | FALSE | Classical | 0.005 |
| SA411189 | Primary tumour | QM-PDA | Squamous | Squamous | Classical | FALSE | Basal-like | 0.860 |
| SA411209 | Primary tumour | Exocrine-like | ADEX | ADEX | Classical | FALSE | Classical | 0.093 |
| SA411241 | Primary tumour | Classical | Pancreatic Progenitor | Pancreatic Progenitor | Classical | FALSE | Classical | 0.005 |
| SA411305 | Primary tumour | QM-PDA | Squamous | ADEX | Classical | FALSE | Basal-like | 0.680 |
| SA411397 | Primary tumour | Classical | Squamous | Immunogenic | Classical | FALSE | Classical | 0.099 |
| SA411406 | Primary tumour | Classical | Immunogenic | Pancreatic Progenitor | Classical | FALSE | Classical | 0.001 |
| SA411430 | Primary tumour | Classical | Immunogenic | Pancreatic Progenitor | | FALSE | Classical | 0.001 |
| SA411557 | Primary tumour | Classical | Immunogenic | Pancreatic Progenitor | | FALSE | Classical | 0.001 |
| SA411578 | Primary tumour | QM-PDA | Squamous | ADEX | Classical | FALSE | Basal-like | 0.902 |
| SA411682 | Cell line | QM-PDA | | Squamous | | FALSE | Basal-like | 0.937 |
| SA411709 | Cell line | QM-PDA | | Squamous | | FALSE | Basal-like | 0.937 |
| SA411721 | Primary tumour | Classical | Pancreatic Progenitor | Pancreatic Progenitor | Classical | FALSE | Classical | 0.001 |
| SA411745 | Primary tumour | Classical | Immunogenic | Pancreatic Progenitor | Classical | FALSE | Classical | 0.001 |
| SA411769 | Primary tumour | Classical | Pancreatic Progenitor | Pancreatic Progenitor | Classical | FALSE | Classical | 0.001 |
| SA411797 | Primary tumour | Classical | Pancreatic Progenitor | Pancreatic Progenitor | | FALSE | Classical | 0.001 |
| SA411833 | Primary tumour | Classical | Immunogenic | Pancreatic Progenitor | Classical | FALSE | Classical | 0.001 |
| SA411841 | Cell line | QM-PDA | | Squamous | | FALSE | Basal-like | 0.937 |
| SA411923 | Primary tumour | Exocrine-like | Squamous | Squamous | Classical | FALSE | Classical | 0.301 |
| SA412003 | Primary tumour | QM-PDA | | ADEX | Classical | FALSE | Classical | 0.092 |
| SA412060 | Cell line | QM-PDA | | Squamous | | FALSE | Basal-like | 0.991 |
| SA412076 | Primary tumour | QM-PDA | Squamous | ADEX | Classical | FALSE | Classical | 0.020 |
| SA412268 | Metastatic tumour | QM-PDA | | Squamous | | FALSE | Basal-like | 0.991 |
| SA412299 | Primary tumour | Exocrine-like | ADEX | ADEX | | FALSE | Classical | 0.020 |
| SA518492 | Cell line | QM-PDA | | Squamous | | FALSE | Basal-like | 0.901 |
| SA518603 | Primary tumour | Classical | Pancreatic Progenitor | Pancreatic Progenitor | Classical | FALSE | Classical | 0.001 |
| SA518614 | Primary tumour | Classical | Immunogenic | Pancreatic Progenitor | | FALSE | Classical | 0.001 |
| SA518615 | Primary tumour | Classical | Immunogenic | Pancreatic Progenitor | Classical | FALSE | Classical | 0.001 |
| SA518624 | | Classical | | Pancreatic Progenitor | | FALSE | Classical | 0.001 |
| SA518630 | Primary tumour | Exocrine-like | ADEX | ADEX | | FALSE | Classical | 0.001 |
| SA518633 | Primary tumour | QM-PDA | Squamous | Squamous | Basal-like | FALSE | Basal-like | 0.991 |
| SA518637 | Primary tumour | QM-PDA | Squamous | Squamous | Basal-like | FALSE | Basal-like | 0.991 |
| SA518665 | Primary tumour | Exocrine-like | ADEX | Pancreatic Progenitor | Classical | FALSE | Classical | 0.001 |
| SA518689 | Primary tumour | Classical | Immunogenic | Pancreatic Progenitor | Classical | FALSE | Classical | 0.001 |
| SA518695 | Primary tumour | Classical | Pancreatic Progenitor | Pancreatic Progenitor | Classical | FALSE | Classical | 0.005 |
| SA518701 | Primary tumour | Exocrine-like | Pancreatic Progenitor | Pancreatic Progenitor | | FALSE | Classical | 0.001 |
| SA518704 | Primary tumour | Exocrine-like | ADEX | ADEX | Classical | FALSE | Classical | 0.013 |
| SA518712 | Primary tumour | Exocrine-like | | ADEX | Classical | FALSE | Classical | 0.013 |
| SA518716 | Primary tumour | Exocrine-like | Immunogenic | Pancreatic Progenitor | Classical | FALSE | Classical | 0.001 |
| SA518724 | Primary tumour | Classical | Pancreatic Progenitor | Pancreatic Progenitor | Classical | FALSE | Classical | 0.001 |
| SA518750 | Primary tumour | Classical | Pancreatic Progenitor | Pancreatic Progenitor | Classical | FALSE | Classical | 0.001 |
| SA518765 | Primary tumour | Classical | Pancreatic Progenitor | Immunogenic | Classical | FALSE | Classical | 0.001 |
| SA518806 | Primary tumour | QM-PDA | Squamous | ADEX | Classical | FALSE | Classical | 0.142 |
| SA518817 | Primary tumour | Classical | Immunogenic | Pancreatic Progenitor | Classical | FALSE | Classical | 0.001 |
| SA518851 | Primary tumour | QM-PDA | Squamous | Squamous | Basal-like | FALSE | Basal-like | 0.991 |
| SA518854 | Primary tumour | Exocrine-like | | ADEX | Classical | FALSE | Classical | 0.092 |
| SA518868 | Primary tumour | QM-PDA | Immunogenic | ADEX | Classical | FALSE | Classical | 0.014 |
| SA518873 | | QM-PDA | | Squamous | | FALSE | Basal-like | 0.991 |
| SA518878 | Primary tumour | QM-PDA | Squamous | ADEX | Classical | FALSE | Classical | 0.001 |
| SA528675 | Primary tumour | Classical | Immunogenic | Pancreatic Progenitor | | FALSE | Classical | 0.001 |

TABLE 15-continued

| PACA_AU_seq | | | | | | | | |
|---|---|---|---|---|---|---|---|---|
| ID | SampleType | Collisson | Balley_original | Bailey | Moffitt | PurIST.training | PurIST | PurIST.basal.prob |
| SA528676 | Primary tumour | QM-PDA | | ADEX | Basal-like | FALSE | Classical | 0.025 |
| SA528677 | Primary tumour | Exocrine-like | ADEX | ADEX | Classical | FALSE | Classical | 0.003 |
| SA528679 | Primary tumour | QM-PDA | Immunogenic | Squamous | Basal-like | FALSE | Basal-like | 0.991 |
| SA528687 | Primary tumour | Classical | Immunogenic | Pancreatic Progenitor | Classical | FALSE | Classical | 0.001 |
| SA528695 | Primary tumour | Classical | Pancreatic Progenitor | Pancreatic Progenitor | Classical | FALSE | Classical | 0.001 |
| SA528701 | Metastatic tumour | Classical | | Pancreatic Progenitor | | FALSE | Classical | 0.014 |
| SA528709 | Primary tumour | QM-PDA | Squamous | Squamous | Basal-like | FALSE | Basal-like | 0.991 |
| SA528711 | Primary tumour | QM-PDA | Pancreatic Progenitor | ADEX | Classical | FALSE | Classical | 0.014 |
| SA528755 | Primary tumour | Classical | Immunogenic | Pancreatic Progenitor | Classical | FALSE | Classical | 0.001 |
| SA528761 | Primary tumour | QM-PDA | Squamous | Squamous | Basal-like | FALSE | Basal-like | 0.762 |
| SA528763 | Primary tumour | QM-PDA | | ADEX | | FALSE | Classical | 0.036 |
| SA528766 | Primary tumour | Exocrine-like | | ADEX | Classical | FALSE | Basal-like | 0.548 |
| SA528767 | Primary tumour | QM-PDA | Squamous | ADEX | Classical | FALSE | Classical | 0.211 |
| SA528768 | Primary tumour | Classical | Pancreatic Progenitor | Pancreatic Progenitor | | FALSE | Classical | 0.002 |
| SA528769 | Primary tumour | Classical | | ADEX | Classical | FALSE | Classical | 0.001 |
| SA528771 | Primary tumour | Classical | | ADEX | Classical | FALSE | Classical | 0.005 |

TABLE 16

| TCGA_PAAD | | | | | | | | |
|---|---|---|---|---|---|---|---|---|
| ID | Collisson_original | Collisson | Bailey_original | Bailey | Moffitt | PurIST.training | PurIST | PurIST.basal.prob |
| TCGA-2L-AAQE-01A | Classical | Classical | Immunogenic | Immunogenic | Classical | FALSE | Classical | 0.436 |
| TCGA-XD-AAUL-01A | Classical | Classical | Immunogenic | Immunogenic | Classical | TRUE | Classical | 0.148 |
| TCGA-2L-AAQJ-01A | Classical | Classical | Progenitor | Pancreatic Progenitor | Classical | TRUE | Classical | 0.001 |
| TCGA-2L-AAQI-01A | Exocrine-like | Exocrine-like | Progenitor | Pancreatic Progenitor | Classical | TRUE | Classical | 0.038 |
| TCGA-3A-A9IB-01A | Exocrine-like | Exocrine-like | ADEX | Squamous | Basal-like | TRUE | Basal-like | 0.548 |
| TCGA-3A-A9IU-01A | Exocrine-like | Exocrine-like | ADEX | Squamous | Basal-like | TRUE | Basal-like | 0.548 |
| TCGA-FB-AAPS-01A | Exocrine-like | Exocrine-like | ADEX | Squamous | Classical | TRUE | Classical | 0.032 |
| TCGA-HV-AA8X-01A | Classical | Classical | Progenitor | Pancreatic Progenitor | Classical | TRUE | Classical | 0.001 |
| TCGA-LB-A9Q5-01A | Exocrine-like | Exocrine-like | Squamous | ADEX | Classical | TRUE | Classical | 0.165 |
| TCGA-HZ-A9TJ-01A | Classical | Classical | Progenitor | Pancreatic Progenitor | Classical | TRUE | Classical | 0.002 |
| TCGA-3A-A9IH-01A | Classical | Classical | Immunogenic | Immunogenic | Classical | TRUE | Basal-like | 0.785 |
| TCGA-RB-AA9M-01A | Classical | Classical | Immunogenic | Immunogenic | Basal-like | FALSE | Classical | 0.308 |
| TCGA-IB-AAUQ-01A | QM-PDA | QM-PDA | ADEX | Squamous | Basal-like | TRUE | Basal-like | 0.939 |
| TCGA-3A-A9J0-01A | Classical | Classical | Immunogenic | Immunogenic | Classical | TRUE | Classical | 0.008 |
| TCGA-FB-AAQ3-01A | Exocrine-like | Exocrine-like | Progenitor | Pancreatic Progenitor | Classical | TRUE | Classical | 0.001 |
| TCGA-FB-AAQ1-01A | Exocrine-like | Exocrine-like | Squamous | ADEX | Basal-like | TRUE | Basal-like | 0.991 |
| TCGA-2J-AAB9-01A | Exocrine-like | Exocrine-like | Squamous | ADEX | Basal-like | FALSE | Classical | 0.090 |
| TCGA-2J-AABA-01A | Classical | Classical | Immunogenic | Immunogenic | Classical | TRUE | Classical | 0.034 |
| TCGA-2J-AABR-01A | Exocrine-like | Exocrine-like | Squamous | ADEX | Classical | FALSE | Basal-like | 0.957 |
| TCGA-FB-AAQ6-01A | Classical | Classical | Progenitor | Pancreatic Progenitor | Classical | TRUE | Classical | 0.001 |
| TCGA-2J-AABE-01A | Classical | Classical | Progenitor | Pancreatic Progenitor | Classical | TRUE | Classical | 0.013 |
| TCGA-2J-AABT-01A | QM-PDA | QM-PDA | Immunogenic | Immunogenic | Classical | TRUE | Classical | 0.003 |
| TCGA-FB-AAPQ-01A | Classical | Classical | Progenitor | Pancreatic Progenitor | Classical | TRUE | Classical | 0.001 |
| TCGA-HV-AA8V-01A | Classical | Classical | ADEX | Squamous | Basal-like | FALSE | Classical | 0.087 |
| TCGA-2J-AABV-01A | Exocrine-like | Exocrine-like | Squamous | ADEX | Classical | TRUE | Classical | 0.001 |
| TCGA-2J-AABF-01A | Exocrine-like | Exocrine-like | Progenitor | Pancreatic Progenitor | Classical | TRUE | Classical | 0.001 |
| TCGA-2J-AABU-01A | QM-PDA | QM-PDA | ADEX | Squamous | Basal-like | TRUE | Basal-like | 0.939 |
| TCGA-FB-AAPU-01A | Classical | Classical | Progenitor | Pancreatic Progenitor | Classical | TRUE | Classical | 0.001 |
| TCGA-2J-AABH-01A | Exocrine-like | Exocrine-like | Progenitor | Pancreatic Progenitor | Classical | TRUE | Classical | 0.005 |
| TCGA-FB-AAPY-01A | Exocrine-like | Exoctine-like | Progenitor | Pancreatic Progenitor | Classical | TRUE | Classical | 0.002 |
| TCGA-2J-AAB1-01A | Classical | Classical | Progenitor | Pancreatic Progenitor | Classical | TRUE | Classical | 0.001 |
| TCGA-XD-AAUG-01A | Exocrine-like | Exocrine-like | Squamous | ADEX | Classical | TRUE | Classical | 0.002 |
| TCGA-2J-AAB4-01A | Classical | Classical | Progenitor | Pancreatic Progenitor | Classical | TRUE | Classical | 0.001 |
| TCGA-2J-AABI-01A | QM-PDA | QM-PDA | ADEX | Squamous | Basal-like | TRUE | Basal-like | 0.991 |
| TCGA-FB-AAPZ-01A | Exocrine-like | Exocrine-like | ADEX | Squamous | Classical | TRUE | Classical | 0.142 |
| TCGA-XD-AAUH-01A | QM-PDA | QM-PDA | ADEX | Squamous | Classical | TRUE | Classical | 0.003 |
| TCGA-3A-A9IX-01A | Exocrine-like | Exocrine-like | Squamous | ADEX | Classical | TRUE | Classical | 0.013 |
| TCGA-2J-AABK-01A | Exocrine-like | Exocrine-like | Progenitor | Pancreatic Progenitor | Classical | TRUE | Classical | 0.002 |
| TCGA-2J-AAB6-01A | QM-PDA | QM-PDA | ADEX | Squamous | Basal-like | TRUE | Basal-like | 0.991 |
| TCGA-FB-AAQ0-01A | Classical | Classical | Progenitor | Pancreatic Progenitor | Classical | TRUE | Classical | 0.001 |
| TCGA-XD-AAUI-01A | Exocrine-like | Exocrine-like | ADEX | Squamous | Classical | TRUE | Classical | 0.096 |
| TCGA-2J-AAB8-01A | Classical | Classical | Immunogenic | Immunogenic | Classical | TRUE | Classical | 0.001 |
| TCGA-3A-A9IZ-01A | QM-PDA | QM-PDA | Immunogenic | Immunogenic | Classical | TRUE | Classical | 0.054 |
| TCGA-2J-AABO-01A | Exocrine-like | Exocrine-like | ADEX | Squamous | Classical | FALSE | Classical | 0.064 |
| TCGA-Z5-AAPL-01A | QM-PDA | QM-PDA | ADEX | Squamous | Classical | TRUE | Classical | 0.004 |
| TCGA-FB-AAQ2-01A | QM-PDA | QM-PDA | ADEX | Squamous | Basal-like | TRUE | Basal-like | 0.991 |
| TCGA-F2-6879-01A | Classical | Classical | Progenitor | Pancreatic Progenitor | Classical | TRUE | Classical | 0.002 |
| TCGA-HZ-7925-01A | QM-PDA | QM-PDA | Immunogenic | Immunogenic | Classical | TRUE | Classical | 0.234 |
| TCGA-IB-7651-01A | Exocrine-like | Exocrine-like | Squamous | ADEX | Classical | TRUE | Classical | 0.008 |

TABLE 16-continued

TCGA_PAAD

| ID | Collisson_original | Collisson | Bailey_original | Bailey | Moffitt | PurIST.training | PurIST | PurIST.basal.prob |
|---|---|---|---|---|---|---|---|---|
| TCGA-HZ-7926-01A | Exocrine-like | Exocrine-like | Immunogenic | Immunogenic | Classical | TRUE | Classical | 0.008 |
| TCGA-IB-7885-01A | QM-PDA | QM-PDA | ADEX | Squamous | Classical | FALSE | Classical | 0.325 |
| TCGA-IB-7652-01A | Exocrine-like | Exocrine-like | Squamous | ADEX | Classical | TRUE | Classical | 0.002 |
| TCGA-IB-7644-01A | Classical | Classical | Progenitor | Pancreatic Progenitor | Classical | TRUE | Classical | 0.001 |
| TCGA-IB-7887-01A | Classical | Classical | Immunogenic | Immunogenic | Basal-like | FALSE | Classical | 0.087 |
| TCGA-IB-7889-01A | Exocrine-like | Exocrine-like | Squamous | ADEX | Classical | TRUE | Classical | 0.016 |
| TCGA-IB-7646-01A | QM-PDA | QM-PDA | ADEX | Squamous | Basal-like | TRUE | Basal-like | 0.991 |
| TCGA-IB-7886-01A | Classical | Classical | Immunogenic | Immunogenic | Classical | TRUE | Classical | 0.005 |
| TCGA-IB-7893-01A | QM-PDA | QM-PDA | ADEX | Squamous | Basal-like | TRUE | Basal-like | 0.855 |
| TCGA-HZ-7919-01A | Classical | Classical | Progenitor | Pancreatic Progenitor | Classical | TRUE | Classical | 0.005 |
| TCGA-HZ-8001-01A | Exocrine-like | Exocrine-like | ADEX | Squamous | Basal-like | TRUE | Basal-like | 0.978 |
| TCGA-IB-7647-01A | Classical | Classical | Immunogenic | Immunogenic | Classical | TRUE | Classical | 0.001 |
| TCGA-IB-7897-01A | QM-PDA | QM-PDA | Squamous | ADEX | Classical | TRUE | Classical | 0.036 |
| TCGA-IB-7888-01A | Classical | Classical | Immunogenic | Immunogenic | Classical | TRUE | Classical | 0.001 |
| TCGA-HZ-8002-01A | Exocrine-like | Exocrine-like | Squamous | ADEX | Classical | TRUE | Classical | 0.200 |
| TCGA-HZ-7922-01A | Exocrine-like | Exocrine-like | Squamous | ADEX | Classical | TRUE | Classical | 0.014 |
| TCGA-HZ-8003-01A | Exocrine-like | Exocrine-like | Squamous | ADEX | Classical | TRUE | Classical | 0.001 |
| TCGA-IB-7649-01A | Exocrine-like | Exocrine-like | Squamous | ADEX | Classical | TRUE | Classical | 0.002 |
| TCGA-IB-7645-01A | QM-PDA | QM-PDA | Immunogenic | Immunogenic | Classical | TRUE | Classical | 0.001 |
| TCGA-IB-7890-01A | QM-PDA | QM-PDA | ADEX | Squamous | Basal-like | TRUE | Basal-like | 0.978 |
| TCGA-IB-7891-01A | Exocrine-like | Exocrine-like | Squamous | ADEX | Classical | TRUE | Classical | 0.005 |
| TCGA-H6-8124-01A | QM-PDA | QM-PDA | ADEX | Squamous | Basal-like | TRUE | Basal-like | 0.937 |
| TCGA-HZ-8315-01A | Exocrine-like | Exocrine-like | Squamous | ADEX | Classical | TRUE | Classical | 0.034 |
| TCGA-HZ-8317-01A | Exocrine-like | Exocrine-like | Squamous | ADEX | Classical | TRUE | Classical | 0.038 |
| TCGA-HZ-8519-01A | Exocrine-like | Exocrine-like | Squamous | ADEX | Classical | TRUE | Classical | 0.008 |
| TCGA-HZ-8636-01A | QM-PDA | QM-PDA | Immunogenic | Immunogenic | Classical | TRUE | Classical | 0.005 |
| TCGA-HZ-8637-01A | QM-PDA | QM-PDA | Immunogenic | Immunogenic | Classical | TRUE | Classical | 0.001 |
| TCGA-IB-8127-01A | Exocrine-like | Exocrine-like | Immunogenic | Immunogenic | Classical | TRUE | Classical | 0.165 |
| TCGA-IB-8126-01A | Exocrine-like | Exocrine-like | Squamous | ADEX | Classical | TRUE | Classical | 0.001 |
| TCGA-F2-A44H-01A | Exocrine-like | Exocrine-like | Squamous | ADEX | Classical | TRUE | Classical | 0.005 |
| TCGA-FB-A4P6-01A | Exocrine-like | Exocrine-like | Squamous | ADEX | Classical | TRUE | Classical | 0.013 |
| TCGA-FB-A4P5-01A | Exocrine-like | Exocrine-like | Squamous | ADEX | Classical | TRUE | Classical | 0.038 |
| TCGA-H6-A45N-01A | Exocrine-like | Exocrine-like | Squamous | ADEX | Classical | TRUE | Classical | 0.002 |
| TCGA-HV-A5A3-01A | Classical | Classical | Immunogenic | Immunogenic | Basal-like | TRUE | Basal-like | 0.902 |
| TCGA-HV-A5A5-01A | Exocrine-like | Exocrine-like | Squamous | ADEX | Classical | TRUE | Classical | 0.002 |
| TCGA-HV-A5A4-01A | Classical | Classical | Progenitor | Pancreatic Progenitor | Classical | TRUE | Classical | 0.002 |
| TCGA-HZ-A49H-01A | Exocrine-like | Exocrine-like | Squamous | ADEX | Classical | TRUE | Classical | 0.002 |
| TCGA-HV-A5A6-01A | Classical | Classical | Immunogenic | Immunogenic | Classical | TRUE | Classical | 0.021 |
| TCGA-HZ-A49G-01A | Exocrine-like | Exocrine-like | Squamous | ADEX | Classical | TRUE | Classical | 0.038 |
| TCGA-HZ-A4BH-01A | Classical | Classical | Immunogenic | Immunogenic | Classical | TRUE | Classical | 0.013 |
| TCGA-HZ-A49I-01A | Classical | Classical | Progenitor | Pancreatic Progenitor | Classical | TRUE | Classical | 0.003 |
| TCGA-HZ-A4BK-01A | Exocrine-like | Exocrine-like | Progenitor | Pancreatic Progenitor | Classical | TRUE | Classical | 0.001 |
| TCGA-M8-A5N4-01A | Classical | Classical | Immunogenic | Immunogenic | Classical | TRUE | Classical | 0.229 |
| TCGA-F2-A44G-01A | Classical | Classical | Immunogenic | Immunogenic | Classical | TRUE | Classical | 0.003 |
| TCGA-HZ-8005-01A | QM-PDA | QM-PDA | ADEX | Squamous | Basal-like | TRUE | Basal-like | 0.902 |
| TCGA-PZ-A5RE-01A | Classical | Classical | Progenitor | Pancreatic Progenitor | Classical | TRUE | Classical | 0.005 |
| TCGA-FB-A78T-01A | Exocrine-like | Exocrine-like | Progenitor | Pancreatic Progenitor | Classical | TRUE | Classical | 0.001 |
| TCGA-FB-A5VM-01A | QM-PDA | QM-PDA | ADEX | Squamous | Basal-like | TRUE | Basal-like | 0.991 |
| TCGA-US-A774-01A | Exocrine-like | Exocrine-like | Squamous | ADEX | Classical | TRUE | Classical | 0.003 |
| TCGA-OE-A75W-01A | Classical | Classical | Progenitor | Pancreatic Progenitor | Classical | TRUE | Classical | 0.002 |
| TCGA-US-A779-01A | Classical | Classical | Progenitor | Pancreatic Progenitor | Classical | TRUE | Classical | 0.001 |
| TCGA-IB-A5SP-01A | Classical | Classical | Progenitor | Pancreatic Progenitor | Classical | TRUE | Classical | 0.001 |
| TCGA-IB-A5SQ-01A | QM-PDA | QM-PDA | ADEX | Squamous | Basal-like | TRUE | Basal-like | 0.965 |
| TCGA-US-A77G-01A | Exocrine-like | Exocrine-like | Progenitor | Pancreatic Progenitor | Classical | TRUE | Classical | 0.001 |
| TCGA-US-A77E-01A | Classical | Classical | Progenitor | Pancreatic Progenitor | Classical | TRUE | Classical | 0.002 |
| TCGA-Q3-A5QY-01A | QM-PDA | QM-PDA | ADEX | Squamous | Basal-like | FALSE | Basal-like | 0.557 |
| TCGA-IB-A5ST-01A | QM-PDA | QM-PDA | ADEX | Squamous | Classical | TRUE | Classical | 0.096 |
| TCGA-IB-A5SO-01A | Classical | Classical | Immunogenic | Immunogenic | Classical | TRUE | Classical | 0.005 |
| TCGA-IB-A5SS-01A | QM-PDA | QM-PDA | ADEX | Squamous | Basal-like | TRUE | Basal-like | 0.902 |
| TCGA-IB-A6UF-01A | Exocrine-like | Exocrine-like | ADEX | Squamous | Basal-like | TRUE | Basal-like | 0.991 |
| TCGA-HV-A7OL-01A | Classical | Classical | Progenitor | Pancreatic Progenitor | Classical | TRUE | Classical | 0.002 |
| TCGA-IB-A6UG-01A | Exocrine-like | Exocrine-like | Squamous | ADEX | Basal-like | TRUE | Basal-like | 0.557 |
| TCGA-HZ-A77P-01A | Exocrine-like | Exocrine-like | Squamous | ADEX | Classical | TRUE | Classical | 0.002 |
| TCGA-HZ-A77O-01A | Exocrine-like | Exocrine-like | Squamous | ADEX | Basal-like | FALSE | Basal-like | 0.548 |
| TCGA-LB-A7SX-01A | Classical | Classical | Immunogenic | Immunogenic | Basal-like | TRUE | Classical | 0.388 |
| TCGA-RB-A7B8-01A | Classical | Classical | Progenitor | Pancreatic Progenitor | Classical | TRUE | Classical | 0.001 |
| TCGA-US-A776-01A | Classical | Classical | Progenitor | Pancreatic Progenitor | Classical | TRUE | Classical | 0.005 |
| TCGA-HZ-A8P0-01A | Exocrine-like | Exocrine-like | Immunogenic | Immunogenic | Classical | TRUE | Classical | 0.004 |
| TCGA-IB-A7LX-01A | QM-PDA | QM-PDA | ADEX | Squamous | Basal-like | TRUE | Basal-like | 0.991 |
| TCGA-HZ-A77Q-01A | QM-PDA | QM-PDA | ADEX | Squamous | Classical | TRUE | Classical | 0.051 |
| TCGA-IB-A7M4-01A | QM-PDA | QM-PDA | ADEX | Squamous | Classical | FALSE | Basal-like | 0.860 |
| TCGA-XN-A8T5-01A | QM-PDA | QM-PDA | ADEX | Squamous | Basal-like | FALSE | Classical | 0.055 |
| TCGA-LB-A8F3-01A | Exocrine-like | Exocrine-like | Squamous | ADEX | Classical | TRUE | Classical | 0.024 |
| TCGA-YB-A89D-01A | Classical | Classical | Progenitor | Pancreatic Progenitor | Classical | TRUE | Classical | 0.002 |
| TCGA-YY-A8LH-01A | Classical | Classical | Progenitor | Pancreatic Progenitor | Classical | TRUE | Classical | 0.001 |

TABLE 16-continued

| TCGA_PAAD | | | | | | | | |
|---|---|---|---|---|---|---|---|---|
| ID | Collisson_original | Collisson | Bailey_original | Bailey | Moffitt | PurIST.training | PurIST | PurIST.basal.prob |
| TCGA-S4-A8RP-01A | Exocrine-like | Exocrine-like | Progenitor | Pancreatic Progenitor | Classical | TRUE | Classical | 0.001 |
| TCGA-XN-A8T3-01A | Exocrine-like | Exocrine-like | Squamous | ADEX | Basal-like | TRUE | Basal-like | 0.902 |
| TCGA-F2-A8YN-01A | Classical | Classical | Immunogenic | Immunogenic | Classical | TRUE | Classical | 0.022 |
| TCGA-S4-A8RO-01A | Classical | Classical | Immunogenic | Immunogenic | Basal-like | FALSE | Basal-like | 0.707 |
| TCGA-HZ-A8P1-01A | Classical | Classical | Progenitor | Pancreatic Progenitor | Classical | TRUE | Classical | 0.001 |
| TCGA-IB-AAUM-01A | Exocrine-like | Exocrine-like | Squamous | ADEX | Classical | TRUE | Classical | 0.001 |
| TCGA-IB-AAUP-01A | QM-PDA | QM-PDA | ADEX | Squamous | Classical | TRUE | Classical | 0.004 |
| TCGA-IB-AAUT-01A | Exocrine-like | Exocrine-like | Squamous | ADEX | Classical | TRUE | Classical | 0.002 |
| TCGA-YH-A8SY-01A | QM-PDA | QM-PDA | ADEX | Squamous | Basal-like | TRUE | Basal-like | 0.779 |
| TCGA-IB-AAUU-01A | Classical | Classical | Progenitor | Pancreatic Progenitor | Classical | TRUE | Classical | 0.001 |
| TCGA-IB-AAUS-01A | Exocrine-like | Exocrine-like | ADEX | Squamous | Classical | TRUE | Classical | 0.090 |
| TCGA-Q3-AA2A-01A | Classical | Classical | Progenitor | Pancreatic Progenitor | Classical | TRUE | Classical | 0.001 |
| TCGA-S4-A8RM-01A | Classical | Classical | Progenitor | Pancreatic Progenitor | Classical | TRUE | Classical | 0.001 |
| TCGA-2L-AAQA-01A | Classical | Classical | Progenitor | Pancreatic Progenitor | Classical | TRUE | Classical | 0.002 |
| TCGA-2L-AAQL-01A | Exocrine-like | Exocrine-like | Progenitor | Pancreatic Progenitor | Classical | TRUE | Classical | 0.001 |
| TCGA-3A-A9I5-01A | Exocrine-like | Exocrine-like | Squamous | ADEX | Basal-like | TRUE | Classical | 0.008 |
| TCGA-3A-A9I9-01A | Exocrine-like | Exocrine-like | Squamous | ADEX | Classical | TRUE | Classical | 0.003 |
| TCGA-3A-A9I7-01A | Exocrine-like | Exocrine-like | Immunogenic | Immunogenic | Classical | TRUE | Classical | 0.064 |
| TCGA-3E-AAAY-01A | Exocrine-like | Exocrine-like | Squamous | ADEX | Classical | TRUE | Classical | 0.002 |
| TCGA-3E-AAAZ-01A | Exocrine-like | Exocrine-like | Immunogenic | Immunogenic | Classical | TRUE | Classical | 0.003 |
| TCGA-F2-A7TX-01A | Exocrine-like | Exocrine-like | Squamous | ADEX | Basal-like | TRUE | Basal-like | 0.902 |
| TCGA-IB-AAUN-01A | Exocrine-like | Exocrine-like | Squamous | ADEX | Basal-like | FALSE | Basal-like | 0.786 |
| TCGA-M-AAUO-01A | QM-PDA | QM-PDA | ADEX | Squamous | Basal-like | TRUE | Basal-like | 0.899 |
| TCGA-3A-A9IC-01A | QM-PDA | QM-PDA | Immunogenic | Immunogenic | Classical | TRUE | Classical | 0.009 |
| TCGA-IB-AAUR-01A | QM-PDA | QM-PDA | ADEX | Squamous | Classical | TRUE | Classical | 0.013 |
| TCGA-FB-A545-01A | QM-PDA | QM-PDA | ADEX | Squamous | Basal-like | TRUE | Basal-like | 0.855 |

TABLE 17

| Yeh_seq | | | | | | | | | | | | |
|---|---|---|---|---|---|---|---|---|---|---|---|---|
| ID | Pathology | TissueType | Sample Type | Moffitt | PurIST | PurIST. basal. prob | SurvivalAnalysis | ClinicalType | Adj. Tx | Adj. Tx. Regimen | Neoadj. Tx | Neoadj. Tx. Regimen |
| S001.FNA.Pi.0422T1 | adeno | Primary PDAC | FNA | Basal-like | Basal-like | 0.762 | TRUE | Panc | yes | gemcitabine | no | |
| S002.FNA.Pi.0825T1 | adeno | Primary PDAC | FNA | Classical | Classical | 0.001 | TRUE | Panc Tumor | yes | gemcitabine | no | |
| S003.FNA.Pi.1119T1 | adeno | Primary PDAC | FNA | Basal-like | Basal-like | 0.991 | TRUE | | yes | (gem w compl and difficulty tol) | no | |
| S004.FNA.Pi.0517T1 | adeno | Primary PDAC | FNA | Classical | Classical | 0.002 | TRUE | | yes | gem + erlotinib | no | |
| S005.FNA.Pi.0818T1 | adeno | Primary PDAC | FNA | Classical | Classical | 0.001 | TRUE | | yes | 5FU/RT | no | |
| S006.FNA.Pi.1012T1 | adeno | Primary PDAC | FNA | Classical | Classical | 0.001 | TRUE | | LTFO | | no | |
| S007.FNA.Pi.1118T1 | adeno | Primary PDAC | FNA | Classical | Classical | 0.039 | TRUE | | yes | gem | no | |
| S008.FNA.Pi.0105T1 | adeno | Primary PDAC | FNA | Classical | Classical | 0.013 | TRUE | | yes | gem | no | |
| S009.FNA.Pi.0119T1 | adeno | Primary PDAC | FNA | Basal-like | Classical | 0.064 | TRUE | | yes | unknown systemic | no | |
| S010.FNA.Pi.0417T1 | adeno | Primary PDAC | FNA | Classical | Classical | 0.013 | TRUE | | yes | gem | no | |
| S011.FNA.Pi.0503T1 | adeno | Primary PDAC | FNA | Classical | Classical | 0.001 | TRUE | | yes | gem + 5fu/rt | no | |
| S012.FNA.Pi.0921T1 | adeno | Primary PDAC | FNA | Classical | Classical | 0.002 | TRUE | | yes | 5FU/RT | no | |
| S013.FNA.Pi.1109T1 | adeno | Primary PDAC | FNA | Classical | Classical | 0.001 | TRUE | Panc Tumor | yes | gem | no | |
| S014.FNA.Pi.1129T1 | adeno | Primary PDAC | FNA | Classical | Classical | 0.002 | TRUE | Panc Tumor | yes | gem + 5FU/RT | no | |
| S015.FNA.Pi.1206T1 | adeno | Primary PDAC | FNA | Classical | Classical | 0.003 | TRUE | Panc Tumor | yes | Folfirinox | yes | folfirinox |
| S016.FNA.Pi.1214T1 | adeno | Primary PDAC | FNA | Classical | Classical | 0.008 | TRUE | Panc Tumor | DOO | | no | |
| S017.FNA.Pi.0124T1 | adeno | Primary PDAC | FNA | Classical | Classical | 0.001 | TRUE | Panc Tumor | yes | gem + 5FU/RT | no | |

TABLE 17-continued

Yeh_seq

| ID | Pathology | TissueType | Sample Type | Moffitt | PurIST | PurIST. basal. prob | SurvivalAnalysis | ClinicalType | Adj. Tx | Adj. Tx. Regimen | Neoadj. Tx | Neoadj. Tx. Regimen |
|---|---|---|---|---|---|---|---|---|---|---|---|---|
| S018.FNA.Pi.0221T1 | adeno | Primary PDAC | FNA | Classical | Classical | 0.001 | TRUE | Panc Tumor | yes | gem | no | |
| S019.FNA.Pi.0222T1 | adeno | Primary PDAC | FNA | Classical | Classical | 0.001 | TRUE | Panc Tumor | yes | gem | no | |
| S020.FNA.Pi.0327T1 | adeno | Primary PDAC | FNA | Classical | Classical | 0.002 | TRUE | Panc Tumor | yes | gem | yes | 5FU/ RT |
| S021.FNA.Pi.0328T1 | adeno | Primary PDAC | FNA | Classical | Classical | 0.001 | TRUE | | yes | RT/gem + gem | no | |
| S022.FNA.Pi.0411T1 | adeno | Primary PDAC | FNA | Classical | Classical | 0.001 | TRUE | | yes | gem | yes | 5FU/ RT |
| S023.FNA.Pi.0417T1 | adeno | Primary PDAC | FNA | Classical | Classical | 0.001 | TRUE | | yes | gem + 5FU/RT | no | |
| S024.FNA.Pi.0425T1 | adeno | Primary PDAC | FNA | Classical | Classical | 0.003 | TRUE | Panc Tumor | yes | gem + 5FU/RT | no | |
| S025.FNA.Pi.0502T2 | adeno | Primary PDAC | FNA | Classical | Classical | 0.001 | TRUE | | yes | gem + 5FU/RT | no | |
| S026.FNA.Pi.0508T1 | adeno | Primary PDAC | FNA | Classical | Classical | 0.040 | TRUE | | yes | gem + 5FU/RT | no | |
| S027.FNA.Pi.0523T1 | adeno | Primary PDAC | FNA | Classical | Classical | 0.002 | TRUE | Panc Tumor | no | | no | |
| S028.FNA.Pi.0524T1 | ampullary | Primary PDAC | FNA | Classical | Classical | 0.001 | FALSE | | | gem + 5FU | | |
| S029.FNA.Pi.0605T1 | adeno | Primary PDAC | FNA | Classical | Classical | 0.001 | TRUE | | yes | gem | no | |
| S030.FNA.Pi.0607T1 | adeno | Primary PDAC | FNA | Classical | Classical | 0.002 | TRUE | | yes | 5FU/RT | no | |
| S031.FNA.Pi.0614T1 | adeno | Primary PDAC | FNA | Classical | Classical | 0.008 | TRUE | | yes | gem + 5FU/RT | no | |
| S032.FNA.Pi.0710T2 | adeno | Primary PDAC | FNA | Classical | Classical | 0.001 | FALSE | Panc Normal, IPMN patient | yes | gem + 5fu/RT | no | |
| S033.FNA.Pi.0711T1 | adeno | Primary PDAC | FNA | Classical | Classical | 0.013 | TRUE | | LTFO | | no | |
| S034.FNA.Pi.0904T1 | adeno | Primary PDAC | FNA | Classical | Classical | 0.001 | TRUE | | yes | gem + RT/5FU | no | |
| S035.FNA.Pi.1009T1 | adeno | Primary PDAC | FNA | Classical | Classical | 0.001 | TRUE | | no | | yes | 5FU/ RT |
| S036.FNA.Pi.1119T1 | adeno | Primary PDAC | FNA | Basal-like | Classical | 0.165 | TRUE | | yes | Folfirinox | no | |
| S037.FNA.Pi.1204T1 | adeno | Primary PDAC | FNA | Classical | Classical | 0.001 | TRUE | | yes | gem | no | |
| S038.FNA.Pi.1205T1 | adeno | Primary PDAC | FNA | Classical | Classical | 0.090 | TRUE | | yes | gem + 5FU/RT | yes | gem |
| S039.FNA.Pi.0129T1 | adeno | Primary PDAC | FNA | Classical | Classical | 0.024 | TRUE | | yes | gem + RT | no | |
| S040.FNA.Pi.0417T1 | adeno | Primary PDAC | FNA | Classical | Classical | 0.008 | TRUE | | yes | Gem + 5FU/RT | no | |
| S041.FNA.Pi.0424T1 | adeno | Primary PDAC | FNA | Basal-like | Classical | 0.002 | TRUE | | yes | gem + 5FU/RT | no | |
| S042.FNA.Pi.0806T1 | adeno | Primary PDAC | FNA | Classical | Classical | 0.001 | TRUE | | yes | gem + 5FU/RT | no | |
| S043.FNA.Pi.0121T1 | adeno | Primary PDAC | FNA | Classical | Classical | 0.001 | TRUE | | yes | gem + 5FU/RT | no | |
| S044.FNA.Pi.0608T1 | adeno | Primary PDAC | FNA | Classical | Classical | 0.001 | TRUE | | yes | gem + 5fu/rt | no | |
| S045.FNA.Pi.1207T1 | adeno | Primary PDAC | FNA | Classical | Classical | 0.002 | TRUE | | yes | gem + 5FU/RT | no | |
| S046.FNA.PDX.0616T1 | adeno | PDX | FNA | Classical | Classical | 0.001 | FALSE | | | | | |
| S047.FNA.PDX.0508T1 | adeno | PDX | FNA | Classical | Classical | 0.013 | FALSE | | | | | |
| S048.FNA.PDX.0902T1B | | PDX | FNA | Classical | Classical | 0.001 | FALSE | | | | | |
| S049.FFPE.PDX.1222T1 | adeno | PDX | FFPE | Classical | Classical | 0.001 | FALSE | | | | | |
| S050.FFPE.PDX.0113T1 | | PDX | FFPE | Basal-like | Classical | 0.223 | FALSE | | | | | |
| S051.FFPE.PDX.1108T1 | adeno | PDX | FFPE | Classical | Classical | 0.005 | FALSE | | | | | |
| S052.FFPE.PDX.1109T1 | adeno | PDX | FFPE | Classical | Classical | 0.002 | FALSE | | | | | |

TABLE 17-continued

| Yeh_seq | | | | | | | | | | | | | |
|---|---|---|---|---|---|---|---|---|---|---|---|---|---|
| ID | Pathology | TissueType | Sample Type | Moffitt | PurIST | PurIST. basal. prob | SurvivalAnalysis | ClinicalType | Adj. Tx | Adj. Tx. Regimen | Neoadj. Tx | Neoadj. Tx. Regimen |
| S053.FFPE.PDX.1109T1 | adeno | PDX | FFPE | Classical | Classical | 0.001 | FALSE | | | | | |
| S054.FFPE.PDX.0417T1 | adeno | PDX | FFPE | Classical | Classical | 0.003 | FALSE | | | | | |
| S055.FFPE.PDX.0910T1 | adeno | PDX | FFPE | Classical | Classical | 0.001 | FALSE | | | | | |
| S056.FF.PDX.1222T1 | adeno | PDX | FF | Classical | Classical | 0.003 | FALSE | | | | | |
| S057.FF.PDX.0113T1 | | PDX | FF | Classical | Classical | 0.021 | FALSE | | | | | |
| S058.FF.PDX.1108T1 | adeno | PDX | FF | Classical | Classical | 0.014 | FALSE | | | | | |
| S059.FF.PDX.1108T1 | adeno | PDX | FF | Classical | Classical | 0.014 | FALSE | | | | | |
| S060.FF.PDX.0411T1 | adeno | PDX | FF | Classical | Classical | 0.001 | FALSE | | | | | |
| S061.FF.PDX.0523T1 | adeno | PDX | FF | Basal-like | Classical | 0.093 | FALSE | | | | | |
| S062.FF.PDX.0319T1 | | PDX | FF | Classical | Classical | 0.005 | FALSE | | | | | |
| S063.FF.PDX.0119T1 | | PDX | FF | Classical | Classical | 0.001 | FALSE | | | | | |
| S064.FF.PDX.0218T2 | | PDX | FF | Classical | Classical | 0.001 | FALSE | | | | | |
| S065.FF.PDX.0225T1 | adenosquamous | PDX | FF | Basal-like | Basal-like | 0.991 | FALSE | | | | | |
| S066.FF.PDX.0616T1 | adeno | PDX | FF | Classical | Classical | 0.001 | FALSE | | | | | |
| S067.FF.PDX.1109T1 | adeno | PDX | FF | Classical | Classical | 0.001 | FALSE | | | | | |
| S068.FF.PDX.0806T1 | adeno | PDX | FF | Classical | Classical | 0.003 | FALSE | | | | | |
| S069.FF.PDX.0508T1 | adeno | PDX | FF | Classical | Classical | 0.013 | FALSE | | | | | |
| S070.FF.PDX.0902T1B | | PDX | FF | Classical | Classical | 0.001 | FALSE | | | | | |
| S071.FF.PDX.1112T1 | | PDX | FF | Classical | Classical | 0.001 | FALSE | | | | | |
| S072.FF.PDX.1125T2 | | PDX | FF | Basal-like | Basal-like | 0.902 | FALSE | | | | | |
| S073.FF.PDX.PancT6 | | PDX | FF | Basal-like | Basal-like | 0.991 | FALSE | | | | | |
| S074.FFPE.Pi.0517T1 | adeno | Primary PDAC | FFPE | Classical | Classical | 0.024 | FALSE | | | | | |
| S075.FFPE.Pi.0503T1 | adeno | Primary PDAC | FFPE | Classical | Classical | 0.038 | FALSE | | | | | |
| S076.FFPE.Pi.0417T1 | adeno | Primary PDAC | FFPE | Classical | Classical | 0.001 | FALSE | | | | | |
| S077.FFPE.Pi.0523T1 | adeno | Primary PDAC | FFPE | Classical | Classical | 0.002 | FALSE | | | | | |
| S078.FFPE.Pi.0806T1 | adeno | Primary PDAC | FFPE | Classical | Classical | 0.013 | FALSE | | | | | |
| S079.FF.Pi.0422T1 | adeno | Primary PDAC | FF | Basal-like | Basal-like | 0.991 | FALSE | | | | | |
| S080.FF.Pi.0825T1 | adeno | Primary PDAC | FF | Classical | Classical | 0.003 | FALSE | | | | | |
| S081.FF.Pi.1119T1 | adeno | Primary PDAC | FF | Basal-like | Basal-like | 0.991 | FALSE | | | | | |
| S082.FF.Pi.0517T1 | adeno | Primary PDAC | FF | Classical | Classical | 0.002 | FALSE | | | | | |
| S083.FF.Pi.0818T1 | adeno | Primary PDAC | FF | Classical | Classical | 0.001 | FALSE | | | | | |
| S084.FF.Pi.1012T1 | adeno | Primary PDAC | FF | Classical | Classical | 0.002 | FALSE | | | | | |
| S085.FF.Pi.1118T1 | adeno | Primary PDAC | FF | Classical | Classical | 0.093 | FALSE | | | | | |
| S086.FF.Pi.0105T1 | adeno | Primary PDAC | FF | Classical | Classical | 0.002 | FALSE | | | | | |
| S087.FF.Pi.0119T1 | adeno | Primary PDAC | FF | Classical | Classical | 0.001 | FALSE | | | | | |
| S088.FF.Pi.0417T1 | adeno | Primary PDAC | FF | Classical | Classical | 0.001 | FALSE | | | | | |

TABLE 17-continued

| Yeh_seq | | | | | | | | | | | | | |
|---|---|---|---|---|---|---|---|---|---|---|---|---|---|
| ID | Pathology | TissueType | Sample Type | Moffitt | PurIST | PurIST. basal. prob | SurvivalAnalysis | ClinicalType | Adj. Tx | Adj. Tx. Regimen | Neoadj. Tx | Neoadj. Tx. Regimen |
| S089.FF.Pi.0503T1 | adeno | Primary PDAC | FF | Classical | Classical | 0.004 | FALSE | | | | | |
| S090.FF.Pi.1109T1 | adeno | Primary PDAC | FF | Classical | Classical | 0.014 | FALSE | | | | | |
| S091.FF.Pi.1129T1 | adeno | Primary PDAC | FF | Classical | Classical | 0.002 | FALSE | | | | | |
| S092.FF.Pi.1206T1 | adeno | Primary PDAC | FF | Classical | Classical | 0.001 | FALSE | | | | | |
| S093.FF.Pi.1214T1 | adeno | Primary PDAC | FF | Classical | Classical | 0.001 | FALSE | | | | | |
| S094.FF.Pi.0124T1 | adeno | Primary PDAC | FF | Classical | Classical | 0.001 | FALSE | | | | | |
| S095.FF.Pi.0221T1 | adeno | Primary PDAC | FF | Classical | Classical | 0.003 | FALSE | | | | | |
| S096.FF.Pi.0222T1 | adeno | Primary PDAC | FF | Classical | Classical | 0.001 | FALSE | | | | | |
| S097.FF.Pi.0327T1 | adeno | Primary PDAC | FF | Classical | Classical | 0.004 | FALSE | | | | | |
| S098.FF.Pi.0328T1 | adeno | Primary PDAC | FF | Classical | Classical | 0.001 | FALSE | | | | | |
| S099.FF.Pi.0411T1 | adeno | Primary PDAC | FF | Classical | Classical | 0.001 | FALSE | | | | | |
| S100.FF.Pi.0417T1 | adeno | Primary PDAC | FF | Classical | Classical | 0.001 | FALSE | | | | | |
| S101.FF.Pi.0425T1 | adeno | Primary PDAC | FF | Classical | Classical | 0.002 | FALSE | | | | | |
| S102.FF.Pi.0502T2 | adeno | Primary PDAC | FF | Classical | Classical | 0.003 | FALSE | | | | | |
| S103.FF.Pi.0508T1 | adeno | Primary PDAC | FF | Classical | Basal-like | 0.557 | FALSE | | | | | |
| S104.FF.Pi.0523T1 | adeno | Primary PDAC | FF | Classical | Classical | 0.002 | FALSE | | | | | |
| S105.FF.Pi.0523T1 | adeno | Primary PDAC | FF | Classical | Classical | 0.002 | FALSE | | | | | |
| S106.FF.Pi.0524T1 | ampullary | Primary PDAC | FF | Classical | Classical | 0.001 | FALSE | | | | | |
| S107.FF.Pi.0605T1 | adeno | Primary PDAC | FF | Classical | Classical | 0.001 | FALSE | | | | | |
| S108.FF.Pi.0607T1 | adeno | Primary PDAC | FF | Classical | Classical | 0.002 | FALSE | | | | | |
| S109.FF.Pi.0614T1 | adeno | Primary PDAC | FF | Classical | Classical | 0.008 | FALSE | | | | | |
| S110.FF.Pi.0710T2 | adeno | Primary PDAC | FF | Classical | Classical | 0.005 | FALSE | | | | | |
| S111.FF.Pi.0711T1 | adeno | Primary PDAC | FF | Classical | Basal-like | 0.860 | FALSE | | | | | |
| S112.FF.Pi.0904T1 | adeno | Primary PDAC | FF | Classical | Classical | 0.034 | FALSE | | | | | |
| S113.FF.Pi.1009T1 | adeno | Primary PDAC | FF | Classical | Classical | 0.033 | FALSE | | | | | |
| S114.FF.Pi.1119T1 | adeno | Primary PDAC | FF | Classical | Classical | 0.021 | FALSE | | | | | |
| S115.FF.Pi.1204T1 | adeno | Primary PDAC | FF | Classical | Classical | 0.001 | FALSE | | | | | |
| S116.FF.Pi.1205T1 | adeno | Primary PDAC | FF | Classical | Classical | 0.013 | FALSE | | | | | |
| S117.FF.Pi.0129T1 | adeno | Primary PDAC | FF | Classical | Classical | 0.002 | FALSE | | | | | |
| S118.FF.Pi.0417T1 | adeno | Primary PDAC | FF | Classical | Classical | 0.013 | FALSE | | | | | |
| S119.FF.Pi.0424T1 | adeno | Primary PDAC | FF | Classical | Classical | 0.001 | FALSE | | | | | |
| S120.FF.Pi.0806T1 | adeno | Primary PDAC | FF | Classical | Classical | 0.005 | FALSE | | | | | |
| S121.FF.Pi.0806T1 | adeno | Primary PDAC | FF | Classical | Classical | 0.001 | FALSE | | | | | |
| S122.FF.Pi.0121T1 | adeno | Primary PDAC | FF | Classical | Classical | 0.002 | FALSE | | | | | |
| S123.FF.Pi.0608T1 | adeno | Primary PDAC | FF | Classical | Classical | 0.005 | FALSE | | | | | |

TABLE 17-continued

| Yeh_seq | | | | | | | | | | | | |
|---|---|---|---|---|---|---|---|---|---|---|---|---|
| ID | Pathology | TissueType | Sample Type | Moffitt | PurIST | PurIST. basal. prob | SurvivalAnalysis | ClinicalType | Adj. Tx | Adj. Tx. Regimen | Neoadj. Tx | Neoadj. Tx. Regimen |
| S124.FF.Pi.1207T1 | adeno | Primary PDAC | FF | Classical | Basal-like | 0.671 | FALSE | | | | | |
| S125.FF.Pi.PancT6 | | Primary PDAC | FF | Basal-like | Basal-like | 0.991 | FALSE | | | | | |

TABLE 18

| Collisson | | | | | | | | | |
|---|---|---|---|---|---|---|---|---|---|
| Dataset | Treatment | # of samples | Collisson | PD (>=20%) | SD (>−30%) & <20%) | PR (<=−30%) | Cochran-Mantel-Haenszel test stratified by treatment | Two-Way ANOVA Model BIC (smaller is better) | Ordinal Regression Model BIC (smaller is better) |
| COMPASS | FFX | 34 | Classical | 0 | 12 | 6 | 0.0024 | 382.8 | 75.77 |
| | | | Exocrine-like | 0 | 3 | 2 | | | |
| | | | QM-PDA | 5 | 5 | 1 | | | |
| | GP | 6 | Classical | 0 | 2 | 1 | | | |
| | | | Exocrine-like | 0 | 0 | 2 | | | |
| | | | QM-PDA | 0 | 1 | 0 | | | |
| Linehan | FOLFIRINOX + PF-04136309 | 24 | Classical | 0 | 4 | 4 | 0.4278 | 254.63 | 61.57 |
| | | | Exocrine-like | 0 | 5 | 3 | | | |
| | | | QM-PDA | 1 | 4 | 3 | | | |
| | FOLFIRINOX | 4 | Classical | 0 | 3 | 0 | | | |
| | | | Exocrine-like | 0 | 0 | 0 | | | |
| | | | QM-PDA | 1 | 0 | 0 | | | |

TABLE 19

| Bailey | | | | | | | | | |
|---|---|---|---|---|---|---|---|---|---|
| Dataset | Treatment | # of samples | Bailey | PD (>=20%) | SD (>−30%) & <20%) | PR (<=−30%) | Cochran-Mantel-Haenszel test stratified by treatment | Two-Way ANOVA Model BIC (smaller is better) | Ordinal Regression Model BIC (smaller is better) |
| COMPASS | FFX | 34 | Squamous | 5 | 3 | 1 | 0.0067 | 385.66 | 78.68 |
| | | | Immunogenic | 0 | 5 | 5 | | | |
| | | | Pancreatic Progenitor | 0 | 6 | 2 | | | |
| | | | ADEX | 0 | 6 | 1 | | | |
| | GP | 6 | Squamous | 0 | 1 | 0 | | | |
| | | | Immunogenic | 0 | 2 | 2 | | | |
| | | | Pancreatic Progenitor | 0 | 0 | 0 | | | |
| | | | ADEX | 0 | 0 | 1 | | | |
| Linehan | FOLFIRINOX + PF-04136309 | 24 | Squamous | 1 | 2 | 1 | 0.1126 | 250.75 | 60.64 |
| | | | Immunogenic | 0 | 3 | 5 | | | |
| | | | Pancreatic Progenitor | 0 | 6 | 2 | | | |
| | | | ADEX | 0 | 2 | 2 | | | |
| | FOLFIRINOX | 4 | Squamous | 1 | 0 | 0 | | | |
| | | | Immunogenic | 0 | 3 | 0 | | | |
| | | | Pancreatic Progenitor | 0 | 0 | 0 | | | |
| | | | ADEX | 0 | 0 | 0 | | | |

TABLE 20

| Moffitt | | | | | | | | | |
|---|---|---|---|---|---|---|---|---|---|
| Dataset | Treatment | # of samples | Moffitt | PD (>=20%) | SD (>−30%) & <20%) | PR (<=−30%) | Cochran-Mantel-Haenszel test stratified by treatment | Two-Way ANOVA Model BIC (smaller is better) | Ordinal Regression Model BIC (smaller is better) |
| COMPASS | FFX | 34 | Basal-like | 5 | 3 | 1 | 0.00098 | 378.75 | 73.07 |
| | | | Classical | 0 | 17 | 8 | | | |
| | GP | 6 | Basal-like | 0 | 1 | 0 | | | |
| | | | Classical | 0 | 2 | 3 | | | |
| Linehan | FOLFIRINOX + PF-04136309 | 24 | Basal-like | 1 | 1 | 0 | 0.01183 | 247.37 | 47.47 |
| | | | Classical | 0 | 12 | 10 | | | |
| | FOLFIRINOX | 4 | Basal-like | 1 | 0 | 0 | | | |
| | | | Classical | 0 | 3 | 0 | | | |

TABLE 21

| SSC | | | | | | | |
|---|---|---|---|---|---|---|---|
| Dataset | Treatment | # of samples | PurIST | PD (>=20%) | SD (>−30% & <20%) | PR (<=−30%) | Cochran-Mantel-Haenszel test stratified by treatment |
| COMPASS | FFX | 34 | Basal-like | 5 | 4 | 1 | 1.20E−03 |
| | | | Classical | 0 | 16 | 8 | |
| | GP | 6 | Basal-like | 0 | 1 | 0 | |
| | | | Classical | 0 | 2 | 3 | |
| Linehan | FOLFIRINOX + PF-04136309 | 24 | Basal-like | 1 | 1 | 0 | 0.0118 |
| | | | Classical | 0 | 12 | 10 | |
| | FOLFIRINOX | 4 | Basal-like | 1 | 0 | 0 | |
| | | | Classical | 0 | 3 | 0 | |

TABLE 22

Summary of Subtype Calls by Schema

| | | | Median Follow-up time (m) | | Overall Survival (m) | | Subtypes | | | | | | | |
|---|---|---|---|---|---|---|---|---|---|---|---|---|---|---|
| Dataset | # Analyzed | # Events | All patients | Censored patients | Median | 95% CI | | Subtype | # of samples | % of samples | Log-rank | HR | HR 95% CI | BIC |
| Linehan_Seq (FOLFIRINOX + PF-04136309) | 28 | 7 | 16.5 | 18 | NA | [25, NA] | Collisson | Classical | 10 | 35.7% | 0.67 | | | 44.503 |
| | | | | | | | | Exocrine-like | 9 | 32.1% | | | | |
| | | | | | | | | QM-PDA | 9 | 32.1% | | | | |
| | | | | | | | Bailey | ADEX | 5 | 17.9% | 0.35 | | | 44.321 |
| | | | | | | | | Immimogenic | 9 | 32.1% | | | | |
| | | | | | | | | Pancreatic Progenitor | 9 | 32.1% | | | | |
| | | | | | | | | Squamous | 5 | 17.9% | | | | |
| | | | | | | | Moffitt | Basal-like | 2 | 7.1% | 0.05 | 6.937 | [0.707, 68.027] | 41.442 |
| | | | | | | | | Classical | 26 | 92.9% | | | | |
| | | | | | | | SSC | Basal-like | 2 | 7.1% | 0.05 | 6.937 | [0.707, 68.027] | 41.442 |
| | | | | | | | | Classical | 26 | 92.9% | | | | |
| Moffitt_GEO_array | 125 | 84 | 13 | 18 | 17 | [13, 20] | Collisson | Classical | 43 | 34.4% | 0.79 | | | 683.915 |
| | | | | | | | | Exocrine-like | 48 | 38.4% | | | | |
| | | | | | | | | QM-PDA | 34 | 27.2% | | | | |
| | | | | | | | Bailey | ADEX | 27 | 21.6% | <0.0001 | | | 677.403 |
| | | | | | | | | Immunogenic | 3 | 2.4% | | | | |

TABLE 22-continued

Summary of Subtype Calls by Schema

| Dataset | # Analyzed | # Events | Median Follow-up time (m) All patients | Median Follow-up time (m) Censored patients | Overall Survival (m) Median | Overall Survival (m) 95% CI | Subtypes Subtype | | Subtypes # of samples | Subtypes % of samples | Subtypes Log-rank | Subtypes HR | Subtypes HR 95% CI | Subtypes BIC |
|---|---|---|---|---|---|---|---|---|---|---|---|---|---|---|
| | | | | | | | | Pancreatic Progenitor | 47 | 37.6% | | | | |
| | | | | | | | | Squamous | 48 | 38.4% % | | | | |
| | | | | | | | Moffitt | Basal-like | 24 | 19.2% | 0.034 | 1.737 | [1.038, 2.906] | 675.985 |
| | | | | | | | | Classical | 101 | 80.8% | | | | |
| | | | | | | | SSC | Basal-like | 20 | 16.0% | 0.14 | 1.502 | [0.870, 2.595] | 678.021 |
| | | | | | | | | Classical | 105 | 84.0% | | | | |
| PACA_AU_array | 71 | 43 | 14 | 21.5 | 16.6 | [13.7, 30.0] | Collisson | Classical | 27 | 38.0% | 0.019 | | | 305.231 |
| | | | | | | | | Exocrine-like | 18 | 25.4% | | | | |
| | | | | | | | | QM-PDA | 26 | 36.6% | | | | |
| | | | | | | | Bailey | ADEX | 12 | 16.9% | 0.12 | | | 311.789 |
| | | | | | | | | Immunogenic | 19 | 26.8% | | | | |
| | | | | | | | | Pancreatic Progenitor | 17 | 23.9% | | | | |
| | | | | | | | | Squamous | 23 | 32.4% | | | | |
| | | | | | | | Moffitt | Basal-like | 13 | 18.3% | 0.009 | 2.516 | [1.228, 5.155] | 304.408 |
| | | | | | | | | Classical | 58 | 81.7% | | | | |
| | | | | | | | SSC | Basal-like | 12 | 16.9% | 0.038 | 2.218 | [1.022, 4.815] | 306.343 |
| | | | | | | | | Classical | 59 | 83.1% | | | | |
| PACA_AU_seq | 57 | 33 | 13.2 | 17.5 | 15 | [13.2, NA] | Collisson | Classical | 24 | 42.1% | 0.006 | | | 211.127 |
| | | | | | | | | Exocrine-like | 11 | 19.3% | | | | |
| | | | | | | | | QM-PDA | 22 | 38.6% | | | | |
| | | | | | | | Bailey | ADEX | 7 | 12.3% | 0.47 | | | 222.647 |
| | | | | | | | | Immunogenic | 16 | 28.1% | | | | |
| | | | | | | | | Pancreatic Progenitor | 14 | 24.6% | | | | |
| | | | | | | | | Squamous | 20 | 35.1% | | | | |
| | | | | | | | Moffitt | Basal-like | 11 | 19.3% | 0.014 | 2.835 | [1.188, 6.766] | 213.574 |
| | | | | | | | | Classical | 46 | 80.7% | | | | |
| | | | | | | | SSC | Basal-like | 14 | 24.6% | 0.072 | 2.016 | [0.921, 4.417] | 215.414 |
| | | | | | | | | Classical | 43 | 75.4% | | | | |
| TCGA_PAAD | 146 | 75 | 14.2 | 15.1 | 20.2 | [16.6, 23.4] | Collisson | Classical | 52 | 35.6% | 0.41 | | | 623.054 |
| | | | | | | | | Exocrine-like | 61 | 41.8% | | | | |
| | | | | | | | | QM-PDA | 33 | 22.6% | | | | |
| | | | | | | | Bailey | ADEX | 38 | 26.0% | 0.54 | | | 626.808 |
| | | | | | | | | Immunogenic | 26 | 17.8% | | | | |
| | | | | | | | | Pancreatic Progenitor | 51 | 34.9% | | | | |
| | | | | | | | | Squamous | 31 | 21.2% | | | | |
| | | | | | | | Moffitt | Basal-like | 37 | 25.3% | 0.0064 | 1.941 | [1.194, 3.156] | 613.865 |
| | | | | | | | | Classical | 109 | 74.7% | | | | |
| | | | | | | | SSC | Basal-like | 33 | 22.6% | 0.0031 | 2.113 | [1.271, 3.512] | 612.969 |
| | | | | | | | | Classical | 113 | 77.4% | | | | |
| Pooled public datasets of primary samples | 376 | 214 | 14.1 | 17 | 19 | [16.6, 22.0] | Collisson | Classical | 134 | 35.6% | 0.0692 | | | 1654.238 |
| | | | | | | | | Exocrine-like | 137 | 36.4% | | | | |
| | | | | | | | | QM-PDA | 105 | 27.9% | | | | |
| | | | | | | | Bailey | ADEX | 83 | 22.1% | 0.0768 | | | 1658.276 |
| | | | | | | | | Immunogenic | 58 | 15.4% | | | | |
| | | | | | | | | Pancreatic Progenitor | 127 | 33.8% | | | | |
| | | | | | | | | Squamous | 108 | 28.7% | | | | |
| | | | | | | | Moffitt | Basal-like | 77 | 20.5% | 1.43E−05 | 1.982 | [1.447, 2.715] | 1637.78 |
| | | | | | | | | Classical | 299 | 79.5% | | | | |
| | | | | | | | SSC | Basal-like | 68 | 18.1% | 0.0001 | 1.896 | [1.361, 2.640] | 1641.295 |
| | | | | | | | | Classical | 308 | 81.9% | | | | |
| | 124 | 63 | 15 | 17.5 | 23.3 | [16.6, 35.8] | SSC excluding | Basal-like | 21 | 16.9% | 0.0107 | 2.436 | [1.2086, 4.9116] | 384.622 |
| | | | | | | | | Classical | 103 | 83.1% | | | | |

TABLE 22-continued

Summary of Subtype Calls by Schema

| Dataset | # Analyzed | # Events | Median Follow-up time (m): All patients | Median Follow-up time (m): Censored patients | Overall Survival (m): Median | Overall Survival (m): 95% CI | | Subtypes: Subtype | Subtypes: # of samples | Subtypes: % of samples | Subtypes: Log-rank | Subtypes: HR | Subtypes: HR 95% CI | Subtypes: BIC |
|---|---|---|---|---|---|---|---|---|---|---|---|---|---|---|
| | | | | | | | training samples) | | | | | | | |
| Aguirre_seq | 48 | 35 | 10 | 15 | 11.5 | [9.73, 19.80] | SSC | Basal-like | 15 | 31.3% | 0.14 | 1.688 | [0.835, 3.407] | 219.125 |
| | | | | | | | | Classical | 33 | 68.8% | | | | |
| Yeh_seq_FNA | 42 | 30 | 12.9 | 24.4 | 17.1 | [10.2, 24.6] | SSC | Basal-like | 2 | 4.8% | 0.017 | 5.289 | [1.151, 24.31] | 178.179 |
| | | | | | | | | Classical | 40 | 95.2% | | | | |

TABLE 23

Collisson Transition Rates

| | | Post-treatment: Classical | Post-treatment: Exocrine | Post-treatment: QM |
|---|---|---|---|---|
| Pre-treatment | QM | 0.22 | 0 | 0.78 |
| | Exocrine | 0.5 | 0.5 | 0 |
| | Classical | 0.45 | 0.27 | 0.27 |

TABLE 24

Bailey Transition Rates

| | | Post-treatment: Squamous | Post-treatment: PP | Post-treatment: Immuno. | Post-treatment: ADEX |
|---|---|---|---|---|---|
| Pre-treatment | Squamous | 0 | 0.2 | 0 | 0.8 |
| | PP | 0.25 | 0.38 | 0.25 | 0.12 |
| | Immuno. | 0 | 0.64 | 0.18 | 0.18 |
| | ADEX | 0.5 | 0.25 | 0.25 | 0 |

TABLE 25

PurIST Coefficients

| Gene A | Gene B | Intercept: −6.815 Coefficient |
|---|---|---|
| GPR87 | REG4 | 1.994 |
| KRT6A | ANXA10 | 2.031 |
| BCAR3 | GATA6 | 1.618 |
| PTGES | CLDN18 | 0.922 |
| ITGA3 | LGALS4 | 1.059 |

TABLE 25-continued

PurIST Coefficients

| Gene A | Gene B | Intercept: −6.815 Coefficient |
|---|---|---|
| C16orf74 | DDC | 0.929 |
| S100A2 | SLC40A1 | 2.505 |
| KRT5 | CLRN3 | 0.485 |

TABLE 26

PurIST-n Coefficients

| Gene A | Gene B | Intercept: −12.414 Coefficients |
|---|---|---|
| GPR87 | REG4 | 3.413 |
| KRT6A | ANXA10 | 3.437 |
| KRT17 | LGALS4 | 2.078 |
| S100A2 | TFF1 | 2.651 |
| C16orf74 | DDC | 0.901 |
| KRT15 | PLA2G10 | 2.677 |
| PTGES | CDH17 | 2.911 |
| DCBLD2 | TSPAN8 | 1.903 |
| PIP5K1B | MUC17 | 0.036 |
| NR1I2 | MYO1A | −0.638 |
| CTSE | LYZ | 0.977 |

TABLE 27

Validation Dataset Individual Study Areas Under the Curves

| Dataset | N | Basal-like | Accuracy | Sensitivity | Specificity | AUC |
|---|---|---|---|---|---|---|
| PACA_AU_seq | 65 | 12 | 0.892 | 0.833 | 0.906 | 0.965 |
| PACA_AU_array | 95 | 14 | 0.958 | 0.929 | 0.963 | 0.973 |
| Moffitt | 37 | 56 | 0.973 | 11 | 0.969 | 11 |
| Linehan_Seq | 66 | 11 | 1 | 0.545 | 1 | 0.984 |
| Connor | 66 | 13 | 0.909 | 1 | 0.982 | 1 |
| COMPASS | 49 | 12 | 0.98 | 0.833 | 0.972 | 0.965 |

TABLE 28

Exemplary PKIs and Their Targets

| Gene Name | Aliases | Compounds | Overexpressed in Subtype |
|---|---|---|---|
| AAK1 | KIAA1048, DKF2p686K16132 | GSK3236425A; LP-935509; UNC-AA-1-0013 (SGC-AAK1-1); UNC-AA-1-0017 | Basal-like |
| ABL1 | JTK7, c-ABL, p150 | asciminib; canertinib, CI-1033; erlotinib, OSI-744; GNF-5; imatinib; LDN-214117; masitinib AB1010; XMD-17-51 | Basal-like |
| CDK1 | CDC28A, CDC2, P34CDC2 | GW276655; GW300657X; GW300660X; GW416981X | Basal-like |
| CDK16 | PCTAIRE, PCTAIRE1, PCTGAIRE, FLJ16665, PCTK1 | CAF-204; SNS-032 | Basal-like |
| CDK17 | PCTAIRE2, PCTK2 | YL-206; SNS-032 | Basal-like |
| CDK4 | CMM3; PSK-J3 | abetnaciclib; LY2857785; palbociclib; ribociclib; PFE-PKIS 32; PFE-PKIS 44; SIHR CDK4/6 compound 83; SIHR CDK4/6 compound 91 | Basal-like |
| CDK7 | CAK1, CDKN7, MO15, STK1, CAK, HCAK, p39MO15 | BMS-387032/SNS-032; BS-181; THZ1 | Basal-like |
| CSNK2A2 | CSNK2A1, CK2α, CK2A2, CK2a2, CK2α2 | G59973, entospletinib; GO289; CX-4945, silmasertib; AZ-G | Basal-like |
| DDR1 | RTK6, CD167, CAK, CD167, DDR, EDDR1, HGK2, MCK10, NEP, NTRK4, PTK3, PTK3A, TRKE | AC220, quizartinib; DDR1 compound 7ae; DDR1-1N-1; imatinib; LY2801653; masitinib AB1010; PD173074; RAF-265, CHIR-265; DDR-TRK-1; GW832467; TPKI-39 | Basal-like |
| EPHA2 | ARCC2, CTPA, CTPP1, CTRCT6, ECK, EphA2 | LY3009120; MLN8237/Alisertib; GW693917A; ALW-II-41-27 | Basal-like |
| FER | PPP1R74, TYK3, p94-Fer | GSK1838705A; PF-06463922, Lorlatinib; GSK1904529 | Basal-like |
| FRK | RAK, GTK, PTK5 | Abbott Compound 530; PF-06463922, Lorlatinib; XMD8-87; GSK1904529; TPKI-113 | Classical |
| GSK3A/G SK3B | | BAY-61-3606; Carna compound 13; CHIR-99021; EHT5372; GW784752X; SB-742609; TPKI-91; ARA014418; LY-317615, enzastaurin; GW513184X; GW810372X; SB-725317; TPKI-85 | Basal-like |
| INSR | CD220, HHF5, IR | OSI-906, linsitinib; GSK1392956A; GSK1904529; GSK2219385 | Basal-like |
| LIMK1 | LIMK, LIMK-1 | CRT0105446; LIMKi compound 3; Amakem tetrahydropyrimido-indole compound 3; Scripps FL 18b; LX7101; TH-257; R10015 | Basal-like |
| LYN | JTK8, p53Lyn, p56Lyn compound 19 | masitinib AB1010; saturated ibrutinib; Maly LYN | Classical |
| MAP2K2 | CFC4, 1VIAPKK2, MEK2, MKK2, PRKMK2 | Trametinib (GSK1120212); cobimetinib/GDC0973; binimetinib; refametinib; ESD0001937 | |
| MAP3K11 | SPRK, MEKK11, MLK-3, PTK1 | PFE-PKIS18; SGK1 Sanofi 14n | Classical |
| MAP3K2 | MEKK2B, MEKK2 | MRKI-19; GSK2656157; AKI00000018a; AK100000021a | Basal-like |
| MAP3K5 | MAPKKK5, ASK1, MEKK5 | Compound 10.HCl; MSC 2032964A; PF3644022; TPKI-58 | Basal-like |
| MAP4K5 | KHSqqq1, GCKR, KHS, MAPKKKK5 | FRAX1036; G-5555 | Basal-like |
| MAPK1 | ERK, ERK2, p41mapk, MAPK2, PRKM2, PRKM1, ERT1, ERK-2, P42MAPK, PRKM1, p38, p40, p41, p42-MAPK, Erk2 | Carna compound 13; SCH772984; Vertex 11e; AZ compound 35 | Basal-like |
| MAPK3 | ERK1, p44mapk, p44erk1, PRKM3, ERK-1, ERT2, HS44KDAP, HUMKER1A, P44ERK1, P44MAPK, p44-ERK1, p44-MAPK, Erk1 | SCH+E:E772984; GAN-305074X (aka GW5074) | Classical |
| PAK4 | | GenentechPAK compound 13; Novartis compound 11 | Basal-like |
| PIP4K2C | PIP5K2C | G1T28 | Basal-like |
| PKM | | TLN-232 (aka CAP-232) | |
| PRKCD | ALPS3, CVID9, Al 71, PKCD, nPKC-delta PKCd | LY-317615; enzastaurn; uprosertib, GSK2141795 | Classical |
| PTK2B | CAKB, PYK2, RAFTK, PTK, CADTK, FADK2, FAK2, PKB | PF-06463922; Lorlatinib; GSK1392956A | Basal-like |
| PIK6 | BtK, p21cdc42Hs, | PLX-4720; Vemurafenib; saturated ibrutinib; XMD8-87; 21a; PF-6698840 | Classical |
| RIPK2 | RICK, RIP2, CARDIAK, CARD3, CCK, GIG30 | LDN-214117; Novartis Compound 2; OD36; OD38; saturated ibrutinib; SB-203580; SB-590885; WEHI-345; GSK583; GSK RIPK2 inhibitor 7 | Basal-like |
| ROCK2 | ROCK-II | GSK269962A; GSK429286; SB-747651A; Scripps compound 35; Netarsudil; netarsudil hydrolysis product; Abbvie ROCK compound 16; Abbvie ROCK compound 58 | Classical |

TABLE 28-continued

Exemplary PKIs and Their Targets

| Gene Name | Aliases | Compounds | Overexpressed in Subtype |
|---|---|---|---|
| SRC | ASV, c-src,ASV1, THC6, c-SRC, p60-Src | many inhibitors, usually src family | Classical |
| sTK10 | LOK, PRO2729 | erlotinib, OSI-744; GSK461364A; RAF-265, CHIR-265; GSK204607; SB-633825 | Basal-like |
| TBK1 | NAK, FTDALS4; T2K | WEHI-112; GSK8612 | Basal-like |
| YES1 | Yes, c-yes, HsT441, P61-YES | PF-477736; saturated ibrutinib; GW621970X | Basal-like |

What is claimed is:

1. A method for treating a subject diagnosed with pancreatic ductal adenocarcinoma (PDAC), the method comprising:

(a) obtaining nucleic acid expression levels for each of the following genes in a biological sample comprising PDAC cells isolated from the subject: GPR87, KRT6A, BCAR3, PTGES, ITGA3, C16orf74, S100A2, KRT5, REG4, ANXA10, GATA6, CLDN18, LGALS4, DDC, SLC40A1, CLRN3, KRT15, KRT17, TFF1, PLA2G10, CDH17, DCBLD2 and TSPAN8, wherein the nucleic acid expression levels were determined using an amplification, hybridization or sequencing assay on the biological sample;

(b) performing a pair-wise comparison of the nucleic acid expression levels for each gene pair in either Gene Pairs 1-8 or Gene Pairs A-H, wherein Gene Pairs 1-8 and Gene Pairs A-H are as follows:

| GENE PAIR | GENE A | GENE B | Coefficient |
|---|---|---|---|
| 1 | GPR87 | REG4 | 1.994 |
| 2 | KRT6A | ANXA10 | 2.031 |
| 3 | BCAR3 | GATA6 | 1.618 |
| 4 | PTGES | CLDN18 | 0.922 |
| 5 | ITGA3 | LGALS4 | 1.059 |
| 6 | C16orf74 | DDC | 0.929 |
| 7 | S100A2 | SLC40A1 | 2.505 |
| 8 | KRT5 | CLRN3 | 0.485 |
| A | GPR87 | REG4 | 3.413 |
| B | KRT6A | ANXA10 | 3.437 |
| C | KRT17 | LGALS4 | 2.078 |
| D | S100A2 | TFF1 | 2.651 |
| E | C16orf74 | DDC | 0.901 |
| F | KRT15 | PLA2G10 | 2.677 |
| G | PTGES | CDH17 | 2.911 |
| H | DCBLD2 | TSPAN8 | 1.903 |

(c) calculating a Raw Score for the biological sample, wherein the calculating comprises:

(i) assigning a value of 1 for each Gene Pair from either Gene Pairs 1-8 or Gene Pairs A-H for which Gene A of the Gene Pair has a higher nucleic acid expression level than Gene B of the Gene Pair, and a value of 0 for each Gene Pair from either Gene Pairs 1-8 or Gene Pairs A-H for which Gene A of the Gene Pair has a lower nucleic acid expression level than Gene B of the Gene Pair;

(ii) multiplying each assigned value by the coefficient listed above for each Gene Pair from either Gene Pairs 1-8 or Gene Pairs A-H to calculate eight individual Gene Pair scores from either Gene Pairs 1-8 or Gene Pairs A-H; and (iii) adding a sum of the eight individual Gene Pair scores from either Gene Pairs 1-8 or Gene Pairs A-H to a respective baseline effect for either Gene Pairs 1-8 or Gene Pairs A-H to calculate a Raw Score for the biological sample, wherein the respective baseline effect is −6.815 for Gene Pairs 1-8 and −12.414 for Gene Pairs A-H, wherein if the calculated Raw Score is greater than or equal to 0, the tumor subtype is determined to be a basal-like subtype, and if the calculated Raw Score if less than 0, the tumor subtype is determined to be a classical subtype;

(d) administering a treatment to the subject based on the subtype assigned, wherein:

(i) if the assigned subtype is a basal-like subtype, the treatment strategy comprises gemcitabine; and (ii) if the assigned subtype is a classical subtype, the treatment comprises FOLFIRINOX.

2. The method of claim 1, wherein the biological sample comprises a biopsy sample, or a frozen or archival sample derived therefrom.

3. The method of claim 2, wherein the biopsy sample comprises a fine needle biopsy aspiration or a percutaneous core needle biopsy.

4. The method of claim 1, wherein the obtaining nucleic acid expression levels employs a technique selected from the group consisting of microarray analysis, RNAseq, quantitative RT-PCR, NanoString, or any combination thereof.

5. The method of claim 4, wherein the technique comprises NanoString and employs probes comprising the following SEQ ID NOs:

| GENE PAIR | GENE A | SEQ ID NO: | GENE B | SEQ ID NO: |
|---|---|---|---|---|
| 1 | GPR87 | 64 | REG4 | 71 |
| 2 | KRT6A | 65 | ANXA10 | 59 |
| 3 | BCAR3 | 81 | GATA6 | 82 |
| 4 | PTGES | 70 | CLDN18 | 84 |
| 5 | ITGA3 | 85 | LGALS4 | 68 |
| 6 | C16orf74 | 60 | DDC | 63 |
| 7 | S100A2 | 72 | SLC40A1 | 86 |
| 8 | KRT5 | 87 | CLRN3 | 83 |
| A | GPR87 | 64 | REG4 | 71 |
| B | KRT6A | 65 | ANXA10 | 59 |
| C | KRT17 | 67 | LGALS4 | 68 |
| D | S100A2 | 72 | TFF1 | 73 |
| E | C16orf74 | 60 | DDC | 63 |
| F | KRT15 | 66 | PLA2G10 | 69 |
| G | PTGES | 70 | CDH17 | 61 |
| H | DCBLD2 | 62 | TSPAN8 | 74. |

6. The method of claim 1, wherein the treatment comprises gemcitabine in combination with nab-paclitaxel.

* * * * *

```
                          SEQUENCE LISTING


<160> NUMBER OF SEQ ID NOS: 102

<210> SEQ ID NO 1
<211> LENGTH: 1441
<212> TYPE: DNA
<213> ORGANISM: Homo sapiens
<220> FEATURE:
<221> NAME/KEY: CDS
<222> LOCATION: (165)..(1139)

<400> SEQUENCE: 1

atccagattt gcttttacat tttcttgcct gagtctgagg tgaacagtga acatatttac      60

atttgattta acagtgaacc ttaattcttt ctggcttcac agtgaaacaa gtttatgcaa     120

tcgatcaaat attttcatcc ctgaggttaa caattaccat caaa atg ttt tgt gga      176
                                                 Met Phe Cys Gly
                                                 1

gac tat gtg caa gga acc atc ttc cca gct ccc aat ttc aat ccc ata       224
Asp Tyr Val Gln Gly Thr Ile Phe Pro Ala Pro Asn Phe Asn Pro Ile
5                   10                  15                  20

atg gat gcc caa atg cta gga gga gca ctc caa gga ttt gac tgt gac       272
Met Asp Ala Gln Met Leu Gly Gly Ala Leu Gln Gly Phe Asp Cys Asp
                25                  30                  35

aaa gac atg ctg atc aac att ctg act cag cgc tgc aat gca caa agg       320
Lys Asp Met Leu Ile Asn Ile Leu Thr Gln Arg Cys Asn Ala Gln Arg
            40                  45                  50

atg atg att gca gag gca tac cag agc atg tat ggc cgg gac ctg att       368
Met Met Ile Ala Glu Ala Tyr Gln Ser Met Tyr Gly Arg Asp Leu Ile
        55                  60                  65

ggg gat atg agg gag cag ctt tcg gat cac ttc aaa gat gtg atg gct       416
Gly Asp Met Arg Glu Gln Leu Ser Asp His Phe Lys Asp Val Met Ala
    70                  75                  80

ggc ctc atg tac cca cca cca ctg tat gat gct cat gag ctc tgg cat       464
Gly Leu Met Tyr Pro Pro Pro Leu Tyr Asp Ala His Glu Leu Trp His
85                  90                  95                  100

gcc atg aag gga gta ggc act gat gag aat tgc ctc att gaa ata cta       512
Ala Met Lys Gly Val Gly Thr Asp Glu Asn Cys Leu Ile Glu Ile Leu
                105                 110                 115

gct tca aga aca aat gga gaa att ttc cag atg cga gaa gcc tac tgc       560
Ala Ser Arg Thr Asn Gly Glu Ile Phe Gln Met Arg Glu Ala Tyr Cys
            120                 125                 130

ttg caa tac agc aat aac ctc caa gag gac att tat tca gag acc tca       608
Leu Gln Tyr Ser Asn Asn Leu Gln Glu Asp Ile Tyr Ser Glu Thr Ser
        135                 140                 145

gga cac ttc aga gat act ctc atg aac ttg gtc cag ggg acc aga gag       656
Gly His Phe Arg Asp Thr Leu Met Asn Leu Val Gln Gly Thr Arg Glu
    150                 155                 160

gaa gga tat aca gac cct gcg atg gct gct cag gat gca atg gtc cta       704
```

```
Glu Gly Tyr Thr Asp Pro Ala Met Ala Ala Gln Asp Ala Met Val Leu
165                 170                 175                 180

tgg gaa gcc tgt cag cag aag acg ggg gag cac aaa acc atg ctg caa      752
Trp Glu Ala Cys Gln Gln Lys Thr Gly Glu His Lys Thr Met Leu Gln
                185                 190                 195

atg atc ctg tgc aac aag agc tac cag cag ctg cgg ctg gtt ttc cag      800
Met Ile Leu Cys Asn Lys Ser Tyr Gln Gln Leu Arg Leu Val Phe Gln
            200                 205                 210

gaa ttt caa aat att tct ggg caa gat atg gta gat gcc att aat gaa      848
Glu Phe Gln Asn Ile Ser Gly Gln Asp Met Val Asp Ala Ile Asn Glu
        215                 220                 225

tgt tat gat gga tac ttt cag gag ctg ctg gtt gca att gtt ctc tgt      896
Cys Tyr Asp Gly Tyr Phe Gln Glu Leu Leu Val Ala Ile Val Leu Cys
    230                 235                 240

gtt cga gac aaa cca gcc tat ttt gct tat aga tta tat agt gca att      944
Val Arg Asp Lys Pro Ala Tyr Phe Ala Tyr Arg Leu Tyr Ser Ala Ile
245                 250                 255                 260

cat gac ttt ggt ttc cat aat aaa act gta atc agg att ctc att gcc      992
His Asp Phe Gly Phe His Asn Lys Thr Val Ile Arg Ile Leu Ile Ala
                265                 270                 275

aga agt gaa ata gac ctg ctg acc ata agg aaa cga tac aaa gag cga     1040
Arg Ser Glu Ile Asp Leu Leu Thr Ile Arg Lys Arg Tyr Lys Glu Arg
            280                 285                 290

tat gga aaa tcc cta ttt cat gat atc aga aat ttt gct tca ggg cat     1088
Tyr Gly Lys Ser Leu Phe His Asp Ile Arg Asn Phe Ala Ser Gly His
        295                 300                 305

tat aag aaa gca ctg ctt gcc atc tgt gct ggt gat gct gag gac tac     1136
Tyr Lys Lys Ala Leu Leu Ala Ile Cys Ala Gly Asp Ala Glu Asp Tyr
    310                 315                 320

taa aatgaagagg acttggagta ctgtgcactc ctctttctag acacttccaa          1189

atagagattt tctcacaaat ttgtactgtt catggcacta ttaacaaaac tatacaatca   1249

tattttctct tctatctttg aaattattct aagccaaaga aaactatgaa tgaaagtata   1309

tgatactgaa tttgcctact atcctgaatt tgcctactat ctaatcagca attaaataaa   1369

ttgtgcatga tggaataata gaaaaattgc attggaatag attttattta aatgtgaacc   1429

atcaacaacc ta                                                       1441

<210> SEQ ID NO 2
<211> LENGTH: 324
<212> TYPE: PRT
<213> ORGANISM: Homo sapiens

<400> SEQUENCE: 2

Met Phe Cys Gly Asp Tyr Val Gln Gly Thr Ile Phe Pro Ala Pro Asn
1               5                   10                  15

Phe Asn Pro Ile Met Asp Ala Gln Met Leu Gly Gly Ala Leu Gln Gly
            20                  25                  30

Phe Asp Cys Asp Lys Asp Met Leu Ile Asn Ile Leu Thr Gln Arg Cys
        35                  40                  45

Asn Ala Gln Arg Met Met Ile Ala Glu Ala Tyr Gln Ser Met Tyr Gly
    50                  55                  60

Arg Asp Leu Ile Gly Asp Met Arg Glu Gln Leu Ser Asp His Phe Lys
65                  70                  75                  80

Asp Val Met Ala Gly Leu Met Tyr Pro Pro Pro Leu Tyr Asp Ala His
                85                  90                  95

Glu Leu Trp His Ala Met Lys Gly Val Gly Thr Asp Glu Asn Cys Leu
            100                 105                 110
```

```
Ile Glu Ile Leu Ala Ser Arg Thr Asn Gly Glu Ile Phe Gln Met Arg
        115                 120                 125

Glu Ala Tyr Cys Leu Gln Tyr Ser Asn Asn Leu Gln Glu Asp Ile Tyr
    130                 135                 140

Ser Glu Thr Ser Gly His Phe Arg Asp Thr Leu Met Asn Leu Val Gln
145                 150                 155                 160

Gly Thr Arg Glu Glu Gly Tyr Thr Asp Pro Ala Met Ala Ala Gln Asp
                165                 170                 175

Ala Met Val Leu Trp Glu Ala Cys Gln Gln Lys Thr Gly Glu His Lys
            180                 185                 190

Thr Met Leu Gln Met Ile Leu Cys Asn Lys Ser Tyr Gln Gln Leu Arg
        195                 200                 205

Leu Val Phe Gln Glu Phe Gln Asn Ile Ser Gly Gln Asp Met Val Asp
    210                 215                 220

Ala Ile Asn Glu Cys Tyr Asp Gly Tyr Phe Gln Glu Leu Leu Val Ala
225                 230                 235                 240

Ile Val Leu Cys Val Arg Asp Lys Pro Ala Tyr Phe Ala Tyr Arg Leu
                245                 250                 255

Tyr Ser Ala Ile His Asp Phe Gly Phe His Asn Lys Thr Val Ile Arg
            260                 265                 270

Ile Leu Ile Ala Arg Ser Glu Ile Asp Leu Leu Thr Ile Arg Lys Arg
        275                 280                 285

Tyr Lys Glu Arg Tyr Gly Lys Ser Leu Phe His Asp Ile Arg Asn Phe
    290                 295                 300

Ala Ser Gly His Tyr Lys Lys Ala Leu Leu Ala Ile Cys Ala Gly Asp
305                 310                 315                 320

Ala Glu Asp Tyr


<210> SEQ ID NO 3
<211> LENGTH: 3336
<212> TYPE: DNA
<213> ORGANISM: Homo sapiens
<220> FEATURE:
<221> NAME/KEY: CDS
<222> LOCATION: (359)..(2836)

<400> SEQUENCE: 3

ctctccggcg gccgctccag cccggccggg accccagagt tgcaggccca ggccagccgt      60

tgcaccgtta agccgggccg gtgacgccgg gcctttacgt cgcgcctgtg agcggccgag     120

gccgagcggc ctcccctcgg gctgcgagac ggagacatta cctcatccct caagattgct     180

cgctgcaaac acaacgctga gaaatggccc aagtaaagcg tgatcagggt cttgcattct     240

tggcacatct aggaagaacg tgcaaggatg cgaattgtga atcgcttctc caaacagagc     300

tgcttcatct gacccaagct ggcctggaga aaggaggaag aggcaagagt tgagaatt       358

atg gct gca gga aaa ttt gca agc ctt ccc aga aac atg ccg gtg aat       406
Met Ala Ala Gly Lys Phe Ala Ser Leu Pro Arg Asn Met Pro Val Asn
1               5                   10                  15

cac cag ttc ccc ctg gcc tca tcc atg gac ctt ctg agc agc agg tcc       454
His Gln Phe Pro Leu Ala Ser Ser Met Asp Leu Leu Ser Ser Arg Ser
            20                  25                  30

cct ctc gct gag cat cgc cca gat gcc tat caa gat gtg tct ata cat       502
Pro Leu Ala Glu His Arg Pro Asp Ala Tyr Gln Asp Val Ser Ile His
        35                  40                  45

ggc acc ctt cca cgg aag aaa aaa ggt cct cct ccc ata agg tcc tgt       550
Gly Thr Leu Pro Arg Lys Lys Lys Gly Pro Pro Pro Ile Arg Ser Cys
```

-continued

```
    50                  55                  60

gat gac ttc agt cac atg ggc acc ctc ccc cac tcc aaa tcc cca cgg      598
Asp Asp Phe Ser His Met Gly Thr Leu Pro His Ser Lys Ser Pro Arg
65                  70                  75                  80

cag aac tcg cct gtg acc cag gat ggc atc cag gag agc cca tgg cag      646
Gln Asn Ser Pro Val Thr Gln Asp Gly Ile Gln Glu Ser Pro Trp Gln
                85                  90                  95

gac cgg cac ggc gaa acc ttc acc ttc agg gat cca cat ctt ctg gac      694
Asp Arg His Gly Glu Thr Phe Thr Phe Arg Asp Pro His Leu Leu Asp
            100                 105                 110

cca act gtg gaa tat gtg aag ttc tcc aag gag agg cac atc atg gac      742
Pro Thr Val Glu Tyr Val Lys Phe Ser Lys Glu Arg His Ile Met Asp
        115                 120                 125

agg acc ccc gag aaa ctg aag aag gag ctg gag gag gag ctg ctc ctg      790
Arg Thr Pro Glu Lys Leu Lys Lys Glu Leu Glu Glu Glu Leu Leu Leu
    130                 135                 140

agc agc gag gac ctg cgc agc cat gcc tgg tac cac ggc cgc atc ccc      838
Ser Ser Glu Asp Leu Arg Ser His Ala Trp Tyr His Gly Arg Ile Pro
145                 150                 155                 160

cga cag gtg tct gaa aac ctt gtg cag cga gat ggt gac ttc cta gtt      886
Arg Gln Val Ser Glu Asn Leu Val Gln Arg Asp Gly Asp Phe Leu Val
                165                 170                 175

cgt gac tct ctg tcc agc cct ggg aac ttt gtc ctg acc tgt cag tgg      934
Arg Asp Ser Leu Ser Ser Pro Gly Asn Phe Val Leu Thr Cys Gln Trp
            180                 185                 190

aag aac ctc gct cag cac ttc aaa atc aac cgg aca gtt ctg cga ctc      982
Lys Asn Leu Ala Gln His Phe Lys Ile Asn Arg Thr Val Leu Arg Leu
        195                 200                 205

agc gag gcc tac agc cgc gtg cag tac cag ttc gag atg gag agc ttc     1030
Ser Glu Ala Tyr Ser Arg Val Gln Tyr Gln Phe Glu Met Glu Ser Phe
    210                 215                 220

gac tcc atc ccc ggc ctg gtg cgc tgc tac gtg ggc aac cgc cgg ccc     1078
Asp Ser Ile Pro Gly Leu Val Arg Cys Tyr Val Gly Asn Arg Arg Pro
225                 230                 235                 240

atc tcc cag cag agt ggc gcc atc atc ttc cag ccc atc aac agg acg     1126
Ile Ser Gln Gln Ser Gly Ala Ile Ile Phe Gln Pro Ile Asn Arg Thr
                245                 250                 255

gtg cct ctg cgg tgc ctg gag gag cat tat ggc acc tcc cca ggc cag     1174
Val Pro Leu Arg Cys Leu Glu Glu His Tyr Gly Thr Ser Pro Gly Gln
            260                 265                 270

gcc cgg gag ggc agc ctc acc aag gga agg ccg gat gtg gcc aag agg     1222
Ala Arg Glu Gly Ser Leu Thr Lys Gly Arg Pro Asp Val Ala Lys Arg
        275                 280                 285

ctg agc ctc acc atg ggt ggc gtc cag gcc cga gag cag aat ttg ccc     1270
Leu Ser Leu Thr Met Gly Gly Val Gln Ala Arg Glu Gln Asn Leu Pro
    290                 295                 300

agg gga aac ctc ctc aga aac aaa gaa aag agt ggt agc cag ccc gcc     1318
Arg Gly Asn Leu Leu Arg Asn Lys Glu Lys Ser Gly Ser Gln Pro Ala
305                 310                 315                 320

tgc ctg gat cac atg cag gac aga aga gcc ttg tcc ctc aaa gcc cac     1366
Cys Leu Asp His Met Gln Asp Arg Arg Ala Leu Ser Leu Lys Ala His
                325                 330                 335

cag tca gag agc tac ctg ccg att ggc tgc aag ctg cca cct cag tcc     1414
Gln Ser Glu Ser Tyr Leu Pro Ile Gly Cys Lys Leu Pro Pro Gln Ser
            340                 345                 350

tcg ggt gtg gac aca agc ccc tgc cca aac tca cct gtg ttc agg acg     1462
Ser Gly Val Asp Thr Ser Pro Cys Pro Asn Ser Pro Val Phe Arg Thr
        355                 360                 365

gga agc gag cct gcc ctg agc cca gca gtg gtt cgg agg gtc tcc tca     1510
```

-continued

```
Gly Ser Glu Pro Ala Leu Ser Pro Ala Val Val Arg Arg Val Ser Ser
    370                 375                 380

gac gcc agg gct ggg gag gcg ctg agg gga tca gac agt caa ctg tgc      1558
Asp Ala Arg Ala Gly Glu Ala Leu Arg Gly Ser Asp Ser Gln Leu Cys
385                 390                 395                 400

cct aag ccc ccg cct aag ccc tgc aag gtg ccg ttc ctc aag gtt ccc      1606
Pro Lys Pro Pro Pro Lys Pro Cys Lys Val Pro Phe Leu Lys Val Pro
                405                 410                 415

tcg tct ccc tct gcc tgg ctc aac tca gag gcc aac tac tgt gaa ctg      1654
Ser Ser Pro Ser Ala Trp Leu Asn Ser Glu Ala Asn Tyr Cys Glu Leu
            420                 425                 430

aac cca gcg ttt gcc aca ggc tgc ggc agg gga gca aag cta ccc tca      1702
Asn Pro Ala Phe Ala Thr Gly Cys Gly Arg Gly Ala Lys Leu Pro Ser
        435                 440                 445

tgt gcc cag gga agc cac aca gaa ctg ctc aca gcc aag cag aat gag      1750
Cys Ala Gln Gly Ser His Thr Glu Leu Leu Thr Ala Lys Gln Asn Glu
    450                 455                 460

gcg cca ggt ccc cgg aac tct ggc gtc aac tac ttg atc ctt gat gat      1798
Ala Pro Gly Pro Arg Asn Ser Gly Val Asn Tyr Leu Ile Leu Asp Asp
465                 470                 475                 480

gat gac agg gaa aga cct tgg gaa cct gcg gca gct cag atg gag aag      1846
Asp Asp Arg Glu Arg Pro Trp Glu Pro Ala Ala Ala Gln Met Glu Lys
                485                 490                 495

ggg cag tgg gac aag ggc gag ttt gtg acg ccc ctc ctg gag act gtc      1894
Gly Gln Trp Asp Lys Gly Glu Phe Val Thr Pro Leu Leu Glu Thr Val
            500                 505                 510

tcc tcc ttc agg ccc aac gag ttt gag tca aag ttc ctt ccc cct gag      1942
Ser Ser Phe Arg Pro Asn Glu Phe Glu Ser Lys Phe Leu Pro Pro Glu
        515                 520                 525

aat aag ccc ctg gaa aca gca atg ttg aaa cgt gca aaa gaa ctg ttc      1990
Asn Lys Pro Leu Glu Thr Ala Met Leu Lys Arg Ala Lys Glu Leu Phe
    530                 535                 540

acc aac aac gac ccc aag gtc atc gcc cag cac gta ctg agc atg gac      2038
Thr Asn Asn Asp Pro Lys Val Ile Ala Gln His Val Leu Ser Met Asp
545                 550                 555                 560

tgc agg gtt gct agg ata ctt gga gtc tct gaa gag atg agg agg aac      2086
Cys Arg Val Ala Arg Ile Leu Gly Val Ser Glu Glu Met Arg Arg Asn
                565                 570                 575

atg ggg gtg agc tca ggc ctg gaa ctc att acc ttg cct cac gga cac      2134
Met Gly Val Ser Ser Gly Leu Glu Leu Ile Thr Leu Pro His Gly His
            580                 585                 590

cag ctg cgc ctg gac ata att gaa aga cac aac aca atg gcc atc ggc      2182
Gln Leu Arg Leu Asp Ile Ile Glu Arg His Asn Thr Met Ala Ile Gly
        595                 600                 605

att gca gtg gac att ctg gga tgc acg ggc act ttg gag gac cga gcg      2230
Ile Ala Val Asp Ile Leu Gly Cys Thr Gly Thr Leu Glu Asp Arg Ala
    610                 615                 620

gcc act ctg agt aag atc atc cag gtg gcg gtg gaa ctg aag gat tcc      2278
Ala Thr Leu Ser Lys Ile Ile Gln Val Ala Val Glu Leu Lys Asp Ser
625                 630                 635                 640

atg ggg gac ctc tat tcc ttc tca gct ctc atg aaa gcc ctg gaa atg      2326
Met Gly Asp Leu Tyr Ser Phe Ser Ala Leu Met Lys Ala Leu Glu Met
                645                 650                 655

cca cag atc aca agg tta gaa aag acg tgg act gct ctg cgg cac cag      2374
Pro Gln Ile Thr Arg Leu Glu Lys Thr Trp Thr Ala Leu Arg His Gln
            660                 665                 670

tac acc caa act gcc att ctc tat gag aaa cag ctg aag ccc ttc agc      2422
Tyr Thr Gln Thr Ala Ile Leu Tyr Glu Lys Gln Leu Lys Pro Phe Ser
        675                 680                 685
```

```
aaa ctc ctg cat gaa ggc aga gag tcc aca tgt gtt ccc cca aac aat      2470
Lys Leu Leu His Glu Gly Arg Glu Ser Thr Cys Val Pro Pro Asn Asn
    690                 695                 700

gta tca gtc cca ctg ctg atg ccg ctt gtg acg tta atg gag cgc cag      2518
Val Ser Val Pro Leu Leu Met Pro Leu Val Thr Leu Met Glu Arg Gln
705                 710                 715                 720

gct gtg act ttt gaa gga acc gac atg tgg gaa aaa aac gac cag agc      2566
Ala Val Thr Phe Glu Gly Thr Asp Met Trp Glu Lys Asn Asp Gln Ser
                725                 730                 735

tgt gaa atc atg ctg aac cat ttg gca aca gcg cga ttc atg gcc gag      2614
Cys Glu Ile Met Leu Asn His Leu Ala Thr Ala Arg Phe Met Ala Glu
            740                 745                 750

gct gca gac agc tac cgg atg aat gct gag agg atc ctg gca ggt ttt      2662
Ala Ala Asp Ser Tyr Arg Met Asn Ala Glu Arg Ile Leu Ala Gly Phe
        755                 760                 765

caa cca gat gaa gaa atg aat gaa atc tgc aag act gaa ttt caa atg      2710
Gln Pro Asp Glu Glu Met Asn Glu Ile Cys Lys Thr Glu Phe Gln Met
    770                 775                 780

cga ttg cta tgg ggc agc aaa ggt gca caa gtc aat cag aca gag aga      2758
Arg Leu Leu Trp Gly Ser Lys Gly Ala Gln Val Asn Gln Thr Glu Arg
785                 790                 795                 800

tat gag aaa ttc aac cag att tta act gcc ctc tcg cgt aaa ttg gaa      2806
Tyr Glu Lys Phe Asn Gln Ile Leu Thr Ala Leu Ser Arg Lys Leu Glu
                805                 810                 815

cct cct cct gta aag cag gca gag ctt tga taactctcca gagaaccttt       2856
Pro Pro Pro Val Lys Gln Ala Glu Leu
            820                 825

agaatatctt ttcaagtttc cccagcttca tctttgggaa agcttactgt ttttgataaa   2916

gtaataatgt gcaaatctga caatatacaa gcttttagta tccacaggat attaaacgtg   2976

taaattgcac agagcacact tatttatgaa ttgtctaaag ttactactga ttttaaaatg   3036

aataatttat tattaaggta actactgcta atgttgatca gcaaatttaa gagaagacct   3096

agctatgttg gctggttgct ttctattatc atggtatttg accattttag ttttaattcc   3156

atgtcagata agtgtaaata gaagagttta aaagcatgaa acatttcaga aggtatcagt   3216

tatatgatat tctttaaaca aatatgaaaa atgtaaatac tcatgaatga aaatacatct   3276

ttttgtgaaa cagttgtatc cagtctcttt catattaaac aactcatctt ggtacaataa   3336


<210> SEQ ID NO 4
<211> LENGTH: 825
<212> TYPE: PRT
<213> ORGANISM: Homo sapiens

<400> SEQUENCE: 4

Met Ala Ala Gly Lys Phe Ala Ser Leu Pro Arg Asn Met Pro Val Asn
1               5                   10                  15

His Gln Phe Pro Leu Ala Ser Ser Met Asp Leu Leu Ser Ser Arg Ser
            20                  25                  30

Pro Leu Ala Glu His Arg Pro Asp Ala Tyr Gln Asp Val Ser Ile His
        35                  40                  45

Gly Thr Leu Pro Arg Lys Lys Lys Gly Pro Pro Pro Ile Arg Ser Cys
    50                  55                  60

Asp Asp Phe Ser His Met Gly Thr Leu Pro His Ser Lys Ser Pro Arg
65                  70                  75                  80

Gln Asn Ser Pro Val Thr Gln Asp Gly Ile Gln Glu Ser Pro Trp Gln
                85                  90                  95

Asp Arg His Gly Glu Thr Phe Thr Phe Arg Asp Pro His Leu Leu Asp
```

-continued

```
            100                 105                 110

Pro Thr Val Glu Tyr Val Lys Phe Ser Lys Glu Arg His Ile Met Asp
        115                 120                 125

Arg Thr Pro Glu Lys Leu Lys Lys Glu Leu Glu Glu Glu Leu Leu Leu
    130                 135                 140

Ser Ser Glu Asp Leu Arg Ser His Ala Trp Tyr His Gly Arg Ile Pro
145                 150                 155                 160

Arg Gln Val Ser Glu Asn Leu Val Gln Arg Asp Gly Asp Phe Leu Val
                165                 170                 175

Arg Asp Ser Leu Ser Ser Pro Gly Asn Phe Val Leu Thr Cys Gln Trp
            180                 185                 190

Lys Asn Leu Ala Gln His Phe Lys Ile Asn Arg Thr Val Leu Arg Leu
        195                 200                 205

Ser Glu Ala Tyr Ser Arg Val Gln Tyr Gln Phe Glu Met Glu Ser Phe
    210                 215                 220

Asp Ser Ile Pro Gly Leu Val Arg Cys Tyr Val Gly Asn Arg Arg Pro
225                 230                 235                 240

Ile Ser Gln Gln Ser Gly Ala Ile Ile Phe Gln Pro Ile Asn Arg Thr
                245                 250                 255

Val Pro Leu Arg Cys Leu Glu Glu His Tyr Gly Thr Ser Pro Gly Gln
            260                 265                 270

Ala Arg Glu Gly Ser Leu Thr Lys Gly Arg Pro Asp Val Ala Lys Arg
        275                 280                 285

Leu Ser Leu Thr Met Gly Gly Val Gln Ala Arg Glu Gln Asn Leu Pro
    290                 295                 300

Arg Gly Asn Leu Leu Arg Asn Lys Glu Lys Ser Gly Ser Gln Pro Ala
305                 310                 315                 320

Cys Leu Asp His Met Gln Asp Arg Arg Ala Leu Ser Leu Lys Ala His
                325                 330                 335

Gln Ser Glu Ser Tyr Leu Pro Ile Gly Cys Lys Leu Pro Pro Gln Ser
            340                 345                 350

Ser Gly Val Asp Thr Ser Pro Cys Pro Asn Ser Pro Val Phe Arg Thr
        355                 360                 365

Gly Ser Glu Pro Ala Leu Ser Pro Ala Val Val Arg Arg Val Ser Ser
    370                 375                 380

Asp Ala Arg Ala Gly Glu Ala Leu Arg Gly Ser Asp Ser Gln Leu Cys
385                 390                 395                 400

Pro Lys Pro Pro Pro Lys Pro Cys Lys Val Pro Phe Leu Lys Val Pro
                405                 410                 415

Ser Ser Pro Ser Ala Trp Leu Asn Ser Glu Ala Asn Tyr Cys Glu Leu
            420                 425                 430

Asn Pro Ala Phe Ala Thr Gly Cys Gly Arg Gly Ala Lys Leu Pro Ser
        435                 440                 445

Cys Ala Gln Gly Ser His Thr Glu Leu Leu Thr Ala Lys Gln Asn Glu
    450                 455                 460

Ala Pro Gly Pro Arg Asn Ser Gly Val Asn Tyr Leu Ile Leu Asp Asp
465                 470                 475                 480

Asp Asp Arg Glu Arg Pro Trp Glu Pro Ala Ala Ala Gln Met Glu Lys
                485                 490                 495

Gly Gln Trp Asp Lys Gly Glu Phe Val Thr Pro Leu Leu Glu Thr Val
            500                 505                 510

Ser Ser Phe Arg Pro Asn Glu Phe Glu Ser Lys Phe Leu Pro Pro Glu
        515                 520                 525
```

```
Asn Lys Pro Leu Glu Thr Ala Met Leu Lys Arg Ala Lys Glu Leu Phe
    530                 535                 540

Thr Asn Asn Asp Pro Lys Val Ile Ala Gln His Val Leu Ser Met Asp
545                 550                 555                 560

Cys Arg Val Ala Arg Ile Leu Gly Val Ser Glu Glu Met Arg Arg Asn
                565                 570                 575

Met Gly Val Ser Ser Gly Leu Glu Leu Ile Thr Leu Pro His Gly His
            580                 585                 590

Gln Leu Arg Leu Asp Ile Ile Glu Arg His Asn Thr Met Ala Ile Gly
        595                 600                 605

Ile Ala Val Asp Ile Leu Gly Cys Thr Gly Thr Leu Glu Asp Arg Ala
    610                 615                 620

Ala Thr Leu Ser Lys Ile Ile Gln Val Ala Val Glu Leu Lys Asp Ser
625                 630                 635                 640

Met Gly Asp Leu Tyr Ser Phe Ser Ala Leu Met Lys Ala Leu Glu Met
                645                 650                 655

Pro Gln Ile Thr Arg Leu Glu Lys Thr Trp Thr Ala Leu Arg His Gln
            660                 665                 670

Tyr Thr Gln Thr Ala Ile Leu Tyr Glu Lys Gln Leu Lys Pro Phe Ser
        675                 680                 685

Lys Leu Leu His Glu Gly Arg Glu Ser Thr Cys Val Pro Pro Asn Asn
    690                 695                 700

Val Ser Val Pro Leu Leu Met Pro Leu Val Thr Leu Met Glu Arg Gln
705                 710                 715                 720

Ala Val Thr Phe Glu Gly Thr Asp Met Trp Glu Lys Asn Asp Gln Ser
                725                 730                 735

Cys Glu Ile Met Leu Asn His Leu Ala Thr Ala Arg Phe Met Ala Glu
            740                 745                 750

Ala Ala Asp Ser Tyr Arg Met Asn Ala Glu Arg Ile Leu Ala Gly Phe
        755                 760                 765

Gln Pro Asp Glu Glu Met Asn Glu Ile Cys Lys Thr Glu Phe Gln Met
    770                 775                 780

Arg Leu Leu Trp Gly Ser Lys Gly Ala Gln Val Asn Gln Thr Glu Arg
785                 790                 795                 800

Tyr Glu Lys Phe Asn Gln Ile Leu Thr Ala Leu Ser Arg Lys Leu Glu
                805                 810                 815

Pro Pro Pro Val Lys Gln Ala Glu Leu
            820                 825

<210> SEQ ID NO 5
<211> LENGTH: 911
<212> TYPE: DNA
<213> ORGANISM: Homo sapiens
<220> FEATURE:
<221> NAME/KEY: CDS
<222> LOCATION: (190)..(420)

<400> SEQUENCE: 5

aggcgcgcgg ctgcccgagc gccggccggg ccatgacccc cgctgctctg tcttgcaggc     60

tcgtcgccgc ggccccccga gcccgaccgc cgccgccacc accaccagcg cccgggcggg    120

cctcgcgcgc ctcgggcgcg gctccgcagt gagcccacca agaaggaagc ggcctgcaga    180

ggtgccgac atg ggg ctt aag atg tcc tgc ctg aaa ggc ttt caa atg tgt     231
          Met Gly Leu Lys Met Ser Cys Leu Lys Gly Phe Gln Met Cys
          1               5                   10
```

```
gtc agc agc agc agc agc agc cac gac gag gcc ccc gtc ctg aac gac      279
Val Ser Ser Ser Ser Ser Ser His Asp Glu Ala Pro Val Leu Asn Asp
15                  20                  25                  30

aag cac ctg gac gtg ccc gac atc atc atc acg ccc ccc acc ccc acg      327
Lys His Leu Asp Val Pro Asp Ile Ile Ile Thr Pro Pro Thr Pro Thr
                35                  40                  45

ggc atg atg ctg ccg agg gac ttg ggg agc aca gtc tgg ctg gat gag      375
Gly Met Met Leu Pro Arg Asp Leu Gly Ser Thr Val Trp Leu Asp Glu
            50                  55                  60

aca ggg tcg tgc cca gat gat gga gaa atc gac cca gaa gcc tga          420
Thr Gly Ser Cys Pro Asp Asp Gly Glu Ile Asp Pro Glu Ala
        65                  70                  75

ggaggtgtcc tgggtttggc tggctggctc ctgctccagc ggcccggctt caggtgtccg    480

ggggcgtggc tgcctggagc aggtgtgctg aataccctgg atgggaactg agcgaacccg    540

ggcctccgct cagagagacg tggcaggacc agcgaggaat ccagcctgtc cacttccaga    600

acagtgtttc ccaggccccg ctgagtggac cggacctctg acacctccag gttcttgctg    660

actccggcct ggtgaaaggg agcgccatgg tcctggctgt tggggtccca gggagaggct    720

ctcttctgga caaacacacc ctcccagccc ccagggctgt gcaaacacat gcccctgcca    780

taagcaccaa caagaacttc ttgcaggtgg agtggctgtt ttttataagt tgttttacag    840

atacggaaac agtccaaaat gggatttata atttcttttt tgcattataa ataaagatcc    900

tctgtaacaa a                                                         911


<210> SEQ ID NO 6
<211> LENGTH: 76
<212> TYPE: PRT
<213> ORGANISM: Homo sapiens

<400> SEQUENCE: 6

Met Gly Leu Lys Met Ser Cys Leu Lys Gly Phe Gln Met Cys Val Ser
1               5                   10                  15

Ser Ser Ser Ser Ser His Asp Glu Ala Pro Val Leu Asn Asp Lys His
            20                  25                  30

Leu Asp Val Pro Asp Ile Ile Ile Thr Pro Pro Thr Pro Thr Gly Met
        35                  40                  45

Met Leu Pro Arg Asp Leu Gly Ser Thr Val Trp Leu Asp Glu Thr Gly
    50                  55                  60

Ser Cys Pro Asp Asp Gly Glu Ile Asp Pro Glu Ala
65                  70                  75


<210> SEQ ID NO 7
<211> LENGTH: 3670
<212> TYPE: DNA
<213> ORGANISM: Homo sapiens
<220> FEATURE:
<221> NAME/KEY: CDS
<222> LOCATION: (94)..(2592)

<400> SEQUENCE: 7

agtcgtagca agagtctcga ccactgaatg gaagaaaagg acttttaacc accattttgt     60

gacttacaga aaggaatttg aataaagaaa act atg ata ctt cag gcc cat ctt     114
                                     Met Ile Leu Gln Ala His Leu
                                     1               5

cac tcc ctg tgt ctt ctt atg ctt tat ttg gca act gga tat ggc caa      162
His Ser Leu Cys Leu Leu Met Leu Tyr Leu Ala Thr Gly Tyr Gly Gln
        10                  15                  20

gag ggg aag ttt agt gga ccc ctg aaa ccc atg aca ttt tct att tat      210
```

-continued

```
Glu Gly Lys Phe Ser Gly Pro Leu Lys Pro Met Thr Phe Ser Ile Tyr
    25                  30                  35

gaa ggc caa gaa ccg agt caa att ata ttc cag ttt aag gcc aat cct      258
Glu Gly Gln Glu Pro Ser Gln Ile Ile Phe Gln Phe Lys Ala Asn Pro
40                  45                  50                  55

cct gct gtg act ttt gaa cta act ggg gag aca gac aac ata ttt gtg      306
Pro Ala Val Thr Phe Glu Leu Thr Gly Glu Thr Asp Asn Ile Phe Val
                60                  65                  70

ata gaa cgg gag gga ctt ctg tat tac aac aga gcc ttg gac agg gaa      354
Ile Glu Arg Glu Gly Leu Leu Tyr Tyr Asn Arg Ala Leu Asp Arg Glu
            75                  80                  85

aca aga tct act cac aat ctc cag gtt gca gcc ctg gac gct aat gga      402
Thr Arg Ser Thr His Asn Leu Gln Val Ala Ala Leu Asp Ala Asn Gly
        90                  95                  100

att ata gtg gag ggt cca gtc cct atc acc ata aaa gtg aag gac atc      450
Ile Ile Val Glu Gly Pro Val Pro Ile Thr Ile Lys Val Lys Asp Ile
    105                 110                 115

aac gac aat cga ccc acg ttt ctc cag tca aag tac gaa ggc tca gta      498
Asn Asp Asn Arg Pro Thr Phe Leu Gln Ser Lys Tyr Glu Gly Ser Val
120                 125                 130                 135

agg cag aac tct cgc cca gga aag ccc ttc ttg tat gtc aat gcc aca      546
Arg Gln Asn Ser Arg Pro Gly Lys Pro Phe Leu Tyr Val Asn Ala Thr
                140                 145                 150

gac ctg gat gat ccg gcc act ccc aat ggc cag ctt tat tac cag att      594
Asp Leu Asp Asp Pro Ala Thr Pro Asn Gly Gln Leu Tyr Tyr Gln Ile
            155                 160                 165

gtc atc cag ctt ccc atg atc aac aat gtc atg tac ttt cag atc aac      642
Val Ile Gln Leu Pro Met Ile Asn Asn Val Met Tyr Phe Gln Ile Asn
        170                 175                 180

aac aaa acg gga gcc atc tct ctt acc cga gag gga tct cag gaa ttg      690
Asn Lys Thr Gly Ala Ile Ser Leu Thr Arg Glu Gly Ser Gln Glu Leu
    185                 190                 195

aat cct gct aag aat cct tcc tat aat ctg gtg atc tca gtg aag gac      738
Asn Pro Ala Lys Asn Pro Ser Tyr Asn Leu Val Ile Ser Val Lys Asp
200                 205                 210                 215

atg gga ggc cag agt gag aat tcc ttc agt gat acc aca tct gtg gat      786
Met Gly Gly Gln Ser Glu Asn Ser Phe Ser Asp Thr Thr Ser Val Asp
                220                 225                 230

atc ata gtg aca gag aat att tgg aaa gca cca aaa cct gtg gag atg      834
Ile Ile Val Thr Glu Asn Ile Trp Lys Ala Pro Lys Pro Val Glu Met
            235                 240                 245

gtg gaa aac tca act gat cct cac ccc atc aaa atc act cag gtg cgg      882
Val Glu Asn Ser Thr Asp Pro His Pro Ile Lys Ile Thr Gln Val Arg
        250                 255                 260

tgg aat gat ccc ggt gca caa tat tcc tta gtt gac aaa gag aag ctg      930
Trp Asn Asp Pro Gly Ala Gln Tyr Ser Leu Val Asp Lys Glu Lys Leu
    265                 270                 275

cca aga ttc cca ttt tca att gac cag gaa gga gat att tac gtg act      978
Pro Arg Phe Pro Phe Ser Ile Asp Gln Glu Gly Asp Ile Tyr Val Thr
280                 285                 290                 295

cag ccc ttg gac cga gaa gaa aag gat gca tat gtt ttt tat gca gtt     1026
Gln Pro Leu Asp Arg Glu Glu Lys Asp Ala Tyr Val Phe Tyr Ala Val
                300                 305                 310

gca aag gat gag tac gga aaa cca ctt tca tat ccg ctg gaa att cat     1074
Ala Lys Asp Glu Tyr Gly Lys Pro Leu Ser Tyr Pro Leu Glu Ile His
            315                 320                 325

gta aaa gtt aaa gat att aat gat aat cca cct aca tgt ccg tca cca     1122
Val Lys Val Lys Asp Ile Asn Asp Asn Pro Pro Thr Cys Pro Ser Pro
        330                 335                 340
```

-continued

```
gta acc gta ttt gag gtc cag gag aat gaa cga ctg ggt aac agt atc     1170
Val Thr Val Phe Glu Val Gln Glu Asn Glu Arg Leu Gly Asn Ser Ile
    345                 350                 355

ggg acc ctt act gca cat gac agg gat gaa gaa aat act gcc aac agt     1218
Gly Thr Leu Thr Ala His Asp Arg Asp Glu Glu Asn Thr Ala Asn Ser
360                 365                 370                 375

ttt cta aac tac agg att gtg gag caa act ccc aaa ctt ccc atg gat     1266
Phe Leu Asn Tyr Arg Ile Val Glu Gln Thr Pro Lys Leu Pro Met Asp
                380                 385                 390

gga ctc ttc cta atc caa acc tat gct gga atg tta cag tta gct aaa     1314
Gly Leu Phe Leu Ile Gln Thr Tyr Ala Gly Met Leu Gln Leu Ala Lys
            395                 400                 405

cag tcc ttg aag aag caa gat act cct cag tac aac tta acg ata gag     1362
Gln Ser Leu Lys Lys Gln Asp Thr Pro Gln Tyr Asn Leu Thr Ile Glu
        410                 415                 420

gtg tct gac aaa gat ttc aag acc ctt tgt ttt gtg caa atc aac gtt     1410
Val Ser Asp Lys Asp Phe Lys Thr Leu Cys Phe Val Gln Ile Asn Val
    425                 430                 435

att gat atc aat gat cag atc ccc atc ttt gaa aaa tca gat tat gga     1458
Ile Asp Ile Asn Asp Gln Ile Pro Ile Phe Glu Lys Ser Asp Tyr Gly
440                 445                 450                 455

aac ctg act ctt gct gaa gac aca aac att ggg tcc acc atc tta acc     1506
Asn Leu Thr Leu Ala Glu Asp Thr Asn Ile Gly Ser Thr Ile Leu Thr
                460                 465                 470

atc cag gcc act gat gct gat gag cca ttt act ggg agt tct aaa att     1554
Ile Gln Ala Thr Asp Ala Asp Glu Pro Phe Thr Gly Ser Ser Lys Ile
            475                 480                 485

ctg tat cat atc ata aag gga gac agt gag gga cgc ctg ggg gtt gac     1602
Leu Tyr His Ile Ile Lys Gly Asp Ser Glu Gly Arg Leu Gly Val Asp
        490                 495                 500

aca gat ccc cat acc aac acc gga tat gtc ata att aaa aag cct ctt     1650
Thr Asp Pro His Thr Asn Thr Gly Tyr Val Ile Ile Lys Lys Pro Leu
    505                 510                 515

gat ttt gaa aca gca gct gtt tcc aac att gtg ttc aaa gca gaa aat     1698
Asp Phe Glu Thr Ala Ala Val Ser Asn Ile Val Phe Lys Ala Glu Asn
520                 525                 530                 535

cct gag cct cta gtg ttt ggt gtg aag tac aat gca agt tct ttt gcc     1746
Pro Glu Pro Leu Val Phe Gly Val Lys Tyr Asn Ala Ser Ser Phe Ala
                540                 545                 550

aag ttc acg ctt att gtg aca gat gtg aat gaa gca cct caa ttt tcc     1794
Lys Phe Thr Leu Ile Val Thr Asp Val Asn Glu Ala Pro Gln Phe Ser
            555                 560                 565

caa cac gta ttc caa gcg aaa gtc agt gag gat gta gct ata ggc act     1842
Gln His Val Phe Gln Ala Lys Val Ser Glu Asp Val Ala Ile Gly Thr
        570                 575                 580

aaa gtg ggc aat gtg act gcc aag gat cca gaa ggt ctg gac ata agc     1890
Lys Val Gly Asn Val Thr Ala Lys Asp Pro Glu Gly Leu Asp Ile Ser
    585                 590                 595

tat tca ctg agg gga gac aca aga ggt tgg ctt aaa att gac cac gtg     1938
Tyr Ser Leu Arg Gly Asp Thr Arg Gly Trp Leu Lys Ile Asp His Val
600                 605                 610                 615

act ggt gag atc ttt agt gtg gct cca ttg gac aga gaa gcc gga agt     1986
Thr Gly Glu Ile Phe Ser Val Ala Pro Leu Asp Arg Glu Ala Gly Ser
                620                 625                 630

cca tat cgg gta caa gtg gtg gcc aca gaa gta ggg ggg tct tcc ttg     2034
Pro Tyr Arg Val Gln Val Val Ala Thr Glu Val Gly Gly Ser Ser Leu
            635                 640                 645

agc tct gtg tca gag ttc cac ctg atc ctt atg gat gtg aat gac aac     2082
Ser Ser Val Ser Glu Phe His Leu Ile Leu Met Asp Val Asn Asp Asn
        650                 655                 660
```

```
cct ccc agg cta gcc aag gac tac acg ggc ttg ttc ttc tgc cat ccc     2130
Pro Pro Arg Leu Ala Lys Asp Tyr Thr Gly Leu Phe Phe Cys His Pro
    665                 670                 675

ctc agt gca cct gga agt ctc att ttc gag gct act gat gat gat cag     2178
Leu Ser Ala Pro Gly Ser Leu Ile Phe Glu Ala Thr Asp Asp Asp Gln
680                 685                 690                 695

cac tta ttt cgg ggt ccc cat ttt aca ttt tcc ctc ggc agt gga agc     2226
His Leu Phe Arg Gly Pro His Phe Thr Phe Ser Leu Gly Ser Gly Ser
                700                 705                 710

tta caa aac gac tgg gaa gtt tcc aaa atc aat ggt act cat gcc cga     2274
Leu Gln Asn Asp Trp Glu Val Ser Lys Ile Asn Gly Thr His Ala Arg
            715                 720                 725

ctg tct acc agg cac aca gag ttt gag gag agg gag tat gtc gtc ttg     2322
Leu Ser Thr Arg His Thr Glu Phe Glu Glu Arg Glu Tyr Val Val Leu
        730                 735                 740

atc cgc atc aat gat ggg ggt cgg cca ccc ttg gaa ggc att gtt tct     2370
Ile Arg Ile Asn Asp Gly Gly Arg Pro Pro Leu Glu Gly Ile Val Ser
    745                 750                 755

tta cca gtt aca ttc tgc agt tgt gtg gaa gga agt tgt ttc cgg cca     2418
Leu Pro Val Thr Phe Cys Ser Cys Val Glu Gly Ser Cys Phe Arg Pro
760                 765                 770                 775

gca ggt cac cag act ggg ata ccc act gtg ggc atg gca gtt ggt ata     2466
Ala Gly His Gln Thr Gly Ile Pro Thr Val Gly Met Ala Val Gly Ile
                780                 785                 790

ctg ctg acc acc ctt ctg gtg att ggt ata att tta gca gtt gtg ttt     2514
Leu Leu Thr Thr Leu Leu Val Ile Gly Ile Ile Leu Ala Val Val Phe
            795                 800                 805

atc cgc ata aag aag gat aaa ggc aaa gat aat gtt gaa agt gct caa     2562
Ile Arg Ile Lys Lys Asp Lys Gly Lys Asp Asn Val Glu Ser Ala Gln
        810                 815                 820

gca tct gaa gtc aaa cct ctg aga agc tga atttgaaaag gaatgtttga       2612
Ala Ser Glu Val Lys Pro Leu Arg Ser
    825                 830

atttatatag caagtgctat ttcagcaaca accatctcat cctattactt ttcatctaac   2672

gtgcattata attttttaaa cagatattcc ctcttgtcct ttaatatttg ctaaatattt   2732

ctttttttgag gtggagtctt gctctgtcgc ccaggctgga gtacagtggt gtgatcccag   2792

ctcactgcaa cctccgcctc ctgggttcac atgattctcc tgcctcagct tcctaagtag   2852

ctgggtttac aggcacccac caccatgccc agctaatttt tgtattttta atagagacgg   2912

ggtttcgcca tttggccagg ctggtcttga actcctgacg tcaagtgatc tgcctgcctt   2972

ggtctcccaa tacaggcatg aaccactgca cccacctact tagatatttc atgtgctata   3032

gacattagag agatttttca tttttccatg acatttttcc tctctgcaaa tggcttagct   3092

acttgtgttt ttcccttttg gggcaagaca gactcattaa atattctgta catttttttct   3152

ttatcaagga gatatatcag tgttgtctca tagaactgcc tggattccat ttatgttttt   3212

tctgattcca tcctgtgtcc ccttcatcct tgactccttt ggtatttcac tgaatttcaa   3272

acatttgtca gagaagaaaa acgtgaggac tcaggaaaaa taaataaata aaagaacagc   3332

cttttccctt agtattaaca gaaatgtttc tgtgtcatta accatcttta atcaatgtga   3392

catgttgctc tttggctgaa attcttcaac ttggaaatga cacagaccca cagaaggtgt   3452

tcaaacacaa cctactctgc aaaccttggt aaaggaacca gtcagctggc cagatttcct   3512

cactacctgc catgcataca tgctgcgcat gttttcttca ttcgtatgtt agtaaagttt   3572

tggttattat atatttaaca tgtggaagaa aacaagacat gaaaagagtg gtgacaaatc   3632
```

aagaataaac actggttgta gtcagttttg tttgttga 3670

<210> SEQ ID NO 8
<211> LENGTH: 832
<212> TYPE: PRT
<213> ORGANISM: Homo sapiens

<400> SEQUENCE: 8

Met Ile Leu Gln Ala His Leu His Ser Leu Cys Leu Leu Met Leu Tyr
1 5 10 15

Leu Ala Thr Gly Tyr Gly Gln Glu Gly Lys Phe Ser Gly Pro Leu Lys
20 25 30

Pro Met Thr Phe Ser Ile Tyr Glu Gly Gln Glu Pro Ser Gln Ile Ile
35 40 45

Phe Gln Phe Lys Ala Asn Pro Pro Ala Val Thr Phe Glu Leu Thr Gly
50 55 60

Glu Thr Asp Asn Ile Phe Val Ile Glu Arg Glu Gly Leu Leu Tyr Tyr
65 70 75 80

Asn Arg Ala Leu Asp Arg Glu Thr Arg Ser Thr His Asn Leu Gln Val
85 90 95

Ala Ala Leu Asp Ala Asn Gly Ile Ile Val Glu Gly Pro Val Pro Ile
100 105 110

Thr Ile Lys Val Lys Asp Ile Asn Asp Asn Arg Pro Thr Phe Leu Gln
115 120 125

Ser Lys Tyr Glu Gly Ser Val Arg Gln Asn Ser Arg Pro Gly Lys Pro
130 135 140

Phe Leu Tyr Val Asn Ala Thr Asp Leu Asp Asp Pro Ala Thr Pro Asn
145 150 155 160

Gly Gln Leu Tyr Tyr Gln Ile Val Ile Gln Leu Pro Met Ile Asn Asn
165 170 175

Val Met Tyr Phe Gln Ile Asn Asn Lys Thr Gly Ala Ile Ser Leu Thr
180 185 190

Arg Glu Gly Ser Gln Glu Leu Asn Pro Ala Lys Asn Pro Ser Tyr Asn
195 200 205

Leu Val Ile Ser Val Lys Asp Met Gly Gly Gln Ser Glu Asn Ser Phe
210 215 220

Ser Asp Thr Thr Ser Val Asp Ile Ile Val Thr Glu Asn Ile Trp Lys
225 230 235 240

Ala Pro Lys Pro Val Glu Met Val Glu Asn Ser Thr Asp Pro His Pro
245 250 255

Ile Lys Ile Thr Gln Val Arg Trp Asn Asp Pro Gly Ala Gln Tyr Ser
260 265 270

Leu Val Asp Lys Glu Lys Leu Pro Arg Phe Pro Phe Ser Ile Asp Gln
275 280 285

Glu Gly Asp Ile Tyr Val Thr Gln Pro Leu Asp Arg Glu Glu Lys Asp
290 295 300

Ala Tyr Val Phe Tyr Ala Val Ala Lys Asp Glu Tyr Gly Lys Pro Leu
305 310 315 320

Ser Tyr Pro Leu Glu Ile His Val Lys Val Lys Asp Ile Asn Asp Asn
325 330 335

Pro Pro Thr Cys Pro Ser Pro Val Thr Val Phe Glu Val Gln Glu Asn
340 345 350

Glu Arg Leu Gly Asn Ser Ile Gly Thr Leu Thr Ala His Asp Arg Asp
355 360 365

```
Glu Glu Asn Thr Ala Asn Ser Phe Leu Asn Tyr Arg Ile Val Glu Gln
    370                 375                 380

Thr Pro Lys Leu Pro Met Asp Gly Leu Phe Leu Ile Gln Thr Tyr Ala
385                 390                 395                 400

Gly Met Leu Gln Leu Ala Lys Gln Ser Leu Lys Lys Gln Asp Thr Pro
                405                 410                 415

Gln Tyr Asn Leu Thr Ile Glu Val Ser Asp Lys Asp Phe Lys Thr Leu
            420                 425                 430

Cys Phe Val Gln Ile Asn Val Ile Asp Ile Asn Asp Gln Ile Pro Ile
        435                 440                 445

Phe Glu Lys Ser Asp Tyr Gly Asn Leu Thr Leu Ala Glu Asp Thr Asn
    450                 455                 460

Ile Gly Ser Thr Ile Leu Thr Ile Gln Ala Thr Asp Ala Asp Glu Pro
465                 470                 475                 480

Phe Thr Gly Ser Ser Lys Ile Leu Tyr His Ile Ile Lys Gly Asp Ser
                485                 490                 495

Glu Gly Arg Leu Gly Val Asp Thr Asp Pro His Thr Asn Thr Gly Tyr
            500                 505                 510

Val Ile Ile Lys Lys Pro Leu Asp Phe Glu Thr Ala Ala Val Ser Asn
        515                 520                 525

Ile Val Phe Lys Ala Glu Asn Pro Glu Pro Leu Val Phe Gly Val Lys
    530                 535                 540

Tyr Asn Ala Ser Ser Phe Ala Lys Phe Thr Leu Ile Val Thr Asp Val
545                 550                 555                 560

Asn Glu Ala Pro Gln Phe Ser Gln His Val Phe Gln Ala Lys Val Ser
                565                 570                 575

Glu Asp Val Ala Ile Gly Thr Lys Val Gly Asn Val Thr Ala Lys Asp
            580                 585                 590

Pro Glu Gly Leu Asp Ile Ser Tyr Ser Leu Arg Gly Asp Thr Arg Gly
        595                 600                 605

Trp Leu Lys Ile Asp His Val Thr Gly Glu Ile Phe Ser Val Ala Pro
    610                 615                 620

Leu Asp Arg Glu Ala Gly Ser Pro Tyr Arg Val Gln Val Val Ala Thr
625                 630                 635                 640

Glu Val Gly Gly Ser Ser Leu Ser Ser Val Ser Glu Phe His Leu Ile
                645                 650                 655

Leu Met Asp Val Asn Asp Asn Pro Pro Arg Leu Ala Lys Asp Tyr Thr
            660                 665                 670

Gly Leu Phe Phe Cys His Pro Leu Ser Ala Pro Gly Ser Leu Ile Phe
        675                 680                 685

Glu Ala Thr Asp Asp Asp Gln His Leu Phe Arg Gly Pro His Phe Thr
    690                 695                 700

Phe Ser Leu Gly Ser Gly Ser Leu Gln Asn Asp Trp Glu Val Ser Lys
705                 710                 715                 720

Ile Asn Gly Thr His Ala Arg Leu Ser Thr Arg His Thr Glu Phe Glu
                725                 730                 735

Glu Arg Glu Tyr Val Val Leu Ile Arg Ile Asn Asp Gly Gly Arg Pro
            740                 745                 750

Pro Leu Glu Gly Ile Val Ser Leu Pro Val Thr Phe Cys Ser Cys Val
        755                 760                 765

Glu Gly Ser Cys Phe Arg Pro Ala Gly His Gln Thr Gly Ile Pro Thr
    770                 775                 780

Val Gly Met Ala Val Gly Ile Leu Leu Thr Thr Leu Leu Val Ile Gly
```

-continued

```
785                 790                 795                 800

Ile Ile Leu Ala Val Val Phe Ile Arg Ile Lys Lys Asp Lys Gly Lys
                805                 810                 815

Asp Asn Val Glu Ser Ala Gln Ala Ser Glu Val Lys Pro Leu Arg Ser
            820                 825                 830


<210> SEQ ID NO 9
<211> LENGTH: 3355
<212> TYPE: DNA
<213> ORGANISM: Homo sapiens
<220> FEATURE:
<221> NAME/KEY: CDS
<222> LOCATION: (62)..(847)

<400> SEQUENCE: 9

acaccttcgg cagcaggagg gcggcagctt ctcgcaggcg gcagggcggg cggccaggat      60

c atg tcc acc acc aca tgc caa gtg gtg gcg ttc ctc ctg tcc atc ctg     109
  Met Ser Thr Thr Thr Cys Gln Val Val Ala Phe Leu Leu Ser Ile Leu
  1               5                   10                  15

ggg ctg gcc ggc tgc atc gcg gcc acc ggg atg gac atg tgg agc acc       157
Gly Leu Ala Gly Cys Ile Ala Ala Thr Gly Met Asp Met Trp Ser Thr
            20                  25                  30

cag gac ctg tac gac aac ccc gtc acc tcc gtg ttc cag tac gaa ggg       205
Gln Asp Leu Tyr Asp Asn Pro Val Thr Ser Val Phe Gln Tyr Glu Gly
        35                  40                  45

ctc tgg agg agc tgc gtg agg cag agt tca ggc ttc acc gaa tgc agg       253
Leu Trp Arg Ser Cys Val Arg Gln Ser Ser Gly Phe Thr Glu Cys Arg
    50                  55                  60

ccc tat ttc acc atc ctg gga ctt cca gcc atg ctg cag gca gtg cga       301
Pro Tyr Phe Thr Ile Leu Gly Leu Pro Ala Met Leu Gln Ala Val Arg
65                  70                  75                  80

gcc ctg atg atc gta ggc atc gtc ctg ggt gcc att ggc ctc ctg gta       349
Ala Leu Met Ile Val Gly Ile Val Leu Gly Ala Ile Gly Leu Leu Val
                85                  90                  95

tcc atc ttt gcc ctg aaa tgc atc cgc att ggc agc atg gag gac tct       397
Ser Ile Phe Ala Leu Lys Cys Ile Arg Ile Gly Ser Met Glu Asp Ser
            100                 105                 110

gcc aaa gcc aac atg aca ctg acc tcc ggg atc atg ttc att gtc tca       445
Ala Lys Ala Asn Met Thr Leu Thr Ser Gly Ile Met Phe Ile Val Ser
        115                 120                 125

ggt ctt tgt gca att gct gga gtg tct gtg ttt gcc aac atg ctg gtg       493
Gly Leu Cys Ala Ile Ala Gly Val Ser Val Phe Ala Asn Met Leu Val
    130                 135                 140

act aac ttc tgg atg tcc aca gct aac atg tac acc ggc atg ggt ggg       541
Thr Asn Phe Trp Met Ser Thr Ala Asn Met Tyr Thr Gly Met Gly Gly
145                 150                 155                 160

atg gtg cag act gtt cag acc agg tac aca ttt ggt gcg gct ctg ttc       589
Met Val Gln Thr Val Gln Thr Arg Tyr Thr Phe Gly Ala Ala Leu Phe
                165                 170                 175

gtg ggc tgg gtc gct gga ggc ctc aca cta att ggg ggt gtg atg atg       637
Val Gly Trp Val Ala Gly Gly Leu Thr Leu Ile Gly Gly Val Met Met
            180                 185                 190

tgc atc gcc tgc cgg ggc ctg gca cca gaa gaa acc aac tac aaa gcc       685
Cys Ile Ala Cys Arg Gly Leu Ala Pro Glu Glu Thr Asn Tyr Lys Ala
        195                 200                 205

gtt tct tat cat gcc tca ggc cac agt gtt gcc tac aag cct gga ggc       733
Val Ser Tyr His Ala Ser Gly His Ser Val Ala Tyr Lys Pro Gly Gly
    210                 215                 220

ttc aag gcc agc act ggc ttt ggg tcc aac acc aaa aac aag aag ata       781
Phe Lys Ala Ser Thr Gly Phe Gly Ser Asn Thr Lys Asn Lys Lys Ile
```

```
225                 230                 235                 240

tac gat gga ggt gcc cgc aca gag gac gag gta caa tct tat cct tcc      829
Tyr Asp Gly Gly Ala Arg Thr Glu Asp Glu Val Gln Ser Tyr Pro Ser
                245                 250                 255

aag cac gac tat gtg taa tgctctaaga cctctcagca cgggcggaag             877
Lys His Asp Tyr Val
            260

aaactcccgg agagctcacc caaaaaacaa ggagatccca tctagatttc ttcttgcttt    937

tgactcacag ctggaagtta gaaaagcctc gatttcatct ttggagaggc caaatggtct    997

tagcctcagt ctctgtctct aaatattcca ccataaaaca gctgagttat ttatgaatta   1057

gaggctatag ctcacatttt caatcctcta tttctttttt taaatataac tttctactct   1117

gatgagagaa tgtggtttta atctctctct cacattttga tgatttagac agactccccc   1177

tcttcctcct agtcaataaa cccattgatg atctatttcc cagcttatcc ccaagaaaac   1237

ttttgaaagg aaagagtaga cccaaagatg ttattttctg ctgtttgaat tttgtctccc   1297

cacccccaac ttggctagta ataaacactt actgaagaag aagcaataag agaaagatat   1357

ttgtaatctc tccagcccat gatctcggtt ttcttacact gtgatcttaa aagttaccaa   1417

accaaagtca ttttcagttt gaggcaacca aacctttcta ctgctgttga catcttctta   1477

ttacagcaac accattctag gagtttcctg agctctccac tggagtcctc tttctgtcgc   1537

gggtcagaaa ttgtccctag atgaatgaga aaattatttt ttttaattta agtcctaaat   1597

atagttaaaa taaataatgt tttagtaaaa tgatacacta tctctgtgaa atagcctcac   1657

ccctacatgt ggatagaagg aaatgaaaaa ataattgctt tgacattgtc tatatggtac   1717

tttgtaaagt catgcttaag tacaaattcc atgaaaagct cactgatcct aattctttcc   1777

ctttgaggtc tctatggctc tgattgtaca tgatagtaag tgtaagccat gtaaaaagta   1837

aataatgtct gggcacagtg gctcacgcct gtaatcctag cactttggga ggctgaggag   1897

gaaggatcac ttgagcccag aagttcgaga ctagcctggg caacatggag aagccctgtc   1957

tctacaaaat acagagagaa aaaatcagcc agtcatggtg gcctacacct gtagtcccag   2017

cattccggga ggctgaggtg ggaggatcac ttgagcccag ggaggttggg gctgcagtga   2077

gccatgatca caccactgca ctccagccag gtgacatagc gagatcctgt ctaaaaaaat   2137

aaaaaataaa taatggaaca cagcaagtcc taggaagtag gttaaaacta attctttaaa   2197

aaaaaaaaaa agttgagcct gaattaaatg taatgtttcc aagtgacagg tatccacatt   2257

tgcatggtta caagccactg ccagttagca gtagcacttt cctggcactg tggtcggttt   2317

tgttttgttt tgctttgttt agagacgggg tctcactttc caggctggcc tcaaactcct   2377

gcactcaagc aattcttcta ccctggcctc ccaagtagct ggaattacag gtgtgcgcca   2437

tcacaactag ctggtggtca gttttgttac tctgagagct gttcacttct ctgaattcac   2497

ctagagtggt tggaccatca gatgtttggg caaaactgaa agctctttgc aaccacacac   2557

cttccctgag cttacatcac tgcccttttg agcagaaagt ctaaattcct tccaagacag   2617

tagaattcca tcccagtacc aaagccagat aggcccccta ggaaactgag gtaagagcag   2677

tctctaaaaa ctacccacag cagcattggt gcaggggaac ttggccatta ggttattatt   2737

tgagaggaaa gtcctcacat caatagtaca tatgaaagtg acctccaagg ggattggtga   2797

atactcataa ggatcttcag gctgaacaga ctatgtctgg ggaaagaacg gattatgccc   2857

cattaaataa caagttgtgt tcaagagtca gagcagtgag ctcagaggcc cttctcactg   2917

agacagcaac atttaaacca aaccagagga agtatttgtg gaactcactg cctcagtttg   2977
```

```
ggtaaaggat gagcagacaa gtcaactaaa gaaaaaagaa aagcaaggag gagggttgag   3037

caatctagag catggagttt gttaagtgct ctctggattt gagttgaaga gcatccattt   3097

gagttgaagg ccacagggca caatgagctc tcccttctac caccagaaag tccctggtca   3157

ggtctcaggt agtgcggtgt ggctcagctg ggtttttaat tagcgcattc tctatccaac   3217

atttaattgt ttgaaagcct ccatatagtt agattgtgct ttgtaatttt gttgttgttg   3277

ctctatctta ttgtatatgc attgagtatt aacctgaatg ttttgttact taaatattaa   3337

aaacactgtt atcctaca                                                  3355
```

<210> SEQ ID NO 10
<211> LENGTH: 261
<212> TYPE: PRT
<213> ORGANISM: Homo sapiens

<400> SEQUENCE: 10

```
Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 11
<211> LENGTH: 1146
<212> TYPE: DNA
<213> ORGANISM: Homo sapiens

```
<220> FEATURE:
<221> NAME/KEY: CDS
<222> LOCATION: (158)..(838)

<400> SEQUENCE: 11

cattagcata acccttcctc aggaagagtg agattttata tttgacaata aagtgttaga     60

ctccatttct aaataccaga cttcaaaaga taaggttcaa aagtgttata agaagatatt    120

ccttttttg tcctagagaa cttattttcc tgtgaaa atg cct acc aca aag aag     175
                                        Met Pro Thr Thr Lys Lys
                                        1               5

aca ttg atg ttc tta tca agc ttt ttc acc agc ctt ggg tcc ttc att      223
Thr Leu Met Phe Leu Ser Ser Phe Phe Thr Ser Leu Gly Ser Phe Ile
            10                  15                  20

gta att tgc tct att ctt ggg aca caa gca tgg atc acc agt aca att      271
Val Ile Cys Ser Ile Leu Gly Thr Gln Ala Trp Ile Thr Ser Thr Ile
        25                  30                  35

gct gtt aga gac tct gct tca aat ggg agc att ttc atc act tac gga      319
Ala Val Arg Asp Ser Ala Ser Asn Gly Ser Ile Phe Ile Thr Tyr Gly
    40                  45                  50

ctt ttt cgt ggg gag agt agt gaa gaa ttg agt cac gga ctt gca gaa      367
Leu Phe Arg Gly Glu Ser Ser Glu Glu Leu Ser His Gly Leu Ala Glu
55                  60                  65                  70

cca aag aaa aag ttt gca gtt tta gag ata ctg aat aat tct tcc caa      415
Pro Lys Lys Lys Phe Ala Val Leu Glu Ile Leu Asn Asn Ser Ser Gln
                75                  80                  85

aaa act ctg cat tcg gtg act atc ctg ttc ctg gtc ctg agt ttg atc      463
Lys Thr Leu His Ser Val Thr Ile Leu Phe Leu Val Leu Ser Leu Ile
            90                  95                  100

acg tcg ctg ctg agc tct ggg ttt acc ttc tac aac agc atc agc aac      511
Thr Ser Leu Leu Ser Ser Gly Phe Thr Phe Tyr Asn Ser Ile Ser Asn
        105                 110                 115

cct tac cag aca ttc ctg ggg ccg acg ggg gtg tac acc tgg aac ggg      559
Pro Tyr Gln Thr Phe Leu Gly Pro Thr Gly Val Tyr Thr Trp Asn Gly
    120                 125                 130

ctc ggt gca tcc ttc gtt ttt gtg acc atg ata ctg ttt gtg gcg aac      607
Leu Gly Ala Ser Phe Val Phe Val Thr Met Ile Leu Phe Val Ala Asn
135                 140                 145                 150

acg cag tcc aac caa ctc tcc gaa gag ttg ttc caa atg ctt tac ccg      655
Thr Gln Ser Asn Gln Leu Ser Glu Glu Leu Phe Gln Met Leu Tyr Pro
                155                 160                 165

gca acc acc agt aaa gga acg acc cac agt tac gga tac tcg ttc tgg      703
Ala Thr Thr Ser Lys Gly Thr Thr His Ser Tyr Gly Tyr Ser Phe Trp
            170                 175                 180

ctc ata ctg ctc gtc att ctt cta aat ata gtc act gta acc atc atc      751
Leu Ile Leu Leu Val Ile Leu Leu Asn Ile Val Thr Val Thr Ile Ile
        185                 190                 195

att ttc tac cag aag gcc aga tac cag cgg aag cag gag cag aga aag      799
Ile Phe Tyr Gln Lys Ala Arg Tyr Gln Arg Lys Gln Glu Gln Arg Lys
    200                 205                 210

cca atg gaa tat gct cca agg gac gga att tta ttc tga attctctttc       848
Pro Met Glu Tyr Ala Pro Arg Asp Gly Ile Leu Phe
215                 220                 225

atctcatttt ggcgttgcat ctattgtaca tcagccctga gtagtaactg gttagcttct    908

ctggacaatt cagcatggta acgtgactgt catctgtgac agcatttgtg tttcatgaca    968

ctgtgttctt cattgatgct gtactcctga aaatttttcc cacaaggttg gggaaatgaa   1028

tgggaaatgt cgctggtctg tgtggtattc aaagcagtag tatcatgatg agcgtaacga   1088

cccttctgac ctggtctcac gatctgaaat aataaaaggc tgtgtcatgt ttcttttc     1146
```

<210> SEQ ID NO 12
<211> LENGTH: 226
<212> TYPE: PRT
<213> ORGANISM: Homo sapiens

<400> SEQUENCE: 12

```
Met Pro Thr Thr Lys Lys Thr Leu Met Phe Leu Ser Ser Phe Phe Thr
1               5                   10                  15

Ser Leu Gly Ser Phe Ile Val Ile Cys Ser Ile Leu Gly Thr Gln Ala
            20                  25                  30

Trp Ile Thr Ser Thr Ile Ala Val Arg Asp Ser Ala Ser Asn Gly Ser
        35                  40                  45

Ile Phe Ile Thr Tyr Gly Leu Phe Arg Gly Glu Ser Ser Glu Glu Leu
    50                  55                  60

Ser His Gly Leu Ala Glu Pro Lys Lys Lys Phe Ala Val Leu Glu Ile
65                  70                  75                  80

Leu Asn Asn Ser Ser Gln Lys Thr Leu His Ser Val Thr Ile Leu Phe
                85                  90                  95

Leu Val Leu Ser Leu Ile Thr Ser Leu Leu Ser Ser Gly Phe Thr Phe
            100                 105                 110

Tyr Asn Ser Ile Ser Asn Pro Tyr Gln Thr Phe Leu Gly Pro Thr Gly
        115                 120                 125

Val Tyr Thr Trp Asn Gly Leu Gly Ala Ser Phe Val Phe Val Thr Met
    130                 135                 140

Ile Leu Phe Val Ala Asn Thr Gln Ser Asn Gln Leu Ser Glu Glu Leu
145                 150                 155                 160

Phe Gln Met Leu Tyr Pro Ala Thr Thr Ser Lys Gly Thr Thr His Ser
                165                 170                 175

Tyr Gly Tyr Ser Phe Trp Leu Ile Leu Leu Val Ile Leu Leu Asn Ile
            180                 185                 190

Val Thr Val Thr Ile Ile Ile Phe Tyr Gln Lys Ala Arg Tyr Gln Arg
        195                 200                 205

Lys Gln Glu Gln Arg Lys Pro Met Glu Tyr Ala Pro Arg Asp Gly Ile
    210                 215                 220

Leu Phe
225
```

<210> SEQ ID NO 13
<211> LENGTH: 2214
<212> TYPE: DNA
<213> ORGANISM: Homo sapiens
<220> FEATURE:
<221> NAME/KEY: CDS
<222> LOCATION: (105)..(1295)

<400> SEQUENCE: 13

```
agactgggct gggcaggtct gagagttagg gaaagtccgt tcccactgcc ctcggggaga      60

gaagaaagga gggggcaagg gagaagctgc tggtcggact caca atg aaa acg ctc      116
                                                 Met Lys Thr Leu
                                                 1

ctt ctt ttg ctg ctg gtg ctc ctg gag ctg gga gag gcc caa gga tcc      164
Leu Leu Leu Leu Leu Val Leu Leu Glu Leu Gly Glu Ala Gln Gly Ser
5                   10                  15                  20

ctt cac agg gtg ccc ctc agg agg cat ccg tcc ctc aag aag aag ctg      212
Leu His Arg Val Pro Leu Arg Arg His Pro Ser Leu Lys Lys Lys Leu
                25                  30                  35
```

-continued

```
cgg gca cgg agc cag ctc tct gag ttc tgg aaa tcc cat aat ttg gac      260
Arg Ala Arg Ser Gln Leu Ser Glu Phe Trp Lys Ser His Asn Leu Asp
            40                  45                  50

atg atc cag ttc acc gag tcc tgc tca atg gac cag agt gcc aag gaa      308
Met Ile Gln Phe Thr Glu Ser Cys Ser Met Asp Gln Ser Ala Lys Glu
        55                  60                  65

ccc ctc atc aac tac ttg gat atg gaa tac ttc ggc act atc tcc att      356
Pro Leu Ile Asn Tyr Leu Asp Met Glu Tyr Phe Gly Thr Ile Ser Ile
    70                  75                  80

ggc tcc cca cca cag aac ttc act gtc atc ttc gac act ggc tcc tcc      404
Gly Ser Pro Pro Gln Asn Phe Thr Val Ile Phe Asp Thr Gly Ser Ser
85                  90                  95                  100

aac ctc tgg gtc ccc tct gtg tac tgc act agc cca gcc tgc aag acg      452
Asn Leu Trp Val Pro Ser Val Tyr Cys Thr Ser Pro Ala Cys Lys Thr
                105                 110                 115

cac agc agg ttc cag cct tcc cag tcc agc aca tac agc cag cca ggt      500
His Ser Arg Phe Gln Pro Ser Gln Ser Ser Thr Tyr Ser Gln Pro Gly
            120                 125                 130

caa tct ttc tcc att cag tat gga acc ggg agc ttg tcc ggg atc att      548
Gln Ser Phe Ser Ile Gln Tyr Gly Thr Gly Ser Leu Ser Gly Ile Ile
        135                 140                 145

gga gcc gac caa gtc tct gtg gaa gga cta acc gtg gtt ggc cag cag      596
Gly Ala Asp Gln Val Ser Val Glu Gly Leu Thr Val Val Gly Gln Gln
    150                 155                 160

ttt gga gaa agt gtc aca gag cca ggc cag acc ttt gtg gat gca gag      644
Phe Gly Glu Ser Val Thr Glu Pro Gly Gln Thr Phe Val Asp Ala Glu
165                 170                 175                 180

ttt gat gga att ctg ggc ctg gga tac ccc tcc ttg gct gtg gga gga      692
Phe Asp Gly Ile Leu Gly Leu Gly Tyr Pro Ser Leu Ala Val Gly Gly
                185                 190                 195

gtg act cca gta ttt gac aac atg atg gct cag aac ctg gtg gac ttg      740
Val Thr Pro Val Phe Asp Asn Met Met Ala Gln Asn Leu Val Asp Leu
            200                 205                 210

ccg atg ttt tct gtc tac atg agc agt aac cca gaa ggt ggt gcg ggg      788
Pro Met Phe Ser Val Tyr Met Ser Ser Asn Pro Glu Gly Gly Ala Gly
        215                 220                 225

agc gag ctg att ttt gga ggc tac gac cac tcc cat ttc tct ggg agc      836
Ser Glu Leu Ile Phe Gly Gly Tyr Asp His Ser His Phe Ser Gly Ser
    230                 235                 240

ctg aat tgg gtc cca gtc acc aag caa gct tac tgg cag att gca ctg      884
Leu Asn Trp Val Pro Val Thr Lys Gln Ala Tyr Trp Gln Ile Ala Leu
245                 250                 255                 260

gat aac atc cag gtg gga ggc act gtt atg ttc tgc tcc gag ggc tgc      932
Asp Asn Ile Gln Val Gly Gly Thr Val Met Phe Cys Ser Glu Gly Cys
                265                 270                 275

cag gcc att gtg gac aca ggg act tcc ctc atc act ggc cct tcc gac      980
Gln Ala Ile Val Asp Thr Gly Thr Ser Leu Ile Thr Gly Pro Ser Asp
            280                 285                 290

aag att aag cag ctg caa aac gcc att ggg gca gcc ccc gtg gat gga     1028
Lys Ile Lys Gln Leu Gln Asn Ala Ile Gly Ala Ala Pro Val Asp Gly
        295                 300                 305

gaa tat gct gtg gag tgt gcc aac ctt aac gtc atg ccg gat gtc acc     1076
Glu Tyr Ala Val Glu Cys Ala Asn Leu Asn Val Met Pro Asp Val Thr
    310                 315                 320

ttc acc att aac gga gtc ccc tat acc ctc agc cca act gcc tac acc     1124
Phe Thr Ile Asn Gly Val Pro Tyr Thr Leu Ser Pro Thr Ala Tyr Thr
325                 330                 335                 340

cta ctg gac ttc gtg gat gga atg cag ttc tgc agc agt ggc ttt caa     1172
Leu Leu Asp Phe Val Asp Gly Met Gln Phe Cys Ser Ser Gly Phe Gln
                345                 350                 355
```

```
gga ctt gac atc cac cct cca gct ggg ccc ctc tgg atc ctg ggg gat      1220
Gly Leu Asp Ile His Pro Pro Ala Gly Pro Leu Trp Ile Leu Gly Asp
            360                 365                 370

gtc ttc att cga cag ttt tac tca gtc ttt gac cgt ggg aat aac cgt      1268
Val Phe Ile Arg Gln Phe Tyr Ser Val Phe Asp Arg Gly Asn Asn Arg
        375                 380                 385

gtg gga ctg gcc cca gca gtc ccc taa ggaggggcct tgtgtctgtg            1315
Val Gly Leu Ala Pro Ala Val Pro
    390                 395

cctgcctgtc tgacagacct tgaatatgtt aggctggggc attctttaca cctacaaaaa   1375

gttattttcc agagaatgta gctgtttcca gggttgcaac ttgaattaag accaaacaga   1435

acatgagaat acacacacac acacacatat acacacacac acacttcaca catacacacc   1495

actcccacca ccgtcatgat ggaggaatta cgttatacat tcatattttg tattgatttt   1555

tgattatgaa aatcaaaaat tttcacattt gattatgaaa atctccaaac atatgcacaa   1615

gcagagatca tggtataata aatccctttg caactccact cagccctgac aacccatcca   1675

cacacggcca ggcctgttta tctacactgc tgcccactcc tctctccagc tccacatgct   1735

gtacctggat cattctgaag caaattccga gcattacatc attttgtcca taaatatttc   1795

taacatcctt aaatatacaa tcggaattca agcatctccc attgtcccac aaatgtttgg   1855

ctgtttttgt agttggattg tttgtattag gattcaagca aggcccatat attgcattta   1915

tttgaaatgt ctgtaagtct ctttccatct acagagttta gcacatttga acgttgctgg   1975

ttgaaatccc gaggtgtcat ttgacatggt tctctgaact tatctttcct ataaaatggt   2035

agttagatct ggaggtctga ttttgtggca aaaatacttc ctaggtggtg ctgggtactt   2095

cttgttgcat cctgtcagga ggcagataat gctggtgcct ctctattggt aatgttaaga   2155

ctgctgggtg ggtttggagt tcttggcttt aatcattcat tacaaagttc agcatttta    2214


<210> SEQ ID NO 14
<211> LENGTH: 396
<212> TYPE: PRT
<213> ORGANISM: Homo sapiens

<400> SEQUENCE: 14

Met Lys Thr Leu Leu Leu Leu Leu Leu Val Leu Leu Glu Leu Gly Glu
1               5                   10                  15

Ala Gln Gly Ser Leu His Arg Val Pro Leu Arg Arg His Pro Ser Leu
            20                  25                  30

Lys Lys Lys Leu Arg Ala Arg Ser Gln Leu Ser Glu Phe Trp Lys Ser
        35                  40                  45

His Asn Leu Asp Met Ile Gln Phe Thr Glu Ser Cys Ser Met Asp Gln
    50                  55                  60

Ser Ala Lys Glu Pro Leu Ile Asn Tyr Leu Asp Met Glu Tyr Phe Gly
65                  70                  75                  80

Thr Ile Ser Ile Gly Ser Pro Pro Gln Asn Phe Thr Val Ile Phe Asp
                85                  90                  95

Thr Gly Ser Ser Asn Leu Trp Val Pro Ser Val Tyr Cys Thr Ser Pro
            100                 105                 110

Ala Cys Lys Thr His Ser Arg Phe Gln Pro Ser Gln Ser Ser Thr Tyr
        115                 120                 125

Ser Gln Pro Gly Gln Ser Phe Ser Ile Gln Tyr Gly Thr Gly Ser Leu
    130                 135                 140

Ser Gly Ile Ile Gly Ala Asp Gln Val Ser Val Glu Gly Leu Thr Val
```

145 150 155 160

Val Gly Gln Gln Phe Gly Glu Ser Val Thr Glu Pro Gly Gln Thr Phe
165 170 175

Val Asp Ala Glu Phe Asp Gly Ile Leu Gly Leu Gly Tyr Pro Ser Leu
180 185 190

Ala Val Gly Gly Val Thr Pro Val Phe Asp Asn Met Met Ala Gln Asn
195 200 205

Leu Val Asp Leu Pro Met Phe Ser Val Tyr Met Ser Ser Asn Pro Glu
210 215 220

Gly Gly Ala Gly Ser Glu Leu Ile Phe Gly Gly Tyr Asp His Ser His
225 230 235 240

Phe Ser Gly Ser Leu Asn Trp Val Pro Val Thr Lys Gln Ala Tyr Trp
245 250 255

Gln Ile Ala Leu Asp Asn Ile Gln Val Gly Gly Thr Val Met Phe Cys
260 265 270

Ser Glu Gly Cys Gln Ala Ile Val Asp Thr Gly Thr Ser Leu Ile Thr
275 280 285

Gly Pro Ser Asp Lys Ile Lys Gln Leu Gln Asn Ala Ile Gly Ala Ala
290 295 300

Pro Val Asp Gly Glu Tyr Ala Val Glu Cys Ala Asn Leu Asn Val Met
305 310 315 320

Pro Asp Val Thr Phe Thr Ile Asn Gly Val Pro Tyr Thr Leu Ser Pro
325 330 335

Thr Ala Tyr Thr Leu Leu Asp Phe Val Asp Gly Met Gln Phe Cys Ser
340 345 350

Ser Gly Phe Gln Gly Leu Asp Ile His Pro Pro Ala Gly Pro Leu Trp
355 360 365

Ile Leu Gly Asp Val Phe Ile Arg Gln Phe Tyr Ser Val Phe Asp Arg
370 375 380

Gly Asn Asn Arg Val Gly Leu Ala Pro Ala Val Pro
385 390 395

<210> SEQ ID NO 15
<211> LENGTH: 6128
<212> TYPE: DNA
<213> ORGANISM: Homo sapiens
<220> FEATURE:
<221> NAME/KEY: CDS
<222> LOCATION: (370)..(2697)

<400> SEQUENCE: 15
gggcctgcct gccagctagc cggagccgcg ggtgagcgcg gcgagcggcg accctggtga 60
ggagcgcggc gcgggaggca cgttccttag ctccgccgcg gccgtcctcc gcggctcgag 120
gactccgctt ccttccctcc cctcccctgc gctccggcct ggggtctcgg cgcggggagc 180
ggagggaagg gacgaaggag gagtaggtga aagcggggtg aggggcggaa gggtcccggc 240
gcggggtgag gcgagggctg cctcttgttc tcccgccgct gccgccgtct cctggtcggg 300
tgccgcggcc agaggcgcgc ggggctgccg aggcacccgc actatgcagg cagactgccg 360 gccgccgcg atg gcg agc cgg gcg gtg gtg aga gcc agg cgc tgc ccg cag 411
Met Ala Ser Arg Ala Val Val Arg Ala Arg Arg Cys Pro Gln
1 5 10 tgt ccc caa gtc cgg gcc gcg gcc gcc gcc ccc gcc tgg gcc gcg ctc 459
Cys Pro Gln Val Arg Ala Ala Ala Ala Ala Pro Ala Trp Ala Ala Leu
15 20 25 30 ccc ctc tcc cgc tcc ctc cct ccc tgc tcc aac tcc tcc tcc ttc tcc 507

-continued

```
Pro Leu Ser Arg Ser Leu Pro Pro Cys Ser Asn Ser Ser Ser Phe Ser
                35                  40                  45

atg cct ctg ttc ctc ctg ctc tta ctt gtc ctg ctc ctg ctg ctc gag      555
Met Pro Leu Phe Leu Leu Leu Leu Leu Val Leu Leu Leu Leu Leu Glu
            50                  55                  60

gac gct gga gcc cag caa ggt gat gga tgt gga cac act gta cta ggc      603
Asp Ala Gly Ala Gln Gln Gly Asp Gly Cys Gly His Thr Val Leu Gly
        65                  70                  75

cct gag agt gga acc ctt aca tcc ata aac tac cca cag acc tat ccc      651
Pro Glu Ser Gly Thr Leu Thr Ser Ile Asn Tyr Pro Gln Thr Tyr Pro
    80                  85                  90

aac agc act gtt tgt gaa tgg gag atc cgt gta aag atg gga gag aga      699
Asn Ser Thr Val Cys Glu Trp Glu Ile Arg Val Lys Met Gly Glu Arg
95                  100                 105                 110

gtt cgc atc aaa ttt ggt gac ttt gac att gaa gat tct gat tct tgt      747
Val Arg Ile Lys Phe Gly Asp Phe Asp Ile Glu Asp Ser Asp Ser Cys
                115                 120                 125

cac ttt aat tac ttg aga att tat aat gga att gga gtc agc aga act      795
His Phe Asn Tyr Leu Arg Ile Tyr Asn Gly Ile Gly Val Ser Arg Thr
            130                 135                 140

gaa ata ggc aaa tac tgt ggt ctg ggg ttg caa atg aac cat tca att      843
Glu Ile Gly Lys Tyr Cys Gly Leu Gly Leu Gln Met Asn His Ser Ile
        145                 150                 155

gaa tca aaa ggc aat gaa atc aca ttg ctg ttc atg agt gga atc cat      891
Glu Ser Lys Gly Asn Glu Ile Thr Leu Leu Phe Met Ser Gly Ile His
    160                 165                 170

gtt tct gga cgc gga ttt ttg gcc tca tac tct gtt ata gat aaa caa      939
Val Ser Gly Arg Gly Phe Leu Ala Ser Tyr Ser Val Ile Asp Lys Gln
175                 180                 185                 190

gat cta att act tgt ttg gac act gca tcc aat ttt ttg gaa cct gag      987
Asp Leu Ile Thr Cys Leu Asp Thr Ala Ser Asn Phe Leu Glu Pro Glu
                195                 200                 205

ttc agt aag tac tgc cca gct ggt tgt ctg ctt cct ttt gct gag ata     1035
Phe Ser Lys Tyr Cys Pro Ala Gly Cys Leu Leu Pro Phe Ala Glu Ile
            210                 215                 220

tct gga aca att cct cat gga tat aga gat tcc tcg cca ttg tgc atg     1083
Ser Gly Thr Ile Pro His Gly Tyr Arg Asp Ser Ser Pro Leu Cys Met
        225                 230                 235

gct ggt gtg cat gca gga gta gtg tca aac acg ttg ggc ggc caa atc     1131
Ala Gly Val His Ala Gly Val Val Ser Asn Thr Leu Gly Gly Gln Ile
    240                 245                 250

agt gtt gta att agt aaa ggt atc ccc tat tat gaa agt tct ttg gct     1179
Ser Val Val Ile Ser Lys Gly Ile Pro Tyr Tyr Glu Ser Ser Leu Ala
255                 260                 265                 270

aac aac gtc aca tct gtg gtg gga cac tta tct aca agt ctt ttt aca     1227
Asn Asn Val Thr Ser Val Val Gly His Leu Ser Thr Ser Leu Phe Thr
                275                 280                 285

ttt aag aca agt gga tgt tat gga aca ctg ggg atg gag tct ggt gtg     1275
Phe Lys Thr Ser Gly Cys Tyr Gly Thr Leu Gly Met Glu Ser Gly Val
            290                 295                 300

atc gcg gat cct caa ata aca gca tca tct gtg ctg gag tgg act gac     1323
Ile Ala Asp Pro Gln Ile Thr Ala Ser Ser Val Leu Glu Trp Thr Asp
        305                 310                 315

cac aca ggg caa gag aac agt tgg aaa ccc aaa aaa gcc agg ctg aaa     1371
His Thr Gly Gln Glu Asn Ser Trp Lys Pro Lys Lys Ala Arg Leu Lys
    320                 325                 330

aaa cct gga ccg cct tgg gct gct ttt gcc act gat gaa tac cag tgg     1419
Lys Pro Gly Pro Pro Trp Ala Ala Phe Ala Thr Asp Glu Tyr Gln Trp
335                 340                 345                 350
```

-continued

```
tta caa ata gat ttg aat aag gaa aag aaa ata aca ggc att ata acc      1467
Leu Gln Ile Asp Leu Asn Lys Glu Lys Lys Ile Thr Gly Ile Ile Thr
                355                 360                 365

act gga tcc acc atg gtg gag cac aat tac tat gtg tct gcc tac aga      1515
Thr Gly Ser Thr Met Val Glu His Asn Tyr Tyr Val Ser Ala Tyr Arg
            370                 375                 380

atc ctg tac agt gat gat ggg cag aaa tgg act gtg tac aga gag cct      1563
Ile Leu Tyr Ser Asp Asp Gly Gln Lys Trp Thr Val Tyr Arg Glu Pro
        385                 390                 395

ggt gtg gag caa gat aag ata ttt caa gga aac aaa gat tat cac cag      1611
Gly Val Glu Gln Asp Lys Ile Phe Gln Gly Asn Lys Asp Tyr His Gln
    400                 405                 410

gat gtg cgt aat aac ttt ttg cca cca att att gca cgt ttt att aga      1659
Asp Val Arg Asn Asn Phe Leu Pro Pro Ile Ile Ala Arg Phe Ile Arg
415                 420                 425                 430

gtg aat cct acc caa tgg cag cag aaa att gcc atg aaa atg gag ctg      1707
Val Asn Pro Thr Gln Trp Gln Gln Lys Ile Ala Met Lys Met Glu Leu
                435                 440                 445

ctc gga tgt cag ttt att cct aaa ggt cgt cct cca aaa ctt act caa      1755
Leu Gly Cys Gln Phe Ile Pro Lys Gly Arg Pro Pro Lys Leu Thr Gln
            450                 455                 460

cct cca cct cct cgg aac agc aat gac ctc aaa aac act aca gcc cct      1803
Pro Pro Pro Pro Arg Asn Ser Asn Asp Leu Lys Asn Thr Thr Ala Pro
        465                 470                 475

cca aaa ata gcc aaa ggt cgt gcc cca aaa ttt acg caa cca cta caa      1851
Pro Lys Ile Ala Lys Gly Arg Ala Pro Lys Phe Thr Gln Pro Leu Gln
    480                 485                 490

cct cgc agt agc aat gaa ttt cct gca cag aca gaa caa aca act gcc      1899
Pro Arg Ser Ser Asn Glu Phe Pro Ala Gln Thr Glu Gln Thr Thr Ala
495                 500                 505                 510

agt cct gat atc aga aat act acc gta act cca aat gta acc aaa gat      1947
Ser Pro Asp Ile Arg Asn Thr Thr Val Thr Pro Asn Val Thr Lys Asp
                515                 520                 525

gta gcg ctg gct gca gtt ctt gtc cct gtg ctg gtc atg gtc ctc act      1995
Val Ala Leu Ala Ala Val Leu Val Pro Val Leu Val Met Val Leu Thr
            530                 535                 540

act ctc att ctc ata tta gtg tgt gct tgg cac tgg aga aac aga aag      2043
Thr Leu Ile Leu Ile Leu Val Cys Ala Trp His Trp Arg Asn Arg Lys
        545                 550                 555

aaa aaa act gaa ggc acc tat gac tta cct tac tgg gac cgg gca ggt      2091
Lys Lys Thr Glu Gly Thr Tyr Asp Leu Pro Tyr Trp Asp Arg Ala Gly
    560                 565                 570

tgg tgg aaa gga atg aag cag ttt ctt cct gca aaa gca gtg gac cat      2139
Trp Trp Lys Gly Met Lys Gln Phe Leu Pro Ala Lys Ala Val Asp His
575                 580                 585                 590

gag gaa acc cca gtt cgc tat agc agc agc gaa gtt aat cac ctg agt      2187
Glu Glu Thr Pro Val Arg Tyr Ser Ser Ser Glu Val Asn His Leu Ser
                595                 600                 605

cca aga gaa gtc acc aca gtg ctg cag gct gac tct gca gag tat gct      2235
Pro Arg Glu Val Thr Thr Val Leu Gln Ala Asp Ser Ala Glu Tyr Ala
            610                 615                 620

cag cca ctg gta gga gga att gtt ggt aca ctt cat caa aga tct acc      2283
Gln Pro Leu Val Gly Gly Ile Val Gly Thr Leu His Gln Arg Ser Thr
        625                 630                 635

ttt aaa cca gaa gaa gga aaa gaa gca ggc tat gca gac cta gat cct      2331
Phe Lys Pro Glu Glu Gly Lys Glu Ala Gly Tyr Ala Asp Leu Asp Pro
    640                 645                 650

tac aac tca cca ggg cag gaa gtt tat cat gcc tat gct gaa cca ctc      2379
Tyr Asn Ser Pro Gly Gln Glu Val Tyr His Ala Tyr Ala Glu Pro Leu
655                 660                 665                 670
```

-continued

```
cca att acg ggg cct gag tat gca acc cca atc atc atg gac atg tca     2427
Pro Ile Thr Gly Pro Glu Tyr Ala Thr Pro Ile Ile Met Asp Met Ser
                675                 680                 685

ggg cac ccc aca act tca gtt ggt cag ccc tcc aca tcc act ttc aag     2475
Gly His Pro Thr Thr Ser Val Gly Gln Pro Ser Thr Ser Thr Phe Lys
            690                 695                 700

gct acg ggg aac caa cct ccc cca cta gtg gga act tac aat aca ctt     2523
Ala Thr Gly Asn Gln Pro Pro Pro Leu Val Gly Thr Tyr Asn Thr Leu
        705                 710                 715

ctc tcc agg act gac agc tgc tcc tca gcc cag gcc cag tat gat acc     2571
Leu Ser Arg Thr Asp Ser Cys Ser Ser Ala Gln Ala Gln Tyr Asp Thr
    720                 725                 730

ccg aaa gct ggg aag cca ggt cta cct gcc cca gac gaa ttg gtg tac     2619
Pro Lys Ala Gly Lys Pro Gly Leu Pro Ala Pro Asp Glu Leu Val Tyr
735                 740                 745                 750

cag gtg cca cag agc aca caa gaa gta tca gga gca gga agg gat ggg     2667
Gln Val Pro Gln Ser Thr Gln Glu Val Ser Gly Ala Gly Arg Asp Gly
                755                 760                 765

gaa tgt gat gtt ttt aaa gaa atc ctt tga agatgatgct gctttttaca       2717
Glu Cys Asp Val Phe Lys Glu Ile Leu
            770                 775

aagcatcgtt ttaaagcaca tggccttttt tttttaatta ttagtggtag taatatatag   2777

aatgtattac ataactgtca ctgaagtggt tggggaaaat gtggtgactg aggtacagga   2837

aactactaat cttgccatct tgctttaagg tgttatggtg gcacagttac tgctcgcctg   2897

ttaaatttca aatgtcctgt ttgatactac tgtagaacac tatttttaat acagaaaaag   2957

ctccctataa tgcacttcag agaaattaaa aatcacagag tatttattac caatgctgca   3017

ggtacattaa tgaactcgag atggctctgt aagcctgact ggcaataacg cacggtactg   3077

ttcttgaaat acctaatggc ttgaaattct agtctgtttg tgaaagatgg gtactatcat   3137

gatttcctct tctattccta tattcttttc tggatttttt ttaataatta gtgatataag   3197

cattgttttt attgcagcca tatccactta tccatcttaa gatctgtagc tgggattttc   3257

tgacttgtaa tgagcagggg gattgctttt tcactttgtg acactcttta gagctttaat   3317

gcttcacagt atatggcctg gtctcatcct tgcgtgttcc acttgaggcc ctttggtgtc   3377

ttgccccatt cttgtgttta taaaatgttt gagtatttct gatgagtgat gcttgcctta   3437

gtctcatgaa ttcagatccc ttcatgtcct ttaagtatgc tcctcaatgt gtaaacagga   3497

acaactttat gatttgaaag ctttaaagga gattcttctc ccaccccccaa ctttatttgc   3557

aatgggattt ttcctaggag agttatgaaa agttgaaggc ttctaaggga atactgtaaa   3617

catgacccac ttatatttat cacagtgaaa ggcaaaatta ttcactcaga agtaatataa   3677

attacctctt taaaaagtaa ccagaatttg tcctttttgg ttttatacat tcacaaacat   3737

atacattttt cttgagtctc aaggtatttt atatttttag tcagaaaaaa taatttttca   3797

tttcagtttt ccataaactg ttacacaaaa tataaaccta acgtgtattt ttcaggactg   3857

cgtgatcgtg cactttgtgt ggtaagaggt ttgagtagtc ctatatgtca cctagggaac   3917

agacattata gcttactagc aaatgaatat tcatgccttg tttttgatac ctcctggcag   3977

cttccatgtc accacttgtt catacctgcc cagagctagt tttagacatg gcaaaataga   4037

aatcatctgt aatttattag ctaacaatgt aaaaccatct tttaaagcct tcagactgtc   4097

aagacgacat gagcagctca ccatatgata aaaatacata aatttgacat tccctcttcc   4157

ataaaccttt gtttgtagat ttaatgttga acagtacttt tccataaagt tctagtcact   4217
```

-continued

```
tctgttggcc tgagccacca gattatgatg ttgccagaat tcactcaatt tgaataaaga   4277

tgaacagtat ttgttttctt gtttccatga attatatcag tattctaaaa catcgcttca   4337

gaaagagaac tgtttatttc tgcaggcttc ctgtcctttt gtggtatggt tttttggcct   4397

tattttcact ggcttttcct tctccaaact ttgaggcgtg atttcattca ttgaagaatc   4457

aatacatatt ttgtttcaaa atgtttgaaa caaaagacat agatggtaga cttttattaa   4517

aacatatatg gatgtggaaa gcacatatat taatgcagtc atcccttttc aggtgggaag   4577

agagcaaacc agttgatttt ttaattcatc cttagtacac agagaatata cttttcctca   4637

agtaatatac ctgtttgaag ctttaagaga gatgtttttg gtaactattt cattttccca   4697

aagaagtttg ctattcttgt gttaattgtg tatacctgat tgttttttcc tggaggtttt   4757

tgttgttgtt gtttagtttt gggttttttt tttttttaaga ggggcaagtg ttttctgaaa   4817

tgatgcatat tttaagactc gattcatatt gccactgtgc tatccttgaa ctaccaataa   4877

tttttataaa atatctagtt tttactactt ttatataaac tttactttcc agatgaagag   4937

ctgagcctga ttcaaatggt ttttctgctt tatacttctt tttagttcat tggtttttat   4997

agtagaggtt ttctattttt tttttttttt tttttactac atttatatgt ctgatacata   5057

tacggctttg gagacaatca agtaacaact gaaaatgtga aagtaaccat atctgacaaa   5117

attcccttga atttttatcc tttgcttgca acatttaaga ctcaaagtca ctggtatatt   5177

ggattaagtt ttttcctgtt aatgcaatta tagaaataca tcggagacac aacaaatgtg   5237

gccattacag gtttcataaa attacactga cttggctgtt acttgatctt aggaaacagc   5297

acagtttaag atattgtgaa ttctgactta tactttatta aatgctgtaa atctaaatag   5357

atcctgttgg atgtgatggg tctagtccag tttatttaag ttcatgtttc actgtttgca   5417

ctttgcattg aacaatgggt ttattcgctg atgtaaacgg ttcgagtgaa gaattaatgc   5477

agtaagtatg acaacacata cacacttgcc tctccccatc tccagaagag gggagcagag   5537

tccgagctta tctaaatatg aatgtggcca caaagctgtg gaaggtgaca aagcttaaac   5597

acctttgccc tggctctgca ttgtcaccta gagagcaaga ggtctataga aacatcatgt   5657

cacatgaaac gattctctgc tttttggttc tgaacttgaa gtccctaaac tgcaaaatct   5717

aagagttggg tggttattaa aatgctttta aagtcaactg tggcaccaat tctaatgtaa   5777

tccaacttgt gactgttttt ttttgttttg ttttgttttt gtgtgtgtgt gtgtggcact   5837

gggaaaagtg gaaacaaaca tgtattgaaa tacatattgg aaataaaaat ggtttgagcg   5897

tcagtgatat tctcccagaa tgtacttatc ttacctcggc atgtactgta gtcactcagt   5957

atttgtatat gttgctagaa tttagattgt aaaatagtga aattttaatg tgttcatttg   6017

tttttaatgt atatatgtct tgctcagatt atttggttta aataaaacaa ccttgaggtt   6077

tgtagctttt ccttatacta taaaatgcca gattcttcta ttttaacctc a            6128
```

<210> SEQ ID NO 16
<211> LENGTH: 775
<212> TYPE: PRT
<213> ORGANISM: Homo sapiens

<400> SEQUENCE: 16

```
Met Ala Ser Arg Ala Val Val Arg Ala Arg Arg Cys Pro Gln Cys Pro
1               5                   10                  15

Gln Val Arg Ala Ala Ala Ala Ala Pro Ala Trp Ala Ala Leu Pro Leu
            20                  25                  30

Ser Arg Ser Leu Pro Pro Cys Ser Asn Ser Ser Ser Phe Ser Met Pro
```

-continued

```
        35                  40                  45

Leu Phe Leu Leu Leu Leu Leu Val Leu Leu Leu Leu Leu Glu Asp Ala
    50                  55                  60

Gly Ala Gln Gln Gly Asp Gly Cys Gly His Thr Val Leu Gly Pro Glu
65                  70                  75                  80

Ser Gly Thr Leu Thr Ser Ile Asn Tyr Pro Gln Thr Tyr Pro Asn Ser
                85                  90                  95

Thr Val Cys Glu Trp Glu Ile Arg Val Lys Met Gly Glu Arg Val Arg
            100                 105                 110

Ile Lys Phe Gly Asp Phe Asp Ile Glu Asp Ser Asp Ser Cys His Phe
        115                 120                 125

Asn Tyr Leu Arg Ile Tyr Asn Gly Ile Gly Val Ser Arg Thr Glu Ile
    130                 135                 140

Gly Lys Tyr Cys Gly Leu Gly Leu Gln Met Asn His Ser Ile Glu Ser
145                 150                 155                 160

Lys Gly Asn Glu Ile Thr Leu Leu Phe Met Ser Gly Ile His Val Ser
                165                 170                 175

Gly Arg Gly Phe Leu Ala Ser Tyr Ser Val Ile Asp Lys Gln Asp Leu
            180                 185                 190

Ile Thr Cys Leu Asp Thr Ala Ser Asn Phe Leu Glu Pro Glu Phe Ser
        195                 200                 205

Lys Tyr Cys Pro Ala Gly Cys Leu Leu Pro Phe Ala Glu Ile Ser Gly
    210                 215                 220

Thr Ile Pro His Gly Tyr Arg Asp Ser Ser Pro Leu Cys Met Ala Gly
225                 230                 235                 240

Val His Ala Gly Val Val Ser Asn Thr Leu Gly Gly Gln Ile Ser Val
                245                 250                 255

Val Ile Ser Lys Gly Ile Pro Tyr Tyr Glu Ser Ser Leu Ala Asn Asn
            260                 265                 270

Val Thr Ser Val Val Gly His Leu Ser Thr Ser Leu Phe Thr Phe Lys
        275                 280                 285

Thr Ser Gly Cys Tyr Gly Thr Leu Gly Met Glu Ser Gly Val Ile Ala
    290                 295                 300

Asp Pro Gln Ile Thr Ala Ser Ser Val Leu Glu Trp Thr Asp His Thr
305                 310                 315                 320

Gly Gln Glu Asn Ser Trp Lys Pro Lys Lys Ala Arg Leu Lys Lys Pro
                325                 330                 335

Gly Pro Pro Trp Ala Ala Phe Ala Thr Asp Glu Tyr Gln Trp Leu Gln
            340                 345                 350

Ile Asp Leu Asn Lys Glu Lys Lys Ile Thr Gly Ile Ile Thr Thr Gly
        355                 360                 365

Ser Thr Met Val Glu His Asn Tyr Tyr Val Ser Ala Tyr Arg Ile Leu
    370                 375                 380

Tyr Ser Asp Asp Gly Gln Lys Trp Thr Val Tyr Arg Glu Pro Gly Val
385                 390                 395                 400

Glu Gln Asp Lys Ile Phe Gln Gly Asn Lys Asp Tyr His Gln Asp Val
                405                 410                 415

Arg Asn Asn Phe Leu Pro Pro Ile Ile Ala Arg Phe Ile Arg Val Asn
            420                 425                 430

Pro Thr Gln Trp Gln Gln Lys Ile Ala Met Lys Met Glu Leu Leu Gly
        435                 440                 445

Cys Gln Phe Ile Pro Lys Gly Arg Pro Pro Lys Leu Thr Gln Pro Pro
    450                 455                 460
```

```
Pro Pro Arg Asn Ser Asn Asp Leu Lys Asn Thr Thr Ala Pro Pro Lys
465                 470                 475                 480

Ile Ala Lys Gly Arg Ala Pro Lys Phe Thr Gln Pro Leu Gln Pro Arg
                485                 490                 495

Ser Ser Asn Glu Phe Pro Ala Gln Thr Glu Gln Thr Thr Ala Ser Pro
            500                 505                 510

Asp Ile Arg Asn Thr Thr Val Thr Pro Asn Val Thr Lys Asp Val Ala
        515                 520                 525

Leu Ala Ala Val Leu Val Pro Val Leu Val Met Val Leu Thr Thr Leu
    530                 535                 540

Ile Leu Ile Leu Val Cys Ala Trp His Trp Arg Asn Arg Lys Lys Lys
545                 550                 555                 560

Thr Glu Gly Thr Tyr Asp Leu Pro Tyr Trp Asp Arg Ala Gly Trp Trp
                565                 570                 575

Lys Gly Met Lys Gln Phe Leu Pro Ala Lys Ala Val Asp His Glu Glu
            580                 585                 590

Thr Pro Val Arg Tyr Ser Ser Ser Glu Val Asn His Leu Ser Pro Arg
        595                 600                 605

Glu Val Thr Thr Val Leu Gln Ala Asp Ser Ala Glu Tyr Ala Gln Pro
    610                 615                 620

Leu Val Gly Gly Ile Val Gly Thr Leu His Gln Arg Ser Thr Phe Lys
625                 630                 635                 640

Pro Glu Glu Gly Lys Glu Ala Gly Tyr Ala Asp Leu Asp Pro Tyr Asn
                645                 650                 655

Ser Pro Gly Gln Glu Val Tyr His Ala Tyr Ala Glu Pro Leu Pro Ile
            660                 665                 670

Thr Gly Pro Glu Tyr Ala Thr Pro Ile Ile Met Asp Met Ser Gly His
        675                 680                 685

Pro Thr Thr Ser Val Gly Gln Pro Ser Thr Ser Thr Phe Lys Ala Thr
    690                 695                 700

Gly Asn Gln Pro Pro Pro Leu Val Gly Thr Tyr Asn Thr Leu Leu Ser
705                 710                 715                 720

Arg Thr Asp Ser Cys Ser Ser Ala Gln Ala Gln Tyr Asp Thr Pro Lys
                725                 730                 735

Ala Gly Lys Pro Gly Leu Pro Ala Pro Asp Glu Leu Val Tyr Gln Val
            740                 745                 750

Pro Gln Ser Thr Gln Glu Val Ser Gly Ala Gly Arg Asp Gly Glu Cys
        755                 760                 765

Asp Val Phe Lys Glu Ile Leu
    770                 775


<210> SEQ ID NO 17
<211> LENGTH: 1949
<212> TYPE: DNA
<213> ORGANISM: Homo sapiens
<220> FEATURE:
<221> NAME/KEY: CDS
<222> LOCATION: (87)..(1529)

<400> SEQUENCE: 17

aactgtcact gtggagagga gagagagagg acagagagca agtcactccc ggctgccttt      60

ttcacctctg acagagccca gacacc atg aac gca agt gaa ttc cga agg aga      113
                             Met Asn Ala Ser Glu Phe Arg Arg Arg
                             1               5

ggg aag gag atg gtg gat tac atg gcc aac tac atg gaa ggc att gag      161
```

-continued

```
Gly Lys Glu Met Val Asp Tyr Met Ala Asn Tyr Met Glu Gly Ile Glu
10                  15                  20                  25

gga cgc cag gtc tac cct gac gtg gag ccc ggg tac ctg cgg ccg ctg      209
Gly Arg Gln Val Tyr Pro Asp Val Glu Pro Gly Tyr Leu Arg Pro Leu
                30                  35                  40

atc cct gcc gct gcc cct cag gag cca gac acg ttt gag gac atc atc      257
Ile Pro Ala Ala Ala Pro Gln Glu Pro Asp Thr Phe Glu Asp Ile Ile
            45                  50                  55

aac gac gtt gag aag ata atc atg cct ggg gtg acg cac tgg cac agc      305
Asn Asp Val Glu Lys Ile Ile Met Pro Gly Val Thr His Trp His Ser
        60                  65                  70

ccc tac ttc ttc gcc tac ttc ccc act gcc agc tcg tac ccg gcc atg      353
Pro Tyr Phe Phe Ala Tyr Phe Pro Thr Ala Ser Ser Tyr Pro Ala Met
    75                  80                  85

ctt gcg gac atg ctg tgc ggg gcc att ggc tgc atc ggc ttc tcc tgg      401
Leu Ala Asp Met Leu Cys Gly Ala Ile Gly Cys Ile Gly Phe Ser Trp
90                  95                  100                 105

gcg gca agc cca gca tgc aca gag ctg gag act gtg atg atg gac tgg      449
Ala Ala Ser Pro Ala Cys Thr Glu Leu Glu Thr Val Met Met Asp Trp
                110                 115                 120

ctc ggg aag atg ctg gaa cta cca aag gca ttt ttg aat gag aaa gct      497
Leu Gly Lys Met Leu Glu Leu Pro Lys Ala Phe Leu Asn Glu Lys Ala
            125                 130                 135

gga gaa ggg gga gga gtg atc cag gga agt gcc agt gaa gcc acc ctg      545
Gly Glu Gly Gly Gly Val Ile Gln Gly Ser Ala Ser Glu Ala Thr Leu
        140                 145                 150

gtg gcc ctg ctg gcc gct cgg acc aaa gtg atc cat cgg ctg cag gca      593
Val Ala Leu Leu Ala Ala Arg Thr Lys Val Ile His Arg Leu Gln Ala
    155                 160                 165

gcg tcc cca gag ctc aca cag gcc gct atc atg gag aag ctg gtg gct      641
Ala Ser Pro Glu Leu Thr Gln Ala Ala Ile Met Glu Lys Leu Val Ala
170                 175                 180                 185

tac tca tcc gat cag gca cac tcc tca gtg gaa aga gct ggg tta att      689
Tyr Ser Ser Asp Gln Ala His Ser Ser Val Glu Arg Ala Gly Leu Ile
                190                 195                 200

ggt gga gtg aaa tta aaa gcc atc ccc tca gat ggc aac ttc gcc atg      737
Gly Gly Val Lys Leu Lys Ala Ile Pro Ser Asp Gly Asn Phe Ala Met
            205                 210                 215

cgt gcg tct gcc ctg cag gaa gcc ctg gag aga gac aaa gcg gct ggc      785
Arg Ala Ser Ala Leu Gln Glu Ala Leu Glu Arg Asp Lys Ala Ala Gly
        220                 225                 230

ctg att cct ttc ttt atg gtt gcc acc ctg ggg acc aca aca tgc tgc      833
Leu Ile Pro Phe Phe Met Val Ala Thr Leu Gly Thr Thr Thr Cys Cys
    235                 240                 245

tcc ttt gac aat ctc tta gaa gtc ggt cct atc tgc aac aag gaa gac      881
Ser Phe Asp Asn Leu Leu Glu Val Gly Pro Ile Cys Asn Lys Glu Asp
250                 255                 260                 265

ata tgg ctg cac gtt gat gca gcc tac gca ggc agt gca ttc atc tgc      929
Ile Trp Leu His Val Asp Ala Ala Tyr Ala Gly Ser Ala Phe Ile Cys
                270                 275                 280

cct gag ttc cgg cac ctt ctg aat gga gtg gag ttt gca gat tca ttc      977
Pro Glu Phe Arg His Leu Leu Asn Gly Val Glu Phe Ala Asp Ser Phe
            285                 290                 295

aac ttt aat ccc cac aaa tgg cta ttg gtg aat ttt gac tgt tct gcc     1025
Asn Phe Asn Pro His Lys Trp Leu Leu Val Asn Phe Asp Cys Ser Ala
        300                 305                 310

atg tgg gtg aaa aag aga aca gac tta acg gga gcc ttt aga ctg gac     1073
Met Trp Val Lys Lys Arg Thr Asp Leu Thr Gly Ala Phe Arg Leu Asp
    315                 320                 325
```

```
ccc act tac ctg aag cac agc cat cag gat tca ggg ctt atc act gac     1121
Pro Thr Tyr Leu Lys His Ser His Gln Asp Ser Gly Leu Ile Thr Asp
330                 335                 340                 345

tac cgg cat tgg cag ata cca ctg ggc aga aga ttt cgc tct ttg aaa     1169
Tyr Arg His Trp Gln Ile Pro Leu Gly Arg Arg Phe Arg Ser Leu Lys
                350                 355                 360

atg tgg ttt gta ttt agg atg tat gga gtc aaa gga ctg cag gct tat     1217
Met Trp Phe Val Phe Arg Met Tyr Gly Val Lys Gly Leu Gln Ala Tyr
            365                 370                 375

atc cgc aag cat gtc cag ctg tcc cat gag ttt gag tca ctg gtg cgc     1265
Ile Arg Lys His Val Gln Leu Ser His Glu Phe Glu Ser Leu Val Arg
        380                 385                 390

cag gat ccc cgc ttt gaa atc tgt gtg gaa gtc att ctg ggg ctt gtc     1313
Gln Asp Pro Arg Phe Glu Ile Cys Val Glu Val Ile Leu Gly Leu Val
    395                 400                 405

tgc ttt cgg cta aag ggt tcc aac aaa gtg aat gaa gct ctt ctg caa     1361
Cys Phe Arg Leu Lys Gly Ser Asn Lys Val Asn Glu Ala Leu Leu Gln
410                 415                 420                 425

aga ata aac agt gcc aaa aaa atc cac ttg gtt cca tgt cac ctc agg     1409
Arg Ile Asn Ser Ala Lys Lys Ile His Leu Val Pro Cys His Leu Arg
                430                 435                 440

gac aag ttt gtc ctg cgc ttt gcc atc tgt tct cgc acg gtg gaa tct     1457
Asp Lys Phe Val Leu Arg Phe Ala Ile Cys Ser Arg Thr Val Glu Ser
            445                 450                 455

gcc cat gtg cag cgg gcc tgg gaa cac atc aaa gag ctg gcg gcc gac     1505
Ala His Val Gln Arg Ala Trp Glu His Ile Lys Glu Leu Ala Ala Asp
        460                 465                 470

gtg ctg cga gca gag agg gag tag gagtgaagcc agctgcagga atcaaaaatt    1559
Val Leu Arg Ala Glu Arg Glu
    475                 480

gaagagagat atatctgaaa actggaataa gaagcaaata aatatcatcc tgccttcatg   1619

gaactcagct gtctgtggct tcccatgtct ttctccaaag ttatccagag ggttgtgatt   1679

ttgtctgctt agtatctcat caacaaagaa atattatttg ctaattaaaa agttaatctt   1739

catggccata gcttttattc attagctgtg atttttgttg attaaaacat tatagatttt   1799

catgttcttg cagtcatcag aagtggtagg aaagcctcac tgatatattt tccagggcaa   1859

tcaatgttca cgcaacttga aattatatct gtggtcttca aattgtcttt tgtcatgtgg   1919

ctaaatgcct aataaacaat tcaagtgaaa                                     1949


<210> SEQ ID NO 18
<211> LENGTH: 480
<212> TYPE: PRT
<213> ORGANISM: Homo sapiens

<400> SEQUENCE: 18

Met Asn Ala Ser Glu Phe Arg Arg Arg Gly Lys Glu Met Val Asp Tyr
1               5                   10                  15

Met Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Ala Pro Gln
        35                  40                  45

Glu Pro Asp Thr Phe Glu Asp Ile Ile Asn Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95
```

```
Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Glu Leu
        115                 120                 125

Pro Lys Ala Phe Leu Asn Glu Lys Ala Gly Glu Gly Gly Gly Val Ile
    130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Asn Phe Ala Met Arg Ala Ser Ala Leu Gln Glu
    210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
            420                 425                 430

Ile His Leu Val Pro Cys His Leu Arg Asp Lys Phe Val Leu Arg Phe
        435                 440                 445

Ala Ile Cys Ser Arg Thr Val Glu Ser Ala His Val Gln Arg Ala Trp
    450                 455                 460

Glu His Ile Lys Glu Leu Ala Ala Asp Val Leu Arg Ala Glu Arg Glu
465                 470                 475                 480
```

<210> SEQ ID NO 19
<211> LENGTH: 3624
<212> TYPE: DNA
<213> ORGANISM: Homo sapiens
<220> FEATURE:

-continued

<221> NAME/KEY: CDS
<222> LOCATION: (132)..(1919)

<400> SEQUENCE: 19

```
ggactcgcgc tcgcccgctg gcgccctcgg cttctctccg cgcctgggag caccctccgc      60

cgcggccgtt ctccatgcgc agcgcccgcc cgaggagcta gacgtcagct tggagcggcg     120

ccggaccgtg g atg gcc ttg act gac ggc ggc tgg tgc ttg ccg aag cgc      170
             Met Ala Leu Thr Asp Gly Gly Trp Cys Leu Pro Lys Arg
             1               5                   10

ttc ggg gcc gcg ggt gcg gac gcc agc gac tcc aga gcc ttt cca gcg      218
Phe Gly Ala Ala Gly Ala Asp Ala Ser Asp Ser Arg Ala Phe Pro Ala
    15                  20                  25

cgg gag ccc tcc acg ccg cct tcc ccc atc tct tcc tcg tcc tcc tcc      266
Arg Glu Pro Ser Thr Pro Pro Ser Pro Ile Ser Ser Ser Ser Ser Ser
30                  35                  40                  45

tgc tcc cgg ggc gga gag cgg ggc ccc ggc ggc gcc agc aac tgc ggg      314
Cys Ser Arg Gly Gly Glu Arg Gly Pro Gly Gly Ala Ser Asn Cys Gly
                50                  55                  60

acg cct cag ctc gac acg gag gcg gcg gcc gga ccc ccg gcc cgc tcg      362
Thr Pro Gln Leu Asp Thr Glu Ala Ala Ala Gly Pro Pro Ala Arg Ser
            65                  70                  75

ctg ctg ctc agt tcc tac gct tcg cat ccc ttc ggg gct ccc cac gga      410
Leu Leu Leu Ser Ser Tyr Ala Ser His Pro Phe Gly Ala Pro His Gly
        80                  85                  90

cct tcg gcg cct ggg gtc gcg ggc ccc ggg ggc aac ctg tcg agc tgg      458
Pro Ser Ala Pro Gly Val Ala Gly Pro Gly Gly Asn Leu Ser Ser Trp
    95                  100                 105

gag gac ttg ctg ctg ttc act gac ctc gac caa gcc gcg acc gcc agc      506
Glu Asp Leu Leu Leu Phe Thr Asp Leu Asp Gln Ala Ala Thr Ala Ser
110                 115                 120                 125

aag ctg ctg tgg tcc agc cgc ggc gcc aag ctg agc ccc ttc gca ccc      554
Lys Leu Leu Trp Ser Ser Arg Gly Ala Lys Leu Ser Pro Phe Ala Pro
                130                 135                 140

gag cag ccg gag gag atg tac cag acc ctc gcc gct ctc tcc agc cag      602
Glu Gln Pro Glu Glu Met Tyr Gln Thr Leu Ala Ala Leu Ser Ser Gln
            145                 150                 155

ggt ccg gcc gcc tac gac ggc gcg ccc ggc ggc ttc gtg cac tct gcg      650
Gly Pro Ala Ala Tyr Asp Gly Ala Pro Gly Gly Phe Val His Ser Ala
        160                 165                 170

gcc gcg gcg gca gca gcc gcg gcg gcg gcc agc tcc ccg gtc tac gtg      698
Ala Ala Ala Ala Ala Ala Ala Ala Ala Ala Ser Ser Pro Val Tyr Val
    175                 180                 185

ccc acc acc cgc gtg ggt tcc atg ctg ccc ggc cta ccg tac cac ctg      746
Pro Thr Thr Arg Val Gly Ser Met Leu Pro Gly Leu Pro Tyr His Leu
190                 195                 200                 205

cag ggg tcg ggc agt ggg cca gcc aac cac gcg ggc ggc gcg ggc gcg      794
Gln Gly Ser Gly Ser Gly Pro Ala Asn His Ala Gly Gly Ala Gly Ala
                210                 215                 220

cac ccc ggc tgg cct cag gcc tcg gcc gac agc cct cca tac ggc agc      842
His Pro Gly Trp Pro Gln Ala Ser Ala Asp Ser Pro Pro Tyr Gly Ser
            225                 230                 235

gga ggc ggc gcg gct ggc ggc ggg gcc gcg ggg cct ggc ggc gct ggc      890
Gly Gly Gly Ala Ala Gly Gly Gly Ala Ala Gly Pro Gly Gly Ala Gly
        240                 245                 250

tca gcc gcg gcg cac gtc tcg gcg cgc ttc ccc tac tct ccc agc ccg      938
Ser Ala Ala Ala His Val Ser Ala Arg Phe Pro Tyr Ser Pro Ser Pro
    255                 260                 265

ccc atg gcc aac ggc gcc gcg cgg gag ccg gga ggc tac gcg gcg gcg      986
Pro Met Ala Asn Gly Ala Ala Arg Glu Pro Gly Gly Tyr Ala Ala Ala
```

-continued

```
270                 275                 280                 285

ggc agt ggg ggc gcg gga ggc gtg agc ggc ggc ggc agt agc ctg gcg      1034
Gly Ser Gly Gly Ala Gly Gly Val Ser Gly Gly Gly Ser Ser Leu Ala
            290                 295                 300

gcc atg ggc ggc cgc gag ccc cag tac agc tcg ctg tcg gcc gcg cgg      1082
Ala Met Gly Gly Arg Glu Pro Gln Tyr Ser Ser Leu Ser Ala Ala Arg
        305                 310                 315

ccg ctg aac ggg acg tac cac cac cac cac cac cac cac cac cac cat      1130
Pro Leu Asn Gly Thr Tyr His His His His His His His His His His
    320                 325                 330

ccg agc ccc tac tcg ccc tac gtg ggg gcg cca ctg acg cct gcc tgg      1178
Pro Ser Pro Tyr Ser Pro Tyr Val Gly Ala Pro Leu Thr Pro Ala Trp
    335                 340                 345

ccc gcc gga ccc ttc gag acc ccg gtg ctg cac agc ctg cag agc cgc      1226
Pro Ala Gly Pro Phe Glu Thr Pro Val Leu His Ser Leu Gln Ser Arg
350                 355                 360                 365

gcc gga gcc ccg ctc ccg gtg ccc cgg ggt ccc agt gca gac ctg ctg      1274
Ala Gly Ala Pro Leu Pro Val Pro Arg Gly Pro Ser Ala Asp Leu Leu
                370                 375                 380

gag gac ctg tcc gag agc cgc gag tgc gtg aac tgc ggc tcc atc cag      1322
Glu Asp Leu Ser Glu Ser Arg Glu Cys Val Asn Cys Gly Ser Ile Gln
            385                 390                 395

acg ccg ctg tgg cgg cgg gac ggc acc ggc cac tac ctg tgc aac gcc      1370
Thr Pro Leu Trp Arg Arg Asp Gly Thr Gly His Tyr Leu Cys Asn Ala
        400                 405                 410

tgc ggg ctc tac agc aag atg aac ggc ctc agc cgg ccc ctc atc aag      1418
Cys Gly Leu Tyr Ser Lys Met Asn Gly Leu Ser Arg Pro Leu Ile Lys
    415                 420                 425

ccg cag aag cgc gtg cct tca tca cgg cgg ctt gga ttg tcc tgt gcc      1466
Pro Gln Lys Arg Val Pro Ser Ser Arg Arg Leu Gly Leu Ser Cys Ala
430                 435                 440                 445

aac tgt cac acc aca act acc acc tta tgg cgc aga aac gcc gag ggt      1514
Asn Cys His Thr Thr Thr Thr Thr Leu Trp Arg Arg Asn Ala Glu Gly
                450                 455                 460

gaa ccc gtg tgc aat gct tgt gga ctc tac atg aaa ctc cat ggg gtg      1562
Glu Pro Val Cys Asn Ala Cys Gly Leu Tyr Met Lys Leu His Gly Val
            465                 470                 475

ccc aga cca ctt gct atg aaa aaa gag gga att caa acc agg aaa cga      1610
Pro Arg Pro Leu Ala Met Lys Lys Glu Gly Ile Gln Thr Arg Lys Arg
        480                 485                 490

aaa cct aag aac ata aat aaa tca aag act tgc tct ggt aat agc aat      1658
Lys Pro Lys Asn Ile Asn Lys Ser Lys Thr Cys Ser Gly Asn Ser Asn
    495                 500                 505

aat tcc att ccc atg act cca act tcc acc tct tct aac tca gat gat      1706
Asn Ser Ile Pro Met Thr Pro Thr Ser Thr Ser Ser Asn Ser Asp Asp
510                 515                 520                 525

tgc agc aaa aat act tcc ccc aca aca caa cct aca gcc tca ggg gcg      1754
Cys Ser Lys Asn Thr Ser Pro Thr Thr Gln Pro Thr Ala Ser Gly Ala
                530                 535                 540

ggt gcc ccg gtg atg act ggt gcg gga gag agc acc aat ccc gag aac      1802
Gly Ala Pro Val Met Thr Gly Ala Gly Glu Ser Thr Asn Pro Glu Asn
            545                 550                 555

agc gag ctc aag tat tcg ggt caa gat ggg ctc tac ata ggc gtc agt      1850
Ser Glu Leu Lys Tyr Ser Gly Gln Asp Gly Leu Tyr Ile Gly Val Ser
        560                 565                 570

ctc gcc tcg ccg gcc gaa gtc acg tcc tcc gtg cga ccg gat tcc tgg      1898
Leu Ala Ser Pro Ala Glu Val Thr Ser Ser Val Arg Pro Asp Ser Trp
    575                 580                 585

tgc gcc ctg gcc ctg gcc tga gcccacgccg ccaggaggca gggagggctc         1949
```

```
Cys Ala Leu Ala Leu Ala
590                 595

cgccgcgggc ctcactccac tcgtgtctgc ttttgtgcag cggtccagac agtggcgact   2009

gcgctgacag aacgtgattc tcgtgccttt attttgaaag agatgttttt cccaagaggc   2069

ttgctgaaag agtgagagaa gatggaaggg aagggccagt gcaactgggc gcttgggcca   2129

ctccagccag cccgcctccg gggcggaccc tgctccactt ccagaagcca ggactaggac   2189

ctgggccttg cctgctatgg aatattgaga gagatttttt aaaaaagatt ttgcattttg   2249

tccaaaatca tgtgcttctt ctgatcaatt ttggttgttc cagaatttct tcataccttt   2309

tccacatcca gatttcatgt gcgttcatgg agaagatcac ttgaggccat ttggtacaca   2369

tctctggagg ctgagtcggt tcatgaggtc tcttatcaaa aatattactc agtttgcaag   2429

actgcattgt aactttaaca tacactgtga ctgacgtttc tcaaagttca tattgtgtgg   2489

ctgatctgaa gtcagtcgga atttgtaaac agggtagcaa acaagatatt tttcttccat   2549

gtatacaata atttttttaa aaagtgcaat ttgcgttgca gcaatcagtg ttaaatcatt   2609

tgcataagat ttaacagcat tttttataat gaatgtaaac attttaactt aatggtactt   2669

aaaataattt aaaagaaaaa tgttaactta gacattctta tgcttctttt acaactacat   2729

cccattttat atttccaatt gttaaagaaa aatatttcaa gaacaaatct tctctcagga   2789

aaattgcctt tctctatttg ttaagaattt ttatacaaga acaccaatat acccccttta   2849

ttttactgtg gaatatgtgc tggaaaaatt gcaacaacac tttactacct aacggatagc   2909

atttgtaaat actctaggta tctgtaaaca ctctgatgaa gtctgtatag tgtgactaac   2969

ccacaggcag gttggtttac attaattttt tttttgaat gggatgtcct atggaaacct    3029

atttcaccag agttttaaaa ataaaaaggg tattgttttg tcttctgtac agtgagttcc   3089

ttccctttc aaagctttct ttttatgctg tatgtgacta tagatattca tataaaacaa    3149

gtgcacgtga agtttgcaaa atgctttaag gccttccttt caaagcatag tccttttgga   3209

gccgttttgt accttttata ccttggctta tttgaagttg acacatgggg ttagttacta   3269

ctctccatgt gcattgggga cagtttttat aagtgggaag gactcagtat tattatattt   3329

gagatgataa gcattttgtt tgggaacaat gcttaaaaat attccagaaa gttcagattt   3389

tttttctttg tgaatgaaat atattctggc ccacgaacag ggcgatttcc tttcagtttt   3449

ttcctttgc aacgtgcctt gaagtctcaa agctcacctg aggttgcaga cgttaccccc    3509

aacagaagat aggtagaaat gattccagtg gcctctttgt attttcttca ttgttgagta   3569

gatttcagga aatcaggagg tgtttcacaa tacagaatga tggcctttaa ctgtg        3624
```

<210> SEQ ID NO 20
<211> LENGTH: 595
<212> TYPE: PRT
<213> ORGANISM: Homo sapiens

<400> SEQUENCE: 20

```
Met Ala Leu Thr Asp Gly Gly Trp Cys Leu Pro Lys Arg Phe Gly Ala
1               5                   10                  15

Ala Gly Ala Asp Ala Ser Asp Ser Arg Ala Phe Pro Ala Arg Glu Pro
            20                  25                  30

Ser Thr Pro Pro Ser Pro Ile Ser Ser Ser Ser Ser Ser Cys Ser Arg
        35                  40                  45

Gly Gly Glu Arg Gly Pro Gly Gly Ala Ser Asn Cys Gly Thr Pro Gln
    50                  55                  60
```

```
Leu Asp Thr Glu Ala Ala Ala Gly Pro Pro Ala Arg Ser Leu Leu Leu
65                  70                  75                  80

Ser Ser Tyr Ala Ser His Pro Phe Gly Ala Pro His Gly Pro Ser Ala
                85                  90                  95

Pro Gly Val Ala Gly Pro Gly Gly Asn Leu Ser Ser Trp Glu Asp Leu
            100                 105                 110

Leu Leu Phe Thr Asp Leu Asp Gln Ala Ala Thr Ala Ser Lys Leu Leu
        115                 120                 125

Trp Ser Ser Arg Gly Ala Lys Leu Ser Pro Phe Ala Pro Glu Gln Pro
    130                 135                 140

Glu Glu Met Tyr Gln Thr Leu Ala Ala Leu Ser Ser Gln Gly Pro Ala
145                 150                 155                 160

Ala Tyr Asp Gly Ala Pro Gly Gly Phe Val His Ser Ala Ala Ala Ala
                165                 170                 175

Ala Ala Ala Ala Ala Ala Ala Ser Ser Pro Val Tyr Val Pro Thr Thr
            180                 185                 190

Arg Val Gly Ser Met Leu Pro Gly Leu Pro Tyr His Leu Gln Gly Ser
        195                 200                 205

Gly Ser Gly Pro Ala Asn His Ala Gly Gly Ala Gly Ala His Pro Gly
    210                 215                 220

Trp Pro Gln Ala Ser Ala Asp Ser Pro Pro Tyr Gly Ser Gly Gly Gly
225                 230                 235                 240

Ala Ala Gly Gly Gly Ala Ala Gly Pro Gly Gly Ala Gly Ser Ala Ala
                245                 250                 255

Ala His Val Ser Ala Arg Phe Pro Tyr Ser Pro Ser Pro Pro Met Ala
            260                 265                 270

Asn Gly Ala Ala Arg Glu Pro Gly Gly Tyr Ala Ala Ala Gly Ser Gly
        275                 280                 285

Gly Ala Gly Gly Val Ser Gly Gly Gly Ser Ser Leu Ala Ala Met Gly
    290                 295                 300

Gly Arg Glu Pro Gln Tyr Ser Ser Leu Ser Ala Ala Arg Pro Leu Asn
305                 310                 315                 320

Gly Thr Tyr His His His His His His His His His His Pro Ser Pro
                325                 330                 335

Tyr Ser Pro Tyr Val Gly Ala Pro Leu Thr Pro Ala Trp Pro Ala Gly
            340                 345                 350

Pro Phe Glu Thr Pro Val Leu His Ser Leu Gln Ser Arg Ala Gly Ala
        355                 360                 365

Pro Leu Pro Val Pro Arg Gly Pro Ser Ala Asp Leu Leu Glu Asp Leu
    370                 375                 380

Ser Glu Ser Arg Glu Cys Val Asn Cys Gly Ser Ile Gln Thr Pro Leu
385                 390                 395                 400

Trp Arg Arg Asp Gly Thr Gly His Tyr Leu Cys Asn Ala Cys Gly Leu
                405                 410                 415

Tyr Ser Lys Met Asn Gly Leu Ser Arg Pro Leu Ile Lys Pro Gln Lys
            420                 425                 430

Arg Val Pro Ser Ser Arg Arg Leu Gly Leu Ser Cys Ala Asn Cys His
        435                 440                 445

Thr Thr Thr Thr Thr Leu Trp Arg Arg Asn Ala Glu Gly Glu Pro Val
    450                 455                 460

Cys Asn Ala Cys Gly Leu Tyr Met Lys Leu His Gly Val Pro Arg Pro
465                 470                 475                 480

Leu Ala Met Lys Lys Glu Gly Ile Gln Thr Arg Lys Arg Lys Pro Lys
```

```
                485                 490                 495

Asn Ile Asn Lys Ser Lys Thr Cys Ser Gly Asn Ser Asn Asn Ser Ile
            500                 505                 510

Pro Met Thr Pro Thr Ser Thr Ser Ser Asn Ser Asp Asp Cys Ser Lys
        515                 520                 525

Asn Thr Ser Pro Thr Thr Gln Pro Thr Ala Ser Gly Ala Gly Ala Pro
    530                 535                 540

Val Met Thr Gly Ala Gly Glu Ser Thr Asn Pro Glu Asn Ser Glu Leu
545                 550                 555                 560

Lys Tyr Ser Gly Gln Asp Gly Leu Tyr Ile Gly Val Ser Leu Ala Ser
                565                 570                 575

Pro Ala Glu Val Thr Ser Ser Val Arg Pro Asp Ser Trp Cys Ala Leu
            580                 585                 590

Ala Leu Ala
        595

<210> SEQ ID NO 21
<211> LENGTH: 1493
<212> TYPE: DNA
<213> ORGANISM: Homo sapiens
<220> FEATURE:
<221> NAME/KEY: CDS
<222> LOCATION: (334)..(1410)

<400> SEQUENCE: 21

agtagtcgcc tggcaggaga atttgaaagg gtgccccaaa ggacaatctc taaaggggta      60

agggagatac ctaccttgtc tggtagggga gatgtttcgt tttcatgctt taccagaaaa     120

tccacttccc tgccgacctt agtttcaaag cttattctta attagagaca agaaacctgt     180

ttcaacttga agacaccgta tgaggtgaat ggacagccag ccaccacaat gaaagaaatc     240

aaaccaggaa taacctatgc tgaacccacg cctcaatcgt ccccaagtgt ttcctgacac     300

gcatctttgc ttacagtgca tcacaactga aga atg ggg ttc aac ttg acg ctt      354
                                     Met Gly Phe Asn Leu Thr Leu
                                     1               5

gca aaa tta cca aat aac gag ctg cac ggc caa gag agt cac aat tca       402
Ala Lys Leu Pro Asn Asn Glu Leu His Gly Gln Glu Ser His Asn Ser
        10                  15                  20

ggc aac agg agc gac ggg cca gga aag aac acc acc ctt cac aat gaa       450
Gly Asn Arg Ser Asp Gly Pro Gly Lys Asn Thr Thr Leu His Asn Glu
    25                  30                  35

ttt gac aca att gtc ttg ccg gtg ctt tat ctc att ata ttt gtg gca       498
Phe Asp Thr Ile Val Leu Pro Val Leu Tyr Leu Ile Ile Phe Val Ala
40                  45                  50                  55

agc atc ttg ctg aat ggt tta gca gtg tgg atc ttc ttc cac att agg       546
Ser Ile Leu Leu Asn Gly Leu Ala Val Trp Ile Phe Phe His Ile Arg
                60                  65                  70

aat aaa acc agc ttc ata ttc tat ctc aaa aac ata gtg gtt gca gac       594
Asn Lys Thr Ser Phe Ile Phe Tyr Leu Lys Asn Ile Val Val Ala Asp
            75                  80                  85

ctc ata atg acg ctg aca ttt cca ttt cga ata gtc cat gat gca gga       642
Leu Ile Met Thr Leu Thr Phe Pro Phe Arg Ile Val His Asp Ala Gly
        90                  95                  100

ttt gga cct tgg tac ttc aag ttt att ctc tgc aga tac act tca gtt       690
Phe Gly Pro Trp Tyr Phe Lys Phe Ile Leu Cys Arg Tyr Thr Ser Val
    105                 110                 115

ttg ttt tat gca aac atg tat act tcc atc gtg ttc ctt ggg ctg ata       738
Leu Phe Tyr Ala Asn Met Tyr Thr Ser Ile Val Phe Leu Gly Leu Ile
120                 125                 130                 135
```

```
agc att gat cgc tat ctg aag gtg gtc aag cca ttt ggg gac tct cgg      786
Ser Ile Asp Arg Tyr Leu Lys Val Val Lys Pro Phe Gly Asp Ser Arg
                140                 145                 150

atg tac agc ata acc ttc acg aag gtt tta tct gtt tgt gtt tgg gtg      834
Met Tyr Ser Ile Thr Phe Thr Lys Val Leu Ser Val Cys Val Trp Val
            155                 160                 165

atc atg gct gtt ttg tct ttg cca aac atc atc cta aca aat ggt cag      882
Ile Met Ala Val Leu Ser Leu Pro Asn Ile Ile Leu Thr Asn Gly Gln
        170                 175                 180

cca aca gag gac aat atc cat gac tgc tca aaa ctt aaa agt cct ttg      930
Pro Thr Glu Asp Asn Ile His Asp Cys Ser Lys Leu Lys Ser Pro Leu
    185                 190                 195

ggg gtc aaa tgg cat acg gca gtc acc tat gtg aac agc tgc ttg ttt      978
Gly Val Lys Trp His Thr Ala Val Thr Tyr Val Asn Ser Cys Leu Phe
200                 205                 210                 215

gtg gcc gtg ctg gtg att ctg atc gga tgt tac ata gcc ata tcc agg     1026
Val Ala Val Leu Val Ile Leu Ile Gly Cys Tyr Ile Ala Ile Ser Arg
                220                 225                 230

tac atc cac aaa tcc agc agg caa ttc ata agt cag tca agc cga aag     1074
Tyr Ile His Lys Ser Ser Arg Gln Phe Ile Ser Gln Ser Ser Arg Lys
            235                 240                 245

cga aaa cat aac cag agc atc agg gtt gtt gtg gct gtg ttt ttt acc     1122
Arg Lys His Asn Gln Ser Ile Arg Val Val Val Ala Val Phe Phe Thr
        250                 255                 260

tgc ttt cta cca tat cac ttg tgc aga att cct ttt act ttt agt cac     1170
Cys Phe Leu Pro Tyr His Leu Cys Arg Ile Pro Phe Thr Phe Ser His
    265                 270                 275

tta gac agg ctt tta gat gaa tct gca caa aaa atc cta tat tac tgc     1218
Leu Asp Arg Leu Leu Asp Glu Ser Ala Gln Lys Ile Leu Tyr Tyr Cys
280                 285                 290                 295

aaa gaa att aca ctt ttc ttg tct gcg tgt aat gtt tgc ctg gat cca     1266
Lys Glu Ile Thr Leu Phe Leu Ser Ala Cys Asn Val Cys Leu Asp Pro
                300                 305                 310

ata att tac ttt ttc atg tgt agg tca ttt tca aga agg ctg ttc aaa     1314
Ile Ile Tyr Phe Phe Met Cys Arg Ser Phe Ser Arg Arg Leu Phe Lys
            315                 320                 325

aaa tca aat atc aga acc agg agt gaa agc atc aga tca ctg caa agt     1362
Lys Ser Asn Ile Arg Thr Arg Ser Glu Ser Ile Arg Ser Leu Gln Ser
        330                 335                 340

gtg aga aga tcg gaa gtt cgc ata tat tat gat tac act gat gtg tag     1410
Val Arg Arg Ser Glu Val Arg Ile Tyr Tyr Asp Tyr Thr Asp Val
    345                 350                 355

gccttttatt gtttgttgga atcgatatgt acaaagtgta aataaatgtt tcttttcatt   1470

atccttgctt gagcccatca aaa                                           1493
```

<210> SEQ ID NO 22
<211> LENGTH: 358
<212> TYPE: PRT
<213> ORGANISM: Homo sapiens

<400> SEQUENCE: 22

```
Met Gly Phe Asn Leu Thr Leu Ala Lys Leu Pro Asn Asn Glu Leu His
1               5                   10                  15

Gly Gln Glu Ser His Asn Ser Gly Asn Arg Ser Asp Gly Pro Gly Lys
            20                  25                  30

Asn Thr Thr Leu His Asn Glu Phe Asp Thr Ile Val Leu Pro Val Leu
        35                  40                  45

Tyr Leu Ile Ile Phe Val Ala Ser Ile Leu Leu Asn Gly Leu Ala Val
```

```
    50                  55                  60

Trp Ile Phe Phe His Ile Arg Asn Lys Thr Ser Phe Ile Phe Tyr Leu
65                  70                  75                  80

Lys Asn Ile Val Val Ala Asp Leu Ile Met Thr Leu Thr Phe Pro Phe
                85                  90                  95

Arg Ile Val His Asp Ala Gly Phe Gly Pro Trp Tyr Phe Lys Phe Ile
            100                 105                 110

Leu Cys Arg Tyr Thr Ser Val Leu Phe Tyr Ala Asn Met Tyr Thr Ser
        115                 120                 125

Ile Val Phe Leu Gly Leu Ile Ser Ile Asp Arg Tyr Leu Lys Val Val
    130                 135                 140

Lys Pro Phe Gly Asp Ser Arg Met Tyr Ser Ile Thr Phe Thr Lys Val
145                 150                 155                 160

Leu Ser Val Cys Val Trp Val Ile Met Ala Val Leu Ser Leu Pro Asn
                165                 170                 175

Ile Ile Leu Thr Asn Gly Gln Pro Thr Glu Asp Asn Ile His Asp Cys
            180                 185                 190

Ser Lys Leu Lys Ser Pro Leu Gly Val Lys Trp His Thr Ala Val Thr
        195                 200                 205

Tyr Val Asn Ser Cys Leu Phe Val Ala Val Leu Val Ile Leu Ile Gly
    210                 215                 220

Cys Tyr Ile Ala Ile Ser Arg Tyr Ile His Lys Ser Ser Arg Gln Phe
225                 230                 235                 240

Ile Ser Gln Ser Ser Arg Lys Arg Lys His Asn Gln Ser Ile Arg Val
                245                 250                 255

Val Val Ala Val Phe Phe Thr Cys Phe Leu Pro Tyr His Leu Cys Arg
            260                 265                 270

Ile Pro Phe Thr Phe Ser His Leu Asp Arg Leu Leu Asp Glu Ser Ala
        275                 280                 285

Gln Lys Ile Leu Tyr Tyr Cys Lys Glu Ile Thr Leu Phe Leu Ser Ala
    290                 295                 300

Cys Asn Val Cys Leu Asp Pro Ile Ile Tyr Phe Phe Met Cys Arg Ser
305                 310                 315                 320

Phe Ser Arg Arg Leu Phe Lys Lys Ser Asn Ile Arg Thr Arg Ser Glu
                325                 330                 335

Ser Ile Arg Ser Leu Gln Ser Val Arg Arg Ser Glu Val Arg Ile Tyr
            340                 345                 350

Tyr Asp Tyr Thr Asp Val
        355
```

<210> SEQ ID NO 23
<211> LENGTH: 4889
<212> TYPE: DNA
<213> ORGANISM: Homo sapiens
<220> FEATURE:
<221> NAME/KEY: CDS
<222> LOCATION: (331)..(3486)

<400> SEQUENCE: 23

```
agatccgccg cgaagccggg atcgaaggcg acagcgcggc caagggggcg cggccgggac      60

aagctggggg ccggttgccc ggggcaggga cggcggcgac ccggccgctg ggggaggcagg    120

aagatagacc cacggatctt aggaagggat ccgagagcgc agctgtgaaa ctggctgggg    180

ctgggggcac gaaaccgatc agcgctacgg agcgcagcgg ccggcgggtt ccagtgtcct    240

ccggcggcgc ggggagcagg tgaacaggtc ctcacgccca gctccgcgcc ctcacgcgct    300
```

```
ctcgccggga ccccgcttcc gctggcagcc atg ggc ccc ggc ccc agc cgc gcg     354
                                 Met Gly Pro Gly Pro Ser Arg Ala
                                 1               5

ccc cgc gcc cca cgc ctg atg ctc tgt gcg ctc gcc ttg atg gtg gcg     402
Pro Arg Ala Pro Arg Leu Met Leu Cys Ala Leu Ala Leu Met Val Ala
    10                  15                  20

gcc ggc ggc tgc gtc gtc tcc gcc ttc aac ctg gat acc cga ttc ctg     450
Ala Gly Gly Cys Val Val Ser Ala Phe Asn Leu Asp Thr Arg Phe Leu
25                  30                  35                  40

gta gtg aag gag gcc ggg aac ccg ggc agc ctc ttc ggc tac tcg gtc     498
Val Val Lys Glu Ala Gly Asn Pro Gly Ser Leu Phe Gly Tyr Ser Val
                45                  50                  55

gcc ctc cat cgg cag aca gag cgg cag cag cgc tac ctg ctc ctg gct     546
Ala Leu His Arg Gln Thr Glu Arg Gln Gln Arg Tyr Leu Leu Leu Ala
            60                  65                  70

ggt gcc ccc cgg gag ctc gct gtg ccc gat ggc tac acc aac cgg act     594
Gly Ala Pro Arg Glu Leu Ala Val Pro Asp Gly Tyr Thr Asn Arg Thr
        75                  80                  85

ggt gct gtg tac ctg tgc cca ctc act gcc cac aag gat gac tgt gag     642
Gly Ala Val Tyr Leu Cys Pro Leu Thr Ala His Lys Asp Asp Cys Glu
    90                  95                  100

cgg atg aac atc aca gtg aaa aat gac cct ggc cat cac att att gag     690
Arg Met Asn Ile Thr Val Lys Asn Asp Pro Gly His His Ile Ile Glu
105                 110                 115                 120

gac atg tgg ctt gga gtg act gtg gcc agc cag ggc cct gca ggc aga     738
Asp Met Trp Leu Gly Val Thr Val Ala Ser Gln Gly Pro Ala Gly Arg
                125                 130                 135

gtt ctg gtc tgt gcc cac cgc tac acc cag gtg ctg tgg tca ggg tca     786
Val Leu Val Cys Ala His Arg Tyr Thr Gln Val Leu Trp Ser Gly Ser
            140                 145                 150

gaa gac cag cgg cgc atg gtg ggc aag tgc tac gtg cga ggc aat gac     834
Glu Asp Gln Arg Arg Met Val Gly Lys Cys Tyr Val Arg Gly Asn Asp
        155                 160                 165

cta gag ctg gac tcc agt gat gac tgg cag acc tac cac aac gag atg     882
Leu Glu Leu Asp Ser Ser Asp Asp Trp Gln Thr Tyr His Asn Glu Met
    170                 175                 180

tgc aat agc aac aca gac tac ctg gag acg ggc atg tgc cag ctg ggc     930
Cys Asn Ser Asn Thr Asp Tyr Leu Glu Thr Gly Met Cys Gln Leu Gly
185                 190                 195                 200

acc agc ggt ggc ttc acc cag aac act gtg tac ttc ggc gcc ccc ggt     978
Thr Ser Gly Gly Phe Thr Gln Asn Thr Val Tyr Phe Gly Ala Pro Gly
                205                 210                 215

gcc tac aac tgg aaa gga aac agc tac atg att cag cgc aag gag tgg    1026
Ala Tyr Asn Trp Lys Gly Asn Ser Tyr Met Ile Gln Arg Lys Glu Trp
            220                 225                 230

gac tta tct gag tat agt tac aag gac cca gag gac caa gga aac ctc    1074
Asp Leu Ser Glu Tyr Ser Tyr Lys Asp Pro Glu Asp Gln Gly Asn Leu
        235                 240                 245

tat att ggg tac acg atg cag gta ggc agc ttc atc ctg cac ccc aaa    1122
Tyr Ile Gly Tyr Thr Met Gln Val Gly Ser Phe Ile Leu His Pro Lys
    250                 255                 260

aac atc acc att gtg aca ggt gcc cca cgg cac cga cat atg ggc gcg    1170
Asn Ile Thr Ile Val Thr Gly Ala Pro Arg His Arg His Met Gly Ala
265                 270                 275                 280

gtg ttc ttg ctg agc cag gag gca ggc gga gac ctg cgg agg agg cag    1218
Val Phe Leu Leu Ser Gln Glu Ala Gly Gly Asp Leu Arg Arg Arg Gln
                285                 290                 295

gtg ctg gag ggc tcg cag gtg ggc gcc tat ttt ggc agc gcc att gcc    1266
Val Leu Glu Gly Ser Gln Val Gly Ala Tyr Phe Gly Ser Ala Ile Ala
```

-continued

```
            300                 305                 310

ctg gca gac ctg aac aat gat ggg tgg cag gac ctc ctg gtg ggc gcc      1314
Leu Ala Asp Leu Asn Asn Asp Gly Trp Gln Asp Leu Leu Val Gly Ala
        315                 320                 325

ccc tac tac ttc gag agg aaa gag gaa gta ggg ggt gcc atc tat gtc      1362
Pro Tyr Tyr Phe Glu Arg Lys Glu Glu Val Gly Gly Ala Ile Tyr Val
    330                 335                 340

ttc atg aac cag gcg gga acc tcc ttc cct gct cac ccc tca ctc ctt      1410
Phe Met Asn Gln Ala Gly Thr Ser Phe Pro Ala His Pro Ser Leu Leu
345                 350                 355                 360

ctt cat ggc ccc agt ggc tct gcc ttt ggt tta tct gtg gcc agc att      1458
Leu His Gly Pro Ser Gly Ser Ala Phe Gly Leu Ser Val Ala Ser Ile
                365                 370                 375

ggt gac atc aac cag gat gga ttt cag gat att gct gtg gga gct ccg      1506
Gly Asp Ile Asn Gln Asp Gly Phe Gln Asp Ile Ala Val Gly Ala Pro
            380                 385                 390

ttt gaa ggc ttg ggc aaa gtg tac atc tat cac agt agc tct aag ggg      1554
Phe Glu Gly Leu Gly Lys Val Tyr Ile Tyr His Ser Ser Ser Lys Gly
        395                 400                 405

ctc ctt aga cag ccc cag cag gta atc cat gga gag aag ctg gga ctg      1602
Leu Leu Arg Gln Pro Gln Gln Val Ile His Gly Glu Lys Leu Gly Leu
    410                 415                 420

cct ggg ttg gcc acc ttc ggc tat tcc ctc agt ggg cag atg gat gtg      1650
Pro Gly Leu Ala Thr Phe Gly Tyr Ser Leu Ser Gly Gln Met Asp Val
425                 430                 435                 440

gat gag aac ttc tac cca gac ctt cta gtg gga agc ctg tca gac cac      1698
Asp Glu Asn Phe Tyr Pro Asp Leu Leu Val Gly Ser Leu Ser Asp His
                445                 450                 455

att gtg ctg ctg cgg gcc cgg ccc gtc atc aac atc gtc cac aag acc      1746
Ile Val Leu Leu Arg Ala Arg Pro Val Ile Asn Ile Val His Lys Thr
            460                 465                 470

ttg gtg ccc agg cca gct gtg ctg gac cct gca ctt tgc acg gcc acc      1794
Leu Val Pro Arg Pro Ala Val Leu Asp Pro Ala Leu Cys Thr Ala Thr
        475                 480                 485

tct tgt gtg caa gtg gag ctg tgc ttt gct tac aac cag agt gcc ggg      1842
Ser Cys Val Gln Val Glu Leu Cys Phe Ala Tyr Asn Gln Ser Ala Gly
    490                 495                 500

aac ccc aac tac agg cga aac atc acc ctg gcc tac act ctg gag gct      1890
Asn Pro Asn Tyr Arg Arg Asn Ile Thr Leu Ala Tyr Thr Leu Glu Ala
505                 510                 515                 520

gac agg gac cgc cgg ccg ccc cgg ctc cgc ttt gcc ggc agt gag tcc      1938
Asp Arg Asp Arg Arg Pro Pro Arg Leu Arg Phe Ala Gly Ser Glu Ser
                525                 530                 535

gct gtc ttc cac ggc ttc ttc tcc atg ccc gag atg cgc tgc cag aag      1986
Ala Val Phe His Gly Phe Phe Ser Met Pro Glu Met Arg Cys Gln Lys
            540                 545                 550

ctg gag ctg ctc ctg atg gac aac ctc cgt gac aaa ctc cgc ccc atc      2034
Leu Glu Leu Leu Leu Met Asp Asn Leu Arg Asp Lys Leu Arg Pro Ile
        555                 560                 565

atc atc tcc atg aac tac tct tta cct ttg cgg atg ccc gat cgc ccc      2082
Ile Ile Ser Met Asn Tyr Ser Leu Pro Leu Arg Met Pro Asp Arg Pro
    570                 575                 580

cgg ctg ggg ctg cgg tcc ctg gac gcc tac ccg atc ctc aac cag gca      2130
Arg Leu Gly Leu Arg Ser Leu Asp Ala Tyr Pro Ile Leu Asn Gln Ala
585                 590                 595                 600

cag gct ctg gag aac cac act gag gtc cag ttc cag aag gag tgc ggg      2178
Gln Ala Leu Glu Asn His Thr Glu Val Gln Phe Gln Lys Glu Cys Gly
                605                 610                 615

cct gac aac aag tgt gag agc aac ttg cag atg cgg gca gcc ttc gtg      2226
```

-continued

```
Pro Asp Asn Lys Cys Glu Ser Asn Leu Gln Met Arg Ala Ala Phe Val
            620                 625                 630

tca gag cag cag cag aag ctg agc agg ctc cag tac agc aga gac gtc      2274
Ser Glu Gln Gln Gln Lys Leu Ser Arg Leu Gln Tyr Ser Arg Asp Val
        635                 640                 645

cgg aaa ttg ctc ctg agc atc aac gtg acg aac acc cgg acc tcg gag      2322
Arg Lys Leu Leu Leu Ser Ile Asn Val Thr Asn Thr Arg Thr Ser Glu
    650                 655                 660

cgc tcc ggg gag gac gcc cac gag gcg ctg ctc acc ctg gtg gtg cct      2370
Arg Ser Gly Glu Asp Ala His Glu Ala Leu Leu Thr Leu Val Val Pro
665                 670                 675                 680

ccc gcc ctg ctg ctg tcc tca gtg cgc ccc ccc ggg gcc tgc caa gct      2418
Pro Ala Leu Leu Leu Ser Ser Val Arg Pro Pro Gly Ala Cys Gln Ala
                685                 690                 695

aat gag acc atc ttt tgc gag ctg ggg aac ccc ttc aaa cgg aac cag      2466
Asn Glu Thr Ile Phe Cys Glu Leu Gly Asn Pro Phe Lys Arg Asn Gln
            700                 705                 710

agg atg gag ctg ctc atc gcc ttt gag gtc atc ggg gtg acc ctg cac      2514
Arg Met Glu Leu Leu Ile Ala Phe Glu Val Ile Gly Val Thr Leu His
        715                 720                 725

aca agg gac ctt cag gtg cag ctg cag ctc tcc acg tcg agt cac cag      2562
Thr Arg Asp Leu Gln Val Gln Leu Gln Leu Ser Thr Ser Ser His Gln
    730                 735                 740

gac aac ctg tgg ccc atg atc ctc act ctg ctg gtg gac tat aca ctc      2610
Asp Asn Leu Trp Pro Met Ile Leu Thr Leu Leu Val Asp Tyr Thr Leu
745                 750                 755                 760

cag acc tcg ctt agc atg gta aat cac cgg cta caa agc ttc ttt ggg      2658
Gln Thr Ser Leu Ser Met Val Asn His Arg Leu Gln Ser Phe Phe Gly
                765                 770                 775

ggg aca gtg atg ggt gag tct ggc atg aaa act gtg gag gat gta gga      2706
Gly Thr Val Met Gly Glu Ser Gly Met Lys Thr Val Glu Asp Val Gly
            780                 785                 790

agc ccc ctc aag tat gaa ttc cag gtg ggc cca atg ggg gag ggg ctg      2754
Ser Pro Leu Lys Tyr Glu Phe Gln Val Gly Pro Met Gly Glu Gly Leu
        795                 800                 805

gtg ggc ctg ggg acc ctg gtc cta ggt ctg gag tgg ccc tac gaa gtc      2802
Val Gly Leu Gly Thr Leu Val Leu Gly Leu Glu Trp Pro Tyr Glu Val
    810                 815                 820

agc aat ggc aag tgg ctg ctg tat ccc acg gag atc acc gtc cat ggc      2850
Ser Asn Gly Lys Trp Leu Leu Tyr Pro Thr Glu Ile Thr Val His Gly
825                 830                 835                 840

aat ggg tcc tgg ccc tgc cga cca cct gga gac ctt atc aac cct ctc      2898
Asn Gly Ser Trp Pro Cys Arg Pro Pro Gly Asp Leu Ile Asn Pro Leu
                845                 850                 855

aac ctc act ctt tct gac cct ggg gac agg cca tca tcc cca cag cgc      2946
Asn Leu Thr Leu Ser Asp Pro Gly Asp Arg Pro Ser Ser Pro Gln Arg
            860                 865                 870

agg cgg cga cag ctg gat cca ggg gga ggc cag ggc ccc cca cct gtc      2994
Arg Arg Arg Gln Leu Asp Pro Gly Gly Gly Gln Gly Pro Pro Pro Val
        875                 880                 885

act ctg gct gct gcc aaa aaa gcc aag tct gag act gtg ctg acc tgt      3042
Thr Leu Ala Ala Ala Lys Lys Ala Lys Ser Glu Thr Val Leu Thr Cys
    890                 895                 900

gcc aca ggg cgt gcc cac tgt gtg tgg cta gag tgc ccc atc cct gat      3090
Ala Thr Gly Arg Ala His Cys Val Trp Leu Glu Cys Pro Ile Pro Asp
905                 910                 915                 920

gcc ccc gtt gtc acc aac gtg act gtg aag gca cga gtg tgg aac agc      3138
Ala Pro Val Val Thr Asn Val Thr Val Lys Ala Arg Val Trp Asn Ser
                925                 930                 935
```

-continued

```
acc ttc atc gag gat tac aga gac ttt gac cga gtc cgg gta aat ggc     3186
Thr Phe Ile Glu Asp Tyr Arg Asp Phe Asp Arg Val Arg Val Asn Gly
            940                 945                 950

tgg gct acc cta ttc ctc cga acc agc atc ccc acc atc aac atg gag     3234
Trp Ala Thr Leu Phe Leu Arg Thr Ser Ile Pro Thr Ile Asn Met Glu
        955                 960                 965

aac aag acc acg tgg ttc tct gtg gac att gac tcg gag ctg gtg gag     3282
Asn Lys Thr Thr Trp Phe Ser Val Asp Ile Asp Ser Glu Leu Val Glu
    970                 975                 980

gag ctg ccg gcc gaa atc gag ctg tgg ctg gtg ctg gtg gcc gtg ggt     3330
Glu Leu Pro Ala Glu Ile Glu Leu Trp Leu Val Leu Val Ala Val Gly
985                 990                 995                 1000

gca ggg ctg ctg ctg  ctg ggg ctg atc atc  ctc ctg ctg tgg aag      3375
Ala Gly Leu Leu Leu  Leu Gly Leu Ile Ile  Leu Leu Leu Trp Lys
               1005                 1010                 1015

tgc ggc ttc ttc aag  cga gcc cgc act cgc  gcc ctg tat gaa gct      3420
Cys Gly Phe Phe Lys  Arg Ala Arg Thr Arg  Ala Leu Tyr Glu Ala
                1020                 1025                 1030

aag agg cag aag gcg  gag atg aag agc cag  ccg tca gag aca gag      3465
Lys Arg Gln Lys Ala  Glu Met Lys Ser Gln  Pro Ser Glu Thr Glu
                1035                 1040                 1045

agg ctg acc gac gac  tac tga gggggcagcc ccccgccccc ggcccacctg      3516
Arg Leu Thr Asp Asp  Tyr
                1050

gtgtgacttc tttaagcgga cccgctatta tcagatcatg cccaagtacc acgcagtgcg   3576

gatccgggag gaggagcgct acccacctcc agggagcacc ctgcccacca agaagcactg   3636

ggtgaccagc tggcagactc gggaccaata ctactgacgt cctccctgat cccaccccct   3696

cctcccccag tgtccccttt cttcctattt atcataagtt atgcctctga cagtccacag   3756

gggccaccac ctttggctgg tagcagcagg ctcaggcaca tacacctcgt caagagcatg   3816

cacatgctgt ctggccctgg ggatcttccc acaggagggc cagcgctgtg gaccttacaa   3876

cgccgagtgc actgcattcc tgtgccctag atgcacgtgg ggcccactgc tcgtggactg   3936

tgctggtgca tcacggatgg tgcatgggct cgccgtgtct cagcctctgc cagcgccaaa   3996

acaagccaaa gagcctccca ccagagccgg gaggaaaagg cccctgcaat gtggtgacac   4056

ctcccccttt cacactggat ccatcttgag ccacagtcac tggattgact ttgctgtcaa   4116

aactactgac agggagcagc ccccgggccg ctggctggtg ggcccccaat gacacccatg   4176

ccagagaggt ggggatcctg cctaaggttg tctacggggg cacttggagg acctggcgtg   4236

ctcagaccca acagcaaagg aactagaaag aaggacccag aacggcttgc tttcctgcat   4296

ctctgtgaag cctctctcct tggccacaga ctgaactcgc agggaatgca gcaggaagga   4356

acaaagacag gcaaacggca acgtagcctg ggctcactgt gctggggcac ggcgggatcc   4416

tccacagaga ggaggggacc aattctggac agacagatgt tgggaggata cagaggagat   4476

gccacttctc actcaccact accagccagc ctcagaaggc cccagagaga ccctgcaaga   4536

ccacggaggg agcgacactt gaatgtagaa taggcagggg gccctgcccc accccatcca   4596

gccagacccc acgctgacca tgcgtcaggg gcctagaggt ggagttctta gctatccttg   4656

gctttcagag ccagcctggc tctgccccct cccccatggg ctgtgtccta aggcccattt   4716

gagaagctga ggctagttcc agaaaacctc tcctgacccc tgcctgttgg caggcccact   4776

ccccagcccc agccccttcc atggtactgt agcaggggaa ttccctcccc ctccttgtgc   4836

cttctttgta tataggcttc tcacggcgac caataaacag ctcccagttt gta          4889
```

-continued

<210> SEQ ID NO 24
<211> LENGTH: 1051
<212> TYPE: PRT
<213> ORGANISM: Homo sapiens

<400> SEQUENCE: 24

```
Met Gly Pro Gly Pro Ser Arg Ala Pro Arg Ala Pro Arg Leu Met Leu
1               5                   10                  15

Cys Ala Leu Ala Leu Met Val Ala Ala Gly Gly Cys Val Val Ser Ala
            20                  25                  30

Phe Asn Leu Asp Thr Arg Phe Leu Val Val Lys Glu Ala Gly Asn Pro
        35                  40                  45

Gly Ser Leu Phe Gly Tyr Ser Val Ala Leu His Arg Gln Thr Glu Arg
    50                  55                  60

Gln Gln Arg Tyr Leu Leu Leu Ala Gly Ala Pro Arg Glu Leu Ala Val
65                  70                  75                  80

Pro Asp Gly Tyr Thr Asn Arg Thr Gly Ala Val Tyr Leu Cys Pro Leu
                85                  90                  95

Thr Ala His Lys Asp Asp Cys Glu Arg Met Asn Ile Thr Val Lys Asn
            100                 105                 110

Asp Pro Gly His His Ile Ile Glu Asp Met Trp Leu Gly Val Thr Val
        115                 120                 125

Ala Ser Gln Gly Pro Ala Gly Arg Val Leu Val Cys Ala His Arg Tyr
    130                 135                 140

Thr Gln Val Leu Trp Ser Gly Ser Glu Asp Gln Arg Arg Met Val Gly
145                 150                 155                 160

Lys Cys Tyr Val Arg Gly Asn Asp Leu Glu Leu Asp Ser Ser Asp Asp
                165                 170                 175

Trp Gln Thr Tyr His Asn Glu Met Cys Asn Ser Asn Thr Asp Tyr Leu
            180                 185                 190

Glu Thr Gly Met Cys Gln Leu Gly Thr Ser Gly Gly Phe Thr Gln Asn
        195                 200                 205

Thr Val Tyr Phe Gly Ala Pro Gly Ala Tyr Asn Trp Lys Gly Asn Ser
    210                 215                 220

Tyr Met Ile Gln Arg Lys Glu Trp Asp Leu Ser Glu Tyr Ser Tyr Lys
225                 230                 235                 240

Asp Pro Glu Asp Gln Gly Asn Leu Tyr Ile Gly Tyr Thr Met Gln Val
                245                 250                 255

Gly Ser Phe Ile Leu His Pro Lys Asn Ile Thr Ile Val Thr Gly Ala
            260                 265                 270

Pro Arg His Arg His Met Gly Ala Val Phe Leu Leu Ser Gln Glu Ala
        275                 280                 285

Gly Gly Asp Leu Arg Arg Arg Gln Val Leu Glu Gly Ser Gln Val Gly
    290                 295                 300

Ala Tyr Phe Gly Ser Ala Ile Ala Leu Ala Asp Leu Asn Asn Asp Gly
305                 310                 315                 320

Trp Gln Asp Leu Leu Val Gly Ala Pro Tyr Tyr Phe Glu Arg Lys Glu
                325                 330                 335

Glu Val Gly Gly Ala Ile Tyr Val Phe Met Asn Gln Ala Gly Thr Ser
            340                 345                 350

Phe Pro Ala His Pro Ser Leu Leu Leu His Gly Pro Ser Gly Ser Ala
        355                 360                 365

Phe Gly Leu Ser Val Ala Ser Ile Gly Asp Ile Asn Gln Asp Gly Phe
    370                 375                 380
```

-continued

```
Gln Asp Ile Ala Val Gly Ala Pro Phe Glu Gly Leu Gly Lys Val Tyr
385                 390                 395                 400

Ile Tyr His Ser Ser Ser Lys Gly Leu Leu Arg Gln Pro Gln Gln Val
                405                 410                 415

Ile His Gly Glu Lys Leu Gly Leu Pro Gly Leu Ala Thr Phe Gly Tyr
            420                 425                 430

Ser Leu Ser Gly Gln Met Asp Val Asp Glu Asn Phe Tyr Pro Asp Leu
        435                 440                 445

Leu Val Gly Ser Leu Ser Asp His Ile Val Leu Leu Arg Ala Arg Pro
    450                 455                 460

Val Ile Asn Ile Val His Lys Thr Leu Val Pro Arg Pro Ala Val Leu
465                 470                 475                 480

Asp Pro Ala Leu Cys Thr Ala Thr Ser Cys Val Gln Val Glu Leu Cys
                485                 490                 495

Phe Ala Tyr Asn Gln Ser Ala Gly Asn Pro Asn Tyr Arg Arg Asn Ile
            500                 505                 510

Thr Leu Ala Tyr Thr Leu Glu Ala Asp Arg Asp Arg Arg Pro Pro Arg
        515                 520                 525

Leu Arg Phe Ala Gly Ser Glu Ser Ala Val Phe His Gly Phe Phe Ser
    530                 535                 540

Met Pro Glu Met Arg Cys Gln Lys Leu Glu Leu Leu Leu Met Asp Asn
545                 550                 555                 560

Leu Arg Asp Lys Leu Arg Pro Ile Ile Ile Ser Met Asn Tyr Ser Leu
                565                 570                 575

Pro Leu Arg Met Pro Asp Arg Pro Arg Leu Gly Leu Arg Ser Leu Asp
            580                 585                 590

Ala Tyr Pro Ile Leu Asn Gln Ala Gln Ala Leu Glu Asn His Thr Glu
        595                 600                 605

Val Gln Phe Gln Lys Glu Cys Gly Pro Asp Asn Lys Cys Glu Ser Asn
    610                 615                 620

Leu Gln Met Arg Ala Ala Phe Val Ser Glu Gln Gln Gln Lys Leu Ser
625                 630                 635                 640

Arg Leu Gln Tyr Ser Arg Asp Val Arg Lys Leu Leu Leu Ser Ile Asn
                645                 650                 655

Val Thr Asn Thr Arg Thr Ser Glu Arg Ser Gly Glu Asp Ala His Glu
            660                 665                 670

Ala Leu Leu Thr Leu Val Val Pro Pro Ala Leu Leu Leu Ser Ser Val
        675                 680                 685

Arg Pro Pro Gly Ala Cys Gln Ala Asn Glu Thr Ile Phe Cys Glu Leu
    690                 695                 700

Gly Asn Pro Phe Lys Arg Asn Gln Arg Met Glu Leu Leu Ile Ala Phe
705                 710                 715                 720

Glu Val Ile Gly Val Thr Leu His Thr Arg Asp Leu Gln Val Gln Leu
                725                 730                 735

Gln Leu Ser Thr Ser Ser His Gln Asp Asn Leu Trp Pro Met Ile Leu
            740                 745                 750

Thr Leu Leu Val Asp Tyr Thr Leu Gln Thr Ser Leu Ser Met Val Asn
        755                 760                 765

His Arg Leu Gln Ser Phe Phe Gly Gly Thr Val Met Gly Glu Ser Gly
    770                 775                 780

Met Lys Thr Val Glu Asp Val Gly Ser Pro Leu Lys Tyr Glu Phe Gln
785                 790                 795                 800

Val Gly Pro Met Gly Glu Gly Leu Val Gly Leu Gly Thr Leu Val Leu
```

```
                805                 810                 815

Gly Leu Glu Trp Pro Tyr Glu Val Ser Asn Gly Lys Trp Leu Leu Tyr
            820                 825                 830

Pro Thr Glu Ile Thr Val His Gly Asn Gly Ser Trp Pro Cys Arg Pro
        835                 840                 845

Pro Gly Asp Leu Ile Asn Pro Leu Asn Leu Thr Leu Ser Asp Pro Gly
    850                 855                 860

Asp Arg Pro Ser Ser Pro Gln Arg Arg Arg Arg Gln Leu Asp Pro Gly
865                 870                 875                 880

Gly Gly Gln Gly Pro Pro Pro Val Thr Leu Ala Ala Ala Lys Lys Ala
                885                 890                 895

Lys Ser Glu Thr Val Leu Thr Cys Ala Thr Gly Arg Ala His Cys Val
            900                 905                 910

Trp Leu Glu Cys Pro Ile Pro Asp Ala Pro Val Val Thr Asn Val Thr
        915                 920                 925

Val Lys Ala Arg Val Trp Asn Ser Thr Phe Ile Glu Asp Tyr Arg Asp
    930                 935                 940

Phe Asp Arg Val Arg Val Asn Gly Trp Ala Thr Leu Phe Leu Arg Thr
945                 950                 955                 960

Ser Ile Pro Thr Ile Asn Met Glu Asn Lys Thr Thr Trp Phe Ser Val
                965                 970                 975

Asp Ile Asp Ser Glu Leu Val Glu Glu Leu Pro Ala Glu Ile Glu Leu
            980                 985                 990

Trp Leu Val Leu Val Ala Val Gly  Ala Gly Leu Leu Leu  Leu Gly Leu
        995                 1000                1005

Ile Ile  Leu Leu Leu Trp Lys  Cys Gly Phe Phe Lys  Arg Ala Arg
    1010                 1015                 1020

Thr Arg  Ala Leu Tyr Glu Ala  Lys Arg Gln Lys Ala  Glu Met Lys
    1025                 1030                 1035

Ser Gln  Pro Ser Glu Thr Glu  Arg Leu Thr Asp Asp  Tyr
    1040                 1045                 1050


<210> SEQ ID NO 25
<211> LENGTH: 2238
<212> TYPE: DNA
<213> ORGANISM: Homo sapiens
<220> FEATURE:
<221> NAME/KEY: CDS
<222> LOCATION: (99)..(1871)

<400> SEQUENCE: 25

aacagagcca ccttctgcgt cctgctgagc tctgttctct ccagcacctc ccaacccact      60

agtgcctggt tctcttgctc caccaggaac aagccacc atg tct cgc cag tca agt     116
                                          Met Ser Arg Gln Ser Ser
                                          1               5

gtg tcc ttc cgg agc ggg ggc agt cgt agc ttc agc acc gcc tct gcc      164
Val Ser Phe Arg Ser Gly Gly Ser Arg Ser Phe Ser Thr Ala Ser Ala
            10                  15                  20

atc acc ccg tct gtc tcc cgc acc agc ttc acc tcc gtg tcc cgg tcc      212
Ile Thr Pro Ser Val Ser Arg Thr Ser Phe Thr Ser Val Ser Arg Ser
        25                  30                  35

ggg ggt ggc ggt ggt ggt ggc ttc ggc agg gtc agc ctt gcg ggt gct      260
Gly Gly Gly Gly Gly Gly Gly Phe Gly Arg Val Ser Leu Ala Gly Ala
    40                  45                  50

tgt gga gtg ggt ggc tat ggc agc cgg agc ctc tac aac ctg ggg ggc      308
Cys Gly Val Gly Gly Tyr Gly Ser Arg Ser Leu Tyr Asn Leu Gly Gly
55                  60                  65                  70
```

-continued

```
tcc aag agg ata tcc atc agc act agt ggt ggc agc ttc agg aac cgg      356
Ser Lys Arg Ile Ser Ile Ser Thr Ser Gly Gly Ser Phe Arg Asn Arg
                75                  80                  85

ttt ggt gct ggt gct gga ggc ggc tat ggc ttt gga ggt ggt gcc ggt      404
Phe Gly Ala Gly Ala Gly Gly Gly Tyr Gly Phe Gly Gly Gly Ala Gly
            90                  95                  100

agt gga ttt ggt ttc ggc ggt gga gct ggt ggt ggc ttt ggg ctc ggt      452
Ser Gly Phe Gly Phe Gly Gly Gly Ala Gly Gly Gly Phe Gly Leu Gly
        105                 110                 115

ggc gga gct ggc ttt gga ggt ggc ttc ggt ggc cct ggc ttt cct gtc      500
Gly Gly Ala Gly Phe Gly Gly Gly Phe Gly Gly Pro Gly Phe Pro Val
    120                 125                 130

tgc cct cct gga ggt atc caa gag gtc act gtc aac cag agt ctc ctg      548
Cys Pro Pro Gly Gly Ile Gln Glu Val Thr Val Asn Gln Ser Leu Leu
135                 140                 145                 150

act ccc ctc aac ctg caa atc gac ccc agc atc cag agg gtg agg acc      596
Thr Pro Leu Asn Leu Gln Ile Asp Pro Ser Ile Gln Arg Val Arg Thr
                155                 160                 165

gag gag cgc gag cag atc aag acc ctc aac aat aag ttt gcc tcc ttc      644
Glu Glu Arg Glu Gln Ile Lys Thr Leu Asn Asn Lys Phe Ala Ser Phe
            170                 175                 180

atc gac aag gtg cgg ttc ctg gag cag cag aac aag gtt ctg gac acc      692
Ile Asp Lys Val Arg Phe Leu Glu Gln Gln Asn Lys Val Leu Asp Thr
        185                 190                 195

aag tgg acc ctg ctg cag gag cag ggc acc aag act gtg agg cag aac      740
Lys Trp Thr Leu Leu Gln Glu Gln Gly Thr Lys Thr Val Arg Gln Asn
    200                 205                 210

ctg gag ccg ttg ttc gag cag tac atc aac aac ctc agg agg cag ctg      788
Leu Glu Pro Leu Phe Glu Gln Tyr Ile Asn Asn Leu Arg Arg Gln Leu
215                 220                 225                 230

gac agc atc gtg ggg gaa cgg ggc cgc ctg gac tca gag ctg aga aac      836
Asp Ser Ile Val Gly Glu Arg Gly Arg Leu Asp Ser Glu Leu Arg Asn
                235                 240                 245

atg cag gac ctg gtg gaa gac ttc aag aac aag tat gag gat gaa atc      884
Met Gln Asp Leu Val Glu Asp Phe Lys Asn Lys Tyr Glu Asp Glu Ile
            250                 255                 260

aac aag cgt acc act gct gag aat gag ttt gtg atg ctg aag aag gat      932
Asn Lys Arg Thr Thr Ala Glu Asn Glu Phe Val Met Leu Lys Lys Asp
        265                 270                 275

gta gat gct gcc tac atg aac aag gtg gag ctg gag gcc aag gtt gat      980
Val Asp Ala Ala Tyr Met Asn Lys Val Glu Leu Glu Ala Lys Val Asp
    280                 285                 290

gca ctg atg gat gag att aac ttc atg aag atg ttc ttt gat gcg gag     1028
Ala Leu Met Asp Glu Ile Asn Phe Met Lys Met Phe Phe Asp Ala Glu
295                 300                 305                 310

ctg tcc cag atg cag acg cat gtc tct gac acc tca gtg gtc ctc tcc     1076
Leu Ser Gln Met Gln Thr His Val Ser Asp Thr Ser Val Val Leu Ser
                315                 320                 325

atg gac aac aac cgc aac ctg gac ctg gat agc atc atc gct gag gtc     1124
Met Asp Asn Asn Arg Asn Leu Asp Leu Asp Ser Ile Ile Ala Glu Val
            330                 335                 340

aag gcc cag tat gag gag att gcc aac cgc agc cgg aca gaa gcc gag     1172
Lys Ala Gln Tyr Glu Glu Ile Ala Asn Arg Ser Arg Thr Glu Ala Glu
        345                 350                 355

tcc tgg tat cag acc aag tat gag gag ctg cag cag aca gct ggc cgg     1220
Ser Trp Tyr Gln Thr Lys Tyr Glu Glu Leu Gln Gln Thr Ala Gly Arg
    360                 365                 370

cat ggc gat gac ctc cgc aac acc aag cat gag atc tct gag atg aac     1268
His Gly Asp Asp Leu Arg Asn Thr Lys His Glu Ile Ser Glu Met Asn
```

-continued

```
375                 380                 385                 390

cgg atg atc cag agg ctg aga gcc gag att gac aat gtc aag aaa cag      1316
Arg Met Ile Gln Arg Leu Arg Ala Glu Ile Asp Asn Val Lys Lys Gln
                395                 400                 405

tgc gcc aat ctg cag aac gcc att gcg gat gcc gag cag cgt ggg gag      1364
Cys Ala Asn Leu Gln Asn Ala Ile Ala Asp Ala Glu Gln Arg Gly Glu
            410                 415                 420

ctg gcc ctc aag gat gcc agg aac aag ctg gcc gag ctg gag gag gcc      1412
Leu Ala Leu Lys Asp Ala Arg Asn Lys Leu Ala Glu Leu Glu Glu Ala
        425                 430                 435

ctg cag aag gcc aag cag gac atg gcc cgg ctg ctg cgt gag tac cag      1460
Leu Gln Lys Ala Lys Gln Asp Met Ala Arg Leu Leu Arg Glu Tyr Gln
    440                 445                 450

gag ctc atg aac acc aag ctg gcc ctg gac gtg gag atc gcc act tac      1508
Glu Leu Met Asn Thr Lys Leu Ala Leu Asp Val Glu Ile Ala Thr Tyr
455                 460                 465                 470

cgc aag ctg ctg gag ggc gag gaa tgc aga ctc agt gga gaa gga gtt      1556
Arg Lys Leu Leu Glu Gly Glu Glu Cys Arg Leu Ser Gly Glu Gly Val
                475                 480                 485

gga cca gtc aac atc tct gtt gtc aca agc agt gtt tcc tct gga tat      1604
Gly Pro Val Asn Ile Ser Val Val Thr Ser Ser Val Ser Ser Gly Tyr
            490                 495                 500

ggc agt ggc agt ggc tat ggc ggt ggc ctc ggt gga ggt ctt ggc ggc      1652
Gly Ser Gly Ser Gly Tyr Gly Gly Gly Leu Gly Gly Gly Leu Gly Gly
        505                 510                 515

ggc ctc ggt gga ggt ctt gcc gga ggt agc agt gga agc tac tac tcc      1700
Gly Leu Gly Gly Gly Leu Ala Gly Gly Ser Ser Gly Ser Tyr Tyr Ser
    520                 525                 530

agc agc agt ggg ggt gtc ggc cta ggt ggt ggg ctc agt gtg ggg ggc      1748
Ser Ser Ser Gly Gly Val Gly Leu Gly Gly Gly Leu Ser Val Gly Gly
535                 540                 545                 550

tct ggc ttc agt gca agc agt ggc cga ggg ctg ggg gtg ggc ttt ggc      1796
Ser Gly Phe Ser Ala Ser Ser Gly Arg Gly Leu Gly Val Gly Phe Gly
                555                 560                 565

agt ggc ggg ggt agc agc tcc agc gtc aaa ttt gtc tcc acc acc tcc      1844
Ser Gly Gly Gly Ser Ser Ser Ser Val Lys Phe Val Ser Thr Thr Ser
            570                 575                 580

tcc tcc cgg aag agc ttc aag agc taa gaacctgctg caagtcactg           1891
Ser Ser Arg Lys Ser Phe Lys Ser
        585                 590

ccttccaagt gcagcaaccc agcccatgga gattgcctct tctaggcagt tgctcaagcc   1951

atgttttatc cttttctgga gagtagtcta gaccaagcca attgcagaac cacattcttt   2011

ggttcccagg agagccccat tcccagcccc tggtctcccg tgccgcagtt ctatattctg   2071

cttcaaatca gccttcaggt ttcccacagc atggcccctg ctgacacgag aacccaaagt   2131

tttcccaaat ctaaatcatc aaaacagaat ccccacccca atcccaaatt ttgttttggt   2191

tctaactacc tccagaatgt gttcaataaa atgcttttat aatataa                 2238


<210> SEQ ID NO 26
<211> LENGTH: 590
<212> TYPE: PRT
<213> ORGANISM: Homo sapiens

<400> SEQUENCE: 26

Met Ser Arg Gln Ser Ser Val Ser Phe Arg Ser Gly Gly Ser Arg Ser
1               5                   10                  15

Phe Ser Thr Ala Ser Ala Ile Thr Pro Ser Val Ser Arg Thr Ser Phe
            20                  25                  30
```

-continued

```
Thr Ser Val Ser Arg Ser Gly Gly Gly Gly Gly Gly Gly Phe Gly Arg
        35                  40                  45

Val Ser Leu Ala Gly Ala Cys Gly Val Gly Gly Tyr Gly Ser Arg Ser
    50                  55                  60

Leu Tyr Asn Leu Gly Gly Ser Lys Arg Ile Ser Ile Ser Thr Ser Gly
65                  70                  75                  80

Gly Ser Phe Arg Asn Arg Phe Gly Ala Gly Ala Gly Gly Gly Tyr Gly
                85                  90                  95

Phe Gly Gly Gly Ala Gly Ser Gly Phe Gly Phe Gly Gly Gly Ala Gly
            100                 105                 110

Gly Gly Phe Gly Leu Gly Gly Gly Ala Gly Phe Gly Gly Gly Phe Gly
        115                 120                 125

Gly Pro Gly Phe Pro Val Cys Pro Pro Gly Gly Ile Gln Glu Val Thr
    130                 135                 140

Val Asn Gln Ser Leu Leu Thr Pro Leu Asn Leu Gln Ile Asp Pro Ser
145                 150                 155                 160

Ile Gln Arg Val Arg Thr Glu Glu Arg Glu Gln Ile Lys Thr Leu Asn
                165                 170                 175

Asn Lys Phe Ala Ser Phe Ile Asp Lys Val Arg Phe Leu Glu Gln Gln
            180                 185                 190

Asn Lys Val Leu Asp Thr Lys Trp Thr Leu Leu Gln Glu Gln Gly Thr
        195                 200                 205

Lys Thr Val Arg Gln Asn Leu Glu Pro Leu Phe Glu Gln Tyr Ile Asn
    210                 215                 220

Asn Leu Arg Arg Gln Leu Asp Ser Ile Val Gly Glu Arg Gly Arg Leu
225                 230                 235                 240

Asp Ser Glu Leu Arg Asn Met Gln Asp Leu Val Glu Asp Phe Lys Asn
                245                 250                 255

Lys Tyr Glu Asp Glu Ile Asn Lys Arg Thr Thr Ala Glu Asn Glu Phe
            260                 265                 270

Val Met Leu Lys Lys Asp Val Asp Ala Ala Tyr Met Asn Lys Val Glu
        275                 280                 285

Leu Glu Ala Lys Val Asp Ala Leu Met Asp Glu Ile Asn Phe Met Lys
    290                 295                 300

Met Phe Phe Asp Ala Glu Leu Ser Gln Met Gln Thr His Val Ser Asp
305                 310                 315                 320

Thr Ser Val Val Leu Ser Met Asp Asn Asn Arg Asn Leu Asp Leu Asp
                325                 330                 335

Ser Ile Ile Ala Glu Val Lys Ala Gln Tyr Glu Glu Ile Ala Asn Arg
            340                 345                 350

Ser Arg Thr Glu Ala Glu Ser Trp Tyr Gln Thr Lys Tyr Glu Glu Leu
        355                 360                 365

Gln Gln Thr Ala Gly Arg His Gly Asp Asp Leu Arg Asn Thr Lys His
    370                 375                 380

Glu Ile Ser Glu Met Asn Arg Met Ile Gln Arg Leu Arg Ala Glu Ile
385                 390                 395                 400

Asp Asn Val Lys Lys Gln Cys Ala Asn Leu Gln Asn Ala Ile Ala Asp
                405                 410                 415

Ala Glu Gln Arg Gly Glu Leu Ala Leu Lys Asp Ala Arg Asn Lys Leu
            420                 425                 430

Ala Glu Leu Glu Glu Ala Leu Gln Lys Ala Lys Gln Asp Met Ala Arg
        435                 440                 445
```

```
Leu Leu Arg Glu Tyr Gln Glu Leu Met Asn Thr Lys Leu Ala Leu Asp
    450                 455                 460

Val Glu Ile Ala Thr Tyr Arg Lys Leu Leu Glu Gly Glu Glu Cys Arg
465                 470                 475                 480

Leu Ser Gly Glu Gly Val Gly Pro Val Asn Ile Ser Val Val Thr Ser
                485                 490                 495

Ser Val Ser Ser Gly Tyr Gly Ser Gly Ser Gly Tyr Gly Gly Gly Leu
            500                 505                 510

Gly Gly Gly Leu Gly Gly Gly Leu Gly Gly Gly Leu Ala Gly Gly Ser
        515                 520                 525

Ser Gly Ser Tyr Tyr Ser Ser Ser Ser Gly Gly Val Gly Leu Gly Gly
    530                 535                 540

Gly Leu Ser Val Gly Gly Ser Gly Phe Ser Ala Ser Ser Gly Arg Gly
545                 550                 555                 560

Leu Gly Val Gly Phe Gly Ser Gly Gly Gly Ser Ser Ser Ser Val Lys
                565                 570                 575

Phe Val Ser Thr Thr Ser Ser Ser Arg Lys Ser Phe Lys Ser
            580                 585                 590


<210> SEQ ID NO 27
<211> LENGTH: 2308
<212> TYPE: DNA
<213> ORGANISM: Homo sapiens
<220> FEATURE:
<221> NAME/KEY: CDS
<222> LOCATION: (70)..(1764)

<400> SEQUENCE: 27

agtcctgctt ctcttccctc tctcctccag cctctcacac tctcctcagc tctctcatct      60

cctggaacc atg gcc agc aca tcc acc acc atc agg agc cac agc agc agc     111
          Met Ala Ser Thr Ser Thr Thr Ile Arg Ser His Ser Ser Ser
          1               5                   10

cgc cgg ggt ttc agt gcc aac tca gcc agg ctc cct ggg gtc agc cgc      159
Arg Arg Gly Phe Ser Ala Asn Ser Ala Arg Leu Pro Gly Val Ser Arg
15                  20                  25                  30

tct ggc ttc agc agc gtc tcc gtg tcc cgc tcc agg ggc agt ggt ggc      207
Ser Gly Phe Ser Ser Val Ser Val Ser Arg Ser Arg Gly Ser Gly Gly
                35                  40                  45

ctg ggt ggt gca tgt gga gga gct ggc ttt ggc agc cgc agt ctg tat      255
Leu Gly Gly Ala Cys Gly Gly Ala Gly Phe Gly Ser Arg Ser Leu Tyr
            50                  55                  60

ggc ctg ggg ggc tcc aag agg atc tcc att gga ggg ggc agc tgt gcc      303
Gly Leu Gly Gly Ser Lys Arg Ile Ser Ile Gly Gly Gly Ser Cys Ala
        65                  70                  75

atc agt ggc ggc tat ggc agc aga gcc gga ggc agc tat ggc ttt ggt      351
Ile Ser Gly Gly Tyr Gly Ser Arg Ala Gly Gly Ser Tyr Gly Phe Gly
    80                  85                  90

ggc gcc ggg agt gga ttt ggt ttc ggt ggt gga gcc ggc att ggc ttt      399
Gly Ala Gly Ser Gly Phe Gly Phe Gly Gly Gly Ala Gly Ile Gly Phe
95                  100                 105                 110

ggt ctg ggt ggt gga gcc ggc ctt gct ggt ggc ttt ggg ggc cct ggc      447
Gly Leu Gly Gly Gly Ala Gly Leu Ala Gly Gly Phe Gly Gly Pro Gly
                115                 120                 125

ttc cct gtg tgc ccc cct gga ggc atc caa gag gtc acc gtc aac cag      495
Phe Pro Val Cys Pro Pro Gly Gly Ile Gln Glu Val Thr Val Asn Gln
            130                 135                 140

agt ctc ctg act ccc ctc aac ctg caa atc gat ccc acc atc cag cgg      543
Ser Leu Leu Thr Pro Leu Asn Leu Gln Ile Asp Pro Thr Ile Gln Arg
        145                 150                 155
```

-continued

```
gtg cgg gct gag gag cgt gaa cag atc aag acc ctc aac aac aag ttt      591
Val Arg Ala Glu Glu Arg Glu Gln Ile Lys Thr Leu Asn Asn Lys Phe
    160                 165                 170

gcc tcc ttc atc gac aag gtg cgg ttc ctg gag cag cag aac aag gtt      639
Ala Ser Phe Ile Asp Lys Val Arg Phe Leu Glu Gln Gln Asn Lys Val
175                 180                 185                 190

ctg gaa aca aag tgg acc ctg ctg cag gag cag ggc acc aag act gtg      687
Leu Glu Thr Lys Trp Thr Leu Leu Gln Glu Gln Gly Thr Lys Thr Val
                195                 200                 205

agg cag aac ctg gag ccg ttg ttc gag cag tac atc aac aac ctc agg      735
Arg Gln Asn Leu Glu Pro Leu Phe Glu Gln Tyr Ile Asn Asn Leu Arg
            210                 215                 220

agg cag ctg gac agc att gtc ggg gaa cgg ggc cgc ctg gac tca gag      783
Arg Gln Leu Asp Ser Ile Val Gly Glu Arg Gly Arg Leu Asp Ser Glu
        225                 230                 235

ctc aga ggc atg cag gac ctg gtg gag gac ttc aag aac aaa tat gag      831
Leu Arg Gly Met Gln Asp Leu Val Glu Asp Phe Lys Asn Lys Tyr Glu
    240                 245                 250

gat gaa atc aac aag cgc aca gca gca gag aat gaa ttt gtg act ctg      879
Asp Glu Ile Asn Lys Arg Thr Ala Ala Glu Asn Glu Phe Val Thr Leu
255                 260                 265                 270

aag aag gat gtg gat gct gcc tac atg aac aag gtt gaa ctg caa gcc      927
Lys Lys Asp Val Asp Ala Ala Tyr Met Asn Lys Val Glu Leu Gln Ala
                275                 280                 285

aag gca gac act ctc aca gac gag atc aac ttc ctg aga gcc ttg tat      975
Lys Ala Asp Thr Leu Thr Asp Glu Ile Asn Phe Leu Arg Ala Leu Tyr
            290                 295                 300

gat gca gag ctg tcc cag atg cag acc cac atc tca gac aca tct gtg     1023
Asp Ala Glu Leu Ser Gln Met Gln Thr His Ile Ser Asp Thr Ser Val
        305                 310                 315

gtg ctg tcc atg gac aac aac cgc aac ctg gac ctg gac agc atc atc     1071
Val Leu Ser Met Asp Asn Asn Arg Asn Leu Asp Leu Asp Ser Ile Ile
    320                 325                 330

gct gag gtc aag gcc caa tat gag gag att gct cag aga agc cgg gct     1119
Ala Glu Val Lys Ala Gln Tyr Glu Glu Ile Ala Gln Arg Ser Arg Ala
335                 340                 345                 350

gag gct gag tcc tgg tac cag acc aag tac gag gag ctg cag gtc aca     1167
Glu Ala Glu Ser Trp Tyr Gln Thr Lys Tyr Glu Glu Leu Gln Val Thr
                355                 360                 365

gca ggc aga cat ggg gac gac ctg cgc aac acc aag cag gag att gct     1215
Ala Gly Arg His Gly Asp Asp Leu Arg Asn Thr Lys Gln Glu Ile Ala
            370                 375                 380

gag atc aac cgc atg atc cag agg ctg aga tct gag atc gac cac gtc     1263
Glu Ile Asn Arg Met Ile Gln Arg Leu Arg Ser Glu Ile Asp His Val
        385                 390                 395

aag aag cag tgc gcc aac ctg cag gcc gcc att gct gat gct gag cag     1311
Lys Lys Gln Cys Ala Asn Leu Gln Ala Ala Ile Ala Asp Ala Glu Gln
    400                 405                 410

cgt ggg gag atg gcc ctc aag gat gcc aag aac aag ctg gaa ggg ctg     1359
Arg Gly Glu Met Ala Leu Lys Asp Ala Lys Asn Lys Leu Glu Gly Leu
415                 420                 425                 430

gag gat gcc ctg cag aag gcc aag cag gac ctg gcc cgg ctg ctg aag     1407
Glu Asp Ala Leu Gln Lys Ala Lys Gln Asp Leu Ala Arg Leu Leu Lys
                435                 440                 445

gag tac cag gag ctg atg aat gtc aag ctg gcc ctg gac gtg gag atc     1455
Glu Tyr Gln Glu Leu Met Asn Val Lys Leu Ala Leu Asp Val Glu Ile
            450                 455                 460

gcc acc tac cgc aag ctg ctg gag ggt gag gag tgc agg ctg aat ggc     1503
Ala Thr Tyr Arg Lys Leu Leu Glu Gly Glu Glu Cys Arg Leu Asn Gly
```

-continued

```
        465                 470                 475

gaa ggc gtt gga caa gtc aac atc tct gtg gtg cag tcc acc gtc tcc      1551
Glu Gly Val Gly Gln Val Asn Ile Ser Val Val Gln Ser Thr Val Ser
    480                 485                 490

agt ggc tat ggc ggt gcc agt ggt gtc ggc agt ggc tta ggc ctg ggt      1599
Ser Gly Tyr Gly Gly Ala Ser Gly Val Gly Ser Gly Leu Gly Leu Gly
495                 500                 505                 510

gga gga agc agc tac tcc tat ggc agt ggt ctt ggc gtt gga ggt ggc      1647
Gly Gly Ser Ser Tyr Ser Tyr Gly Ser Gly Leu Gly Val Gly Gly Gly
                515                 520                 525

ttc agt tcc agc agt ggc aga gcc att ggg ggt ggc ctc agc tct gtt      1695
Phe Ser Ser Ser Ser Gly Arg Ala Ile Gly Gly Gly Leu Ser Ser Val
            530                 535                 540

gga ggc ggc agt tcc acc atc aag tac acc acc acc tcc tcc tcc agc      1743
Gly Gly Gly Ser Ser Thr Ile Lys Tyr Thr Thr Thr Ser Ser Ser Ser
        545                 550                 555

agg aag agc tat aag cac taa agtgcgtctg ctagctctcg gtcccacagt        1794
Arg Lys Ser Tyr Lys His
    560

cctcaggccc ctctctggct gcagagccct ctcctcaggt tgcctttcct ctcctggcct   1854

ccagtctccc ctgctgtccc aggtagagct gggtatggat gcttagtgcc ctcacttctt   1914

ctctctctct ctataccatc tgagcaccca ttgctcacca tcagatcaac ctctgatttt   1974

acatcatgat gtaatcacca ctggagcttc actgttacta aattattaat ttcttgcctc   2034

cagtgttcta tctctgaggc tgagcattat aagaaaatga cctctgctcc ttttcattgc   2094

agaaaattgc caggggctta tttcagaaca acttccactt actttccact ggctctcaaa   2154

ctctctaact tataagtgtt gtgaaccccc acccaggcag tatccatgaa agcacaagtg   2214

actagtccta tgatgtacaa agcctgtatc tctgtgatga tttctgtgct cttcgctgtt   2274

tgcaattgct aaataaagca gatttataat acaa                               2308


<210> SEQ ID NO 28
<211> LENGTH: 564
<212> TYPE: PRT
<213> ORGANISM: Homo sapiens

<400> SEQUENCE: 28

Met Ala Ser Thr Ser Thr Thr Ile Arg Ser His Ser Ser Ser Arg Arg
1               5                   10                  15

Gly Phe Ser Ala Asn Ser Ala Arg Leu Pro Gly Val Ser Arg Ser Gly
            20                  25                  30

Phe Ser Ser Val Ser Val Ser Arg Ser Arg Gly Ser Gly Gly Leu Gly
        35                  40                  45

Gly Ala Cys Gly Gly Ala Gly Phe Gly Ser Arg Ser Leu Tyr Gly Leu
    50                  55                  60

Gly Gly Ser Lys Arg Ile Ser Ile Gly Gly Gly Ser Cys Ala Ile Ser
65                  70                  75                  80

Gly Gly Tyr Gly Ser Arg Ala Gly Gly Ser Tyr Gly Phe Gly Gly Ala
                85                  90                  95

Gly Ser Gly Phe Gly Phe Gly Gly Gly Ala Gly Ile Gly Phe Gly Leu
            100                 105                 110

Gly Gly Gly Ala Gly Leu Ala Gly Gly Phe Gly Gly Pro Gly Phe Pro
        115                 120                 125

Val Cys Pro Pro Gly Gly Ile Gln Glu Val Thr Val Asn Gln Ser Leu
    130                 135                 140
```

-continued

```
Leu Thr Pro Leu Asn Leu Gln Ile Asp Pro Thr Ile Gln Arg Val Arg
145                 150                 155                 160

Ala Glu Glu Arg Glu Gln Ile Lys Thr Leu Asn Asn Lys Phe Ala Ser
                165                 170                 175

Phe Ile Asp Lys Val Arg Phe Leu Glu Gln Gln Asn Lys Val Leu Glu
            180                 185                 190

Thr Lys Trp Thr Leu Leu Gln Glu Gln Gly Thr Lys Thr Val Arg Gln
        195                 200                 205

Asn Leu Glu Pro Leu Phe Glu Gln Tyr Ile Asn Asn Leu Arg Arg Gln
    210                 215                 220

Leu Asp Ser Ile Val Gly Glu Arg Gly Arg Leu Asp Ser Glu Leu Arg
225                 230                 235                 240

Gly Met Gln Asp Leu Val Glu Asp Phe Lys Asn Lys Tyr Glu Asp Glu
                245                 250                 255

Ile Asn Lys Arg Thr Ala Ala Glu Asn Glu Phe Val Thr Leu Lys Lys
            260                 265                 270

Asp Val Asp Ala Ala Tyr Met Asn Lys Val Glu Leu Gln Ala Lys Ala
        275                 280                 285

Asp Thr Leu Thr Asp Glu Ile Asn Phe Leu Arg Ala Leu Tyr Asp Ala
    290                 295                 300

Glu Leu Ser Gln Met Gln Thr His Ile Ser Asp Thr Ser Val Val Leu
305                 310                 315                 320

Ser Met Asp Asn Asn Arg Asn Leu Asp Leu Asp Ser Ile Ile Ala Glu
                325                 330                 335

Val Lys Ala Gln Tyr Glu Glu Ile Ala Gln Arg Ser Arg Ala Glu Ala
            340                 345                 350

Glu Ser Trp Tyr Gln Thr Lys Tyr Glu Glu Leu Gln Val Thr Ala Gly
        355                 360                 365

Arg His Gly Asp Asp Leu Arg Asn Thr Lys Gln Glu Ile Ala Glu Ile
    370                 375                 380

Asn Arg Met Ile Gln Arg Leu Arg Ser Glu Ile Asp His Val Lys Lys
385                 390                 395                 400

Gln Cys Ala Asn Leu Gln Ala Ala Ile Ala Asp Ala Glu Gln Arg Gly
                405                 410                 415

Glu Met Ala Leu Lys Asp Ala Lys Asn Lys Leu Glu Gly Leu Glu Asp
            420                 425                 430

Ala Leu Gln Lys Ala Lys Gln Asp Leu Ala Arg Leu Leu Lys Glu Tyr
        435                 440                 445

Gln Glu Leu Met Asn Val Lys Leu Ala Leu Asp Val Glu Ile Ala Thr
    450                 455                 460

Tyr Arg Lys Leu Leu Glu Gly Glu Glu Cys Arg Leu Asn Gly Glu Gly
465                 470                 475                 480

Val Gly Gln Val Asn Ile Ser Val Val Gln Ser Thr Val Ser Ser Gly
                485                 490                 495

Tyr Gly Gly Ala Ser Gly Val Gly Ser Gly Leu Gly Leu Gly Gly Gly
            500                 505                 510

Ser Ser Tyr Ser Tyr Gly Ser Gly Leu Gly Val Gly Gly Gly Phe Ser
        515                 520                 525

Ser Ser Ser Gly Arg Ala Ile Gly Gly Gly Leu Ser Ser Val Gly Gly
    530                 535                 540

Gly Ser Ser Thr Ile Lys Tyr Thr Thr Thr Ser Ser Ser Ser Arg Lys
545                 550                 555                 560

Ser Tyr Lys His
```

<210> SEQ ID NO 29
<211> LENGTH: 1712
<212> TYPE: DNA
<213> ORGANISM: Homo sapiens
<220> FEATURE:
<221> NAME/KEY: CDS
<222> LOCATION: (64)..(1434)

<400> SEQUENCE: 29

```
ctggtacctc ctgccagcat ctcttgggtt tgctgagaac tcacgggctc cagctacctg     60

gcc atg acc acc aca ttt ctg caa act tct tcc tcc acc ttt ggg ggt      108
    Met Thr Thr Thr Phe Leu Gln Thr Ser Ser Ser Thr Phe Gly Gly
    1               5                   10                  15

ggc tca acc cga ggg ggt tcc ctc ctg gct ggg gga ggt ggc ttt ggt      156
Gly Ser Thr Arg Gly Gly Ser Leu Leu Ala Gly Gly Gly Gly Phe Gly
                20                  25                  30

ggg ggg agt ctc tct ggg gga ggt gga agc cga agt atc tca gct tct      204
Gly Gly Ser Leu Ser Gly Gly Gly Gly Ser Arg Ser Ile Ser Ala Ser
            35                  40                  45

tct gct agg ttt gtc tct tca ggg tca gga gga gga tat ggg ggt ggc      252
Ser Ala Arg Phe Val Ser Ser Gly Ser Gly Gly Gly Tyr Gly Gly Gly
        50                  55                  60

atg agg gtc tgt ggc ttt ggt gga ggg gct ggt agt gtt ttc ggt gga      300
Met Arg Val Cys Gly Phe Gly Gly Gly Ala Gly Ser Val Phe Gly Gly
    65                  70                  75

ggc ttt gga ggg ggc gtt ggt ggg ggt ttt ggt ggt ggc ttt ggt ggt      348
Gly Phe Gly Gly Gly Val Gly Gly Gly Phe Gly Gly Gly Phe Gly Gly
80                  85                  90                  95

ggc gat ggt ggt ctc ctc tct ggc aat gag aaa att acc atg cag aac      396
Gly Asp Gly Gly Leu Leu Ser Gly Asn Glu Lys Ile Thr Met Gln Asn
                100                 105                 110

ctc aat gac cgc ctg gcc tcc tac ctg gac aag gta cgt gcc ctg gag      444
Leu Asn Asp Arg Leu Ala Ser Tyr Leu Asp Lys Val Arg Ala Leu Glu
            115                 120                 125

gag gcc aat gct gac ctg gag gtg aag atc cat gac tgg tac cag aag      492
Glu Ala Asn Ala Asp Leu Glu Val Lys Ile His Asp Trp Tyr Gln Lys
        130                 135                 140

cag acc cca acc agc cca gaa tgc gac tac agc caa tac ttc aag acc      540
Gln Thr Pro Thr Ser Pro Glu Cys Asp Tyr Ser Gln Tyr Phe Lys Thr
    145                 150                 155

att gaa gag ctc cgg gac aag atc atg gcc acc acc atc gac aac tcc      588
Ile Glu Glu Leu Arg Asp Lys Ile Met Ala Thr Thr Ile Asp Asn Ser
160                 165                 170                 175

cgg gtc atc ctg gag atc gac aat gcc agg ctg gct gcg gac gac ttc      636
Arg Val Ile Leu Glu Ile Asp Asn Ala Arg Leu Ala Ala Asp Asp Phe
                180                 185                 190

agg ctc aag tat gag aat gag ctg gcc ctg cgc cag ggc gtt gag gct      684
Arg Leu Lys Tyr Glu Asn Glu Leu Ala Leu Arg Gln Gly Val Glu Ala
            195                 200                 205

gac atc aac ggc ttg cgc cga gtc ctg gat gag ctg acc ctg gcc agg      732
Asp Ile Asn Gly Leu Arg Arg Val Leu Asp Glu Leu Thr Leu Ala Arg
        210                 215                 220

act gac ctg gag atg cag atc gag ggc ctg aat gag gag cta gcc tac      780
Thr Asp Leu Glu Met Gln Ile Glu Gly Leu Asn Glu Glu Leu Ala Tyr
    225                 230                 235

ctg aag aag aac cac gaa gag gag atg aag gag ttc agc agc cag ctg      828
Leu Lys Lys Asn His Glu Glu Glu Met Lys Glu Phe Ser Ser Gln Leu
240                 245                 250                 255

gcc ggc cag gtc aat gtg gag atg gac gca gca ccg ggt gtg gac ctg      876
```

```
Ala Gly Gln Val Asn Val Glu Met Asp Ala Ala Pro Gly Val Asp Leu
                260                 265                 270

acc cgt gtg ctg gca gag atg agg gag cag tac gag gcc atg gcg gag      924
Thr Arg Val Leu Ala Glu Met Arg Glu Gln Tyr Glu Ala Met Ala Glu
            275                 280                 285

aag aac cgc cgg gat gtc gag gcc tgg ttc ttc agc aag act gag gag      972
Lys Asn Arg Arg Asp Val Glu Ala Trp Phe Phe Ser Lys Thr Glu Glu
        290                 295                 300

ctg aac aaa gag gtg gcc tcc aac aca gaa atg atc cag acc agc aag     1020
Leu Asn Lys Glu Val Ala Ser Asn Thr Glu Met Ile Gln Thr Ser Lys
    305                 310                 315

acg gag atc aca gac ctg aga cgc acg atg cag gag ctg gag atc gag     1068
Thr Glu Ile Thr Asp Leu Arg Arg Thr Met Gln Glu Leu Glu Ile Glu
320                 325                 330                 335

ctg cag tcc cag ctc agc atg aaa gct ggg ctg gag aac tca ctg gcc     1116
Leu Gln Ser Gln Leu Ser Met Lys Ala Gly Leu Glu Asn Ser Leu Ala
                340                 345                 350

gag aca gag tgc cgc tat gcc acg cag ctg cag cag atc cag ggg ctc     1164
Glu Thr Glu Cys Arg Tyr Ala Thr Gln Leu Gln Gln Ile Gln Gly Leu
            355                 360                 365

att ggt ggc ctg gag gcc cag ctg agt gag ctc cga tgc gag atg gag     1212
Ile Gly Gly Leu Glu Ala Gln Leu Ser Glu Leu Arg Cys Glu Met Glu
        370                 375                 380

gct cag aac cag gag tac aag atg ctg ctt gac ata aag aca cgg ctg     1260
Ala Gln Asn Gln Glu Tyr Lys Met Leu Leu Asp Ile Lys Thr Arg Leu
    385                 390                 395

gag cag gag atc gct act tac cgc agc ctg ctc gag ggc cag gat gcc     1308
Glu Gln Glu Ile Ala Thr Tyr Arg Ser Leu Leu Glu Gly Gln Asp Ala
400                 405                 410                 415

aag atg gct ggc att gcc atc agg gaa gcc tct tca gga ggt ggt ggt     1356
Lys Met Ala Gly Ile Ala Ile Arg Glu Ala Ser Ser Gly Gly Gly Gly
                420                 425                 430

agc agc agc aat ttc cac atc aat gta gaa gag tca gtg gat gga cag     1404
Ser Ser Ser Asn Phe His Ile Asn Val Glu Glu Ser Val Asp Gly Gln
            435                 440                 445

gtg gtt tct tcc cac aag aga gaa atc taa gtgtctattg caggagaaac       1454
Val Val Ser Ser His Lys Arg Glu Ile
        450                 455

gtcccttgcc actccccact ctcatcaggc caagtggagg actggccaga gggcctgcac   1514

atgcaaactc cagtccctgc cttcagagag ctgaaaaggg tccctcggtc ttttatttca   1574

gggctttgca tgcgctctat tccccctctg cctctcccca ccttctttgg agcaaggaga   1634

tgcagctgta ttgtgtaaca agctcatttg tacagtgtct gttcatgtaa taaagaatta   1694

cttttccttt tgcaaata                                                 1712


<210> SEQ ID NO 30
<211> LENGTH: 456
<212> TYPE: PRT
<213> ORGANISM: Homo sapiens

<400> SEQUENCE: 30

Met Thr Thr Thr Phe Leu Gln Thr Ser Ser Ser Thr Phe Gly Gly Gly
1               5                   10                  15

Ser Thr Arg Gly Gly Ser Leu Leu Ala Gly Gly Gly Gly Phe Gly Gly
            20                  25                  30

Gly Ser Leu Ser Gly Gly Gly Gly Ser Arg Ser Ile Ser Ala Ser Ser
        35                  40                  45

Ala Arg Phe Val Ser Ser Gly Ser Gly Gly Gly Tyr Gly Gly Gly Met
```

```
    50                  55                  60

Arg Val Cys Gly Phe Gly Gly Gly Ala Gly Ser Val Phe Gly Gly Gly
65                  70                  75                  80

Phe Gly Gly Gly Val Gly Gly Gly Phe Gly Gly Gly Phe Gly Gly Gly
                85                  90                  95

Asp Gly Gly Leu Leu Ser Gly Asn Glu Lys Ile Thr Met Gln Asn Leu
            100                 105                 110

Asn Asp Arg Leu Ala Ser Tyr Leu Asp Lys Val Arg Ala Leu Glu Glu
        115                 120                 125

Ala Asn Ala Asp Leu Glu Val Lys Ile His Asp Trp Tyr Gln Lys Gln
    130                 135                 140

Thr Pro Thr Ser Pro Glu Cys Asp Tyr Ser Gln Tyr Phe Lys Thr Ile
145                 150                 155                 160

Glu Glu Leu Arg Asp Lys Ile Met Ala Thr Thr Ile Asp Asn Ser Arg
                165                 170                 175

Val Ile Leu Glu Ile Asp Asn Ala Arg Leu Ala Ala Asp Asp Phe Arg
            180                 185                 190

Leu Lys Tyr Glu Asn Glu Leu Ala Leu Arg Gln Gly Val Glu Ala Asp
        195                 200                 205

Ile Asn Gly Leu Arg Arg Val Leu Asp Glu Leu Thr Leu Ala Arg Thr
    210                 215                 220

Asp Leu Glu Met Gln Ile Glu Gly Leu Asn Glu Glu Leu Ala Tyr Leu
225                 230                 235                 240

Lys Lys Asn His Glu Glu Glu Met Lys Glu Phe Ser Ser Gln Leu Ala
                245                 250                 255

Gly Gln Val Asn Val Glu Met Asp Ala Ala Pro Gly Val Asp Leu Thr
            260                 265                 270

Arg Val Leu Ala Glu Met Arg Glu Gln Tyr Glu Ala Met Ala Glu Lys
        275                 280                 285

Asn Arg Arg Asp Val Glu Ala Trp Phe Phe Ser Lys Thr Glu Glu Leu
    290                 295                 300

Asn Lys Glu Val Ala Ser Asn Thr Glu Met Ile Gln Thr Ser Lys Thr
305                 310                 315                 320

Glu Ile Thr Asp Leu Arg Arg Thr Met Gln Glu Leu Glu Ile Glu Leu
                325                 330                 335

Gln Ser Gln Leu Ser Met Lys Ala Gly Leu Glu Asn Ser Leu Ala Glu
            340                 345                 350

Thr Glu Cys Arg Tyr Ala Thr Gln Leu Gln Gln Ile Gln Gly Leu Ile
        355                 360                 365

Gly Gly Leu Glu Ala Gln Leu Ser Glu Leu Arg Cys Glu Met Glu Ala
    370                 375                 380

Gln Asn Gln Glu Tyr Lys Met Leu Leu Asp Ile Lys Thr Arg Leu Glu
385                 390                 395                 400

Gln Glu Ile Ala Thr Tyr Arg Ser Leu Leu Glu Gly Gln Asp Ala Lys
                405                 410                 415

Met Ala Gly Ile Ala Ile Arg Glu Ala Ser Ser Gly Gly Gly Gly Ser
            420                 425                 430

Ser Ser Asn Phe His Ile Asn Val Glu Glu Ser Val Asp Gly Gln Val
        435                 440                 445

Val Ser Ser His Lys Arg Glu Ile
    450                 455
```

<210> SEQ ID NO 31

```
<211> LENGTH: 1517
<212> TYPE: DNA
<213> ORGANISM: Homo sapiens
<220> FEATURE:
<221> NAME/KEY: CDS
<222> LOCATION: (67)..(1365)

<400> SEQUENCE: 31

acacaacttg gggcccctct cctctccagc ccttctcctg tgtgcctgcc tcctgccgcc      60

gccacc atg acc acc tcc atc cgc cag ttc acc tcc tcc agc tcc atc        108
       Met Thr Thr Ser Ile Arg Gln Phe Thr Ser Ser Ser Ser Ile
       1               5                   10

aag ggc tcc tcc ggc ctg ggg ggc ggc tcg tcc cgc acc tcc tgc cgg       156
Lys Gly Ser Ser Gly Leu Gly Gly Gly Ser Ser Arg Thr Ser Cys Arg
15                  20                  25                  30

ctg tct ggc ggc ctg ggt gcc ggc tcc tgc agg ctg gga tct gct ggc       204
Leu Ser Gly Gly Leu Gly Ala Gly Ser Cys Arg Leu Gly Ser Ala Gly
                35                  40                  45

ggc ctg ggc agc acc ctc ggg ggt agc agc tac tcc agc tgc tac agc       252
Gly Leu Gly Ser Thr Leu Gly Gly Ser Ser Tyr Ser Ser Cys Tyr Ser
            50                  55                  60

ttt ggc tct ggt ggt ggc tat ggc agc agc ttt ggg ggt gtt gat ggg       300
Phe Gly Ser Gly Gly Gly Tyr Gly Ser Ser Phe Gly Gly Val Asp Gly
        65                  70                  75

ctg ctg gct gga ggt gag aag gcc acc atg cag aac ctc aat gac cgc       348
Leu Leu Ala Gly Gly Glu Lys Ala Thr Met Gln Asn Leu Asn Asp Arg
    80                  85                  90

ctg gcc tcc tac ctg gac aag gtg cgt gcc ctg gag gag gcc aac act       396
Leu Ala Ser Tyr Leu Asp Lys Val Arg Ala Leu Glu Glu Ala Asn Thr
95                  100                 105                 110

gag ctg gag gtg aag atc cgt gac tgg tac cag agg cag gcc ccg ggg       444
Glu Leu Glu Val Lys Ile Arg Asp Trp Tyr Gln Arg Gln Ala Pro Gly
                115                 120                 125

ccc gcc cgt gac tac agc cag tac tac agg aca att gag gag ctg cag       492
Pro Ala Arg Asp Tyr Ser Gln Tyr Tyr Arg Thr Ile Glu Glu Leu Gln
            130                 135                 140

aac aag atc ctc aca gcc acc gtg gac aat gcc aac atc ctg cta cag       540
Asn Lys Ile Leu Thr Ala Thr Val Asp Asn Ala Asn Ile Leu Leu Gln
        145                 150                 155

att gac aat gcc cgt ctg gct gct gat gac ttc cgc acc aag ttt gag       588
Ile Asp Asn Ala Arg Leu Ala Ala Asp Asp Phe Arg Thr Lys Phe Glu
    160                 165                 170

aca gag cag gcc ctg cgc ctg agt gtg gag gcc gac atc aat ggc ctg       636
Thr Glu Gln Ala Leu Arg Leu Ser Val Glu Ala Asp Ile Asn Gly Leu
175                 180                 185                 190

cgc agg gtg ctg gat gag ctg acc ctg gcc aga gcc gac ctg gag atg       684
Arg Arg Val Leu Asp Glu Leu Thr Leu Ala Arg Ala Asp Leu Glu Met
                195                 200                 205

cag att gag aac ctc aag gag gag ctg gcc tac ctg aag aag aac cac       732
Gln Ile Glu Asn Leu Lys Glu Glu Leu Ala Tyr Leu Lys Lys Asn His
            210                 215                 220

gag gag gag atg aac gcc ctg cga ggc cag gtg ggt ggt gag atc aat       780
Glu Glu Glu Met Asn Ala Leu Arg Gly Gln Val Gly Gly Glu Ile Asn
        225                 230                 235

gtg gag atg gac gct gcc cca ggc gtg gac ctg agc cgc atc ctc aac       828
Val Glu Met Asp Ala Ala Pro Gly Val Asp Leu Ser Arg Ile Leu Asn
    240                 245                 250

gag atg cgt gac cag tat gag aag atg gca gag aag aac cgc aag gat       876
Glu Met Arg Asp Gln Tyr Glu Lys Met Ala Glu Lys Asn Arg Lys Asp
255                 260                 265                 270
```

```
gcc gag gat tgg ttc ttc agc aag aca gag gaa ctg aac cgc gag gtg      924
Ala Glu Asp Trp Phe Phe Ser Lys Thr Glu Glu Leu Asn Arg Glu Val
                275                 280                 285

gcc acc aac agt gag ctg gtg cag agt ggc aag agt gag atc tcg gag      972
Ala Thr Asn Ser Glu Leu Val Gln Ser Gly Lys Ser Glu Ile Ser Glu
            290                 295                 300

ctc cgg cgc acc atg cag gcc ttg gag ata gag ctg cag tcc cag ctc     1020
Leu Arg Arg Thr Met Gln Ala Leu Glu Ile Glu Leu Gln Ser Gln Leu
        305                 310                 315

agc atg aaa gca tcc ctg gag ggc aac ctg gcg gag aca gag aac cgc     1068
Ser Met Lys Ala Ser Leu Glu Gly Asn Leu Ala Glu Thr Glu Asn Arg
    320                 325                 330

tac tgc gtg cag ctg tcc cag atc cag ggg ctg att ggc agc gtg gag     1116
Tyr Cys Val Gln Leu Ser Gln Ile Gln Gly Leu Ile Gly Ser Val Glu
335                 340                 345                 350

gag cag ctg gcc cag ctt cgc tgc gag atg gag cag cag aac cag gaa     1164
Glu Gln Leu Ala Gln Leu Arg Cys Glu Met Glu Gln Gln Asn Gln Glu
                355                 360                 365

tac aaa atc ctg ctg gat gtg aag acg cgg ctg gag cag gag att gcc     1212
Tyr Lys Ile Leu Leu Asp Val Lys Thr Arg Leu Glu Gln Glu Ile Ala
            370                 375                 380

acc tac cgc cgc ctg ctg gag gga gag gat gcc cac ctg act cag tac     1260
Thr Tyr Arg Arg Leu Leu Glu Gly Glu Asp Ala His Leu Thr Gln Tyr
        385                 390                 395

aag aaa gaa ccg gtg acc acc cgt cag gtg cgt acc att gtg gaa gag     1308
Lys Lys Glu Pro Val Thr Thr Arg Gln Val Arg Thr Ile Val Glu Glu
    400                 405                 410

gtc cag gat ggc aag gtc atc tcc tcc cgc gag cag gtc cac cag acc     1356
Val Gln Asp Gly Lys Val Ile Ser Ser Arg Glu Gln Val His Gln Thr
415                 420                 425                 430

acc cgc tga ggactcagct accccggccg gccacccagg aggcagggag             1405
Thr Arg

gcagccgccc catctgcccc acagtctccg gcctctccag cctcagcccc ctgcttcagt   1465

cccttcccca tgcttccttg cctgatgaca ataaagcttg ttgactcagc ta           1517


<210> SEQ ID NO 32
<211> LENGTH: 432
<212> TYPE: PRT
<213> ORGANISM: Homo sapiens

<400> SEQUENCE: 32

Met Thr Thr Ser Ile Arg Gln Phe Thr Ser Ser Ser Ser Ile Lys Gly
1               5                   10                  15

Ser Ser Gly Leu Gly Gly Gly Ser Ser Arg Thr Ser Cys Arg Leu Ser
            20                  25                  30

Gly Gly Leu Gly Ala Gly Ser Cys Arg Leu Gly Ser Ala Gly Gly Leu
        35                  40                  45

Gly Ser Thr Leu Gly Gly Ser Ser Tyr Ser Ser Cys Tyr Ser Phe Gly
    50                  55                  60

Ser Gly Gly Gly Tyr Gly Ser Ser Phe Gly Gly Val Asp Gly Leu Leu
65                  70                  75                  80

Ala Gly Gly Glu Lys Ala Thr Met Gln Asn Leu Asn Asp Arg Leu Ala
                85                  90                  95

Ser Tyr Leu Asp Lys Val Arg Ala Leu Glu Glu Ala Asn Thr Glu Leu
            100                 105                 110

Glu Val Lys Ile Arg Asp Trp Tyr Gln Arg Gln Ala Pro Gly Pro Ala
        115                 120                 125
```

-continued

Arg Asp Tyr Ser Gln Tyr Tyr Arg Thr Ile Glu Glu Leu Gln Asn Lys
    130                 135                 140

Ile Leu Thr Ala Thr Val Asp Asn Ala Asn Ile Leu Leu Gln Ile Asp
145                 150                 155                 160

Asn Ala Arg Leu Ala Ala Asp Asp Phe Arg Thr Lys Phe Glu Thr Glu
                165                 170                 175

Gln Ala Leu Arg Leu Ser Val Glu Ala Asp Ile Asn Gly Leu Arg Arg
            180                 185                 190

Val Leu Asp Glu Leu Thr Leu Ala Arg Ala Asp Leu Glu Met Gln Ile
        195                 200                 205

Glu Asn Leu Lys Glu Glu Leu Ala Tyr Leu Lys Lys Asn His Glu Glu
    210                 215                 220

Glu Met Asn Ala Leu Arg Gly Gln Val Gly Gly Glu Ile Asn Val Glu
225                 230                 235                 240

Met Asp Ala Ala Pro Gly Val Asp Leu Ser Arg Ile Leu Asn Glu Met
                245                 250                 255

Arg Asp Gln Tyr Glu Lys Met Ala Glu Lys Asn Arg Lys Asp Ala Glu
            260                 265                 270

Asp Trp Phe Phe Ser Lys Thr Glu Glu Leu Asn Arg Glu Val Ala Thr
        275                 280                 285

Asn Ser Glu Leu Val Gln Ser Gly Lys Ser Glu Ile Ser Glu Leu Arg
    290                 295                 300

Arg Thr Met Gln Ala Leu Glu Ile Glu Leu Gln Ser Gln Leu Ser Met
305                 310                 315                 320

Lys Ala Ser Leu Glu Gly Asn Leu Ala Glu Thr Glu Asn Arg Tyr Cys
                325                 330                 335

Val Gln Leu Ser Gln Ile Gln Gly Leu Ile Gly Ser Val Glu Glu Gln
            340                 345                 350

Leu Ala Gln Leu Arg Cys Glu Met Glu Gln Gln Asn Gln Glu Tyr Lys
        355                 360                 365

Ile Leu Leu Asp Val Lys Thr Arg Leu Glu Gln Glu Ile Ala Thr Tyr
    370                 375                 380

Arg Arg Leu Leu Glu Gly Glu Asp Ala His Leu Thr Gln Tyr Lys Lys
385                 390                 395                 400

Glu Pro Val Thr Thr Arg Gln Val Arg Thr Ile Val Glu Glu Val Gln
                405                 410                 415

Asp Gly Lys Val Ile Ser Ser Arg Glu Gln Val His Gln Thr Thr Arg
            420                 425                 430

<210> SEQ ID NO 33
<211> LENGTH: 1121
<212> TYPE: DNA
<213> ORGANISM: Homo sapiens
<220> FEATURE:
<221> NAME/KEY: CDS
<222> LOCATION: (60)..(1031)

<400> SEQUENCE: 33
accatctccc actcctgcag ctcttctcac aggaccagcc actagcgcag cctcgagcg      59 atg gcc tat gtc ccc gca ccg ggc tac cag ccc acc tac aac ccg acg      107
Met Ala Tyr Val Pro Ala Pro Gly Tyr Gln Pro Thr Tyr Asn Pro Thr
1               5                   10                  15 ctg cct tac tac cag ccc atc ccg ggc ggg ctc aac gtg gga atg tct      155
Leu Pro Tyr Tyr Gln Pro Ile Pro Gly Gly Leu Asn Val Gly Met Ser
            20                  25                  30 gtt tac atc caa gga gtg gcc agc gag cac atg aag cgg ttc ttc gtg      203

```
Val Tyr Ile Gln Gly Val Ala Ser Glu His Met Lys Arg Phe Phe Val
        35                  40                  45

aac ttt gtg gtt ggg cag gat ccg ggc tca gac gtc gcc ttc cac ttc      251
Asn Phe Val Val Gly Gln Asp Pro Gly Ser Asp Val Ala Phe His Phe
    50                  55                  60

aat ccg cgg ttt gac ggc tgg gac aag gtg gtc ttc aac acg ttg cag      299
Asn Pro Arg Phe Asp Gly Trp Asp Lys Val Val Phe Asn Thr Leu Gln
65                  70                  75                  80

ggc ggg aag tgg ggc agc gag gag agg aag agg agc atg ccc ttc aaa      347
Gly Gly Lys Trp Gly Ser Glu Glu Arg Lys Arg Ser Met Pro Phe Lys
                85                  90                  95

aag ggt gcc gcc ttt gag ctg gtc ttc ata gtc ctg gct gag cac tac      395
Lys Gly Ala Ala Phe Glu Leu Val Phe Ile Val Leu Ala Glu His Tyr
            100                 105                 110

aag gtg gtg gta aat gga aat ccc ttc tat gag tac ggg cac cgg ctt      443
Lys Val Val Val Asn Gly Asn Pro Phe Tyr Glu Tyr Gly His Arg Leu
        115                 120                 125

ccc cta cag atg gtc acc cac ctg caa gtg gat ggg gat ctg caa ctt      491
Pro Leu Gln Met Val Thr His Leu Gln Val Asp Gly Asp Leu Gln Leu
    130                 135                 140

caa tca atc aac ttc atc gga ggc cag ccc ctc cgg ccc cag gga ccc      539
Gln Ser Ile Asn Phe Ile Gly Gly Gln Pro Leu Arg Pro Gln Gly Pro
145                 150                 155                 160

ccg atg atg cca cct tac cct ggt ccc gga cat tgc cat caa cag ctg      587
Pro Met Met Pro Pro Tyr Pro Gly Pro Gly His Cys His Gln Gln Leu
                165                 170                 175

aac agc ctg ccc acc atg gaa gga ccc cca acc ttc aac ccg cct gtg      635
Asn Ser Leu Pro Thr Met Glu Gly Pro Pro Thr Phe Asn Pro Pro Val
            180                 185                 190

cca tat ttc ggg agg ctg caa gga ggg ctc aca gct cga aga acc atc      683
Pro Tyr Phe Gly Arg Leu Gln Gly Gly Leu Thr Ala Arg Arg Thr Ile
        195                 200                 205

atc atc aag ggc tat gtg cct ccc aca ggc aag agc ttt gct atc aac      731
Ile Ile Lys Gly Tyr Val Pro Pro Thr Gly Lys Ser Phe Ala Ile Asn
    210                 215                 220

ttc aag gtg ggc tcc tca ggg gac ata gct ctg cac att aat ccc cgc      779
Phe Lys Val Gly Ser Ser Gly Asp Ile Ala Leu His Ile Asn Pro Arg
225                 230                 235                 240

atg ggc aac ggt acc gtg gtc cgg aac agc ctt ctg aat ggc tcg tgg      827
Met Gly Asn Gly Thr Val Val Arg Asn Ser Leu Leu Asn Gly Ser Trp
                245                 250                 255

gga tcc gag gag aag aag atc acc cac aac cca ttt ggt ccc gga cag      875
Gly Ser Glu Glu Lys Lys Ile Thr His Asn Pro Phe Gly Pro Gly Gln
            260                 265                 270

ttc ttt gat ctg tcc att cgc tgt ggc ttg gat cgc ttc aag gtt tac      923
Phe Phe Asp Leu Ser Ile Arg Cys Gly Leu Asp Arg Phe Lys Val Tyr
        275                 280                 285

gcc aat ggc cag cac ctc ttt gac ttt gcc cat cgc ctc tcg gcc ttc      971
Ala Asn Gly Gln His Leu Phe Asp Phe Ala His Arg Leu Ser Ala Phe
    290                 295                 300

cag agg gtg gac aca ttg gaa atc cag ggt gat gtc acc ttg tcc tat     1019
Gln Arg Val Asp Thr Leu Glu Ile Gln Gly Asp Val Thr Leu Ser Tyr
305                 310                 315                 320

gtc cag atc taa tctattcctg gggccataac tcatgggaaa acagaattat         1071
Val Gln Ile

cccctaggac tcctttctaa gcccctaata aaatgtctga gggtgtctca              1121


<210> SEQ ID NO 34
<211> LENGTH: 323
```

<212> TYPE: PRT
<213> ORGANISM: Homo sapiens

<400> SEQUENCE: 34

```
Met Ala Tyr Val Pro Ala Pro Gly Tyr Gln Pro Thr Tyr Asn Pro Thr
1               5                   10                  15

Leu Pro Tyr Tyr Gln Pro Ile Pro Gly Gly Leu Asn Val Gly Met Ser
            20                  25                  30

Val Tyr Ile Gln Gly Val Ala Ser Glu His Met Lys Arg Phe Phe Val
        35                  40                  45

Asn Phe Val Val Gly Gln Asp Pro Gly Ser Asp Val Ala Phe His Phe
    50                  55                  60

Asn Pro Arg Phe Asp Gly Trp Asp Lys Val Val Phe Asn Thr Leu Gln
65                  70                  75                  80

Gly Gly Lys Trp Gly Ser Glu Glu Arg Lys Arg Ser Met Pro Phe Lys
                85                  90                  95

Lys Gly Ala Ala Phe Glu Leu Val Phe Ile Val Leu Ala Glu His Tyr
            100                 105                 110

Lys Val Val Val Asn Gly Asn Pro Phe Tyr Glu Tyr Gly His Arg Leu
        115                 120                 125

Pro Leu Gln Met Val Thr His Leu Gln Val Asp Gly Asp Leu Gln Leu
    130                 135                 140

Gln Ser Ile Asn Phe Ile Gly Gly Gln Pro Leu Arg Pro Gln Gly Pro
145                 150                 155                 160

Pro Met Met Pro Pro Tyr Pro Gly Pro Gly His Cys His Gln Gln Leu
                165                 170                 175

Asn Ser Leu Pro Thr Met Glu Gly Pro Pro Thr Phe Asn Pro Pro Val
            180                 185                 190

Pro Tyr Phe Gly Arg Leu Gln Gly Gly Leu Thr Ala Arg Arg Thr Ile
        195                 200                 205

Ile Ile Lys Gly Tyr Val Pro Pro Thr Gly Lys Ser Phe Ala Ile Asn
    210                 215                 220

Phe Lys Val Gly Ser Ser Gly Asp Ile Ala Leu His Ile Asn Pro Arg
225                 230                 235                 240

Met Gly Asn Gly Thr Val Val Arg Asn Ser Leu Leu Asn Gly Ser Trp
                245                 250                 255

Gly Ser Glu Glu Lys Lys Ile Thr His Asn Pro Phe Gly Pro Gly Gln
            260                 265                 270

Phe Phe Asp Leu Ser Ile Arg Cys Gly Leu Asp Arg Phe Lys Val Tyr
        275                 280                 285

Ala Asn Gly Gln His Leu Phe Asp Phe Ala His Arg Leu Ser Ala Phe
    290                 295                 300

Gln Arg Val Asp Thr Leu Glu Ile Gln Gly Asp Val Thr Leu Ser Tyr
305                 310                 315                 320

Val Gln Ile
```

<210> SEQ ID NO 35
<211> LENGTH: 1490
<212> TYPE: DNA
<213> ORGANISM: Homo sapiens
<220> FEATURE:
<221> NAME/KEY: CDS
<222> LOCATION: (29)..(475)

<400> SEQUENCE: 35

```
agcctagcac tctgacctag cagtcaac atg aag gct ctc att gtt ctg ggg        52
```

```
                              Met Lys Ala Leu Ile Val Leu Gly
                              1               5

ctt gtc ctc ctt tct gtt acg gtc cag ggc aag gtc ttt gaa agg tgt      100
Leu Val Leu Leu Ser Val Thr Val Gln Gly Lys Val Phe Glu Arg Cys
    10                  15                  20

gag ttg gcc aga act ctg aaa aga ttg gga atg gat ggc tac agg gga      148
Glu Leu Ala Arg Thr Leu Lys Arg Leu Gly Met Asp Gly Tyr Arg Gly
25                  30                  35                  40

atc agc cta gca aac tgg atg tgt ttg gcc aaa tgg gag agt ggt tac      196
Ile Ser Leu Ala Asn Trp Met Cys Leu Ala Lys Trp Glu Ser Gly Tyr
                45                  50                  55

aac aca cga gct aca aac tac aat gct gga gac aga agc act gat tat      244
Asn Thr Arg Ala Thr Asn Tyr Asn Ala Gly Asp Arg Ser Thr Asp Tyr
            60                  65                  70

ggg ata ttt cag atc aat agc cgc tac tgg tgt aat gat ggc aaa acc      292
Gly Ile Phe Gln Ile Asn Ser Arg Tyr Trp Cys Asn Asp Gly Lys Thr
        75                  80                  85

cca gga gca gtt aat gcc tgt cat tta tcc tgc agt gct ttg ctg caa      340
Pro Gly Ala Val Asn Ala Cys His Leu Ser Cys Ser Ala Leu Leu Gln
    90                  95                  100

gat aac atc gct gat gct gta gct tgt gca aag agg gtt gtc cgt gat      388
Asp Asn Ile Ala Asp Ala Val Ala Cys Ala Lys Arg Val Val Arg Asp
105                 110                 115                 120

cca caa ggc att aga gca tgg gtg gca tgg aga aat cgt tgt caa aac      436
Pro Gln Gly Ile Arg Ala Trp Val Ala Trp Arg Asn Arg Cys Gln Asn
                125                 130                 135

aga gat gtc cgt cag tat gtt caa ggt tgt gga gtg taa ctccagaatt       485
Arg Asp Val Arg Gln Tyr Val Gln Gly Cys Gly Val
            140                 145

ttccttcttc agctcatttt gtctctctca cattaaggga gtaggaatta agtgaaaggt    545

cacactacca ttatttcccc ttcaaacaaa taatattttt acagaagcag gagcaaaata    605

tggcctttct tctaagagat ataatgttca ctaatgtggt tattttacat taagcctaca    665

acatttttca gtttgcaaat agaactaata ctggtgaaaa tttacctaaa accttggtta    725

tcaaatacat ctccagtaca ttccgttctt tttttttttg agacagtctc gctctgtcgc    785

ccaggctgga gtgcagtggc gcaatctcgg ctcactgcaa cctccacctc ccgggttcac    845

gccattctcc tgcctcagcc tcccgagtag ctgggattac gggcgcccgc caccacgccc    905

ggctaatttt ttgtattttt agtagagaca gggtttcacc gtgttagcca ggatggtctc    965

gatctcctga ccttgtgatc cacccacctc ggcctcccaa agtgctggga ttacaggcgt   1025

gagccactgc gcccggccac attcagttct tatcaaagaa ataacccaga cttaatcttg   1085

aatgatacga ttatgcccaa tattaagtaa aaaatataag aaaaggttat cttaaataga   1145

tcttaggcaa aataccagct gatgaaggca tctgatgcct tcatctgttc agtcatctcc   1205

aaaaacagta aaaataacca ctttttgttg ggcaatatga aatttttaaa ggagtagaat   1265

accaaatgat agaaacagac tgcctgaatt gagaattttg atttcttaaa gtgtgtttct   1325

ttctaaattg ctgttcctta atttgattaa tttaattcat gtattatgat taaatctgag   1385

gcagatgagc ttacaagtat tgaaataatt actaattaat cacaaatgtg aagttatgca   1445

tgatgtaaaa aatacaaaca ttctaattaa aggctttgca acaca                   1490


<210> SEQ ID NO 36
<211> LENGTH: 148
<212> TYPE: PRT
<213> ORGANISM: Homo sapiens
```

<400> SEQUENCE: 36

Met Lys Ala Leu Ile Val Leu Gly Leu Val Leu Leu Ser Val Thr Val
1               5                   10                  15

Gln Gly Lys Val Phe Glu Arg Cys Glu Leu Ala Arg Thr Leu Lys Arg
            20                  25                  30

Leu Gly Met Asp Gly Tyr Arg Gly Ile Ser Leu Ala Asn Trp Met Cys
        35                  40                  45

Leu Ala Lys Trp Glu Ser Gly Tyr Asn Thr Arg Ala Thr Asn Tyr Asn
    50                  55                  60

Ala Gly Asp Arg Ser Thr Asp Tyr Gly Ile Phe Gln Ile Asn Ser Arg
65                  70                  75                  80

Tyr Trp Cys Asn Asp Gly Lys Thr Pro Gly Ala Val Asn Ala Cys His
                85                  90                  95

Leu Ser Cys Ser Ala Leu Leu Gln Asp Asn Ile Ala Asp Ala Val Ala
            100                 105                 110

Cys Ala Lys Arg Val Val Arg Asp Pro Gln Gly Ile Arg Ala Trp Val
        115                 120                 125

Ala Trp Arg Asn Arg Cys Gln Asn Arg Asp Val Arg Gln Tyr Val Gln
    130                 135                 140

Gly Cys Gly Val
145

<210> SEQ ID NO 37
<211> LENGTH: 14352
<212> TYPE: DNA
<213> ORGANISM: Homo sapiens
<220> FEATURE:
<221> NAME/KEY: CDS
<222> LOCATION: (56)..(13537)

<400> SEQUENCE: 37
catttcgcca gctcctctgg gggtgacagg caagtgagac gtgctcagag ctccg atg      58
                                                             Met
                                                             1 cca agg cca ggg acc atg gcg ctg tgt ctg ctg acc ttg gtc ctc tcg      106
Pro Arg Pro Gly Thr Met Ala Leu Cys Leu Leu Thr Leu Val Leu Ser
            5                   10                  15 ctc ttg ccc cca caa gct gct gca gaa cag gac ctc agt gtg aac agg      154
Leu Leu Pro Pro Gln Ala Ala Ala Glu Gln Asp Leu Ser Val Asn Arg
        20                  25                  30 gct gtg tgg gat gga gga ggg tgc atc tcc caa ggg gac gtc ttg aac      202
Ala Val Trp Asp Gly Gly Gly Cys Ile Ser Gln Gly Asp Val Leu Asn
    35                  40                  45 cgt cag tgc cag cag ctg tct cag cac gtt agg aca ggt tct gcg gca      250
Arg Gln Cys Gln Gln Leu Ser Gln His Val Arg Thr Gly Ser Ala Ala
50                  55                  60                  65 aac acc gcc aca ggt aca aca tct aca aat gtc gtg gag cca aga atg      298
Asn Thr Ala Thr Gly Thr Thr Ser Thr Asn Val Val Glu Pro Arg Met
                70                  75                  80 tat ttg agt tgc agc acc aac cct gag atg acc tcg att gag tcc agt      346
Tyr Leu Ser Cys Ser Thr Asn Pro Glu Met Thr Ser Ile Glu Ser Ser
            85                  90                  95 gtg act tca gac act cct ggt gtc tcc agt acc agg atg aca cca aca      394
Val Thr Ser Asp Thr Pro Gly Val Ser Ser Thr Arg Met Thr Pro Thr
        100                 105                 110 gaa tcc aga aca act tca gaa tct acc agt gac agc acc aca ctt ttc      442
Glu Ser Arg Thr Thr Ser Glu Ser Thr Ser Asp Ser Thr Thr Leu Phe
    115                 120                 125

-continued

```
ccc agt tct act gaa gac act tca tct cct aca act cct gaa ggc acc      490
Pro Ser Ser Thr Glu Asp Thr Ser Ser Pro Thr Thr Pro Glu Gly Thr
130                 135                 140                 145

gac gtg ccc atg tca aca cca agt gaa gaa agc att tca tca aca atg      538
Asp Val Pro Met Ser Thr Pro Ser Glu Glu Ser Ile Ser Ser Thr Met
                150                 155                 160

gct ttt gtc agc act gca cct ctt ccc agt ttt gag gcc tac aca tct      586
Ala Phe Val Ser Thr Ala Pro Leu Pro Ser Phe Glu Ala Tyr Thr Ser
            165                 170                 175

tta aca tat aag gtt gat atg agc aca cct ctg acc act tct act cag      634
Leu Thr Tyr Lys Val Asp Met Ser Thr Pro Leu Thr Thr Ser Thr Gln
        180                 185                 190

gca agt tca tct cct act act cct gaa agc acc acc ata ccc aaa tca      682
Ala Ser Ser Ser Pro Thr Thr Pro Glu Ser Thr Thr Ile Pro Lys Ser
    195                 200                 205

act aac agt gaa gga agc act cca tta aca agt atg cct gcc agc acc      730
Thr Asn Ser Glu Gly Ser Thr Pro Leu Thr Ser Met Pro Ala Ser Thr
210                 215                 220                 225

atg aag gtg gcc agt tca gag gct atc acc ctt ttg aca act cct gtt      778
Met Lys Val Ala Ser Ser Glu Ala Ile Thr Leu Leu Thr Thr Pro Val
                230                 235                 240

gaa atc agc aca cct gtg acc att tct gct caa gcc agt tca tct cct      826
Glu Ile Ser Thr Pro Val Thr Ile Ser Ala Gln Ala Ser Ser Ser Pro
            245                 250                 255

aca act gct gaa ggt ccc agc ctg tca aac tca gct cct agt gga gga      874
Thr Thr Ala Glu Gly Pro Ser Leu Ser Asn Ser Ala Pro Ser Gly Gly
        260                 265                 270

agc act cca tta aca aga atg cct ctc agc gtg atg ctg gtg gtc agt      922
Ser Thr Pro Leu Thr Arg Met Pro Leu Ser Val Met Leu Val Val Ser
    275                 280                 285

tct gag gct agc acc ctt tca aca act cct gct gcc acc aac att cct      970
Ser Glu Ala Ser Thr Leu Ser Thr Thr Pro Ala Ala Thr Asn Ile Pro
290                 295                 300                 305

gtg atc act tct act gaa gcc agt tca tct cct aca acg gct gaa ggc     1018
Val Ile Thr Ser Thr Glu Ala Ser Ser Ser Pro Thr Thr Ala Glu Gly
                310                 315                 320

acc agc ata cca acc tca act tat act gaa gga agc act cca tta aca     1066
Thr Ser Ile Pro Thr Ser Thr Tyr Thr Glu Gly Ser Thr Pro Leu Thr
            325                 330                 335

agt acg cct gcc agc acc atg ccg gtt gcc act tct gaa atg agc aca     1114
Ser Thr Pro Ala Ser Thr Met Pro Val Ala Thr Ser Glu Met Ser Thr
        340                 345                 350

ctt tca ata act cct gtt gac acc agc aca ctt gtg acc act tct act     1162
Leu Ser Ile Thr Pro Val Asp Thr Ser Thr Leu Val Thr Thr Ser Thr
    355                 360                 365

gaa ccc agt tca ctt cct aca act gct gaa gct acc agc atg cta acc     1210
Glu Pro Ser Ser Leu Pro Thr Thr Ala Glu Ala Thr Ser Met Leu Thr
370                 375                 380                 385

tca act ctt agt gaa gga agc act cca tta aca aat atg cct gtc agc     1258
Ser Thr Leu Ser Glu Gly Ser Thr Pro Leu Thr Asn Met Pro Val Ser
                390                 395                 400

acc ata ttg gtg gcc agt tct gag gct agc acc act tca aca att cct     1306
Thr Ile Leu Val Ala Ser Ser Glu Ala Ser Thr Thr Ser Thr Ile Pro
            405                 410                 415

gtt gac tcc aaa act ttt gtg acc act gct agt gaa gcc agc tca tct     1354
Val Asp Ser Lys Thr Phe Val Thr Thr Ala Ser Glu Ala Ser Ser Ser
        420                 425                 430

ccc aca act gct gaa gat acc agc att gca acc tca act cct agt gaa     1402
Pro Thr Thr Ala Glu Asp Thr Ser Ile Ala Thr Ser Thr Pro Ser Glu
    435                 440                 445
```

-continued

```
gga agc act cca tta aca agt atg cct gtc agc acc act cca gtg gcc      1450
Gly Ser Thr Pro Leu Thr Ser Met Pro Val Ser Thr Thr Pro Val Ala
450                 455                 460                 465

agt tct gag gct agc aac ctt tca aca act cct gtt gac tcc aaa act      1498
Ser Ser Glu Ala Ser Asn Leu Ser Thr Thr Pro Val Asp Ser Lys Thr
                470                 475                 480

cag gtg acc act tct act gaa gcc agt tca tct cct cca act gct gaa      1546
Gln Val Thr Thr Ser Thr Glu Ala Ser Ser Ser Pro Pro Thr Ala Glu
            485                 490                 495

gtt aac agc atg cca acc tca act cct agt gaa gga agc act cca tta      1594
Val Asn Ser Met Pro Thr Ser Thr Pro Ser Glu Gly Ser Thr Pro Leu
        500                 505                 510

aca agt atg tct gtc agc acc atg ccg gtg gcc agt tct gag gct agc      1642
Thr Ser Met Ser Val Ser Thr Met Pro Val Ala Ser Ser Glu Ala Ser
    515                 520                 525

acc ctt tca aca act cct gtt gac acc agc aca cct gtg acc act tct      1690
Thr Leu Ser Thr Thr Pro Val Asp Thr Ser Thr Pro Val Thr Thr Ser
530                 535                 540                 545

agt gaa gcc agt tca tct tct aca act cct gaa ggt acc agc ata cca      1738
Ser Glu Ala Ser Ser Ser Ser Thr Thr Pro Glu Gly Thr Ser Ile Pro
                550                 555                 560

acc tca act cct agt gaa gga agc act cca tta aca aac atg cct gtc      1786
Thr Ser Thr Pro Ser Glu Gly Ser Thr Pro Leu Thr Asn Met Pro Val
            565                 570                 575

agc acc agg ctg gtg gtc agt tct gag gct agc acc act tca aca act      1834
Ser Thr Arg Leu Val Val Ser Ser Glu Ala Ser Thr Thr Ser Thr Thr
        580                 585                 590

cct gct gac tcc aac act ttt gtg acc act tct agt gaa gct agt tca      1882
Pro Ala Asp Ser Asn Thr Phe Val Thr Thr Ser Ser Glu Ala Ser Ser
    595                 600                 605

tct tct aca act gct gaa ggt acc agc atg cca acc tca act tac agt      1930
Ser Ser Thr Thr Ala Glu Gly Thr Ser Met Pro Thr Ser Thr Tyr Ser
610                 615                 620                 625

gaa aga ggc act aca ata aca agt atg tct gtc agc acc aca ctg gtg      1978
Glu Arg Gly Thr Thr Ile Thr Ser Met Ser Val Ser Thr Thr Leu Val
                630                 635                 640

gcc agt tct gag gct agc acc ctt tca aca act cct gtt gac tcc aac      2026
Ala Ser Ser Glu Ala Ser Thr Leu Ser Thr Thr Pro Val Asp Ser Asn
            645                 650                 655

act cct gtg acc act tca act gaa gcc act tca tct tct aca act gcg      2074
Thr Pro Val Thr Thr Ser Thr Glu Ala Thr Ser Ser Ser Thr Thr Ala
        660                 665                 670

gaa ggt acc agc atg cca acc tca act tat act gaa gga agc act cca      2122
Glu Gly Thr Ser Met Pro Thr Ser Thr Tyr Thr Glu Gly Ser Thr Pro
    675                 680                 685

tta aca agt atg cct gtc aac acc aca ctg gtg gcc agt tct gag gct      2170
Leu Thr Ser Met Pro Val Asn Thr Thr Leu Val Ala Ser Ser Glu Ala
690                 695                 700                 705

agc acc ctt tca aca act cct gtt gac acc agc aca cct gtg acc act      2218
Ser Thr Leu Ser Thr Thr Pro Val Asp Thr Ser Thr Pro Val Thr Thr
                710                 715                 720

tca act gaa gcc agt tcc tct cct aca act gct gat ggt gcc agt atg      2266
Ser Thr Glu Ala Ser Ser Ser Pro Thr Thr Ala Asp Gly Ala Ser Met
            725                 730                 735

cca acc tca act cct agt gaa gga agc act cca tta aca agt atg cct      2314
Pro Thr Ser Thr Pro Ser Glu Gly Ser Thr Pro Leu Thr Ser Met Pro
        740                 745                 750

gtc agc aaa acg ctg ttg acc agt tct gag gct agc acc ctt tca aca      2362
Val Ser Lys Thr Leu Leu Thr Ser Ser Glu Ala Ser Thr Leu Ser Thr
```

```
    755                 760                 765

act cct ctt gac aca agc aca cat atc acc act tct act gaa gcc agt     2410
Thr Pro Leu Asp Thr Ser Thr His Ile Thr Thr Ser Thr Glu Ala Ser
770                 775                 780                 785

tgc tct cct aca acc act gaa ggt acc agc atg cca atc tca act cct     2458
Cys Ser Pro Thr Thr Thr Glu Gly Thr Ser Met Pro Ile Ser Thr Pro
                790                 795                 800

agt gaa gga agt cct tta tta aca agt ata cct gtc agc atc aca ccg     2506
Ser Glu Gly Ser Pro Leu Leu Thr Ser Ile Pro Val Ser Ile Thr Pro
            805                 810                 815

gtg acc agt cct gag gct agc acc ctt tca aca act cct gtt gac tcc     2554
Val Thr Ser Pro Glu Ala Ser Thr Leu Ser Thr Thr Pro Val Asp Ser
        820                 825                 830

aac agt cct gtg acc act tct act gaa gtc agt tca tct cct aca cct     2602
Asn Ser Pro Val Thr Thr Ser Thr Glu Val Ser Ser Ser Pro Thr Pro
    835                 840                 845

gct gaa ggt acc agc atg cca acc tca act tat agt gaa gga aga act     2650
Ala Glu Gly Thr Ser Met Pro Thr Ser Thr Tyr Ser Glu Gly Arg Thr
850                 855                 860                 865

cct tta aca agt atg cct gtc agc acc aca ctg gtg gcc act tct gca     2698
Pro Leu Thr Ser Met Pro Val Ser Thr Thr Leu Val Ala Thr Ser Ala
                870                 875                 880

atc agc acc ctt tca aca act cct gtt gac acc agc aca cct gtg acc     2746
Ile Ser Thr Leu Ser Thr Thr Pro Val Asp Thr Ser Thr Pro Val Thr
            885                 890                 895

aat tct act gaa gcc cgt tcg tct cct aca act tct gaa ggt acc agc     2794
Asn Ser Thr Glu Ala Arg Ser Ser Pro Thr Thr Ser Glu Gly Thr Ser
        900                 905                 910

atg cca acc tca act cct ggg gaa gga agc act cca tta aca agt atg     2842
Met Pro Thr Ser Thr Pro Gly Glu Gly Ser Thr Pro Leu Thr Ser Met
    915                 920                 925

cct gac agc acc acg ccg gta gtc agt tct gag gct aga aca ctt tca     2890
Pro Asp Ser Thr Thr Pro Val Val Ser Ser Glu Ala Arg Thr Leu Ser
930                 935                 940                 945

gca act cct gtt gac acc agc aca cct gtg acc act tct act gaa gcc     2938
Ala Thr Pro Val Asp Thr Ser Thr Pro Val Thr Thr Ser Thr Glu Ala
                950                 955                 960

act tca tct cct aca act gct gaa ggt acc agc ata cca acc tcg act     2986
Thr Ser Ser Pro Thr Thr Ala Glu Gly Thr Ser Ile Pro Thr Ser Thr
            965                 970                 975

cct agt gaa gga acg act cca tta aca agc aca cct gtc agc cac acg     3034
Pro Ser Glu Gly Thr Thr Pro Leu Thr Ser Thr Pro Val Ser His Thr
        980                 985                 990

ctg gtg gcc aat tct gag gct  agc acc ctt tca aca  act cct gtt gac   3082
Leu Val Ala Asn Ser Glu Ala  Ser Thr Leu Ser Thr  Thr Pro Val Asp
    995                 1000                1005

tcc  aac act cct ttg acc  act tct act gaa gcc  agt tca cct cct     3127
Ser  Asn Thr Pro Leu Thr  Thr Ser Thr Glu Ala  Ser Ser Pro Pro
1010                 1015                 1020

ccc  act gct gaa ggt acc  agc atg cca acc tca  act cct agt gaa     3172
Pro  Thr Ala Glu Gly Thr  Ser Met Pro Thr Ser  Thr Pro Ser Glu
1025                 1030                 1035

gga  agc act cca tta aca  cgt atg cct gtc agc  acc aca atg gtg     3217
Gly  Ser Thr Pro Leu Thr  Arg Met Pro Val Ser  Thr Thr Met Val
1040                 1045                 1050

gcc  agt tct gaa acg agc  aca ctt tca aca act  cct gct gac acc     3262
Ala  Ser Ser Glu Thr Ser  Thr Leu Ser Thr Thr  Pro Ala Asp Thr
1055                 1060                 1065

agc  aca cct gtg acc act  tat tct caa gcc agt  tca tct tct aca     3307
```

```
Ser  Thr Pro Val Thr Thr  Tyr Ser Gln Ala Ser  Ser Ser Ser Thr
1070                1075                1080

act  gct gac ggt acc agc  atg cca acc tca act  tat agt gaa gga      3352
Thr  Ala Asp Gly Thr Ser  Met Pro Thr Ser Thr  Tyr Ser Glu Gly
1085                1090                1095

agc  act cca cta aca agt  gtg cct gtc agc acc  agg ctg gtg gtc      3397
Ser  Thr Pro Leu Thr Ser  Val Pro Val Ser Thr  Arg Leu Val Val
1100                1105                1110

agt  tct gag gct agc acc  ctt tcc aca act cct  gtc gac acc agc      3442
Ser  Ser Glu Ala Ser Thr  Leu Ser Thr Thr Pro  Val Asp Thr Ser
1115                1120                1125

ata  cct gtc acc act tct  act gaa gcc agt tca  tct cct aca act      3487
Ile  Pro Val Thr Thr Ser  Thr Glu Ala Ser Ser  Ser Pro Thr Thr
1130                1135                1140

gct  gaa ggt acc agc ata  cca acc tca cct ccc  agt gaa gga acc      3532
Ala  Glu Gly Thr Ser Ile  Pro Thr Ser Pro Pro  Ser Glu Gly Thr
1145                1150                1155

act  ccg tta gca agt atg  cct gtc agc acc acg  ctg gtg gtc agt      3577
Thr  Pro Leu Ala Ser Met  Pro Val Ser Thr Thr  Leu Val Val Ser
1160                1165                1170

tct  gag gct aac acc ctt  tca aca act cct gtg  gac tcc aaa act      3622
Ser  Glu Ala Asn Thr Leu  Ser Thr Thr Pro Val  Asp Ser Lys Thr
1175                1180                1185

cag  gtg gcc act tct act  gaa gcc agt tca cct  cct cca act gct      3667
Gln  Val Ala Thr Ser Thr  Glu Ala Ser Ser Pro  Pro Pro Thr Ala
1190                1195                1200

gaa  gtt acc agc atg cca  acc tca act cct gga  gaa aga agc act      3712
Glu  Val Thr Ser Met Pro  Thr Ser Thr Pro Gly  Glu Arg Ser Thr
1205                1210                1215

cca  tta aca agt atg cct  gtc aga cac acg cca  gtg gcc agt tct      3757
Pro  Leu Thr Ser Met Pro  Val Arg His Thr Pro  Val Ala Ser Ser
1220                1225                1230

gag  gct agc acc ctt tca  aca tct ccc gtt gac  acc agc aca cct      3802
Glu  Ala Ser Thr Leu Ser  Thr Ser Pro Val Asp  Thr Ser Thr Pro
1235                1240                1245

gtg  acc act tct gct gaa  acc agt tcc tct cct  aca acc gct gaa      3847
Val  Thr Thr Ser Ala Glu  Thr Ser Ser Ser Pro  Thr Thr Ala Glu
1250                1255                1260

ggt  acc agc ttg cca acc  tca act act agt gaa  gga agt act cta      3892
Gly  Thr Ser Leu Pro Thr  Ser Thr Thr Ser Glu  Gly Ser Thr Leu
1265                1270                1275

tta  aca agt ata cct gtc  agc acc acg ctg gtg  acc agt cct gag      3937
Leu  Thr Ser Ile Pro Val  Ser Thr Thr Leu Val  Thr Ser Pro Glu
1280                1285                1290

gct  agc acc ctt tta aca  act cct gtt gac act  aaa ggt cct gtg      3982
Ala  Ser Thr Leu Leu Thr  Thr Pro Val Asp Thr  Lys Gly Pro Val
1295                1300                1305

gtc  act tct aat gaa gtc  agt tca tct cct aca  cct gct gaa ggt      4027
Val  Thr Ser Asn Glu Val  Ser Ser Ser Pro Thr  Pro Ala Glu Gly
1310                1315                1320

acc  agc atg cca acc tca  act tat agt gaa gga  aga act cct tta      4072
Thr  Ser Met Pro Thr Ser  Thr Tyr Ser Glu Gly  Arg Thr Pro Leu
1325                1330                1335

aca  agt ata cct gtc aac  acc aca ctg gtg gcc  agt tct gca atc      4117
Thr  Ser Ile Pro Val Asn  Thr Thr Leu Val Ala  Ser Ser Ala Ile
1340                1345                1350

agc  atc ctt tca aca act  cct gtt gac aac agc  aca cct gtg acc      4162
Ser  Ile Leu Ser Thr Thr  Pro Val Asp Asn Ser  Thr Pro Val Thr
1355                1360                1365
```

-continued

```
act  tct act gaa gcc tgt  tca tct cct aca act  tct gaa ggt acc      4207
Thr  Ser Thr Glu Ala Cys  Ser Ser Pro Thr Thr  Ser Glu Gly Thr
1370                 1375                 1380

agc  atg cca aac tca aat  cct agt gaa gga acc  act ccg tta aca      4252
Ser  Met Pro Asn Ser Asn  Pro Ser Glu Gly Thr  Thr Pro Leu Thr
1385                 1390                 1395

agt  ata cct gtc agc acc  acg ccg gta gtc agt  tct gag gct agc      4297
Ser  Ile Pro Val Ser Thr  Thr Pro Val Val Ser  Ser Glu Ala Ser
1400                 1405                 1410

acc  ctt tca gca act cct  gtt gac acc agc acc  cct ggg acc act      4342
Thr  Leu Ser Ala Thr Pro  Val Asp Thr Ser Thr  Pro Gly Thr Thr
1415                 1420                 1425

tct  gct gaa gcc act tca  tct cct aca act gct  gaa ggt atc agc      4387
Ser  Ala Glu Ala Thr Ser  Ser Pro Thr Thr Ala  Glu Gly Ile Ser
1430                 1435                 1440

ata  cca acc tca act cct  agt gaa gga aag act  cca tta aaa agt      4432
Ile  Pro Thr Ser Thr Pro  Ser Glu Gly Lys Thr  Pro Leu Lys Ser
1445                 1450                 1455

ata  cct gtc agc aac acg  ccg gtg gcc aat tct  gag gct agc acc      4477
Ile  Pro Val Ser Asn Thr  Pro Val Ala Asn Ser  Glu Ala Ser Thr
1460                 1465                 1470

ctt  tca aca act cct gtt  gac tct aac agt cct  gtg gtc act tct      4522
Leu  Ser Thr Thr Pro Val  Asp Ser Asn Ser Pro  Val Val Thr Ser
1475                 1480                 1485

aca  gca gtc agt tca tct  cct aca cct gct gaa  ggt acc agc ata      4567
Thr  Ala Val Ser Ser Ser  Pro Thr Pro Ala Glu  Gly Thr Ser Ile
1490                 1495                 1500

gca  atc tca acg cct agt  gaa gga agc act gca  tta aca agt ata      4612
Ala  Ile Ser Thr Pro Ser  Glu Gly Ser Thr Ala  Leu Thr Ser Ile
1505                 1510                 1515

cct  gtc agc acc aca aca  gtg gcc agt tct gaa  atc aac agc ctt      4657
Pro  Val Ser Thr Thr Thr  Val Ala Ser Ser Glu  Ile Asn Ser Leu
1520                 1525                 1530

tca  aca act cct gct gtc  acc agc aca cct gtg  acc act tat tct      4702
Ser  Thr Thr Pro Ala Val  Thr Ser Thr Pro Val  Thr Thr Tyr Ser
1535                 1540                 1545

caa  gcc agt tca tct cct  aca act gct gac ggt  acc agc atg caa      4747
Gln  Ala Ser Ser Ser Pro  Thr Thr Ala Asp Gly  Thr Ser Met Gln
1550                 1555                 1560

acc  tca act tat agt gaa  gga agc act cca cta  aca agt ttg cct      4792
Thr  Ser Thr Tyr Ser Glu  Gly Ser Thr Pro Leu  Thr Ser Leu Pro
1565                 1570                 1575

gtc  agc acc atg ctg gtg  gtc agt tct gag gct  aac acc ctt tca      4837
Val  Ser Thr Met Leu Val  Val Ser Ser Glu Ala  Asn Thr Leu Ser
1580                 1585                 1590

aca  acc cct att gac tcc  aaa act cag gtg acc  gct tct act gaa      4882
Thr  Thr Pro Ile Asp Ser  Lys Thr Gln Val Thr  Ala Ser Thr Glu
1595                 1600                 1605

gcc  agt tca tct aca acc  gct gaa ggt agc agc  atg aca atc tca      4927
Ala  Ser Ser Ser Thr Thr  Ala Glu Gly Ser Ser  Met Thr Ile Ser
1610                 1615                 1620

act  cct agt gaa gga agt  cct cta tta aca agt  ata cct gtc agc      4972
Thr  Pro Ser Glu Gly Ser  Pro Leu Leu Thr Ser  Ile Pro Val Ser
1625                 1630                 1635

acc  acg ccg gtg gcc agt  cct gag gct agc acc  ctt tca aca act      5017
Thr  Thr Pro Val Ala Ser  Pro Glu Ala Ser Thr  Leu Ser Thr Thr
1640                 1645                 1650

cct  gtt gac tcc aac agt  cct gtg atc act tct  act gaa gtc agt      5062
Pro  Val Asp Ser Asn Ser  Pro Val Ile Thr Ser  Thr Glu Val Ser
1655                 1660                 1665
```

```
tca  tct cct aca cct gct  gaa ggt acc agc atg  cca acc tca act      5107
Ser  Ser Pro Thr Pro Ala  Glu Gly Thr Ser Met  Pro Thr Ser Thr
1670                 1675                 1680

tat  act gaa gga aga act  cct tta aca agt ata  act gtc aga aca      5152
Tyr  Thr Glu Gly Arg Thr  Pro Leu Thr Ser Ile  Thr Val Arg Thr
1685                 1690                 1695

aca  ccg gtg gcc agc tct  gca atc agc acc ctt  tca aca act ccc      5197
Thr  Pro Val Ala Ser Ser  Ala Ile Ser Thr Leu  Ser Thr Thr Pro
1700                 1705                 1710

gtt  gac aac agc aca cct  gtg acc act tct act  gaa gcc cgt tca      5242
Val  Asp Asn Ser Thr Pro  Val Thr Thr Ser Thr  Glu Ala Arg Ser
1715                 1720                 1725

tct  cct aca act tct gaa  ggt acc agc atg cca  aac tca act cct      5287
Ser  Pro Thr Thr Ser Glu  Gly Thr Ser Met Pro  Asn Ser Thr Pro
1730                 1735                 1740

agt  gaa gga acc act cca  tta aca agt ata cct  gtc agc acc acg      5332
Ser  Glu Gly Thr Thr Pro  Leu Thr Ser Ile Pro  Val Ser Thr Thr
1745                 1750                 1755

ccg  gta ctc agt tct gag  gct agc acc ctt tca  gca act cct att      5377
Pro  Val Leu Ser Ser Glu  Ala Ser Thr Leu Ser  Ala Thr Pro Ile
1760                 1765                 1770

gac  acc agc acc cct gtg  acc act tct act gaa  gcc act tcg tct      5422
Asp  Thr Ser Thr Pro Val  Thr Thr Ser Thr Glu  Ala Thr Ser Ser
1775                 1780                 1785

cct  aca act gct gaa ggt  acc agc ata cca acc  tcg act ctt agt      5467
Pro  Thr Thr Ala Glu Gly  Thr Ser Ile Pro Thr  Ser Thr Leu Ser
1790                 1795                 1800

gaa  gga atg act cca tta  aca agc aca cct gtc  agc cac acg ctg      5512
Glu  Gly Met Thr Pro Leu  Thr Ser Thr Pro Val  Ser His Thr Leu
1805                 1810                 1815

gtg  gcc aat tct gag gct  agc acc ctt tca aca  act cct gtt gac      5557
Val  Ala Asn Ser Glu Ala  Ser Thr Leu Ser Thr  Thr Pro Val Asp
1820                 1825                 1830

tct  aac agt cct gtg gtc  act tct aca gca gtc  agt tca tct cct      5602
Ser  Asn Ser Pro Val Val  Thr Ser Thr Ala Val  Ser Ser Ser Pro
1835                 1840                 1845

aca  cct gct gaa ggt acc  agc ata gca acc tca  acg cct agt gaa      5647
Thr  Pro Ala Glu Gly Thr  Ser Ile Ala Thr Ser  Thr Pro Ser Glu
1850                 1855                 1860

gga  agc act gca tta aca  agt ata cct gtc agc  acc aca aca gtg      5692
Gly  Ser Thr Ala Leu Thr  Ser Ile Pro Val Ser  Thr Thr Thr Val
1865                 1870                 1875

gcc  agt tct gaa acc aac  acc ctt tca aca act  ccc gct gtc acc      5737
Ala  Ser Ser Glu Thr Asn  Thr Leu Ser Thr Thr  Pro Ala Val Thr
1880                 1885                 1890

agc  aca cct gtg acc act  tat gct caa gtc agt  tca tct cct aca      5782
Ser  Thr Pro Val Thr Thr  Tyr Ala Gln Val Ser  Ser Ser Pro Thr
1895                 1900                 1905

act  gct gac ggt agc agc  atg cca acc tca act  cct agg gaa gga      5827
Thr  Ala Asp Gly Ser Ser  Met Pro Thr Ser Thr  Pro Arg Glu Gly
1910                 1915                 1920

agg  cct cca tta aca agt  ata cct gtc agc acc  aca aca gtg gcc      5872
Arg  Pro Pro Leu Thr Ser  Ile Pro Val Ser Thr  Thr Thr Val Ala
1925                 1930                 1935

agt  tct gaa atc aac acc  ctt tca aca act ctt  gct gac acc agg      5917
Ser  Ser Glu Ile Asn Thr  Leu Ser Thr Thr Leu  Ala Asp Thr Arg
1940                 1945                 1950

aca  cct gtg acc act tat  tct caa gcc agt tca  tct cct aca act      5962
Thr  Pro Val Thr Thr Tyr  Ser Gln Ala Ser Ser  Ser Pro Thr Thr
```

-continued

```
1955                1960                1965

gct  gat ggt acc agc atg  cca acc cca gct tat  agt gaa gga agc      6007
Ala  Asp Gly Thr Ser Met  Pro Thr Pro Ala Tyr  Ser Glu Gly Ser
1970                1975                1980

act  cca cta aca agt atg  cct ctc agc acc acg  ctg gtg gtc agt      6052
Thr  Pro Leu Thr Ser Met  Pro Leu Ser Thr Thr  Leu Val Val Ser
1985                1990                1995

tct  gag gct agc act ctt  tcc aca act cct gtt  gac acc agc act      6097
Ser  Glu Ala Ser Thr Leu  Ser Thr Thr Pro Val  Asp Thr Ser Thr
2000                2005                2010

cct  gcc acc act tct act  gaa ggc agt tca tct  cct aca act gca      6142
Pro  Ala Thr Thr Ser Thr  Glu Gly Ser Ser Ser  Pro Thr Thr Ala
2015                2020                2025

gga  ggt acc agc ata caa  acc tca act cct agt  gaa cgg acc act      6187
Gly  Gly Thr Ser Ile Gln  Thr Ser Thr Pro Ser  Glu Arg Thr Thr
2030                2035                2040

cca  tta gca ggt atg cct  gtc agc act acg ctt  gtg gtc agt tct      6232
Pro  Leu Ala Gly Met Pro  Val Ser Thr Thr Leu  Val Val Ser Ser
2045                2050                2055

gag  ggt aac acc ctt tca  aca act cct gtt gac  tcc aaa act cag      6277
Glu  Gly Asn Thr Leu Ser  Thr Thr Pro Val Asp  Ser Lys Thr Gln
2060                2065                2070

gtg  acc aat tct act gaa  gcc agt tca tct gca  acc gct gaa ggt      6322
Val  Thr Asn Ser Thr Glu  Ala Ser Ser Ser Ala  Thr Ala Glu Gly
2075                2080                2085

agc  agc atg aca atc tca  gct cct agt gaa gga  agt cct cta cta      6367
Ser  Ser Met Thr Ile Ser  Ala Pro Ser Glu Gly  Ser Pro Leu Leu
2090                2095                2100

aca  agt ata cct ctc agc  acc acg ccg gtg gcc  agt cct gag gct      6412
Thr  Ser Ile Pro Leu Ser  Thr Thr Pro Val Ala  Ser Pro Glu Ala
2105                2110                2115

agc  acc ctt tca aca act  cct gtt gac tcc aac  agt cct gtg atc      6457
Ser  Thr Leu Ser Thr Thr  Pro Val Asp Ser Asn  Ser Pro Val Ile
2120                2125                2130

act  tct act gaa gtc agt  tca tct cct ata cct  act gaa ggt acc      6502
Thr  Ser Thr Glu Val Ser  Ser Ser Pro Ile Pro  Thr Glu Gly Thr
2135                2140                2145

agc  atg caa acc tca act  tat agt gac aga aga  act cct tta aca      6547
Ser  Met Gln Thr Ser Thr  Tyr Ser Asp Arg Arg  Thr Pro Leu Thr
2150                2155                2160

agt  atg cct gtc agc acc  aca gtg gtg gcc agt  tct gca atc agc      6592
Ser  Met Pro Val Ser Thr  Thr Val Val Ala Ser  Ser Ala Ile Ser
2165                2170                2175

acc  ctt tca aca act cct  gtt gac acc agc aca  cct gtg acc aat      6637
Thr  Leu Ser Thr Thr Pro  Val Asp Thr Ser Thr  Pro Val Thr Asn
2180                2185                2190

tct  act gaa gcc cgt tca  tct cct aca act tct  gaa ggt acc agc      6682
Ser  Thr Glu Ala Arg Ser  Ser Pro Thr Thr Ser  Glu Gly Thr Ser
2195                2200                2205

atg  cca acc tca act cct  agt gaa gga agc act  cca ttc aca agt      6727
Met  Pro Thr Ser Thr Pro  Ser Glu Gly Ser Thr  Pro Phe Thr Ser
2210                2215                2220

atg  cct gtc agc acc atg  ccg gta gtt act tct  gag gct agc acc      6772
Met  Pro Val Ser Thr Met  Pro Val Val Thr Ser  Glu Ala Ser Thr
2225                2230                2235

ctt  tca gca act cct gtt  gac acc agc aca cct  gtg acc act tct      6817
Leu  Ser Ala Thr Pro Val  Asp Thr Ser Thr Pro  Val Thr Thr Ser
2240                2245                2250

act  gaa gcc act tca tct  cct aca act gct gaa  ggt acc agc ata      6862
```

-continued

```
Thr  Glu Ala Thr Ser Ser  Pro Thr Thr Ala Glu  Gly Thr Ser Ile
2255                2260                2265

cca  act tca act ctt agt  gaa gga acg act cca  tta aca agt ata      6907
Pro  Thr Ser Thr Leu Ser  Glu Gly Thr Thr Pro  Leu Thr Ser Ile
2270                2275                2280

cct  gtc agc cac acg ctg  gtg gcc aat tct gag  gtt agc acc ctt      6952
Pro  Val Ser His Thr Leu  Val Ala Asn Ser Glu  Val Ser Thr Leu
2285                2290                2295

tca  aca act cct gtt gac  tcc aac act cct ttc  act act tct act      6997
Ser  Thr Thr Pro Val Asp  Ser Asn Thr Pro Phe  Thr Thr Ser Thr
2300                2305                2310

gaa  gcc agt tca cct cct  ccc act gct gaa ggt  acc agc atg cca      7042
Glu  Ala Ser Ser Pro Pro  Pro Thr Ala Glu Gly  Thr Ser Met Pro
2315                2320                2325

acc  tca act tct agt gaa  gga aac act cca tta  aca cgt atg cct      7087
Thr  Ser Thr Ser Ser Glu  Gly Asn Thr Pro Leu  Thr Arg Met Pro
2330                2335                2340

gtc  agc acc aca atg gtg  gcc agt ttt gaa aca  agc aca ctt tct      7132
Val  Ser Thr Thr Met Val  Ala Ser Phe Glu Thr  Ser Thr Leu Ser
2345                2350                2355

aca  act cct gct gac acc  agc aca cct gtg act  act tat tct caa      7177
Thr  Thr Pro Ala Asp Thr  Ser Thr Pro Val Thr  Thr Tyr Ser Gln
2360                2365                2370

gcc  ggt tca tct cct aca  act gct gac gat act  agc atg cca acc      7222
Ala  Gly Ser Ser Pro Thr  Thr Ala Asp Asp Thr  Ser Met Pro Thr
2375                2380                2385

tca  act tat agt gaa gga  agc act cca cta aca  agt gtg cct gtc      7267
Ser  Thr Tyr Ser Glu Gly  Ser Thr Pro Leu Thr  Ser Val Pro Val
2390                2395                2400

agc  acc atg ccg gtg gtc  agt tct gag gct agc  acc cat tcc aca      7312
Ser  Thr Met Pro Val Val  Ser Ser Glu Ala Ser  Thr His Ser Thr
2405                2410                2415

act  cct gtt gac acc agc  aca cct gtc acc act  tct act gaa gcc      7357
Thr  Pro Val Asp Thr Ser  Thr Pro Val Thr Thr  Ser Thr Glu Ala
2420                2425                2430

agt  tca tct cct aca act  gct gaa ggt acc agc  ata cca acc tca      7402
Ser  Ser Ser Pro Thr Thr  Ala Glu Gly Thr Ser  Ile Pro Thr Ser
2435                2440                2445

cct  cct agt gaa gga acc  act ccg tta gca agt  atg cct gtc agc      7447
Pro  Pro Ser Glu Gly Thr  Thr Pro Leu Ala Ser  Met Pro Val Ser
2450                2455                2460

acc  acg ccg gtg gtc agt  tct gag gct ggc acc  ctt tcc aca act      7492
Thr  Thr Pro Val Val Ser  Ser Glu Ala Gly Thr  Leu Ser Thr Thr
2465                2470                2475

cct  gtt gac acc agc aca  cct atg acc act tct  act gaa gcc agt      7537
Pro  Val Asp Thr Ser Thr  Pro Met Thr Thr Ser  Thr Glu Ala Ser
2480                2485                2490

tca  tct cct aca act gct  gaa gat atc gtc gtg  cca atc tca act      7582
Ser  Ser Pro Thr Thr Ala  Glu Asp Ile Val Val  Pro Ile Ser Thr
2495                2500                2505

gct  agt gaa gga agt act  cta tta aca agt ata  cct gtc agc acc      7627
Ala  Ser Glu Gly Ser Thr  Leu Leu Thr Ser Ile  Pro Val Ser Thr
2510                2515                2520

acg  cca gtg gcc agt cct  gag gct agc acc ctt  tca aca act cct      7672
Thr  Pro Val Ala Ser Pro  Glu Ala Ser Thr Leu  Ser Thr Thr Pro
2525                2530                2535

gtt  gac tcc aac agt cct  gtg gtc act tct act  gaa atc agt tca      7717
Val  Asp Ser Asn Ser Pro  Val Val Thr Ser Thr  Glu Ile Ser Ser
2540                2545                2550
```

```
tct  gct aca tcc gct gaa  ggt acc agc atg cct  acc tca act tat      7762
Ser  Ala Thr Ser Ala Glu  Gly Thr Ser Met Pro  Thr Ser Thr Tyr
2555                2560                2565

agt  gaa gga agc act cca  tta aga agt atg cct  gtc agc acc aag      7807
Ser  Glu Gly Ser Thr Pro  Leu Arg Ser Met Pro  Val Ser Thr Lys
2570                2575                2580

ccg  ttg gcc agt tct gag  gct agc act ctt tca  aca act cct gtt      7852
Pro  Leu Ala Ser Ser Glu  Ala Ser Thr Leu Ser  Thr Thr Pro Val
2585                2590                2595

gac  acc agc ata cct gtc  acc act tct act gaa  acc agt tca tct      7897
Asp  Thr Ser Ile Pro Val  Thr Thr Ser Thr Glu  Thr Ser Ser Ser
2600                2605                2610

cct  aca act gca aaa gat  acc agc atg cca atc  tca act cct agt      7942
Pro  Thr Thr Ala Lys Asp  Thr Ser Met Pro Ile  Ser Thr Pro Ser
2615                2620                2625

gaa  gta agt act tca tta  aca agt ata ctt gtc  agc acc atg cca      7987
Glu  Val Ser Thr Ser Leu  Thr Ser Ile Leu Val  Ser Thr Met Pro
2630                2635                2640

gtg  gcc agt tct gag gct  agc acc ctt tca aca  act cct gtt gac      8032
Val  Ala Ser Ser Glu Ala  Ser Thr Leu Ser Thr  Thr Pro Val Asp
2645                2650                2655

acc  agg aca ctt gtg acc  act tcc act gga acc  agt tca tct cct      8077
Thr  Arg Thr Leu Val Thr  Thr Ser Thr Gly Thr  Ser Ser Ser Pro
2660                2665                2670

aca  act gct gaa ggt agc  agc atg cca acc tca  act cct ggt gaa      8122
Thr  Thr Ala Glu Gly Ser  Ser Met Pro Thr Ser  Thr Pro Gly Glu
2675                2680                2685

aga  agc act cca tta aca  aat ata ctt gtc agc  acc acg ctg ttg      8167
Arg  Ser Thr Pro Leu Thr  Asn Ile Leu Val Ser  Thr Thr Leu Leu
2690                2695                2700

gcc  aat tct gag gct agc  acc ctt tca aca act  cct gtt gac acc      8212
Ala  Asn Ser Glu Ala Ser  Thr Leu Ser Thr Thr  Pro Val Asp Thr
2705                2710                2715

agc  aca cct gtc acc act  tct gct gaa gcc agt  tct tct cct aca      8257
Ser  Thr Pro Val Thr Thr  Ser Ala Glu Ala Ser  Ser Ser Pro Thr
2720                2725                2730

act  gct gaa ggt acc agc  atg cga atc tca act  cct agt gat gga      8302
Thr  Ala Glu Gly Thr Ser  Met Arg Ile Ser Thr  Pro Ser Asp Gly
2735                2740                2745

agt  act cca tta aca agt  ata ctt gtc agc acc  ctg cca gtg gcc      8347
Ser  Thr Pro Leu Thr Ser  Ile Leu Val Ser Thr  Leu Pro Val Ala
2750                2755                2760

agt  tct gag gct agc acc  gtt tca aca act gct  gtt gac acc agc      8392
Ser  Ser Glu Ala Ser Thr  Val Ser Thr Thr Ala  Val Asp Thr Ser
2765                2770                2775

ata  cct gtc acc act tct  act gaa gcc agt tcc  tct cct aca act      8437
Ile  Pro Val Thr Thr Ser  Thr Glu Ala Ser Ser  Ser Pro Thr Thr
2780                2785                2790

gct  gaa gtt acc agc atg  cca acc tca act cct  agt gaa aca agt      8482
Ala  Glu Val Thr Ser Met  Pro Thr Ser Thr Pro  Ser Glu Thr Ser
2795                2800                2805

act  cca tta act agt atg  cct gtc aac cac acg  cca gtg gcc agt      8527
Thr  Pro Leu Thr Ser Met  Pro Val Asn His Thr  Pro Val Ala Ser
2810                2815                2820

tct  gag gct ggc acc ctt  tca aca act cct gtt  gac acc agc aca      8572
Ser  Glu Ala Gly Thr Leu  Ser Thr Thr Pro Val  Asp Thr Ser Thr
2825                2830                2835

cct  gtg acc act tct act  aaa gcc agt tca tct  cct aca act gct      8617
Pro  Val Thr Thr Ser Thr  Lys Ala Ser Ser Ser  Pro Thr Thr Ala
2840                2845                2850
```

gaa ggt atc gtc gtg cca atc tca act gct agt gaa gga agt act 8662
Glu Gly Ile Val Val Pro Ile Ser Thr Ala Ser Glu Gly Ser Thr
2855 2860 2865 cta tta aca agt ata cct gtc agc acc acg ccg gtg gcc agt tct 8707
Leu Leu Thr Ser Ile Pro Val Ser Thr Thr Pro Val Ala Ser Ser
2870 2875 2880 gag gct agc acc ctt tca aca act cct gtt gat acc agc ata cct 8752
Glu Ala Ser Thr Leu Ser Thr Thr Pro Val Asp Thr Ser Ile Pro
2885 2890 2895 gtc acc act tct act gaa ggc agt tct tct cct aca act gct gaa 8797
Val Thr Thr Ser Thr Glu Gly Ser Ser Ser Pro Thr Thr Ala Glu
2900 2905 2910 ggt acc agc atg cca atc tca act cct agt gaa gta agt act cca 8842
Gly Thr Ser Met Pro Ile Ser Thr Pro Ser Glu Val Ser Thr Pro
2915 2920 2925 tta aca agt ata ctt gtc agc acc gtg cca gtg gcc ggt tct gag 8887
Leu Thr Ser Ile Leu Val Ser Thr Val Pro Val Ala Gly Ser Glu
2930 2935 2940 gct agc acc ctt tca aca act cct gtt gac acc agg aca cct gtc 8932
Ala Ser Thr Leu Ser Thr Thr Pro Val Asp Thr Arg Thr Pro Val
2945 2950 2955 acc act tct gct gaa gct agt tct tct cct aca act gct gaa ggt 8977
Thr Thr Ser Ala Glu Ala Ser Ser Ser Pro Thr Thr Ala Glu Gly
2960 2965 2970 acc agc atg cca atc tca act cct ggc gaa aga aga act cca tta 9022
Thr Ser Met Pro Ile Ser Thr Pro Gly Glu Arg Arg Thr Pro Leu
2975 2980 2985 aca agt atg tct gtc agc acc atg ccg gtg gcc agt tct gag gct 9067
Thr Ser Met Ser Val Ser Thr Met Pro Val Ala Ser Ser Glu Ala
2990 2995 3000 agc acc ctt tca aga act cct gct gac acc agc aca cct gtg acc 9112
Ser Thr Leu Ser Arg Thr Pro Ala Asp Thr Ser Thr Pro Val Thr
3005 3010 3015 act tct act gaa gcc agt tcc tct cct aca act gct gaa ggt acc 9157
Thr Ser Thr Glu Ala Ser Ser Ser Pro Thr Thr Ala Glu Gly Thr
3020 3025 3030 ggc ata cca atc tca act cct agt gaa gga agt act cca tta aca 9202
Gly Ile Pro Ile Ser Thr Pro Ser Glu Gly Ser Thr Pro Leu Thr
3035 3040 3045 agt ata cct gtc agc acc acg cca gtg gcc att cct gag gct agc 9247
Ser Ile Pro Val Ser Thr Thr Pro Val Ala Ile Pro Glu Ala Ser
3050 3055 3060 acc ctt tca aca act cct gtt gac tcc aac agt cct gtg gtc act 9292
Thr Leu Ser Thr Thr Pro Val Asp Ser Asn Ser Pro Val Val Thr
3065 3070 3075 tct act gaa gtc agt tca tct cct aca cct gct gaa ggt acc agc 9337
Ser Thr Glu Val Ser Ser Ser Pro Thr Pro Ala Glu Gly Thr Ser
3080 3085 3090 atg cca atc tca act tat agt gaa gga agc act cca tta aca ggt 9382
Met Pro Ile Ser Thr Tyr Ser Glu Gly Ser Thr Pro Leu Thr Gly
3095 3100 3105 gtg cct gtc agc acc aca ccg gtg acc agt tct gca atc agc acc 9427
Val Pro Val Ser Thr Thr Pro Val Thr Ser Ser Ala Ile Ser Thr
3110 3115 3120 ctt tca aca act cct gtt gac acc agc aca cct gtg acc act tct 9472
Leu Ser Thr Thr Pro Val Asp Thr Ser Thr Pro Val Thr Thr Ser
3125 3130 3135 act gaa gcc cat tca tct cct aca act tct gaa ggt acc agc atg 9517
Thr Glu Ala His Ser Ser Pro Thr Thr Ser Glu Gly Thr Ser Met -continued

```
3140                3145                3150

cca  acc tca act cct agt  gaa gga agt act cca  tta aca tat atg      9562
Pro  Thr Ser Thr Pro Ser  Glu Gly Ser Thr Pro  Leu Thr Tyr Met
3155                3160                3165

cct  gtc agc acc atg ctg  gta gtc agt tct gag  gat agc acc ctt      9607
Pro  Val Ser Thr Met Leu  Val Val Ser Ser Glu  Asp Ser Thr Leu
3170                3175                3180

tca  gca act cct gtt gac  acc agc aca cct gtg  acc act tct act      9652
Ser  Ala Thr Pro Val Asp  Thr Ser Thr Pro Val  Thr Thr Ser Thr
3185                3190                3195

gaa  gcc act tca tct aca  act gct gaa ggt acc  agc att cca acc      9697
Glu  Ala Thr Ser Ser Thr  Thr Ala Glu Gly Thr  Ser Ile Pro Thr
3200                3205                3210

tca  act cct agt gaa gga  atg act cca tta act  agt gta cct gtc      9742
Ser  Thr Pro Ser Glu Gly  Met Thr Pro Leu Thr  Ser Val Pro Val
3215                3220                3225

agc  aac acg ccg gtg gcc  agt tct gag gct agc  atc ctt tca aca      9787
Ser  Asn Thr Pro Val Ala  Ser Ser Glu Ala Ser  Ile Leu Ser Thr
3230                3235                3240

act  cct gtt gac tcc aac  act cct ttg acc act  tct act gaa gcc      9832
Thr  Pro Val Asp Ser Asn  Thr Pro Leu Thr Thr  Ser Thr Glu Ala
3245                3250                3255

agt  tca tct cct ccc act  gct gaa ggt acc agc  atg cca acc tca      9877
Ser  Ser Ser Pro Pro Thr  Ala Glu Gly Thr Ser  Met Pro Thr Ser
3260                3265                3270

act  cct agt gaa gga agc  act cca tta aca agt  atg cct gtc agc      9922
Thr  Pro Ser Glu Gly Ser  Thr Pro Leu Thr Ser  Met Pro Val Ser
3275                3280                3285

acc  aca acg gtg gcc agt  tct gaa acg agc acc  ctt tca aca act      9967
Thr  Thr Thr Val Ala Ser  Ser Glu Thr Ser Thr  Leu Ser Thr Thr
3290                3295                3300

cct  gct gac acc agc aca  cct gtg acc act tat  tct caa gcc agt     10012
Pro  Ala Asp Thr Ser Thr  Pro Val Thr Thr Tyr  Ser Gln Ala Ser
3305                3310                3315

tca  tct cct cca att gct  gac ggt act agc atg  cca acc tca act     10057
Ser  Ser Pro Pro Ile Ala  Asp Gly Thr Ser Met  Pro Thr Ser Thr
3320                3325                3330

tat  agt gaa gga agc act  cca cta aca aat atg  tct ttc agc acc     10102
Tyr  Ser Glu Gly Ser Thr  Pro Leu Thr Asn Met  Ser Phe Ser Thr
3335                3340                3345

acg  cca gtg gtc agt tct  gag gct agc acc ctt  tcc aca act cct     10147
Thr  Pro Val Val Ser Ser  Glu Ala Ser Thr Leu  Ser Thr Thr Pro
3350                3355                3360

gtt  gac acc agc aca cct  gtc acc act tct act  gaa gcc agt tta     10192
Val  Asp Thr Ser Thr Pro  Val Thr Thr Ser Thr  Glu Ala Ser Leu
3365                3370                3375

tct  cct aca act gct gaa  ggt acc agc ata cca  acc tca agt cct     10237
Ser  Pro Thr Thr Ala Glu  Gly Thr Ser Ile Pro  Thr Ser Ser Pro
3380                3385                3390

agt  gaa gga acc act cca  tta gca agt atg cct  gtc agc acc acg     10282
Ser  Glu Gly Thr Thr Pro  Leu Ala Ser Met Pro  Val Ser Thr Thr
3395                3400                3405

ccg  gtg gtc agt tct gag  gtt aac acc ctt tca  aca act cct gtg     10327
Pro  Val Val Ser Ser Glu  Val Asn Thr Leu Ser  Thr Thr Pro Val
3410                3415                3420

gac  tcc aac act ctg gtg  acc act tct act gaa  gcc agt tca tct     10372
Asp  Ser Asn Thr Leu Val  Thr Thr Ser Thr Glu  Ala Ser Ser Ser
3425                3430                3435

cct  aca atc gct gaa ggt  acc agc ttg cca acc  tca act act agt     10417
```

-continued

```
Pro  Thr Ile Ala Glu Gly  Thr Ser Leu Pro Thr  Ser Thr Thr Ser
3440                 3445                 3450

gaa  gga agc act cca tta  tca att atg cct ctc  agt acc acg ccg     10462
Glu  Gly Ser Thr Pro Leu  Ser Ile Met Pro Leu  Ser Thr Thr Pro
3455                 3460                 3465

gtg  gcc agt tct gag gct  agc acc ctt tca aca  act cct gtt gac     10507
Val  Ala Ser Ser Glu Ala  Ser Thr Leu Ser Thr  Thr Pro Val Asp
3470                 3475                 3480

acc  agc aca cct gtg acc  act tct tct cca acc  aat tca tct cct     10552
Thr  Ser Thr Pro Val Thr  Thr Ser Ser Pro Thr  Asn Ser Ser Pro
3485                 3490                 3495

aca  act gct gaa gtt acc  agc atg cca aca tca  act gct ggt gaa     10597
Thr  Thr Ala Glu Val Thr  Ser Met Pro Thr Ser  Thr Ala Gly Glu
3500                 3505                 3510

gga  agc act cca tta aca  aat atg cct gtc agc  acc aca ccg gtg     10642
Gly  Ser Thr Pro Leu Thr  Asn Met Pro Val Ser  Thr Thr Pro Val
3515                 3520                 3525

gcc  agt tct gag gct agc  acc ctt tca aca act  cct gtt gac tcc     10687
Ala  Ser Ser Glu Ala Ser  Thr Leu Ser Thr Thr  Pro Val Asp Ser
3530                 3535                 3540

aac  act ttt gtt acc agt  tct agt caa gcc agt  tca tct cca gca     10732
Asn  Thr Phe Val Thr Ser  Ser Ser Gln Ala Ser  Ser Ser Pro Ala
3545                 3550                 3555

act  ctt cag gtc acc act  atg cgt atg tct act  cca agt gaa gga     10777
Thr  Leu Gln Val Thr Thr  Met Arg Met Ser Thr  Pro Ser Glu Gly
3560                 3565                 3570

agc  tct tca tta aca act  atg ctc ctc agc agc  aca tat gtg acc     10822
Ser  Ser Ser Leu Thr Thr  Met Leu Leu Ser Ser  Thr Tyr Val Thr
3575                 3580                 3585

agt  tct gag gct agc aca  cct tcc act cct tct  gtt gac aga agc     10867
Ser  Ser Glu Ala Ser Thr  Pro Ser Thr Pro Ser  Val Asp Arg Ser
3590                 3595                 3600

aca  cct gtg acc act tct  act cag agc aat tct  act cct aca cct     10912
Thr  Pro Val Thr Thr Ser  Thr Gln Ser Asn Ser  Thr Pro Thr Pro
3605                 3610                 3615

cct  gaa gtt atc acc ctg  cca atg tca act cct  agt gaa gta agc     10957
Pro  Glu Val Ile Thr Leu  Pro Met Ser Thr Pro  Ser Glu Val Ser
3620                 3625                 3630

act  cca tta acc att atg  cct gtc agc acc aca  tcg gtg acc att     11002
Thr  Pro Leu Thr Ile Met  Pro Val Ser Thr Thr  Ser Val Thr Ile
3635                 3640                 3645

tct  gag gct ggc aca gct  tca aca ctt cct gtt  gac acc agc aca     11047
Ser  Glu Ala Gly Thr Ala  Ser Thr Leu Pro Val  Asp Thr Ser Thr
3650                 3655                 3660

cct  gtg atc act tct acc  caa gtc agt tca tct  cct gtg act cct     11092
Pro  Val Ile Thr Ser Thr  Gln Val Ser Ser Ser  Pro Val Thr Pro
3665                 3670                 3675

gaa  ggt acc acc atg cca  atc tgg acg cct agt  gaa gga agc act     11137
Glu  Gly Thr Thr Met Pro  Ile Trp Thr Pro Ser  Glu Gly Ser Thr
3680                 3685                 3690

cca  tta aca act atg cct  gtc agc acc aca cgt  gtg acc agc tct     11182
Pro  Leu Thr Thr Met Pro  Val Ser Thr Thr Arg  Val Thr Ser Ser
3695                 3700                 3705

gag  ggt agc acc ctt tca  aca cct tct gtt gtc  acc agc aca cct     11227
Glu  Gly Ser Thr Leu Ser  Thr Pro Ser Val Val  Thr Ser Thr Pro
3710                 3715                 3720

gtg  acc act tct act gaa  gcc att tca tct tct  gca act ctt gac     11272
Val  Thr Thr Ser Thr Glu  Ala Ile Ser Ser Ser  Ala Thr Leu Asp
3725                 3730                 3735
```

```
agc  acc acc atg tct gtg  tca atg ccc atg gaa  ata agc acc ctt     11317
Ser  Thr Thr Met Ser Val  Ser Met Pro Met Glu  Ile Ser Thr Leu
3740                 3745                 3750

ggg  acc act att ctt gtc  agt acc aca cct gtt  acg agg ttt cct     11362
Gly  Thr Thr Ile Leu Val  Ser Thr Thr Pro Val  Thr Arg Phe Pro
3755                 3760                 3765

gag  agt agc acc cct tcc  ata cca tct gtt tac  acc agc atg tct     11407
Glu  Ser Ser Thr Pro Ser  Ile Pro Ser Val Tyr  Thr Ser Met Ser
3770                 3775                 3780

atg  acc act gcc tct gaa  ggc agt tca tct cct  aca act ctt gaa     11452
Met  Thr Thr Ala Ser Glu  Gly Ser Ser Ser Pro  Thr Thr Leu Glu
3785                 3790                 3795

ggc  acc acc acc atg cct  atg tca act acg agt  gaa aga agc act     11497
Gly  Thr Thr Thr Met Pro  Met Ser Thr Thr Ser  Glu Arg Ser Thr
3800                 3805                 3810

tta  ttg aca act gtc ctc  atc agc cct ata tct  gtg atg agt cct     11542
Leu  Leu Thr Thr Val Leu  Ile Ser Pro Ile Ser  Val Met Ser Pro
3815                 3820                 3825

tct  gag gcc agc aca ctt  tca aca cct cct ggt  gat acc agc aca     11587
Ser  Glu Ala Ser Thr Leu  Ser Thr Pro Pro Gly  Asp Thr Ser Thr
3830                 3835                 3840

cct  ttg ctc acc tct acc  aaa gcc ggt tca ttc  tcc ata cct gct     11632
Pro  Leu Leu Thr Ser Thr  Lys Ala Gly Ser Phe  Ser Ile Pro Ala
3845                 3850                 3855

gaa  gtc act acc ata cgt  att tca att acc agt  gaa aga agc act     11677
Glu  Val Thr Thr Ile Arg  Ile Ser Ile Thr Ser  Glu Arg Ser Thr
3860                 3865                 3870

cca  tta aca act ctc ctt  gtc agc acc aca ctt  cca act agc ttt     11722
Pro  Leu Thr Thr Leu Leu  Val Ser Thr Thr Leu  Pro Thr Ser Phe
3875                 3880                 3885

cct  ggg gcc agc ata gct  tcg aca cct cct ctt  gac aca agc aca     11767
Pro  Gly Ala Ser Ile Ala  Ser Thr Pro Pro Leu  Asp Thr Ser Thr
3890                 3895                 3900

act  ttt acc cct tct act  gac act gcc tca act  ccc aca att cct     11812
Thr  Phe Thr Pro Ser Thr  Asp Thr Ala Ser Thr  Pro Thr Ile Pro
3905                 3910                 3915

gta  gcc acc acc ata tct  gta tca gtg atc aca  gaa gga agc aca     11857
Val  Ala Thr Thr Ile Ser  Val Ser Val Ile Thr  Glu Gly Ser Thr
3920                 3925                 3930

cct  ggg aca acc att ttt  att ccc agc act cct  gtc acc agt tct     11902
Pro  Gly Thr Thr Ile Phe  Ile Pro Ser Thr Pro  Val Thr Ser Ser
3935                 3940                 3945

act  gct gat gtc ttt cct  gca aca act ggt gct  gta tct acc cct     11947
Thr  Ala Asp Val Phe Pro  Ala Thr Thr Gly Ala  Val Ser Thr Pro
3950                 3955                 3960

gtg  ata act tcc act gaa  cta aac aca cca tca  acc tcc agt agt     11992
Val  Ile Thr Ser Thr Glu  Leu Asn Thr Pro Ser  Thr Ser Ser Ser
3965                 3970                 3975

agt  acc acc aca tct ttt  tca act act aag gaa  ttt aca aca ccc     12037
Ser  Thr Thr Thr Ser Phe  Ser Thr Thr Lys Glu  Phe Thr Thr Pro
3980                 3985                 3990

gca  atg act act gca gct  ccc ctc aca tat gtg  acc atg tct act     12082
Ala  Met Thr Thr Ala Ala  Pro Leu Thr Tyr Val  Thr Met Ser Thr
3995                 4000                 4005

gcc  ccc agc aca ccc aga  aca acc agc aga ggc  tgc act act tct     12127
Ala  Pro Ser Thr Pro Arg  Thr Thr Ser Arg Gly  Cys Thr Thr Ser
4010                 4015                 4020

gca  tca acg ctt tct gca  acc agt aca cct cac  acc tct act tct     12172
Ala  Ser Thr Leu Ser Ala  Thr Ser Thr Pro His  Thr Ser Thr Ser
4025                 4030                 4035
```

```
gtc  acc acc cgt cct gtg  acc cct tca tca gaa  tcc agc agg ccg      12217
Val  Thr Thr Arg Pro Val  Thr Pro Ser Ser Glu  Ser Ser Arg Pro
4040                4045                4050

tca  aca att act tct cac  acc atc cca cct aca  ttt cct cct gct      12262
Ser  Thr Ile Thr Ser His  Thr Ile Pro Pro Thr  Phe Pro Pro Ala
4055                4060                4065

cac  tcc agt aca cct cca  aca acc tct gcc tcc  tcc acg act gtg      12307
His  Ser Ser Thr Pro Pro  Thr Thr Ser Ala Ser  Ser Thr Thr Val
4070                4075                4080

aac  cct gag gct gtc acc  acc atg acc acc agg  aca aaa ccc agc      12352
Asn  Pro Glu Ala Val Thr  Thr Met Thr Thr Arg  Thr Lys Pro Ser
4085                4090                4095

aca  cgg acc act tcc ttc  ccc acg gtg acc acc  acc gct gtc ccc      12397
Thr  Arg Thr Thr Ser Phe  Pro Thr Val Thr Thr  Thr Ala Val Pro
4100                4105                4110

acg  aat act aca att aag  agc aac ccc acc tca  act cct act gtg      12442
Thr  Asn Thr Thr Ile Lys  Ser Asn Pro Thr Ser  Thr Pro Thr Val
4115                4120                4125

cca  aga acc aca aca tgc  ttt gga gat ggg tgc  cag aat acg gcc      12487
Pro  Arg Thr Thr Thr Cys  Phe Gly Asp Gly Cys  Gln Asn Thr Ala
4130                4135                4140

tct  cgc tgc aag aat gga  ggc acc tgg gat ggg  ctc aag tgc cag      12532
Ser  Arg Cys Lys Asn Gly  Gly Thr Trp Asp Gly  Leu Lys Cys Gln
4145                4150                4155

tgt  ccc aac ctc tat tat  ggg gag ttg tgt gag  gag gtg gtc agc      12577
Cys  Pro Asn Leu Tyr Tyr  Gly Glu Leu Cys Glu  Glu Val Val Ser
4160                4165                4170

agc  att gac ata ggg cca  ccg gag act atc tct  gcc caa atg gaa      12622
Ser  Ile Asp Ile Gly Pro  Pro Glu Thr Ile Ser  Ala Gln Met Glu
4175                4180                4185

ctg  act gtg aca gtg acc  agt gtg aag ttc acc  gaa gag cta aaa      12667
Leu  Thr Val Thr Val Thr  Ser Val Lys Phe Thr  Glu Glu Leu Lys
4190                4195                4200

aac  cac tct tcc cag gaa  ttc cag gag ttc aaa  cag aca ttc acg      12712
Asn  His Ser Ser Gln Glu  Phe Gln Glu Phe Lys  Gln Thr Phe Thr
4205                4210                4215

gaa  cag atg aat att gtg  tat tcc ggg atc cct  gag tat gtc ggg      12757
Glu  Gln Met Asn Ile Val  Tyr Ser Gly Ile Pro  Glu Tyr Val Gly
4220                4225                4230

gtg  aac atc aca aag cta  cgt ctt ggc agt gtg  gtg gtg gag cat      12802
Val  Asn Ile Thr Lys Leu  Arg Leu Gly Ser Val  Val Val Glu His
4235                4240                4245

gac  gtc ctc cta aga acc  aag tac aca cca gaa  tac aag aca gta      12847
Asp  Val Leu Leu Arg Thr  Lys Tyr Thr Pro Glu  Tyr Lys Thr Val
4250                4255                4260

ttg  gac aat gcc acc gaa  gta gtg aaa gag aaa  atc aca aaa gtg      12892
Leu  Asp Asn Ala Thr Glu  Val Val Lys Glu Lys  Ile Thr Lys Val
4265                4270                4275

acc  aca cag caa ata atg  att aat gat att tgc  tca gac atg atg      12937
Thr  Thr Gln Gln Ile Met  Ile Asn Asp Ile Cys  Ser Asp Met Met
4280                4285                4290

tgt  ttc aac acc act ggc  acc caa gtg caa aac  att acg gtg acc      12982
Cys  Phe Asn Thr Thr Gly  Thr Gln Val Gln Asn  Ile Thr Val Thr
4295                4300                4305

cag  tac gac cct gaa gag  gac tgc cgg aag atg  gcc aag gaa tat      13027
Gln  Tyr Asp Pro Glu Glu  Asp Cys Arg Lys Met  Ala Lys Glu Tyr
4310                4315                4320

gga  gac tac ttc gta gtg  gag tac cgg gac cag  aag cca tac tgc      13072
Gly  Asp Tyr Phe Val Val  Glu Tyr Arg Asp Gln  Lys Pro Tyr Cys
```

```
4325                4330                4335

atc  agc ccc tgt gag cct  ggc ttc agt gtc tcc  aag aac tgt aac     13117
Ile  Ser Pro Cys Glu Pro  Gly Phe Ser Val Ser  Lys Asn Cys Asn
4340                4345                4350

ctc  ggc aag tgc cag atg  tct cta agt gga cct  cag tgc ctc tgc     13162
Leu  Gly Lys Cys Gln Met  Ser Leu Ser Gly Pro  Gln Cys Leu Cys
4355                4360                4365

gtg  acc acg gaa act cac  tgg tac agt ggg gag  acc tgt aac cag     13207
Val  Thr Thr Glu Thr His  Trp Tyr Ser Gly Glu  Thr Cys Asn Gln
4370                4375                4380

ggc  acc cag aag agt ctg  gtg tac ggc ctc gtg  ggg gca ggg gtc     13252
Gly  Thr Gln Lys Ser Leu  Val Tyr Gly Leu Val  Gly Ala Gly Val
4385                4390                4395

gtg  ctg atg ctg atc atc  ctg gta gct ctc ctg  atg ctc gtt ttc     13297
Val  Leu Met Leu Ile Ile  Leu Val Ala Leu Leu  Met Leu Val Phe
4400                4405                4410

cgc  tcc aag aga gag gtg  aaa cgg caa aag tac  aga ttg tct cag     13342
Arg  Ser Lys Arg Glu Val  Lys Arg Gln Lys Tyr  Arg Leu Ser Gln
4415                4420                4425

tta  tac aag tgg caa gaa  gag gac agt gga cca  gct cct ggg acc     13387
Leu  Tyr Lys Trp Gln Glu  Glu Asp Ser Gly Pro  Ala Pro Gly Thr
4430                4435                4440

ttc  caa aac att ggc ttt  gac atc tgc caa gat  gat gat tcc atc     13432
Phe  Gln Asn Ile Gly Phe  Asp Ile Cys Gln Asp  Asp Asp Ser Ile
4445                4450                4455

cac  ctg gag tcc atc tat  agt aat ttc cag ccc  tcc ttg aga cac     13477
His  Leu Glu Ser Ile Tyr  Ser Asn Phe Gln Pro  Ser Leu Arg His
4460                4465                4470

ata  gac cct gaa aca aag  atc cga att cag agg  cct cag gta atg     13522
Ile  Asp Pro Glu Thr Lys  Ile Arg Ile Gln Arg  Pro Gln Val Met
4475                4480                4485

acg  aca tca ttt taa ggcatggagc tgagaagtct gggagtgagg agatcccagt   13577
Thr  Thr Ser Phe
4490

ccggctaagc ttggtggagc attttcccat tgagagcctt ccatgggaac tcaatgttcc  13637

cattgtaagt acaggaaaca agccctgtac ttaccaagga gaaagaggag agacagcagt  13697

gctgggagat tctcaaatag aaacccgtgg acgctccaat gggcttgtca tgatatcagg  13757

ctaggctttc ctgctcattt ttcaaagacg ctccagattt gagggtactc tgactgcaac  13817

atctttcacc ccattgatcg ccaggattga tttggttgat ctggctgagc aggcgggtgt  13877

ccccgtcctc cctcactgcc ccatatgtgt ccctcctaaa gctgcatgct cagttgaaga  13937

ggacgagagg acgaccttct ctgatagagg aggaccacgc ttcagtcaaa ggcatacaag  13997

tatctatctg gacttccctg ctagcacttc caaacaagct cagagatgtt cctcccctca  14057

tctgcccggg ttcagtacca tggacagcgc cctcgacccg ctgtttacaa ccatgacccc  14117

ttggacactg gactgcatgc actttacata tcacaaaatg ctctcataag aattattgca  14177

taccatcttc atgaaaaaca cctgtattta aatatagagc atttaccttt tggtatataa  14237

gattgtgggt attttttaag ttcttattgt tatgagttct gatttttttcc ttagtaaata  14297

ttataatata tatttgtagt aactaaaaat aataaagcaa ttttattaca atttt       14352
```

<210> SEQ ID NO 38
<211> LENGTH: 4493
<212> TYPE: PRT
<213> ORGANISM: Homo sapiens

<400> SEQUENCE: 38

-continued

```
Met Pro Arg Pro Gly Thr Met Ala Leu Cys Leu Leu Thr Leu Val Leu
1               5                   10                  15

Ser Leu Leu Pro Pro Gln Ala Ala Ala Glu Gln Asp Leu Ser Val Asn
            20                  25                  30

Arg Ala Val Trp Asp Gly Gly Gly Cys Ile Ser Gln Gly Asp Val Leu
        35                  40                  45

Asn Arg Gln Cys Gln Gln Leu Ser Gln His Val Arg Thr Gly Ser Ala
    50                  55                  60

Ala Asn Thr Ala Thr Gly Thr Thr Ser Thr Asn Val Val Glu Pro Arg
65                  70                  75                  80

Met Tyr Leu Ser Cys Ser Thr Asn Pro Glu Met Thr Ser Ile Glu Ser
                85                  90                  95

Ser Val Thr Ser Asp Thr Pro Gly Val Ser Ser Thr Arg Met Thr Pro
            100                 105                 110

Thr Glu Ser Arg Thr Thr Ser Glu Ser Thr Ser Asp Ser Thr Thr Leu
        115                 120                 125

Phe Pro Ser Ser Thr Glu Asp Thr Ser Ser Pro Thr Thr Pro Glu Gly
    130                 135                 140

Thr Asp Val Pro Met Ser Thr Pro Ser Glu Glu Ser Ile Ser Ser Thr
145                 150                 155                 160

Met Ala Phe Val Ser Thr Ala Pro Leu Pro Ser Phe Glu Ala Tyr Thr
                165                 170                 175

Ser Leu Thr Tyr Lys Val Asp Met Ser Thr Pro Leu Thr Thr Ser Thr
            180                 185                 190

Gln Ala Ser Ser Ser Pro Thr Thr Pro Glu Ser Thr Thr Ile Pro Lys
        195                 200                 205

Ser Thr Asn Ser Glu Gly Ser Thr Pro Leu Thr Ser Met Pro Ala Ser
    210                 215                 220

Thr Met Lys Val Ala Ser Ser Glu Ala Ile Thr Leu Leu Thr Thr Pro
225                 230                 235                 240

Val Glu Ile Ser Thr Pro Val Thr Ile Ser Ala Gln Ala Ser Ser Ser
                245                 250                 255

Pro Thr Thr Ala Glu Gly Pro Ser Leu Ser Asn Ser Ala Pro Ser Gly
            260                 265                 270

Gly Ser Thr Pro Leu Thr Arg Met Pro Leu Ser Val Met Leu Val Val
        275                 280                 285

Ser Ser Glu Ala Ser Thr Leu Ser Thr Thr Pro Ala Ala Thr Asn Ile
    290                 295                 300

Pro Val Ile Thr Ser Thr Glu Ala Ser Ser Ser Pro Thr Thr Ala Glu
305                 310                 315                 320

Gly Thr Ser Ile Pro Thr Ser Thr Tyr Thr Glu Gly Ser Thr Pro Leu
                325                 330                 335

Thr Ser Thr Pro Ala Ser Thr Met Pro Val Ala Thr Ser Glu Met Ser
            340                 345                 350

Thr Leu Ser Ile Thr Pro Val Asp Thr Ser Thr Leu Val Thr Thr Ser
        355                 360                 365

Thr Glu Pro Ser Ser Leu Pro Thr Thr Ala Glu Ala Thr Ser Met Leu
    370                 375                 380

Thr Ser Thr Leu Ser Glu Gly Ser Thr Pro Leu Thr Asn Met Pro Val
385                 390                 395                 400

Ser Thr Ile Leu Val Ala Ser Ser Glu Ala Ser Thr Thr Ser Thr Ile
                405                 410                 415
```

-continued

```
Pro Val Asp Ser Lys Thr Phe Val Thr Thr Ala Ser Glu Ala Ser Ser
                420                 425                 430

Ser Pro Thr Thr Ala Glu Asp Thr Ser Ile Ala Thr Ser Thr Pro Ser
            435                 440                 445

Glu Gly Ser Thr Pro Leu Thr Ser Met Pro Val Ser Thr Thr Pro Val
    450                 455                 460

Ala Ser Ser Glu Ala Ser Asn Leu Ser Thr Thr Pro Val Asp Ser Lys
465                 470                 475                 480

Thr Gln Val Thr Thr Ser Thr Glu Ala Ser Ser Ser Pro Pro Thr Ala
                485                 490                 495

Glu Val Asn Ser Met Pro Thr Ser Thr Pro Ser Glu Gly Ser Thr Pro
                500                 505                 510

Leu Thr Ser Met Ser Val Ser Thr Met Pro Val Ala Ser Ser Glu Ala
            515                 520                 525

Ser Thr Leu Ser Thr Thr Pro Val Asp Thr Ser Thr Pro Val Thr Thr
    530                 535                 540

Ser Ser Glu Ala Ser Ser Ser Ser Thr Thr Pro Glu Gly Thr Ser Ile
545                 550                 555                 560

Pro Thr Ser Thr Pro Ser Glu Gly Ser Thr Pro Leu Thr Asn Met Pro
                565                 570                 575

Val Ser Thr Arg Leu Val Val Ser Ser Glu Ala Ser Thr Thr Ser Thr
                580                 585                 590

Thr Pro Ala Asp Ser Asn Thr Phe Val Thr Thr Ser Ser Glu Ala Ser
            595                 600                 605

Ser Ser Ser Thr Thr Ala Glu Gly Thr Ser Met Pro Thr Ser Thr Tyr
    610                 615                 620

Ser Glu Arg Gly Thr Thr Ile Thr Ser Met Ser Val Ser Thr Thr Leu
625                 630                 635                 640

Val Ala Ser Ser Glu Ala Ser Thr Leu Ser Thr Thr Pro Val Asp Ser
                645                 650                 655

Asn Thr Pro Val Thr Thr Ser Thr Glu Ala Thr Ser Ser Ser Thr Thr
                660                 665                 670

Ala Glu Gly Thr Ser Met Pro Thr Ser Thr Tyr Thr Glu Gly Ser Thr
            675                 680                 685

Pro Leu Thr Ser Met Pro Val Asn Thr Thr Leu Val Ala Ser Ser Glu
    690                 695                 700

Ala Ser Thr Leu Ser Thr Thr Pro Val Asp Thr Ser Thr Pro Val Thr
705                 710                 715                 720

Thr Ser Thr Glu Ala Ser Ser Ser Pro Thr Thr Ala Asp Gly Ala Ser
                725                 730                 735

Met Pro Thr Ser Thr Pro Ser Glu Gly Ser Thr Pro Leu Thr Ser Met
                740                 745                 750

Pro Val Ser Lys Thr Leu Leu Thr Ser Ser Glu Ala Ser Thr Leu Ser
            755                 760                 765

Thr Thr Pro Leu Asp Thr Ser Thr His Ile Thr Thr Ser Thr Glu Ala
    770                 775                 780

Ser Cys Ser Pro Thr Thr Thr Glu Gly Thr Ser Met Pro Ile Ser Thr
785                 790                 795                 800

Pro Ser Glu Gly Ser Pro Leu Leu Thr Ser Ile Pro Val Ser Ile Thr
                805                 810                 815

Pro Val Thr Ser Pro Glu Ala Ser Thr Leu Ser Thr Thr Pro Val Asp
                820                 825                 830

Ser Asn Ser Pro Val Thr Thr Ser Thr Glu Val Ser Ser Ser Pro Thr
```

-continued

```
        835                 840                 845

Pro Ala Glu Gly Thr Ser Met Pro Thr Ser Thr Tyr Ser Glu Gly Arg
    850                 855                 860

Thr Pro Leu Thr Ser Met Pro Val Ser Thr Thr Leu Val Ala Thr Ser
865                 870                 875                 880

Ala Ile Ser Thr Leu Ser Thr Thr Pro Val Asp Thr Ser Thr Pro Val
                885                 890                 895

Thr Asn Ser Thr Glu Ala Arg Ser Ser Pro Thr Thr Ser Glu Gly Thr
            900                 905                 910

Ser Met Pro Thr Ser Thr Pro Gly Glu Gly Ser Thr Pro Leu Thr Ser
        915                 920                 925

Met Pro Asp Ser Thr Thr Pro Val Val Ser Ser Glu Ala Arg Thr Leu
    930                 935                 940

Ser Ala Thr Pro Val Asp Thr Ser Thr Pro Val Thr Thr Ser Thr Glu
945                 950                 955                 960

Ala Thr Ser Ser Pro Thr Thr Ala Glu Gly Thr Ser Ile Pro Thr Ser
                965                 970                 975

Thr Pro Ser Glu Gly Thr Thr Pro Leu Thr Ser Thr Pro Val Ser His
            980                 985                 990

Thr Leu Val Ala Asn Ser Glu Ala  Ser Thr Leu Ser Thr  Thr Pro Val
        995                 1000                1005

Asp Ser  Asn Thr Pro Leu Thr  Thr Ser Thr Glu Ala  Ser Ser Pro
    1010                1015                1020

Pro Pro  Thr Ala Glu Gly Thr  Ser Met Pro Thr Ser  Thr Pro Ser
    1025                1030                1035

Glu Gly  Ser Thr Pro Leu Thr  Arg Met Pro Val Ser  Thr Thr Met
    1040                1045                1050

Val Ala  Ser Ser Glu Thr Ser  Thr Leu Ser Thr Thr  Pro Ala Asp
    1055                1060                1065

Thr Ser  Thr Pro Val Thr Thr  Tyr Ser Gln Ala Ser  Ser Ser Ser
    1070                1075                1080

Thr Thr  Ala Asp Gly Thr Ser  Met Pro Thr Ser Thr  Tyr Ser Glu
    1085                1090                1095

Gly Ser  Thr Pro Leu Thr Ser  Val Pro Val Ser Thr  Arg Leu Val
    1100                1105                1110

Val Ser  Ser Glu Ala Ser Thr  Leu Ser Thr Thr Pro  Val Asp Thr
    1115                1120                1125

Ser Ile  Pro Val Thr Thr Ser  Thr Glu Ala Ser Ser  Ser Pro Thr
    1130                1135                1140

Thr Ala  Glu Gly Thr Ser Ile  Pro Thr Ser Pro Pro  Ser Glu Gly
    1145                1150                1155

Thr Thr  Pro Leu Ala Ser Met  Pro Val Ser Thr Thr  Leu Val Val
    1160                1165                1170

Ser Ser  Glu Ala Asn Thr Leu  Ser Thr Thr Pro Val  Asp Ser Lys
    1175                1180                1185

Thr Gln  Val Ala Thr Ser Thr  Glu Ala Ser Ser Pro  Pro Pro Thr
    1190                1195                1200

Ala Glu  Val Thr Ser Met Pro  Thr Ser Thr Pro Gly  Glu Arg Ser
    1205                1210                1215

Thr Pro  Leu Thr Ser Met Pro  Val Arg His Thr Pro  Val Ala Ser
    1220                1225                1230

Ser Glu  Ala Ser Thr Leu Ser  Thr Ser Pro Val Asp  Thr Ser Thr
    1235                1240                1245
```

```
Pro Val Thr Thr Ser Ala Glu Thr Ser Ser Ser Pro Thr Thr Ala
    1250                1255                1260

Glu Gly Thr Ser Leu Pro Thr Ser Thr Thr Ser Glu Gly Ser Thr
    1265                1270                1275

Leu Leu Thr Ser Ile Pro Val Ser Thr Thr Leu Val Thr Ser Pro
    1280                1285                1290

Glu Ala Ser Thr Leu Leu Thr Thr Pro Val Asp Thr Lys Gly Pro
    1295                1300                1305

Val Val Thr Ser Asn Glu Val Ser Ser Ser Pro Thr Pro Ala Glu
    1310                1315                1320

Gly Thr Ser Met Pro Thr Ser Thr Tyr Ser Glu Gly Arg Thr Pro
    1325                1330                1335

Leu Thr Ser Ile Pro Val Asn Thr Thr Leu Val Ala Ser Ser Ala
    1340                1345                1350

Ile Ser Ile Leu Ser Thr Thr Pro Val Asp Asn Ser Thr Pro Val
    1355                1360                1365

Thr Thr Ser Thr Glu Ala Cys Ser Ser Pro Thr Thr Ser Glu Gly
    1370                1375                1380

Thr Ser Met Pro Asn Ser Asn Pro Ser Glu Gly Thr Thr Pro Leu
    1385                1390                1395

Thr Ser Ile Pro Val Ser Thr Thr Pro Val Val Ser Ser Glu Ala
    1400                1405                1410

Ser Thr Leu Ser Ala Thr Pro Val Asp Thr Ser Thr Pro Gly Thr
    1415                1420                1425

Thr Ser Ala Glu Ala Thr Ser Ser Pro Thr Thr Ala Glu Gly Ile
    1430                1435                1440

Ser Ile Pro Thr Ser Thr Pro Ser Glu Gly Lys Thr Pro Leu Lys
    1445                1450                1455

Ser Ile Pro Val Ser Asn Thr Pro Val Ala Asn Ser Glu Ala Ser
    1460                1465                1470

Thr Leu Ser Thr Thr Pro Val Asp Ser Asn Ser Pro Val Val Thr
    1475                1480                1485

Ser Thr Ala Val Ser Ser Ser Pro Thr Pro Ala Glu Gly Thr Ser
    1490                1495                1500

Ile Ala Ile Ser Thr Pro Ser Glu Gly Ser Thr Ala Leu Thr Ser
    1505                1510                1515

Ile Pro Val Ser Thr Thr Thr Val Ala Ser Ser Glu Ile Asn Ser
    1520                1525                1530

Leu Ser Thr Thr Pro Ala Val Thr Ser Thr Pro Val Thr Thr Tyr
    1535                1540                1545

Ser Gln Ala Ser Ser Ser Pro Thr Thr Ala Asp Gly Thr Ser Met
    1550                1555                1560

Gln Thr Ser Thr Tyr Ser Glu Gly Ser Thr Pro Leu Thr Ser Leu
    1565                1570                1575

Pro Val Ser Thr Met Leu Val Val Ser Ser Glu Ala Asn Thr Leu
    1580                1585                1590

Ser Thr Thr Pro Ile Asp Ser Lys Thr Gln Val Thr Ala Ser Thr
    1595                1600                1605

Glu Ala Ser Ser Ser Thr Thr Ala Glu Gly Ser Ser Met Thr Ile
    1610                1615                1620

Ser Thr Pro Ser Glu Gly Ser Pro Leu Leu Thr Ser Ile Pro Val
    1625                1630                1635
```

```
Ser Thr  Thr Pro Val Ala Ser  Pro Glu Ala Ser Thr  Leu Ser Thr
    1640                 1645                 1650

Thr Pro  Val Asp Ser Asn Ser  Pro Val Ile Thr Ser  Thr Glu Val
    1655                 1660                 1665

Ser Ser  Ser Pro Thr Pro Ala  Glu Gly Thr Ser Met  Pro Thr Ser
    1670                 1675                 1680

Thr Tyr  Thr Glu Gly Arg Thr  Pro Leu Thr Ser Ile  Thr Val Arg
    1685                 1690                 1695

Thr Thr  Pro Val Ala Ser Ser  Ala Ile Ser Thr Leu  Ser Thr Thr
    1700                 1705                 1710

Pro Val  Asp Asn Ser Thr Pro  Val Thr Thr Ser Thr  Glu Ala Arg
    1715                 1720                 1725

Ser Ser  Pro Thr Thr Ser Glu  Gly Thr Ser Met Pro  Asn Ser Thr
    1730                 1735                 1740

Pro Ser  Glu Gly Thr Thr Pro  Leu Thr Ser Ile Pro  Val Ser Thr
    1745                 1750                 1755

Thr Pro  Val Leu Ser Ser Glu  Ala Ser Thr Leu Ser  Ala Thr Pro
    1760                 1765                 1770

Ile Asp  Thr Ser Thr Pro Val  Thr Thr Ser Thr Glu  Ala Thr Ser
    1775                 1780                 1785

Ser Pro  Thr Thr Ala Glu Gly  Thr Ser Ile Pro Thr  Ser Thr Leu
    1790                 1795                 1800

Ser Glu  Gly Met Thr Pro Leu  Thr Ser Thr Pro Val  Ser His Thr
    1805                 1810                 1815

Leu Val  Ala Asn Ser Glu Ala  Ser Thr Leu Ser Thr  Thr Pro Val
    1820                 1825                 1830

Asp Ser  Asn Ser Pro Val Val  Thr Ser Thr Ala Val  Ser Ser Ser
    1835                 1840                 1845

Pro Thr  Pro Ala Glu Gly Thr  Ser Ile Ala Thr Ser  Thr Pro Ser
    1850                 1855                 1860

Glu Gly  Ser Thr Ala Leu Thr  Ser Ile Pro Val Ser  Thr Thr Thr
    1865                 1870                 1875

Val Ala  Ser Ser Glu Thr Asn  Thr Leu Ser Thr Thr  Pro Ala Val
    1880                 1885                 1890

Thr Ser  Thr Pro Val Thr Thr  Tyr Ala Gln Val Ser  Ser Ser Pro
    1895                 1900                 1905

Thr Thr  Ala Asp Gly Ser Ser  Met Pro Thr Ser Thr  Pro Arg Glu
    1910                 1915                 1920

Gly Arg  Pro Pro Leu Thr Ser  Ile Pro Val Ser Thr  Thr Thr Val
    1925                 1930                 1935

Ala Ser  Ser Glu Ile Asn Thr  Leu Ser Thr Thr Leu  Ala Asp Thr
    1940                 1945                 1950

Arg Thr  Pro Val Thr Thr Tyr  Ser Gln Ala Ser Ser  Ser Pro Thr
    1955                 1960                 1965

Thr Ala  Asp Gly Thr Ser Met  Pro Thr Pro Ala Tyr  Ser Glu Gly
    1970                 1975                 1980

Ser Thr  Pro Leu Thr Ser Met  Pro Leu Ser Thr Thr  Leu Val Val
    1985                 1990                 1995

Ser Ser  Glu Ala Ser Thr Leu  Ser Thr Thr Pro Val  Asp Thr Ser
    2000                 2005                 2010

Thr Pro  Ala Thr Thr Ser Thr  Glu Gly Ser Ser Ser  Pro Thr Thr
    2015                 2020                 2025

Ala Gly  Gly Thr Ser Ile Gln  Thr Ser Thr Pro Ser  Glu Arg Thr
```

```
    2030                2035                2040

Thr Pro  Leu Ala Gly Met Pro  Val Ser Thr Thr Leu  Val Val Ser
    2045                2050                2055

Ser Glu  Gly Asn Thr Leu Ser  Thr Thr Pro Val Asp  Ser Lys Thr
    2060                2065                2070

Gln Val  Thr Asn Ser Thr Glu  Ala Ser Ser Ser Ala  Thr Ala Glu
    2075                2080                2085

Gly Ser  Ser Met Thr Ile Ser  Ala Pro Ser Glu Gly  Ser Pro Leu
    2090                2095                2100

Leu Thr  Ser Ile Pro Leu Ser  Thr Thr Pro Val Ala  Ser Pro Glu
    2105                2110                2115

Ala Ser  Thr Leu Ser Thr Thr  Pro Val Asp Ser Asn  Ser Pro Val
    2120                2125                2130

Ile Thr  Ser Thr Glu Val Ser  Ser Ser Pro Ile Pro  Thr Glu Gly
    2135                2140                2145

Thr Ser  Met Gln Thr Ser Thr  Tyr Ser Asp Arg Arg  Thr Pro Leu
    2150                2155                2160

Thr Ser  Met Pro Val Ser Thr  Thr Val Val Ala Ser  Ser Ala Ile
    2165                2170                2175

Ser Thr  Leu Ser Thr Thr Pro  Val Asp Thr Ser Thr  Pro Val Thr
    2180                2185                2190

Asn Ser  Thr Glu Ala Arg Ser  Ser Pro Thr Thr Ser  Glu Gly Thr
    2195                2200                2205

Ser Met  Pro Thr Ser Thr Pro  Ser Glu Gly Ser Thr  Pro Phe Thr
    2210                2215                2220

Ser Met  Pro Val Ser Thr Met  Pro Val Val Thr Ser  Glu Ala Ser
    2225                2230                2235

Thr Leu  Ser Ala Thr Pro Val  Asp Thr Ser Thr Pro  Val Thr Thr
    2240                2245                2250

Ser Thr  Glu Ala Thr Ser Ser  Pro Thr Thr Ala Glu  Gly Thr Ser
    2255                2260                2265

Ile Pro  Thr Ser Thr Leu Ser  Glu Gly Thr Thr Pro  Leu Thr Ser
    2270                2275                2280

Ile Pro  Val Ser His Thr Leu  Val Ala Asn Ser Glu  Val Ser Thr
    2285                2290                2295

Leu Ser  Thr Thr Pro Val Asp  Ser Asn Thr Pro Phe  Thr Thr Ser
    2300                2305                2310

Thr Glu  Ala Ser Ser Pro Pro  Pro Thr Ala Glu Gly  Thr Ser Met
    2315                2320                2325

Pro Thr  Ser Thr Ser Ser Glu  Gly Asn Thr Pro Leu  Thr Arg Met
    2330                2335                2340

Pro Val  Ser Thr Thr Met Val  Ala Ser Phe Glu Thr  Ser Thr Leu
    2345                2350                2355

Ser Thr  Thr Pro Ala Asp Thr  Ser Thr Pro Val Thr  Thr Tyr Ser
    2360                2365                2370

Gln Ala  Gly Ser Ser Pro Thr  Thr Ala Asp Asp Thr  Ser Met Pro
    2375                2380                2385

Thr Ser  Thr Tyr Ser Glu Gly  Ser Thr Pro Leu Thr  Ser Val Pro
    2390                2395                2400

Val Ser  Thr Met Pro Val Val  Ser Ser Glu Ala Ser  Thr His Ser
    2405                2410                2415

Thr Thr  Pro Val Asp Thr Ser  Thr Pro Val Thr Thr  Ser Thr Glu
    2420                2425                2430
```

```
Ala Ser Ser Ser Pro Thr Thr Ala Glu Gly Thr Ser Ile Pro Thr
    2435                2440                2445

Ser Pro Pro Ser Glu Gly Thr Thr Pro Leu Ala Ser Met Pro Val
    2450                2455                2460

Ser Thr Thr Pro Val Val Ser Ser Glu Ala Gly Thr Leu Ser Thr
    2465                2470                2475

Thr Pro Val Asp Thr Ser Thr Pro Met Thr Thr Ser Thr Glu Ala
    2480                2485                2490

Ser Ser Ser Pro Thr Thr Ala Glu Asp Ile Val Val Pro Ile Ser
    2495                2500                2505

Thr Ala Ser Glu Gly Ser Thr Leu Leu Thr Ser Ile Pro Val Ser
    2510                2515                2520

Thr Thr Pro Val Ala Ser Pro Glu Ala Ser Thr Leu Ser Thr Thr
    2525                2530                2535

Pro Val Asp Ser Asn Ser Pro Val Val Thr Ser Thr Glu Ile Ser
    2540                2545                2550

Ser Ser Ala Thr Ser Ala Glu Gly Thr Ser Met Pro Thr Ser Thr
    2555                2560                2565

Tyr Ser Glu Gly Ser Thr Pro Leu Arg Ser Met Pro Val Ser Thr
    2570                2575                2580

Lys Pro Leu Ala Ser Ser Glu Ala Ser Thr Leu Ser Thr Thr Pro
    2585                2590                2595

Val Asp Thr Ser Ile Pro Val Thr Thr Ser Thr Glu Thr Ser Ser
    2600                2605                2610

Ser Pro Thr Thr Ala Lys Asp Thr Ser Met Pro Ile Ser Thr Pro
    2615                2620                2625

Ser Glu Val Ser Thr Ser Leu Thr Ser Ile Leu Val Ser Thr Met
    2630                2635                2640

Pro Val Ala Ser Ser Glu Ala Ser Thr Leu Ser Thr Thr Pro Val
    2645                2650                2655

Asp Thr Arg Thr Leu Val Thr Thr Ser Thr Gly Thr Ser Ser Ser
    2660                2665                2670

Pro Thr Thr Ala Glu Gly Ser Ser Met Pro Thr Ser Thr Pro Gly
    2675                2680                2685

Glu Arg Ser Thr Pro Leu Thr Asn Ile Leu Val Ser Thr Thr Leu
    2690                2695                2700

Leu Ala Asn Ser Glu Ala Ser Thr Leu Ser Thr Thr Pro Val Asp
    2705                2710                2715

Thr Ser Thr Pro Val Thr Thr Ser Ala Glu Ala Ser Ser Ser Pro
    2720                2725                2730

Thr Thr Ala Glu Gly Thr Ser Met Arg Ile Ser Thr Pro Ser Asp
    2735                2740                2745

Gly Ser Thr Pro Leu Thr Ser Ile Leu Val Ser Thr Leu Pro Val
    2750                2755                2760

Ala Ser Ser Glu Ala Ser Thr Val Ser Thr Thr Ala Val Asp Thr
    2765                2770                2775

Ser Ile Pro Val Thr Thr Ser Thr Glu Ala Ser Ser Ser Pro Thr
    2780                2785                2790

Thr Ala Glu Val Thr Ser Met Pro Thr Ser Thr Pro Ser Glu Thr
    2795                2800                2805

Ser Thr Pro Leu Thr Ser Met Pro Val Asn His Thr Pro Val Ala
    2810                2815                2820
```

Ser Ser Glu Ala Gly Thr Leu Ser Thr Thr Pro Val Asp Thr Ser
2825 2830 2835

Thr Pro Val Thr Thr Ser Thr Lys Ala Ser Ser Ser Pro Thr Thr
2840 2845 2850

Ala Glu Gly Ile Val Val Pro Ile Ser Thr Ala Ser Glu Gly Ser
2855 2860 2865

Thr Leu Leu Thr Ser Ile Pro Val Ser Thr Thr Pro Val Ala Ser
2870 2875 2880

Ser Glu Ala Ser Thr Leu Ser Thr Thr Pro Val Asp Thr Ser Ile
2885 2890 2895

Pro Val Thr Thr Ser Thr Glu Gly Ser Ser Ser Pro Thr Thr Ala
2900 2905 2910

Glu Gly Thr Ser Met Pro Ile Ser Thr Pro Ser Glu Val Ser Thr
2915 2920 2925

Pro Leu Thr Ser Ile Leu Val Ser Thr Val Pro Val Ala Gly Ser
2930 2935 2940

Glu Ala Ser Thr Leu Ser Thr Thr Pro Val Asp Thr Arg Thr Pro
2945 2950 2955

Val Thr Thr Ser Ala Glu Ala Ser Ser Ser Pro Thr Thr Ala Glu
2960 2965 2970

Gly Thr Ser Met Pro Ile Ser Thr Pro Gly Glu Arg Arg Thr Pro
2975 2980 2985

Leu Thr Ser Met Ser Val Ser Thr Met Pro Val Ala Ser Ser Glu
2990 2995 3000

Ala Ser Thr Leu Ser Arg Thr Pro Ala Asp Thr Ser Thr Pro Val
3005 3010 3015

Thr Thr Ser Thr Glu Ala Ser Ser Ser Pro Thr Thr Ala Glu Gly
3020 3025 3030

Thr Gly Ile Pro Ile Ser Thr Pro Ser Glu Gly Ser Thr Pro Leu
3035 3040 3045

Thr Ser Ile Pro Val Ser Thr Thr Pro Val Ala Ile Pro Glu Ala
3050 3055 3060

Ser Thr Leu Ser Thr Thr Pro Val Asp Ser Asn Ser Pro Val Val
3065 3070 3075

Thr Ser Thr Glu Val Ser Ser Ser Pro Thr Pro Ala Glu Gly Thr
3080 3085 3090

Ser Met Pro Ile Ser Thr Tyr Ser Glu Gly Ser Thr Pro Leu Thr
3095 3100 3105

Gly Val Pro Val Ser Thr Thr Pro Val Thr Ser Ser Ala Ile Ser
3110 3115 3120

Thr Leu Ser Thr Thr Pro Val Asp Thr Ser Thr Pro Val Thr Thr
3125 3130 3135

Ser Thr Glu Ala His Ser Ser Pro Thr Thr Ser Glu Gly Thr Ser
3140 3145 3150

Met Pro Thr Ser Thr Pro Ser Glu Gly Ser Thr Pro Leu Thr Tyr
3155 3160 3165

Met Pro Val Ser Thr Met Leu Val Val Ser Ser Glu Asp Ser Thr
3170 3175 3180

Leu Ser Ala Thr Pro Val Asp Thr Ser Thr Pro Val Thr Thr Ser
3185 3190 3195

Thr Glu Ala Thr Ser Ser Thr Thr Ala Glu Gly Thr Ser Ile Pro
3200 3205 3210

Thr Ser Thr Pro Ser Glu Gly Met Thr Pro Leu Thr Ser Val Pro 3215 3220 3225

Val Ser Asn Thr Pro Val Ala Ser Ser Glu Ala Ser Ile Leu Ser
3230 3235 3240

Thr Thr Pro Val Asp Ser Asn Thr Pro Leu Thr Thr Ser Thr Glu
3245 3250 3255

Ala Ser Ser Ser Pro Pro Thr Ala Glu Gly Thr Ser Met Pro Thr
3260 3265 3270

Ser Thr Pro Ser Glu Gly Ser Thr Pro Leu Thr Ser Met Pro Val
3275 3280 3285

Ser Thr Thr Thr Val Ala Ser Ser Glu Thr Ser Thr Leu Ser Thr
3290 3295 3300

Thr Pro Ala Asp Thr Ser Thr Pro Val Thr Thr Tyr Ser Gln Ala
3305 3310 3315

Ser Ser Ser Pro Pro Ile Ala Asp Gly Thr Ser Met Pro Thr Ser
3320 3325 3330

Thr Tyr Ser Glu Gly Ser Thr Pro Leu Thr Asn Met Ser Phe Ser
3335 3340 3345

Thr Thr Pro Val Val Ser Ser Glu Ala Ser Thr Leu Ser Thr Thr
3350 3355 3360

Pro Val Asp Thr Ser Thr Pro Val Thr Thr Ser Thr Glu Ala Ser
3365 3370 3375

Leu Ser Pro Thr Thr Ala Glu Gly Thr Ser Ile Pro Thr Ser Ser
3380 3385 3390

Pro Ser Glu Gly Thr Thr Pro Leu Ala Ser Met Pro Val Ser Thr
3395 3400 3405

Thr Pro Val Val Ser Ser Glu Val Asn Thr Leu Ser Thr Thr Pro
3410 3415 3420

Val Asp Ser Asn Thr Leu Val Thr Thr Ser Thr Glu Ala Ser Ser
3425 3430 3435

Ser Pro Thr Ile Ala Glu Gly Thr Ser Leu Pro Thr Ser Thr Thr
3440 3445 3450

Ser Glu Gly Ser Thr Pro Leu Ser Ile Met Pro Leu Ser Thr Thr
3455 3460 3465

Pro Val Ala Ser Ser Glu Ala Ser Thr Leu Ser Thr Thr Pro Val
3470 3475 3480

Asp Thr Ser Thr Pro Val Thr Thr Ser Ser Pro Thr Asn Ser Ser
3485 3490 3495

Pro Thr Thr Ala Glu Val Thr Ser Met Pro Thr Ser Thr Ala Gly
3500 3505 3510

Glu Gly Ser Thr Pro Leu Thr Asn Met Pro Val Ser Thr Thr Pro
3515 3520 3525

Val Ala Ser Ser Glu Ala Ser Thr Leu Ser Thr Thr Pro Val Asp
3530 3535 3540

Ser Asn Thr Phe Val Thr Ser Ser Ser Gln Ala Ser Ser Ser Pro
3545 3550 3555

Ala Thr Leu Gln Val Thr Thr Met Arg Met Ser Thr Pro Ser Glu
3560 3565 3570

Gly Ser Ser Ser Leu Thr Thr Met Leu Leu Ser Ser Thr Tyr Val
3575 3580 3585

Thr Ser Ser Glu Ala Ser Thr Pro Ser Thr Pro Ser Val Asp Arg
3590 3595 3600

Ser Thr Pro Val Thr Thr Ser Thr Gln Ser Asn Ser Thr Pro Thr
3605 3610 3615

```
Pro Pro Glu Val Ile Thr Leu Pro Met Ser Thr Pro Ser Glu Val
    3620                3625                3630

Ser Thr Pro Leu Thr Ile Met Pro Val Ser Thr Thr Ser Val Thr
    3635                3640                3645

Ile Ser Glu Ala Gly Thr Ala Ser Thr Leu Pro Val Asp Thr Ser
    3650                3655                3660

Thr Pro Val Ile Thr Ser Thr Gln Val Ser Ser Ser Pro Val Thr
    3665                3670                3675

Pro Glu Gly Thr Thr Met Pro Ile Trp Thr Pro Ser Glu Gly Ser
    3680                3685                3690

Thr Pro Leu Thr Thr Met Pro Val Ser Thr Thr Arg Val Thr Ser
    3695                3700                3705

Ser Glu Gly Ser Thr Leu Ser Thr Pro Ser Val Val Thr Ser Thr
    3710                3715                3720

Pro Val Thr Thr Ser Thr Glu Ala Ile Ser Ser Ser Ala Thr Leu
    3725                3730                3735

Asp Ser Thr Thr Met Ser Val Ser Met Pro Met Glu Ile Ser Thr
    3740                3745                3750

Leu Gly Thr Thr Ile Leu Val Ser Thr Thr Pro Val Thr Arg Phe
    3755                3760                3765

Pro Glu Ser Ser Thr Pro Ser Ile Pro Ser Val Tyr Thr Ser Met
    3770                3775                3780

Ser Met Thr Thr Ala Ser Glu Gly Ser Ser Ser Pro Thr Thr Leu
    3785                3790                3795

Glu Gly Thr Thr Thr Met Pro Met Ser Thr Thr Ser Glu Arg Ser
    3800                3805                3810

Thr Leu Leu Thr Thr Val Leu Ile Ser Pro Ile Ser Val Met Ser
    3815                3820                3825

Pro Ser Glu Ala Ser Thr Leu Ser Thr Pro Pro Gly Asp Thr Ser
    3830                3835                3840

Thr Pro Leu Leu Thr Ser Thr Lys Ala Gly Ser Phe Ser Ile Pro
    3845                3850                3855

Ala Glu Val Thr Thr Ile Arg Ile Ser Ile Thr Ser Glu Arg Ser
    3860                3865                3870

Thr Pro Leu Thr Thr Leu Leu Val Ser Thr Thr Leu Pro Thr Ser
    3875                3880                3885

Phe Pro Gly Ala Ser Ile Ala Ser Thr Pro Pro Leu Asp Thr Ser
    3890                3895                3900

Thr Thr Phe Thr Pro Ser Thr Asp Thr Ala Ser Thr Pro Thr Ile
    3905                3910                3915

Pro Val Ala Thr Thr Ile Ser Val Ser Val Ile Thr Glu Gly Ser
    3920                3925                3930

Thr Pro Gly Thr Thr Ile Phe Ile Pro Ser Thr Pro Val Thr Ser
    3935                3940                3945

Ser Thr Ala Asp Val Phe Pro Ala Thr Thr Gly Ala Val Ser Thr
    3950                3955                3960

Pro Val Ile Thr Ser Thr Glu Leu Asn Thr Pro Ser Thr Ser Ser
    3965                3970                3975

Ser Ser Thr Thr Thr Ser Phe Ser Thr Thr Lys Glu Phe Thr Thr
    3980                3985                3990

Pro Ala Met Thr Thr Ala Ala Pro Leu Thr Tyr Val Thr Met Ser
    3995                4000                4005
```

-continued

Thr Ala Pro Ser Thr Pro Arg Thr Thr Ser Arg Gly Cys Thr Thr
4010 4015 4020

Ser Ala Ser Thr Leu Ser Ala Thr Ser Thr Pro His Thr Ser Thr
4025 4030 4035

Ser Val Thr Thr Arg Pro Val Thr Pro Ser Ser Glu Ser Ser Arg
4040 4045 4050

Pro Ser Thr Ile Thr Ser His Thr Ile Pro Pro Thr Phe Pro Pro
4055 4060 4065

Ala His Ser Ser Thr Pro Pro Thr Thr Ser Ala Ser Ser Thr Thr
4070 4075 4080

Val Asn Pro Glu Ala Val Thr Thr Met Thr Thr Arg Thr Lys Pro
4085 4090 4095

Ser Thr Arg Thr Thr Ser Phe Pro Thr Val Thr Thr Thr Ala Val
4100 4105 4110

Pro Thr Asn Thr Thr Ile Lys Ser Asn Pro Thr Ser Thr Pro Thr
4115 4120 4125

Val Pro Arg Thr Thr Thr Cys Phe Gly Asp Gly Cys Gln Asn Thr
4130 4135 4140

Ala Ser Arg Cys Lys Asn Gly Gly Thr Trp Asp Gly Leu Lys Cys
4145 4150 4155

Gln Cys Pro Asn Leu Tyr Tyr Gly Glu Leu Cys Glu Glu Val Val
4160 4165 4170

Ser Ser Ile Asp Ile Gly Pro Pro Glu Thr Ile Ser Ala Gln Met
4175 4180 4185

Glu Leu Thr Val Thr Val Thr Ser Val Lys Phe Thr Glu Glu Leu
4190 4195 4200

Lys Asn His Ser Ser Gln Glu Phe Gln Glu Phe Lys Gln Thr Phe
4205 4210 4215

Thr Glu Gln Met Asn Ile Val Tyr Ser Gly Ile Pro Glu Tyr Val
4220 4225 4230

Gly Val Asn Ile Thr Lys Leu Arg Leu Gly Ser Val Val Val Glu
4235 4240 4245

His Asp Val Leu Leu Arg Thr Lys Tyr Thr Pro Glu Tyr Lys Thr
4250 4255 4260

Val Leu Asp Asn Ala Thr Glu Val Val Lys Glu Lys Ile Thr Lys
4265 4270 4275

Val Thr Thr Gln Gln Ile Met Ile Asn Asp Ile Cys Ser Asp Met
4280 4285 4290

Met Cys Phe Asn Thr Thr Gly Thr Gln Val Gln Asn Ile Thr Val
4295 4300 4305

Thr Gln Tyr Asp Pro Glu Glu Asp Cys Arg Lys Met Ala Lys Glu
4310 4315 4320

Tyr Gly Asp Tyr Phe Val Val Glu Tyr Arg Asp Gln Lys Pro Tyr
4325 4330 4335

Cys Ile Ser Pro Cys Glu Pro Gly Phe Ser Val Ser Lys Asn Cys
4340 4345 4350

Asn Leu Gly Lys Cys Gln Met Ser Leu Ser Gly Pro Gln Cys Leu
4355 4360 4365

Cys Val Thr Thr Glu Thr His Trp Tyr Ser Gly Glu Thr Cys Asn
4370 4375 4380

Gln Gly Thr Gln Lys Ser Leu Val Tyr Gly Leu Val Gly Ala Gly
4385 4390 4395

Val Val Leu Met Leu Ile Ile Leu Val Ala Leu Leu Met Leu Val

```
    4400                4405                4410

Phe Arg  Ser Lys Arg Glu Val  Lys Arg Gln Lys Tyr  Arg Leu Ser
    4415                4420                4425

Gln Leu  Tyr Lys Trp Gln Glu  Glu Asp Ser Gly Pro  Ala Pro Gly
    4430                4435                4440

Thr Phe  Gln Asn Ile Gly Phe  Asp Ile Cys Gln Asp  Asp Asp Ser
    4445                4450                4455

Ile His  Leu Glu Ser Ile Tyr  Ser Asn Phe Gln Pro  Ser Leu Arg
    4460                4465                4470

His Ile  Asp Pro Glu Thr Lys  Ile Arg Ile Gln Arg  Pro Gln Val
    4475                4480                4485

Met Thr  Thr Ser Phe
    4490

<210> SEQ ID NO 39
<211> LENGTH: 3633
<212> TYPE: DNA
<213> ORGANISM: Homo sapiens
<220> FEATURE:
<221> NAME/KEY: CDS
<222> LOCATION: (264)..(3395)

<400> SEQUENCE: 39

ctctcctggt ttgactggca cagggagcct gggctggaag aggcagcaaa agggaaaatc     60

agaagagtgg acactggcaa gaggagggca gcctttttcc cagcttcctt gcaccatgga    120

cagctcccat taagccacct ctccatcctg gggccaggac tcttatgccc cattcctgtc    180

aaattgagat ttcatccacc attctccaag gacagtgaag ttatacccta gttccagtgt    240

tgggatcagt ggcccctctg gac atg cct ctc ctg gaa ggt tct gtg ggg gtg    293
                          Met Pro Leu Leu Glu Gly Ser Val Gly Val
                          1               5                   10

gag gat ctt gtc ctc ctg gaa ccc ttg gtg gag gag tca ctg ctc aag      341
Glu Asp Leu Val Leu Leu Glu Pro Leu Val Glu Glu Ser Leu Leu Lys
                15                  20                  25

aat ctt cag ctt cgc tat gaa aac aag gag att tat acc tac att ggg      389
Asn Leu Gln Leu Arg Tyr Glu Asn Lys Glu Ile Tyr Thr Tyr Ile Gly
            30                  35                  40

aat gtg gtg atc tca gtg aat ccc tat caa cag ctt ccc atc tat ggg      437
Asn Val Val Ile Ser Val Asn Pro Tyr Gln Gln Leu Pro Ile Tyr Gly
        45                  50                  55

cca gag ttc att gcc aaa tat caa gac tat act ttc tat gag ctg aag      485
Pro Glu Phe Ile Ala Lys Tyr Gln Asp Tyr Thr Phe Tyr Glu Leu Lys
    60                  65                  70

ccc cat atc tac gca ttg gca aat gtg gcg tac cag tca ctg agg gac      533
Pro His Ile Tyr Ala Leu Ala Asn Val Ala Tyr Gln Ser Leu Arg Asp
75                  80                  85                  90

agg gac cga gac cag tgt atc ctc atc aca ggc gag agt gga tca ggg      581
Arg Asp Arg Asp Gln Cys Ile Leu Ile Thr Gly Glu Ser Gly Ser Gly
                95                  100                 105

aag act gag gcc agc aag ctg gtg atg tct tat gtg gct gcc gtc tgt      629
Lys Thr Glu Ala Ser Lys Leu Val Met Ser Tyr Val Ala Ala Val Cys
            110                 115                 120

ggg aaa gga gag cag gtg aac tct gtg aag gag cag ctg cta cag tct      677
Gly Lys Gly Glu Gln Val Asn Ser Val Lys Glu Gln Leu Leu Gln Ser
        125                 130                 135

aac cca gtg ctg gag gct ttt ggc aat gcc aag acc att cgc aac aac      725
Asn Pro Val Leu Glu Ala Phe Gly Asn Ala Lys Thr Ile Arg Asn Asn
    140                 145                 150
```

-continued

```
aat tcc tcc cga ttt gga aaa tac atg gat att gaa ttt gac ttc aag      773
Asn Ser Ser Arg Phe Gly Lys Tyr Met Asp Ile Glu Phe Asp Phe Lys
155                 160                 165                 170

gga tcc ccc ctc ggt ggt gtc atc aca aac tat ctg ctt gag aaa tcc      821
Gly Ser Pro Leu Gly Gly Val Ile Thr Asn Tyr Leu Leu Glu Lys Ser
                175                 180                 185

cga tta gtg aag cag ctc aaa gga gaa agg aac ttc cac atc ttc tat      869
Arg Leu Val Lys Gln Leu Lys Gly Glu Arg Asn Phe His Ile Phe Tyr
            190                 195                 200

cag ctg ctg gct gga gca gat gaa cag ctg ctg aag gcc ctg aag ctt      917
Gln Leu Leu Ala Gly Ala Asp Glu Gln Leu Leu Lys Ala Leu Lys Leu
        205                 210                 215

gag cgg gat aca act ggc tat gcc tat ctg aat cat gaa gta tcc aga      965
Glu Arg Asp Thr Thr Gly Tyr Ala Tyr Leu Asn His Glu Val Ser Arg
    220                 225                 230

gtg gat ggc atg gac gac gcc tcc agc ttc agg gct gta cag agt gca     1013
Val Asp Gly Met Asp Asp Ala Ser Ser Phe Arg Ala Val Gln Ser Ala
235                 240                 245                 250

atg gca gtg att ggg ttc tcg gag gag gag att cga caa gtg cta gag     1061
Met Ala Val Ile Gly Phe Ser Glu Glu Glu Ile Arg Gln Val Leu Glu
                255                 260                 265

gtg aca tcc atg gtg cta aag ctg ggg aac gtg ttg gtg gct gat gag     1109
Val Thr Ser Met Val Leu Lys Leu Gly Asn Val Leu Val Ala Asp Glu
            270                 275                 280

ttc cag gcc agt ggg ata cca gca agt ggc atc cgt gat ggg aga ggt     1157
Phe Gln Ala Ser Gly Ile Pro Ala Ser Gly Ile Arg Asp Gly Arg Gly
        285                 290                 295

gtt cgg gag att ggg gag atg gtg ggc ttg aat tca gaa gaa gta gag     1205
Val Arg Glu Ile Gly Glu Met Val Gly Leu Asn Ser Glu Glu Val Glu
    300                 305                 310

aga gct ttg tgc tcg agg acc atg gaa aca gcc aag gaa aag gtg gtc     1253
Arg Ala Leu Cys Ser Arg Thr Met Glu Thr Ala Lys Glu Lys Val Val
315                 320                 325                 330

act gca ctg aat gtt atg cag gct cag tat gct cgg gac gcc ctg gct     1301
Thr Ala Leu Asn Val Met Gln Ala Gln Tyr Ala Arg Asp Ala Leu Ala
                335                 340                 345

aag aac atc tac agc cgc ctc ttt gac tgg ata gtg aat cga atc aat     1349
Lys Asn Ile Tyr Ser Arg Leu Phe Asp Trp Ile Val Asn Arg Ile Asn
            350                 355                 360

gag agc atc aag gtg ggc atc ggg gaa aag aag aag gta atg gga gtc     1397
Glu Ser Ile Lys Val Gly Ile Gly Glu Lys Lys Lys Val Met Gly Val
        365                 370                 375

ctt gat atc tac ggt ttt gag ata tta gag gat aat agc ttt gag caa     1445
Leu Asp Ile Tyr Gly Phe Glu Ile Leu Glu Asp Asn Ser Phe Glu Gln
    380                 385                 390

ttt gtg atc aac tac tgc aat gag aag ctg cag cag gtg ttc ata gag     1493
Phe Val Ile Asn Tyr Cys Asn Glu Lys Leu Gln Gln Val Phe Ile Glu
395                 400                 405                 410

atg acc ctg aaa gaa gag caa gag gaa tat aag aga gaa ggc ata ccg     1541
Met Thr Leu Lys Glu Glu Gln Glu Glu Tyr Lys Arg Glu Gly Ile Pro
                415                 420                 425

tgg aca aag gtg gac tac ttt gat aat ggc atc att tgt aag ctc att     1589
Trp Thr Lys Val Asp Tyr Phe Asp Asn Gly Ile Ile Cys Lys Leu Ile
            430                 435                 440

gag cat aat cag cga ggt atc ctg gcc atg ttg gat gag gag tgc ctg     1637
Glu His Asn Gln Arg Gly Ile Leu Ala Met Leu Asp Glu Glu Cys Leu
        445                 450                 455

cgg cct ggg gtg gtc agt gac tcc act ttc cta gca aag ctg aac cag     1685
Arg Pro Gly Val Val Ser Asp Ser Thr Phe Leu Ala Lys Leu Asn Gln
    460                 465                 470
```

```
ctc ttc tcc aag cat ggc cac tac gag agc aaa gtc acc cag aat gcc      1733
Leu Phe Ser Lys His Gly His Tyr Glu Ser Lys Val Thr Gln Asn Ala
475                 480                 485                 490

cag cgt cag tat gac cac acc atg ggc ctc agc tgc ttc cgc atc tgc      1781
Gln Arg Gln Tyr Asp His Thr Met Gly Leu Ser Cys Phe Arg Ile Cys
                495                 500                 505

cac tat gcg ggc aag gtg aca tac aac gtg acc agc ttt att gac aag      1829
His Tyr Ala Gly Lys Val Thr Tyr Asn Val Thr Ser Phe Ile Asp Lys
            510                 515                 520

aat aat gac cta ctc ttc cga gac ctg ttg cag gcc atg tgg aag gcc      1877
Asn Asn Asp Leu Leu Phe Arg Asp Leu Leu Gln Ala Met Trp Lys Ala
        525                 530                 535

cag cac ccc ctc ctt cgg tcc ttg ttt cct gag ggc aat cct aag cag      1925
Gln His Pro Leu Leu Arg Ser Leu Phe Pro Glu Gly Asn Pro Lys Gln
    540                 545                 550

gca tct ctc aaa cgc ccc ccg act gct ggg gcc cag ttc aag agt tct      1973
Ala Ser Leu Lys Arg Pro Pro Thr Ala Gly Ala Gln Phe Lys Ser Ser
555                 560                 565                 570

gtg gcc atc ctc atg aag aat ctg tat tcc aag agc ccc aac tac atc      2021
Val Ala Ile Leu Met Lys Asn Leu Tyr Ser Lys Ser Pro Asn Tyr Ile
                575                 580                 585

agg tgc ata aag ccc aat gag cat cag cag cga ggt cag ttc tct tca      2069
Arg Cys Ile Lys Pro Asn Glu His Gln Gln Arg Gly Gln Phe Ser Ser
            590                 595                 600

gac ctg gtg gca acc cag gct cgg tac ctg gga ctg ctg gag aac gta      2117
Asp Leu Val Ala Thr Gln Ala Arg Tyr Leu Gly Leu Leu Glu Asn Val
        605                 610                 615

cgg gtg cga cgg gca ggc tat gcc cac cgc cag ggt tat ggg ccc ttc      2165
Arg Val Arg Arg Ala Gly Tyr Ala His Arg Gln Gly Tyr Gly Pro Phe
    620                 625                 630

ctg gaa agg tac cga ttg ctg agc cgg agc acc tgg cct cac tgg aat      2213
Leu Glu Arg Tyr Arg Leu Leu Ser Arg Ser Thr Trp Pro His Trp Asn
635                 640                 645                 650

ggg gga gac cgg gaa ggt gtt gag aag gtc ctg ggg gag ctg agc atg      2261
Gly Gly Asp Arg Glu Gly Val Glu Lys Val Leu Gly Glu Leu Ser Met
                655                 660                 665

tcc tcg ggg gag ctg gcc ttt ggc aag aca aag atc ttc att aga agc      2309
Ser Ser Gly Glu Leu Ala Phe Gly Lys Thr Lys Ile Phe Ile Arg Ser
            670                 675                 680

ccc aag act ctt ttc tac ctc gaa gaa cag agg cgc ctg aga ctc cag      2357
Pro Lys Thr Leu Phe Tyr Leu Glu Glu Gln Arg Arg Leu Arg Leu Gln
        685                 690                 695

cag ctg gcc aca ctc ata cag aag att tac cga ggc tgg cgc tgc cgc      2405
Gln Leu Ala Thr Leu Ile Gln Lys Ile Tyr Arg Gly Trp Arg Cys Arg
    700                 705                 710

acc cac tac caa ctg atg cga aag agt cag atc ctc atc tcc tct tgg      2453
Thr His Tyr Gln Leu Met Arg Lys Ser Gln Ile Leu Ile Ser Ser Trp
715                 720                 725                 730

ttt cgg gga aac atg caa aag aaa tgc tat ggg aag ata aag gca tcc      2501
Phe Arg Gly Asn Met Gln Lys Lys Cys Tyr Gly Lys Ile Lys Ala Ser
                735                 740                 745

gtg tta ttg atc cag gct ttt gtg aga ggg tgg aag gcc cga aag aat      2549
Val Leu Leu Ile Gln Ala Phe Val Arg Gly Trp Lys Ala Arg Lys Asn
            750                 755                 760

tat cgc aaa tat ttc cgg tca gag gct gcc ctc acc ttg gca gat ttc      2597
Tyr Arg Lys Tyr Phe Arg Ser Glu Ala Ala Leu Thr Leu Ala Asp Phe
        765                 770                 775

atc tac aag agc atg gta cag aaa ttc cta ctg ggg ctg aag aac aat      2645
Ile Tyr Lys Ser Met Val Gln Lys Phe Leu Leu Gly Leu Lys Asn Asn
```

```
    780                 785                 790

ttg cca tcc aca aac gtc tta gac aag aca tgg cca gcc gcc ccc tac     2693
Leu Pro Ser Thr Asn Val Leu Asp Lys Thr Trp Pro Ala Ala Pro Tyr
795                 800                 805                 810

aag tgc ctc agc aca gca aat cag gag ctg cag cag ctc ttc tac cag     2741
Lys Cys Leu Ser Thr Ala Asn Gln Glu Leu Gln Gln Leu Phe Tyr Gln
                815                 820                 825

tgg aag tgc aag agg ttc cgg gat cag ctg tcc ccg aag cag gta gag     2789
Trp Lys Cys Lys Arg Phe Arg Asp Gln Leu Ser Pro Lys Gln Val Glu
            830                 835                 840

atc ctg agg gaa aag ctc tgt gcc agt gaa ctg ttc aag ggc aag aag     2837
Ile Leu Arg Glu Lys Leu Cys Ala Ser Glu Leu Phe Lys Gly Lys Lys
        845                 850                 855

gct tca tat ccc cag agt gtc ccc att cca ttc tgt ggt gac tac att     2885
Ala Ser Tyr Pro Gln Ser Val Pro Ile Pro Phe Cys Gly Asp Tyr Ile
    860                 865                 870

ggg ctg caa ggg aac ccc aag ctg cag aag ctg aaa ggc ggg gag gag     2933
Gly Leu Gln Gly Asn Pro Lys Leu Gln Lys Leu Lys Gly Gly Glu Glu
875                 880                 885                 890

ggg cct gtt ctg atg gca gag gcc gtg aag aag gtc aat cgt ggc aat     2981
Gly Pro Val Leu Met Ala Glu Ala Val Lys Lys Val Asn Arg Gly Asn
                895                 900                 905

ggc aag act tct tct cgg att ctc ctc ctg acc aag ggc cat gtg att     3029
Gly Lys Thr Ser Ser Arg Ile Leu Leu Leu Thr Lys Gly His Val Ile
            910                 915                 920

ctc aca gac acc aag aag tcc cag gcc aaa att gtc att ggg cta gac     3077
Leu Thr Asp Thr Lys Lys Ser Gln Ala Lys Ile Val Ile Gly Leu Asp
        925                 930                 935

aat gtg gct ggg gtg tca gtc acc agc ctc aag gat ggg ctc ttt agc     3125
Asn Val Ala Gly Val Ser Val Thr Ser Leu Lys Asp Gly Leu Phe Ser
    940                 945                 950

ttg cat ctg agt gag atg tca tcg gtg ggc tcc aag ggg gac ttc ctg     3173
Leu His Leu Ser Glu Met Ser Ser Val Gly Ser Lys Gly Asp Phe Leu
955                 960                 965                 970

ctg gtc agc gag cat gtg att gaa ctg ctg acc aaa atg tac cgg gct     3221
Leu Val Ser Glu His Val Ile Glu Leu Leu Thr Lys Met Tyr Arg Ala
                975                 980                 985

gtg ctg gat gcc acg cag agg cag ctt aca gtc acc gtg act  gag aag     3269
Val Leu Asp Ala Thr Gln Arg Gln Leu Thr Val Thr Val Thr  Glu Lys
            990                 995                 1000

ttc tca gtg  agg ttc aag gag aac  agt gtg gct gtc aag  gtc gtc     3314
Phe Ser Val  Arg Phe Lys Glu Asn  Ser Val Ala Val Lys  Val Val
        1005                 1010                 1015

cag ggc cct  gca ggt ggt gac aac  agc aag cta cgc tac  aaa aaa     3359
Gln Gly Pro  Ala Gly Gly Asp Asn  Ser Lys Leu Arg Tyr  Lys Lys
        1020                 1025                 1030

aag ggg agt  cat tgc ttg gag gtg  act gtg cag tga ggagggggca       3405
Lys Gly Ser  His Cys Leu Glu Val  Thr Val Gln
        1035                 1040

ccatgcagag atggcagttg cttcctcctg aaccagcact aatccccctc tgccctcctg   3465

tgtgggagga tctctaaccc ctctgatcgt ggcgcatggc ttggggatta aactaccctt   3525

gaagaggacc cttgtcccaa acccttcttg ttctctcctc caaaagtagc ttcctccaac   3585

ccgcagcctc tctgcacact aataaaacat gtggcttgga aaggttca                3633
```

<210> SEQ ID NO 40
<211> LENGTH: 1043
<212> TYPE: PRT
<213> ORGANISM: Homo sapiens

<400> SEQUENCE: 40

```
Met Pro Leu Leu Glu Gly Ser Val Gly Val Glu Asp Leu Val Leu Leu
1               5                   10                  15

Glu Pro Leu Val Glu Glu Ser Leu Leu Lys Asn Leu Gln Leu Arg Tyr
            20                  25                  30

Glu Asn Lys Glu Ile Tyr Thr Tyr Ile Gly Asn Val Val Ile Ser Val
        35                  40                  45

Asn Pro Tyr Gln Gln Leu Pro Ile Tyr Gly Pro Glu Phe Ile Ala Lys
    50                  55                  60

Tyr Gln Asp Tyr Thr Phe Tyr Glu Leu Lys Pro His Ile Tyr Ala Leu
65                  70                  75                  80

Ala Asn Val Ala Tyr Gln Ser Leu Arg Asp Arg Asp Arg Asp Gln Cys
                85                  90                  95

Ile Leu Ile Thr Gly Glu Ser Gly Ser Gly Lys Thr Glu Ala Ser Lys
            100                 105                 110

Leu Val Met Ser Tyr Val Ala Ala Val Cys Gly Lys Gly Glu Gln Val
        115                 120                 125

Asn Ser Val Lys Glu Gln Leu Leu Gln Ser Asn Pro Val Leu Glu Ala
    130                 135                 140

Phe Gly Asn Ala Lys Thr Ile Arg Asn Asn Asn Ser Ser Arg Phe Gly
145                 150                 155                 160

Lys Tyr Met Asp Ile Glu Phe Asp Phe Lys Gly Ser Pro Leu Gly Gly
                165                 170                 175

Val Ile Thr Asn Tyr Leu Leu Glu Lys Ser Arg Leu Val Lys Gln Leu
            180                 185                 190

Lys Gly Glu Arg Asn Phe His Ile Phe Tyr Gln Leu Leu Ala Gly Ala
        195                 200                 205

Asp Glu Gln Leu Leu Lys Ala Leu Lys Leu Glu Arg Asp Thr Thr Gly
    210                 215                 220

Tyr Ala Tyr Leu Asn His Glu Val Ser Arg Val Asp Gly Met Asp Asp
225                 230                 235                 240

Ala Ser Ser Phe Arg Ala Val Gln Ser Ala Met Ala Val Ile Gly Phe
                245                 250                 255

Ser Glu Glu Glu Ile Arg Gln Val Leu Glu Val Thr Ser Met Val Leu
            260                 265                 270

Lys Leu Gly Asn Val Leu Val Ala Asp Glu Phe Gln Ala Ser Gly Ile
        275                 280                 285

Pro Ala Ser Gly Ile Arg Asp Gly Arg Gly Val Arg Glu Ile Gly Glu
    290                 295                 300

Met Val Gly Leu Asn Ser Glu Glu Val Glu Arg Ala Leu Cys Ser Arg
305                 310                 315                 320

Thr Met Glu Thr Ala Lys Glu Lys Val Val Thr Ala Leu Asn Val Met
                325                 330                 335

Gln Ala Gln Tyr Ala Arg Asp Ala Leu Ala Lys Asn Ile Tyr Ser Arg
            340                 345                 350

Leu Phe Asp Trp Ile Val Asn Arg Ile Asn Glu Ser Ile Lys Val Gly
        355                 360                 365

Ile Gly Glu Lys Lys Lys Val Met Gly Val Leu Asp Ile Tyr Gly Phe
    370                 375                 380

Glu Ile Leu Glu Asp Asn Ser Phe Glu Gln Phe Val Ile Asn Tyr Cys
385                 390                 395                 400

Asn Glu Lys Leu Gln Gln Val Phe Ile Glu Met Thr Leu Lys Glu Glu
```

-continued

```
                405                 410                 415

Gln Glu Glu Tyr Lys Arg Glu Gly Ile Pro Trp Thr Lys Val Asp Tyr
            420                 425                 430

Phe Asp Asn Gly Ile Ile Cys Lys Leu Ile Glu His Asn Gln Arg Gly
        435                 440                 445

Ile Leu Ala Met Leu Asp Glu Glu Cys Leu Arg Pro Gly Val Val Ser
    450                 455                 460

Asp Ser Thr Phe Leu Ala Lys Leu Asn Gln Leu Phe Ser Lys His Gly
465                 470                 475                 480

His Tyr Glu Ser Lys Val Thr Gln Asn Ala Gln Arg Gln Tyr Asp His
                485                 490                 495

Thr Met Gly Leu Ser Cys Phe Arg Ile Cys His Tyr Ala Gly Lys Val
            500                 505                 510

Thr Tyr Asn Val Thr Ser Phe Ile Asp Lys Asn Asn Asp Leu Leu Phe
        515                 520                 525

Arg Asp Leu Leu Gln Ala Met Trp Lys Ala Gln His Pro Leu Leu Arg
    530                 535                 540

Ser Leu Phe Pro Glu Gly Asn Pro Lys Gln Ala Ser Leu Lys Arg Pro
545                 550                 555                 560

Pro Thr Ala Gly Ala Gln Phe Lys Ser Ser Val Ala Ile Leu Met Lys
                565                 570                 575

Asn Leu Tyr Ser Lys Ser Pro Asn Tyr Ile Arg Cys Ile Lys Pro Asn
            580                 585                 590

Glu His Gln Gln Arg Gly Gln Phe Ser Ser Asp Leu Val Ala Thr Gln
        595                 600                 605

Ala Arg Tyr Leu Gly Leu Leu Glu Asn Val Arg Val Arg Arg Ala Gly
    610                 615                 620

Tyr Ala His Arg Gln Gly Tyr Gly Pro Phe Leu Glu Arg Tyr Arg Leu
625                 630                 635                 640

Leu Ser Arg Ser Thr Trp Pro His Trp Asn Gly Gly Asp Arg Glu Gly
                645                 650                 655

Val Glu Lys Val Leu Gly Glu Leu Ser Met Ser Ser Gly Glu Leu Ala
            660                 665                 670

Phe Gly Lys Thr Lys Ile Phe Ile Arg Ser Pro Lys Thr Leu Phe Tyr
        675                 680                 685

Leu Glu Glu Gln Arg Arg Leu Arg Leu Gln Gln Leu Ala Thr Leu Ile
    690                 695                 700

Gln Lys Ile Tyr Arg Gly Trp Arg Cys Arg Thr His Tyr Gln Leu Met
705                 710                 715                 720

Arg Lys Ser Gln Ile Leu Ile Ser Ser Trp Phe Arg Gly Asn Met Gln
                725                 730                 735

Lys Lys Cys Tyr Gly Lys Ile Lys Ala Ser Val Leu Leu Ile Gln Ala
            740                 745                 750

Phe Val Arg Gly Trp Lys Ala Arg Lys Asn Tyr Arg Lys Tyr Phe Arg
        755                 760                 765

Ser Glu Ala Ala Leu Thr Leu Ala Asp Phe Ile Tyr Lys Ser Met Val
    770                 775                 780

Gln Lys Phe Leu Leu Gly Leu Lys Asn Asn Leu Pro Ser Thr Asn Val
785                 790                 795                 800

Leu Asp Lys Thr Trp Pro Ala Ala Pro Tyr Lys Cys Leu Ser Thr Ala
                805                 810                 815

Asn Gln Glu Leu Gln Gln Leu Phe Tyr Gln Trp Lys Cys Lys Arg Phe
            820                 825                 830
```

```
Arg Asp Gln Leu Ser Pro Lys Gln Val Glu Ile Leu Arg Glu Lys Leu
        835                 840                 845

Cys Ala Ser Glu Leu Phe Lys Gly Lys Lys Ala Ser Tyr Pro Gln Ser
    850                 855                 860

Val Pro Ile Pro Phe Cys Gly Asp Tyr Ile Gly Leu Gln Gly Asn Pro
865                 870                 875                 880

Lys Leu Gln Lys Leu Lys Gly Gly Glu Glu Gly Pro Val Leu Met Ala
                885                 890                 895

Glu Ala Val Lys Lys Val Asn Arg Gly Asn Gly Lys Thr Ser Ser Arg
            900                 905                 910

Ile Leu Leu Leu Thr Lys Gly His Val Ile Leu Thr Asp Thr Lys Lys
        915                 920                 925

Ser Gln Ala Lys Ile Val Ile Gly Leu Asp Asn Val Ala Gly Val Ser
    930                 935                 940

Val Thr Ser Leu Lys Asp Gly Leu Phe Ser Leu His Leu Ser Glu Met
945                 950                 955                 960

Ser Ser Val Gly Ser Lys Gly Asp Phe Leu Leu Val Ser Glu His Val
                965                 970                 975

Ile Glu Leu Leu Thr Lys Met Tyr Arg Ala Val Leu Asp Ala Thr Gln
            980                 985                 990

Arg Gln Leu Thr Val Thr Val Thr  Glu Lys Phe Ser Val  Arg Phe Lys
        995                 1000                1005

Glu Asn  Ser Val Ala Val Lys  Val Val Gln Gly Pro  Ala Gly Gly
    1010                1015                1020

Asp Asn  Ser Lys Leu Arg Tyr  Lys Lys Lys Gly Ser  His Cys Leu
    1025                1030                1035

Glu Val  Thr Val Gln
    1040


<210> SEQ ID NO 41
<211> LENGTH: 2772
<212> TYPE: DNA
<213> ORGANISM: Homo sapiens
<220> FEATURE:
<221> NAME/KEY: CDS
<222> LOCATION: (49)..(1470)

<400> SEQUENCE: 41

ggcctgctgg gttagtgctg gcagccccct gaggccaagg acagcagc atg aca gtc      57
                                                     Met Thr Val
                                                     1

acc agg act cac cac ttc aag gag ggg tcc ctc aga gca cct gcc ata      105
Thr Arg Thr His His Phe Lys Glu Gly Ser Leu Arg Ala Pro Ala Ile
    5                   10                  15

ccc ctg cac agt gct gcg gct gag ttg gct tca aac cat cca aga ggc      153
Pro Leu His Ser Ala Ala Ala Glu Leu Ala Ser Asn His Pro Arg Gly
20                  25                  30                  35

cca gaa gca aac ctg gag gtg aga ccc aaa gaa agc tgg aac cat gct      201
Pro Glu Ala Asn Leu Glu Val Arg Pro Lys Glu Ser Trp Asn His Ala
                40                  45                  50

gac ttt gta cac tgt gag gac aca gag tct gtt cct gga aag ccc agt      249
Asp Phe Val His Cys Glu Asp Thr Glu Ser Val Pro Gly Lys Pro Ser
            55                  60                  65

gtc aac gca gat gag gaa gtc gga ggt ccc caa atc tgc cgt gta tgt      297
Val Asn Ala Asp Glu Glu Val Gly Gly Pro Gln Ile Cys Arg Val Cys
        70                  75                  80

ggg gac aag gcc act ggc tat cac ttc aat gtc atg aca tgt gaa gga      345
```

```
Gly Asp Lys Ala Thr Gly Tyr His Phe Asn Val Met Thr Cys Glu Gly
    85                  90                  95

tgc aag ggc ttt ttc agg agg gcc atg aaa cgc aac gcc cgg ctg agg      393
Cys Lys Gly Phe Phe Arg Arg Ala Met Lys Arg Asn Ala Arg Leu Arg
100                 105                 110                 115

tgc ccc ttc cgg aag ggc gcc tgc gag atc acc cgg aag acc cgg cga      441
Cys Pro Phe Arg Lys Gly Ala Cys Glu Ile Thr Arg Lys Thr Arg Arg
                120                 125                 130

cag tgc cag gcc tgc cgc ctg cgc aag tgc ctg gag agc ggc atg aag      489
Gln Cys Gln Ala Cys Arg Leu Arg Lys Cys Leu Glu Ser Gly Met Lys
            135                 140                 145

aag gag atg atc atg tcc gac gag gcc gtg gag gag agg cgg gcc ttg      537
Lys Glu Met Ile Met Ser Asp Glu Ala Val Glu Glu Arg Arg Ala Leu
        150                 155                 160

atc aag cgg aag aaa agt gaa cgg aca ggg act cag cca ctg gga gtg      585
Ile Lys Arg Lys Lys Ser Glu Arg Thr Gly Thr Gln Pro Leu Gly Val
    165                 170                 175

cag ggg ctg aca gag gag cag cgg atg atg atc agg gag ctg atg gac      633
Gln Gly Leu Thr Glu Glu Gln Arg Met Met Ile Arg Glu Leu Met Asp
180                 185                 190                 195

gct cag atg aaa acc ttt gac act acc ttc tcc cat ttc aag aat ttc      681
Ala Gln Met Lys Thr Phe Asp Thr Thr Phe Ser His Phe Lys Asn Phe
                200                 205                 210

cgg ctg cca ggg gtg ctt agc agt ggc tgc gag ttg cca gag tct ctg      729
Arg Leu Pro Gly Val Leu Ser Ser Gly Cys Glu Leu Pro Glu Ser Leu
            215                 220                 225

cag gcc cca tcg agg gaa gaa gct gcc aag tgg agc cag gtc cgg aaa      777
Gln Ala Pro Ser Arg Glu Glu Ala Ala Lys Trp Ser Gln Val Arg Lys
        230                 235                 240

gat ctg tgc tct ttg aag gtc tct ctg cag ctg cgg ggg gag gat ggc      825
Asp Leu Cys Ser Leu Lys Val Ser Leu Gln Leu Arg Gly Glu Asp Gly
    245                 250                 255

agt gtc tgg aac tac aaa ccc cca gcc gac agt ggc ggg aaa gag atc      873
Ser Val Trp Asn Tyr Lys Pro Pro Ala Asp Ser Gly Gly Lys Glu Ile
260                 265                 270                 275

ttc tcc ctg ctg ccc cac atg gct gac atg tca acc tac atg ttc aaa      921
Phe Ser Leu Leu Pro His Met Ala Asp Met Ser Thr Tyr Met Phe Lys
                280                 285                 290

ggc atc atc agc ttt gcc aaa gtc atc tcc tac ttc agg gac ttg ccc      969
Gly Ile Ile Ser Phe Ala Lys Val Ile Ser Tyr Phe Arg Asp Leu Pro
            295                 300                 305

atc gag gac cag atc tcc ctg ctg aag ggg gcc gct ttc gag ctg tgt     1017
Ile Glu Asp Gln Ile Ser Leu Leu Lys Gly Ala Ala Phe Glu Leu Cys
        310                 315                 320

caa ctg aga ttc aac aca gtg ttc aac gcg gag act gga acc tgg gag     1065
Gln Leu Arg Phe Asn Thr Val Phe Asn Ala Glu Thr Gly Thr Trp Glu
    325                 330                 335

tgt ggc cgg ctg tcc tac tgc ttg gaa gac act gca ggt ggc ttc cag     1113
Cys Gly Arg Leu Ser Tyr Cys Leu Glu Asp Thr Ala Gly Gly Phe Gln
340                 345                 350                 355

caa ctt cta ctg gag ccc atg ctg aaa ttc cac tac atg ctg aag aag     1161
Gln Leu Leu Leu Glu Pro Met Leu Lys Phe His Tyr Met Leu Lys Lys
                360                 365                 370

ctg cag ctg cat gag gag gag tat gtg ctg atg cag gcc atc tcc ctc     1209
Leu Gln Leu His Glu Glu Glu Tyr Val Leu Met Gln Ala Ile Ser Leu
            375                 380                 385

ttc tcc cca gac cgc cca ggt gtg ctg cag cac cgc gtg gtg gac cag     1257
Phe Ser Pro Asp Arg Pro Gly Val Leu Gln His Arg Val Val Asp Gln
        390                 395                 400
```

-continued

```
ctg cag gag caa ttc gcc att act ctg aag tcc tac att gaa tgc aat     1305
Leu Gln Glu Gln Phe Ala Ile Thr Leu Lys Ser Tyr Ile Glu Cys Asn
    405                 410                 415

cgg ccc cag cct gct cat agg ttc ttg ttc ctg aag atc atg gct atg     1353
Arg Pro Gln Pro Ala His Arg Phe Leu Phe Leu Lys Ile Met Ala Met
420                 425                 430                 435

ctc acc gag ctc cgc agc atc aat gct cag cac acc cag cgg ctg ctg     1401
Leu Thr Glu Leu Arg Ser Ile Asn Ala Gln His Thr Gln Arg Leu Leu
                440                 445                 450

cgc atc cag gac ata cac ccc ttt gct acg ccc ctc atg cag gag ttg     1449
Arg Ile Gln Asp Ile His Pro Phe Ala Thr Pro Leu Met Gln Glu Leu
            455                 460                 465

ttc ggc atc aca ggt agc tga gcggctgccc ttgggtgaca cctccgagag       1500
Phe Gly Ile Thr Gly Ser
        470

gcagccagac ccagagccct ctgagccgcc actcccgggc caagacagat ggacactgcc   1560

aagagccgac aatgccctgc tggcctgtct ccctagggaa ttcctgctat gacagctggc   1620

tagcattcct caggaaggac atgggtgccc cccaccccca gttcagtctg tagggagtga   1680

agccacagac tcttacgtgg agagtgcact gacctgtagg tcaggaccat cagagaggca   1740

aggttgccct ttcctttaa aaggccctgt ggtctgggga gaaatccctc agatcccact   1800

aaagtgtcaa ggtgtggaag ggaccaagcg accaaggatg ggccatctgg ggtctatgcc   1860

cacataccca cgtttgttcg cttcctgagt cttttcattg ctacctctaa tagtcctgtc   1920

tcccacttcc cactcgttcc cctcctcttc cgagctgctt tgtgggctcc aggcctgtac   1980

tcatcggcag gcgcatgagt atctgtggga gtcctctaga gagatgagaa gccaggaggc   2040

ctgcaccaaa tgtcagaagc ttggcatgac ctcattccgg ccacatcatt ctgtgtctct   2100

gcatccattt gaacacatta ttaagcaccg ataataggta gcctgctgtg gggtatacag   2160

cattgactca gatatagatc ctgagctcac agagtttata gttaaaaaaa caaacagaaa   2220

cacaaacaat ttggatcaaa aggagaaatg ataagtgaca aaagcagcac aaggaatttc   2280

cctgtgtgga tgctgagctg tgatggcggg cactgggtac ccaagtgaag gttcccgagg   2340

acatgagtct gtaggagcaa gggcacaaac tgcagctgtg agtgcgtgtg tgtgatttgg   2400

tgtaggtagg tctgtttgcc acttgatggg gcctgggttt gttcctgggg ctggaatgct   2460

gggtatgctc tgtgacaagg ctacgctgac aatcagttaa acacaccgga gaagaaccat   2520

ttacatgcac cttatatttc tgtgtacaca tctattctca aagctaaagg gtatgaaagt   2580

gcctgccttg tttatagcca cttgtgagta aaaatttttt tgcattttca caaattatac   2640

tttatataag gcattccaca cctaagaact agttttggga aatgtagccc tgggtttaat   2700

gtcaaatcaa ggcaaaagga attaaataat gtacttttgg ctaaaaaaaa aaaaaaaaaa   2760

aaaaaaaaaa aa                                                       2772
```

<210> SEQ ID NO 42
<211> LENGTH: 473
<212> TYPE: PRT
<213> ORGANISM: Homo sapiens

<400> SEQUENCE: 42

```
Met Thr Val Thr Arg Thr His His Phe Lys Glu Gly Ser Leu Arg Ala
1               5                   10                  15

Pro Ala Ile Pro Leu His Ser Ala Ala Ala Glu Leu Ala Ser Asn His
            20                  25                  30

Pro Arg Gly Pro Glu Ala Asn Leu Glu Val Arg Pro Lys Glu Ser Trp
```

-continued

```
        35                  40                  45

Asn His Ala Asp Phe Val His Cys Glu Asp Thr Glu Ser Val Pro Gly
    50                  55                  60

Lys Pro Ser Val Asn Ala Asp Glu Glu Val Gly Gly Pro Gln Ile Cys
65                  70                  75                  80

Arg Val Cys Gly Asp Lys Ala Thr Gly Tyr His Phe Asn Val Met Thr
                85                  90                  95

Cys Glu Gly Cys Lys Gly Phe Phe Arg Arg Ala Met Lys Arg Asn Ala
            100                 105                 110

Arg Leu Arg Cys Pro Phe Arg Lys Gly Ala Cys Glu Ile Thr Arg Lys
        115                 120                 125

Thr Arg Arg Gln Cys Gln Ala Cys Arg Leu Arg Lys Cys Leu Glu Ser
    130                 135                 140

Gly Met Lys Lys Glu Met Ile Met Ser Asp Glu Ala Val Glu Glu Arg
145                 150                 155                 160

Arg Ala Leu Ile Lys Arg Lys Lys Ser Glu Arg Thr Gly Thr Gln Pro
                165                 170                 175

Leu Gly Val Gln Gly Leu Thr Glu Glu Gln Arg Met Met Ile Arg Glu
            180                 185                 190

Leu Met Asp Ala Gln Met Lys Thr Phe Asp Thr Thr Phe Ser His Phe
        195                 200                 205

Lys Asn Phe Arg Leu Pro Gly Val Leu Ser Ser Gly Cys Glu Leu Pro
    210                 215                 220

Glu Ser Leu Gln Ala Pro Ser Arg Glu Glu Ala Ala Lys Trp Ser Gln
225                 230                 235                 240

Val Arg Lys Asp Leu Cys Ser Leu Lys Val Ser Leu Gln Leu Arg Gly
                245                 250                 255

Glu Asp Gly Ser Val Trp Asn Tyr Lys Pro Pro Ala Asp Ser Gly Gly
            260                 265                 270

Lys Glu Ile Phe Ser Leu Leu Pro His Met Ala Asp Met Ser Thr Tyr
        275                 280                 285

Met Phe Lys Gly Ile Ile Ser Phe Ala Lys Val Ile Ser Tyr Phe Arg
    290                 295                 300

Asp Leu Pro Ile Glu Asp Gln Ile Ser Leu Leu Lys Gly Ala Ala Phe
305                 310                 315                 320

Glu Leu Cys Gln Leu Arg Phe Asn Thr Val Phe Asn Ala Glu Thr Gly
                325                 330                 335

Thr Trp Glu Cys Gly Arg Leu Ser Tyr Cys Leu Glu Asp Thr Ala Gly
            340                 345                 350

Gly Phe Gln Gln Leu Leu Leu Glu Pro Met Leu Lys Phe His Tyr Met
        355                 360                 365

Leu Lys Lys Leu Gln Leu His Glu Glu Glu Tyr Val Leu Met Gln Ala
    370                 375                 380

Ile Ser Leu Phe Ser Pro Asp Arg Pro Gly Val Leu Gln His Arg Val
385                 390                 395                 400

Val Asp Gln Leu Gln Glu Gln Phe Ala Ile Thr Leu Lys Ser Tyr Ile
                405                 410                 415

Glu Cys Asn Arg Pro Gln Pro Ala His Arg Phe Leu Phe Leu Lys Ile
            420                 425                 430

Met Ala Met Leu Thr Glu Leu Arg Ser Ile Asn Ala Gln His Thr Gln
        435                 440                 445

Arg Leu Leu Arg Ile Gln Asp Ile His Pro Phe Ala Thr Pro Leu Met
    450                 455                 460
```

```
Gln Glu Leu Phe Gly Ile Thr Gly Ser
465                 470


<210> SEQ ID NO 43
<211> LENGTH: 3115
<212> TYPE: DNA
<213> ORGANISM: Homo sapiens
<220> FEATURE:
<221> NAME/KEY: CDS
<222> LOCATION: (766)..(2388)

<400> SEQUENCE: 43

ctctctgcgc ctcgctccga ctccggcgcg caccaagcgg gaacccgcgc ccgagcccgg      60

cgggcgccgc tgctgctcct ctcggtcccc ggttcccggt ccccgaacgc gccgcggcga     120

ggctgcgccc ggcagtggag ccgctcggag ctgctgggct ttggcggccg ctcgctgctc     180

cgtctggccg gaggaccggc ggggaaggaa ggggaaagcg gggacacaca cactcgccgc     240

ggcgcgcgcg cactgcacac tcgtagccgc gcgcccccgc caaggcgcgt ccggagcgag     300

tttggccccg cggctccagc cccggcacct gcccgccctc agcgttgccc ccggccccgg     360

ccccgcccgc cgccccctcc gccctcccgc ccctcccgcc cctcccgccc ctcgcctgca     420

ctgctctccc ttcgctgtgg ggaagcgaca acgtcccgat aacttgcaga ctgtggcgca     480

actggtcttg gtagcggagg cacccgaatg ctgcccgggt gagatgagga agccaaggcc     540

cagcagagct gagatgtgac tgcagagccg tccaacccca gtcctgtgac ctttctctgg     600

tgcctgatac ctctcagcat ttgagggcct tttctcttcc tgcttcatct ctaaaggtcc     660

ttctaggaga gaggtgaaag aaacctggca aagaaaacgg tctcgacaat gagtaggcca     720

cccatcacta ctaactacag atgacttgcc atttcattta caaag atg tct tct gct     777
                                                  Met Ser Ser Ala
                                                  1

gct gaa aat gga gag gca gca cct gga aaa caa aat gaa gaa aaa acc       825
Ala Glu Asn Gly Glu Ala Ala Pro Gly Lys Gln Asn Glu Glu Lys Thr
5                   10                  15                  20

tat aaa aag act gca tca tct gct att aaa ggt gct att cag ctg gga       873
Tyr Lys Lys Thr Ala Ser Ser Ala Ile Lys Gly Ala Ile Gln Leu Gly
                25                  30                  35

ata gga tac aca gtg ggt aat ctc act tcc aag cca gaa cga gat gtt       921
Ile Gly Tyr Thr Val Gly Asn Leu Thr Ser Lys Pro Glu Arg Asp Val
            40                  45                  50

ctt atg caa gac ttt tat gtg gtg gaa agt gtg ttc cta ccc agc gaa       969
Leu Met Gln Asp Phe Tyr Val Val Glu Ser Val Phe Leu Pro Ser Glu
        55                  60                  65

ggg agc aat ctg acc cca gca cat cac tac cca gac ttt aga ttt aag      1017
Gly Ser Asn Leu Thr Pro Ala His His Tyr Pro Asp Phe Arg Phe Lys
    70                  75                  80

aca tac gct cca tta gca ttc cga tat ttc aga gaa ctt ttt ggt atc      1065
Thr Tyr Ala Pro Leu Ala Phe Arg Tyr Phe Arg Glu Leu Phe Gly Ile
85                  90                  95                  100

aag cct gat gat tac ttg tat tcc atc tgc agt gaa cct cta ata gaa      1113
Lys Pro Asp Asp Tyr Leu Tyr Ser Ile Cys Ser Glu Pro Leu Ile Glu
                105                 110                 115

ctg tct aac cct gga gcc agt gga tcc ttg ttt ttt gtg acc agt gat      1161
Leu Ser Asn Pro Gly Ala Ser Gly Ser Leu Phe Phe Val Thr Ser Asp
            120                 125                 130

gat gaa ttt atc atc aaa aca gtt cag cac aaa gaa gct gag ttt ctt      1209
Asp Glu Phe Ile Ile Lys Thr Val Gln His Lys Glu Ala Glu Phe Leu
        135                 140                 145
```

-continued

```
cag aag cta ctg cca ggc tat tac atg aat tta aac cag aat cca agg      1257
Gln Lys Leu Leu Pro Gly Tyr Tyr Met Asn Leu Asn Gln Asn Pro Arg
    150                 155                 160

act ctt ttg cca aaa ttt tac gga ctg tat tgt atg caa tca gga ggc      1305
Thr Leu Leu Pro Lys Phe Tyr Gly Leu Tyr Cys Met Gln Ser Gly Gly
165                 170                 175                 180

att aat atc agg att gtg gtg atg aac aac gtt ttg cca cgc tcc atg      1353
Ile Asn Ile Arg Ile Val Val Met Asn Asn Val Leu Pro Arg Ser Met
                185                 190                 195

aga atg cac ttt aca tat gac ttg aaa ggc tca acg tat aag cga aga      1401
Arg Met His Phe Thr Tyr Asp Leu Lys Gly Ser Thr Tyr Lys Arg Arg
            200                 205                 210

gca tcc cgt aaa gag aga gag aaa tcc aac ccc aca ttt aag gac tta      1449
Ala Ser Arg Lys Glu Arg Glu Lys Ser Asn Pro Thr Phe Lys Asp Leu
        215                 220                 225

gat ttc ctg caa gac atg cac gaa ggg ttg tat ttt gat acg gaa aca      1497
Asp Phe Leu Gln Asp Met His Glu Gly Leu Tyr Phe Asp Thr Glu Thr
    230                 235                 240

tac aac gcg ctt atg aaa aca ctt cag aga gac tgc cgg gtg cta gaa      1545
Tyr Asn Ala Leu Met Lys Thr Leu Gln Arg Asp Cys Arg Val Leu Glu
245                 250                 255                 260

agc ttc aag atc atg gat tat agc ctt ctg ttg gga att cat ttc ctg      1593
Ser Phe Lys Ile Met Asp Tyr Ser Leu Leu Leu Gly Ile His Phe Leu
                265                 270                 275

gac cat tcc ctc aaa gag aaa gag gag gag acc cca caa aat gtg cct      1641
Asp His Ser Leu Lys Glu Lys Glu Glu Glu Thr Pro Gln Asn Val Pro
            280                 285                 290

gat gct aag cgg act ggg atg cag aag gtt ctc tac tca aca gcc atg      1689
Asp Ala Lys Arg Thr Gly Met Gln Lys Val Leu Tyr Ser Thr Ala Met
        295                 300                 305

gaa tct atc cag ggt cca ggg aaa tct gga gat ggg ata atc aca gag      1737
Glu Ser Ile Gln Gly Pro Gly Lys Ser Gly Asp Gly Ile Ile Thr Glu
    310                 315                 320

aac cca gac aca atg gga ggc att cca gct aaa agc cat agg gga gaa      1785
Asn Pro Asp Thr Met Gly Gly Ile Pro Ala Lys Ser His Arg Gly Glu
325                 330                 335                 340

aaa cta ctt tta ttt atg ggc att att gac att ctg caa tca tat agg      1833
Lys Leu Leu Leu Phe Met Gly Ile Ile Asp Ile Leu Gln Ser Tyr Arg
                345                 350                 355

tta atg aag aag tta gaa cat tcc tgg aaa gct ctt gtt tat gat ggg      1881
Leu Met Lys Lys Leu Glu His Ser Trp Lys Ala Leu Val Tyr Asp Gly
            360                 365                 370

gac act gtt tct gtt cat aga cca agc ttt tat gca gac aga ttt ctt      1929
Asp Thr Val Ser Val His Arg Pro Ser Phe Tyr Ala Asp Arg Phe Leu
        375                 380                 385

aag ttc atg aat tcc aga gtt ttc aag aaa att caa gct ttg aag gct      1977
Lys Phe Met Asn Ser Arg Val Phe Lys Lys Ile Gln Ala Leu Lys Ala
    390                 395                 400

tca ccg tct aag aaa cgg tgc aat tca atc gcc gcc cta aag gcc act      2025
Ser Pro Ser Lys Lys Arg Cys Asn Ser Ile Ala Ala Leu Lys Ala Thr
405                 410                 415                 420

tca cag gag att gtg tcc tca att agc cag gaa tgg aag gat gag aag      2073
Ser Gln Glu Ile Val Ser Ser Ile Ser Gln Glu Trp Lys Asp Glu Lys
                425                 430                 435

cgg gat ttg ctg act gaa gga caa agt ttt agc agc ctt gat gaa gaa      2121
Arg Asp Leu Leu Thr Glu Gly Gln Ser Phe Ser Ser Leu Asp Glu Glu
            440                 445                 450

gcc ctg gga tcc cga cac agg cca gac ctg gtc cct agc act cca tca      2169
Ala Leu Gly Ser Arg His Arg Pro Asp Leu Val Pro Ser Thr Pro Ser
        455                 460                 465
```

```
ctg ttt gaa gct gct tcc ttg gca acc aca att tca tct tct tcc tta     2217
Leu Phe Glu Ala Ala Ser Leu Ala Thr Thr Ile Ser Ser Ser Ser Leu
    470                 475                 480

tac gtc aat gag cac tat cca cac gac agg cct aca ctc tat tca aac     2265
Tyr Val Asn Glu His Tyr Pro His Asp Arg Pro Thr Leu Tyr Ser Asn
485                 490                 495                 500

agc aaa ggg tta cct tcc agt tca aca ttt acc ttg gaa gag ggg acc     2313
Ser Lys Gly Leu Pro Ser Ser Ser Thr Phe Thr Leu Glu Glu Gly Thr
                505                 510                 515

atc tac ttg acc gct gag ccc aac act ctg gaa gtg cag gat gac aat     2361
Ile Tyr Leu Thr Ala Glu Pro Asn Thr Leu Glu Val Gln Asp Asp Asn
            520                 525                 530

gct tct gtg ctt gac gtc tat tta taa gtgaaaatgg tgatcaccta           2408
Ala Ser Val Leu Asp Val Tyr Leu
        535                 540

agcacatgga tgagacgtga gcacagttat ggcagagaag tttctccgca ccagaattat   2468

ccacagcaac ttggctgagc cccactacac acagagaaat catcaacctg acttaagagt   2528

tttcaagatg tcaacttcag gctgatcagc agatgggatg tgaaaaatac taccctattc   2588

tatcatttgc tgttgcttgc tgaactgtga agaactgcat gaactatatt taagctgctt   2648

tctgtaccat tgccaatcac ctttttggag ttggaagtgc tattttccta tggacttttg   2708

cattatttca ttgtgcatgc atccagtgat tatacataag caacatatgt aatctgctta   2768

tatattttta aaaatccatc cacacacatg gtaaattaag tataaattct tttgcaaaat   2828

tatagttcat gtcattgaaa gtttaaattg gtttcattta aagatcaata tactaggtct   2888

gccttcactt tatagaaaac tagcttctat aaagattttt tcactgttta ctagtgaaat   2948

gagaaaagca aagctattta taaaaggcct tatgtcgtgt acatacattg tctttgaaat   3008

atttgtgatc tagtttattg cttgtaaaag agaaattata taatttattt agtaaatact   3068

actgtaaact atagttttgt gagagaaata aaatattttg ttctcaa                 3115


<210> SEQ ID NO 44
<211> LENGTH: 540
<212> TYPE: PRT
<213> ORGANISM: Homo sapiens

<400> SEQUENCE: 44

Met Ser Ser Ala Ala Glu Asn Gly Glu Ala Ala Pro Gly Lys Gln Asn
1               5                   10                  15

Glu Glu Lys Thr Tyr Lys Lys Thr Ala Ser Ser Ala Ile Lys Gly Ala
            20                  25                  30

Ile Gln Leu Gly Ile Gly Tyr Thr Val Gly Asn Leu Thr Ser Lys Pro
        35                  40                  45

Glu Arg Asp Val Leu Met Gln Asp Phe Tyr Val Val Glu Ser Val Phe
    50                  55                  60

Leu Pro Ser Glu Gly Ser Asn Leu Thr Pro Ala His His Tyr Pro Asp
65                  70                  75                  80

Phe Arg Phe Lys Thr Tyr Ala Pro Leu Ala Phe Arg Tyr Phe Arg Glu
                85                  90                  95

Leu Phe Gly Ile Lys Pro Asp Asp Tyr Leu Tyr Ser Ile Cys Ser Glu
            100                 105                 110

Pro Leu Ile Glu Leu Ser Asn Pro Gly Ala Ser Gly Ser Leu Phe Phe
        115                 120                 125

Val Thr Ser Asp Asp Glu Phe Ile Ile Lys Thr Val Gln His Lys Glu
    130                 135                 140
```

```
Ala Glu Phe Leu Gln Lys Leu Leu Pro Gly Tyr Tyr Met Asn Leu Asn
145                 150                 155                 160

Gln Asn Pro Arg Thr Leu Leu Pro Lys Phe Tyr Gly Leu Tyr Cys Met
                165                 170                 175

Gln Ser Gly Gly Ile Asn Ile Arg Ile Val Val Met Asn Asn Val Leu
            180                 185                 190

Pro Arg Ser Met Arg Met His Phe Thr Tyr Asp Leu Lys Gly Ser Thr
        195                 200                 205

Tyr Lys Arg Arg Ala Ser Arg Lys Glu Arg Glu Lys Ser Asn Pro Thr
    210                 215                 220

Phe Lys Asp Leu Asp Phe Leu Gln Asp Met His Glu Gly Leu Tyr Phe
225                 230                 235                 240

Asp Thr Glu Thr Tyr Asn Ala Leu Met Lys Thr Leu Gln Arg Asp Cys
                245                 250                 255

Arg Val Leu Glu Ser Phe Lys Ile Met Asp Tyr Ser Leu Leu Leu Gly
            260                 265                 270

Ile His Phe Leu Asp His Ser Leu Lys Glu Lys Glu Glu Glu Thr Pro
        275                 280                 285

Gln Asn Val Pro Asp Ala Lys Arg Thr Gly Met Gln Lys Val Leu Tyr
    290                 295                 300

Ser Thr Ala Met Glu Ser Ile Gln Gly Pro Gly Lys Ser Gly Asp Gly
305                 310                 315                 320

Ile Ile Thr Glu Asn Pro Asp Thr Met Gly Gly Ile Pro Ala Lys Ser
                325                 330                 335

His Arg Gly Glu Lys Leu Leu Leu Phe Met Gly Ile Ile Asp Ile Leu
            340                 345                 350

Gln Ser Tyr Arg Leu Met Lys Lys Leu Glu His Ser Trp Lys Ala Leu
        355                 360                 365

Val Tyr Asp Gly Asp Thr Val Ser Val His Arg Pro Ser Phe Tyr Ala
    370                 375                 380

Asp Arg Phe Leu Lys Phe Met Asn Ser Arg Val Phe Lys Lys Ile Gln
385                 390                 395                 400

Ala Leu Lys Ala Ser Pro Ser Lys Lys Arg Cys Asn Ser Ile Ala Ala
                405                 410                 415

Leu Lys Ala Thr Ser Gln Glu Ile Val Ser Ser Ile Ser Gln Glu Trp
            420                 425                 430

Lys Asp Glu Lys Arg Asp Leu Leu Thr Glu Gly Gln Ser Phe Ser Ser
        435                 440                 445

Leu Asp Glu Glu Ala Leu Gly Ser Arg His Arg Pro Asp Leu Val Pro
    450                 455                 460

Ser Thr Pro Ser Leu Phe Glu Ala Ala Ser Leu Ala Thr Thr Ile Ser
465                 470                 475                 480

Ser Ser Ser Leu Tyr Val Asn Glu His Tyr Pro His Asp Arg Pro Thr
                485                 490                 495

Leu Tyr Ser Asn Ser Lys Gly Leu Pro Ser Ser Ser Thr Phe Thr Leu
            500                 505                 510

Glu Glu Gly Thr Ile Tyr Leu Thr Ala Glu Pro Asn Thr Leu Glu Val
        515                 520                 525

Gln Asp Asp Asn Ala Ser Val Leu Asp Val Tyr Leu
    530                 535                 540
```

<210> SEQ ID NO 45
<211> LENGTH: 636

```
<212> TYPE: DNA
<213> ORGANISM: Homo sapiens
<220> FEATURE:
<221> NAME/KEY: CDS
<222> LOCATION: (80)..(577)

<400> SEQUENCE: 45

gtgacagccg gggtgtgtgt ccgccgggct tggtgcctcc ggtggccctg cagcaccgtc      60

ccacctctgc caccctccg atg ggg ccg cta cct gtg tgc ctg cca atc atg      112
                     Met Gly Pro Leu Pro Val Cys Leu Pro Ile Met
                     1               5                   10

ctg ctc ctg cta ctg ccg tcg ctg ctg ctg ctg ctg ctt cta cct ggc      160
Leu Leu Leu Leu Leu Pro Ser Leu Leu Leu Leu Leu Leu Leu Pro Gly
            15                  20                  25

ccc ggg tcc ggc gag gcc tcc agg ata tta cgt gtg cac cgg cgt ggg      208
Pro Gly Ser Gly Glu Ala Ser Arg Ile Leu Arg Val His Arg Arg Gly
        30                  35                  40

atc ctg gaa ctg gca gga act gtg ggt tgt gtt ggt ccc cga acc ccc      256
Ile Leu Glu Leu Ala Gly Thr Val Gly Cys Val Gly Pro Arg Thr Pro
    45                  50                  55

atc gcc tat atg aaa tat ggt tgc ttt tgt ggc ttg gga ggc cat ggc      304
Ile Ala Tyr Met Lys Tyr Gly Cys Phe Cys Gly Leu Gly Gly His Gly
60                  65                  70                  75

cag ccc cgc gat gcc att gac tgg tgc tgc cat ggc cac gac tgt tgt      352
Gln Pro Arg Asp Ala Ile Asp Trp Cys Cys His Gly His Asp Cys Cys
                80                  85                  90

tac act cga gct gag gag gcc ggc tgc agc ccc aag aca gag cgc tac      400
Tyr Thr Arg Ala Glu Glu Ala Gly Cys Ser Pro Lys Thr Glu Arg Tyr
            95                  100                 105

tcc tgg cag tgc gtc aat cag agc gtc ctg tgc gga ccg gca gag aac      448
Ser Trp Gln Cys Val Asn Gln Ser Val Leu Cys Gly Pro Ala Glu Asn
        110                 115                 120

aaa tgc caa gaa ctg ttg tgc aag tgt gac cag gag att gct aac tgc      496
Lys Cys Gln Glu Leu Leu Cys Lys Cys Asp Gln Glu Ile Ala Asn Cys
    125                 130                 135

tta gcc caa act gag tac aac tta aag tac ctc ttc tac ccc cag ttc      544
Leu Ala Gln Thr Glu Tyr Asn Leu Lys Tyr Leu Phe Tyr Pro Gln Phe
140                 145                 150                 155

cta tgt gag ccg gac tcg ccc aag tgt gac tga ctaccttgac ttgaaatgct    597
Leu Cys Glu Pro Asp Ser Pro Lys Cys Asp
                160                 165

cttttgcaca aggaaataaa gcgtcctctc agtaatgaa                           636

<210> SEQ ID NO 46
<211> LENGTH: 165
<212> TYPE: PRT
<213> ORGANISM: Homo sapiens

<400> SEQUENCE: 46

Met Gly Pro Leu Pro Val Cys Leu Pro Ile Met Leu Leu Leu Leu Leu
1               5                   10                  15

Pro Ser Leu Leu Leu Leu Leu Leu Leu Pro Gly Pro Gly Ser Gly Glu
            20                  25                  30

Ala Ser Arg Ile Leu Arg Val His Arg Arg Gly Ile Leu Glu Leu Ala
        35                  40                  45

Gly Thr Val Gly Cys Val Gly Pro Arg Thr Pro Ile Ala Tyr Met Lys
    50                  55                  60

Tyr Gly Cys Phe Cys Gly Leu Gly Gly His Gly Gln Pro Arg Asp Ala
65                  70                  75                  80
```

```
Ile Asp Trp Cys Cys His Gly His Asp Cys Cys Tyr Thr Arg Ala Glu
                85                  90                  95

Glu Ala Gly Cys Ser Pro Lys Thr Glu Arg Tyr Ser Trp Gln Cys Val
            100                 105                 110

Asn Gln Ser Val Leu Cys Gly Pro Ala Glu Asn Lys Cys Gln Glu Leu
        115                 120                 125

Leu Cys Lys Cys Asp Gln Glu Ile Ala Asn Cys Leu Ala Gln Thr Glu
    130                 135                 140

Tyr Asn Leu Lys Tyr Leu Phe Tyr Pro Gln Phe Leu Cys Glu Pro Asp
145                 150                 155                 160

Ser Pro Lys Cys Asp
                165


<210> SEQ ID NO 47
<211> LENGTH: 1751
<212> TYPE: DNA
<213> ORGANISM: Homo sapiens
<220> FEATURE:
<221> NAME/KEY: CDS
<222> LOCATION: (31)..(489)

<400> SEQUENCE: 47

acacccacag ttgagctgcg ctggccagag atg cct gcc cac agc ctg gtg atg      54
                                 Met Pro Ala His Ser Leu Val Met
                                 1               5

agc agc ccg gcc ctc ccg gcc ttc ctg ctc tgc agc acg ctg ctg gtc      102
Ser Ser Pro Ala Leu Pro Ala Phe Leu Leu Cys Ser Thr Leu Leu Val
    10                  15                  20

atc aag atg tac gtg gtg gcc atc atc acg ggc caa gtg agg ctg cgg      150
Ile Lys Met Tyr Val Val Ala Ile Ile Thr Gly Gln Val Arg Leu Arg
25                  30                  35                  40

aag aag gcc ttt gcc aac ccc gag gat gcc ctg aga cac gga ggc ccc      198
Lys Lys Ala Phe Ala Asn Pro Glu Asp Ala Leu Arg His Gly Gly Pro
                45                  50                  55

cag tat tgc agg agc gac ccc gac gtg gaa cgc tgc ctc agg gcc cac      246
Gln Tyr Cys Arg Ser Asp Pro Asp Val Glu Arg Cys Leu Arg Ala His
            60                  65                  70

cgg aac gac atg gag acc atc tac ccc ttc ctt ttc ctg ggc ttc gtc      294
Arg Asn Asp Met Glu Thr Ile Tyr Pro Phe Leu Phe Leu Gly Phe Val
        75                  80                  85

tac tcc ttt ctg ggt cct aac cct ttt gtc gcc tgg atg cac ttc ctg      342
Tyr Ser Phe Leu Gly Pro Asn Pro Phe Val Ala Trp Met His Phe Leu
    90                  95                  100

gtc ttc ctc gtg ggc cgt gtg gca cac acc gtg gcc tac ctg ggg aag      390
Val Phe Leu Val Gly Arg Val Ala His Thr Val Ala Tyr Leu Gly Lys
105                 110                 115                 120

ctg cgg gca ccc atc cgc tcc gtg acc tac acc ctg gcc cag ctc ccc      438
Leu Arg Ala Pro Ile Arg Ser Val Thr Tyr Thr Leu Ala Gln Leu Pro
                125                 130                 135

tgc gcc tcc atg gct ctg cag atc ctc tgg gaa gcg gcc cgc cac ctg      486
Cys Ala Ser Met Ala Leu Gln Ile Leu Trp Glu Ala Ala Arg His Leu
            140                 145                 150

tga ccagcagctg atgcctcctt ggccaccaga ccatgggcca agagccgccg           539

tggctatacc tggggacttg atgttccttc cagattgtgg tgggccctga gtcctggttt    599

cctggcagcc tgctgcgcgt gtgggtctct gggcacagtg ggcctgtgtg tgtgcccgtg    659

tgtgtgtatg tgtgtgtgta tgtttcttag ccccttggat tcctgcacga agtggctgat    719

gggaaccatt tcaagacaga ttgtgaagat tgatagaaaa tccttcagct aaagtaacag    779
```

```
agcatcaaaa acatcactcc ctctccctcc ctaacagtga aaagagagaa gggagactct    839

atttaagatt cccaaaccta atgatcatct gaatcccggg ctaagaatgc agacttttca    899

gactgacccc agaaattctg gcccagccaa tctagaggca agcctggcca tctgtatttt    959

tttttttcca agacagagtc ttgctctgtt gcccaagctg gagtgaagtg gtacaatctg   1019

gctcactgca gcctccgcct cccgggttca agcgattctc ccgcctcagc ctcctgagta   1079

gctgggatta caggcgcgta tcaccatacc cagctaattt ttgtattttt agtagagacg   1139

ggttcaccat gttgcccagg agggtctcga actcctggcc tcaagtgatc caccggcctc   1199

ggcctcccaa agtgctggga tgacaggcat gaatcactgt gctcagccac catctggagt   1259

tttaaaaggc tcccatgtga gtccctgtga tggccaggcc aggggacccc tgccagttct   1319

ctgtggaagc aaggctgggg tcttgggttc ctgtatggtg gaagctgggt gagccaagga   1379

cagggctggc tcctctgccc ccgctgacgc ttcccttgcc gttggctttg gatgtctttg   1439

ctgcagtctt ctctctggct caggtgtggg tgggaggggc ccacaggaag ctcagccttc   1499

tcctcccaag gtttgagtcc ctccaaaggg cagtgggtgg aggaccggga gctttgggtg   1559

accagccact caaaggaact ttctggtccc ttcagtatct tcaaggtttg gaaactgcaa   1619

atgtcccctt gatggggaat ccgtgtgtgt gtgtgtgtgt gtgtgtgtgt gtgtgtgtgt   1679

gtgtgtgtgt tttctcctag acccgtgacc tgagatgtgt gatttttagt cattaaatgg   1739

aagtgtctgc ca                                                       1751
```

<210> SEQ ID NO 48
<211> LENGTH: 152
<212> TYPE: PRT
<213> ORGANISM: Homo sapiens

<400> SEQUENCE: 48

```
Met Pro Ala His Ser Leu Val Met Ser Ser Pro Ala Leu Pro Ala Phe
1               5                   10                  15

Leu Leu Cys Ser Thr Leu Leu Val Ile Lys Met Tyr Val Val Ala Ile
            20                  25                  30

Ile Thr Gly Gln Val Arg Leu Arg Lys Lys Ala Phe Ala Asn Pro Glu
        35                  40                  45

Asp Ala Leu Arg His Gly Gly Pro Gln Tyr Cys Arg Ser Asp Pro Asp
    50                  55                  60

Val Glu Arg Cys Leu Arg Ala His Arg Asn Asp Met Glu Thr Ile Tyr
65                  70                  75                  80

Pro Phe Leu Phe Leu Gly Phe Val Tyr Ser Phe Leu Gly Pro Asn Pro
                85                  90                  95

Phe Val Ala Trp Met His Phe Leu Val Phe Leu Val Gly Arg Val Ala
            100                 105                 110

His Thr Val Ala Tyr Leu Gly Lys Leu Arg Ala Pro Ile Arg Ser Val
        115                 120                 125

Thr Tyr Thr Leu Ala Gln Leu Pro Cys Ala Ser Met Ala Leu Gln Ile
    130                 135                 140

Leu Trp Glu Ala Ala Arg His Leu
145                 150
```

<210> SEQ ID NO 49
<211> LENGTH: 1224
<212> TYPE: DNA
<213> ORGANISM: Homo sapiens
<220> FEATURE:
<221> NAME/KEY: CDS

```
<222> LOCATION: (147)..(623)

<400> SEQUENCE: 49

actggagaca ctgaagaagg caggggccct tagagtcttg gttgccaaac agatttgcag      60

atcaaggaga acccaggagt ttcaaagaag cgctagtaag gtctctgaga tccttgcact     120

agctacatcc tcagggtagg aggaag atg gct tcc aga agc atg cgg ctg ctc      173
                             Met Ala Ser Arg Ser Met Arg Leu Leu
                             1               5

cta ttg ctg agc tgc ctg gcc aaa aca gga gtc ctg ggt gat atc atc       221
Leu Leu Leu Ser Cys Leu Ala Lys Thr Gly Val Leu Gly Asp Ile Ile
10                  15                  20                  25

atg aga ccc agc tgt gct cct gga tgg ttt tac cac aag tcc aat tgc       269
Met Arg Pro Ser Cys Ala Pro Gly Trp Phe Tyr His Lys Ser Asn Cys
                30                  35                  40

tat ggt tac ttc agg aag ctg agg aac tgg tct gat gcc gag ctc gag       317
Tyr Gly Tyr Phe Arg Lys Leu Arg Asn Trp Ser Asp Ala Glu Leu Glu
            45                  50                  55

tgt cag tct tac gga aac gga gcc cac ctg gca tct atc ctg agt tta       365
Cys Gln Ser Tyr Gly Asn Gly Ala His Leu Ala Ser Ile Leu Ser Leu
        60                  65                  70

aag gaa gcc agc acc ata gca gag tac ata agt ggc tat cag aga agc       413
Lys Glu Ala Ser Thr Ile Ala Glu Tyr Ile Ser Gly Tyr Gln Arg Ser
    75                  80                  85

cag ccg ata tgg att ggc ctg cac gac cca cag aag agg cag cag tgg       461
Gln Pro Ile Trp Ile Gly Leu His Asp Pro Gln Lys Arg Gln Gln Trp
90                  95                  100                 105

cag tgg att gat ggg gcc atg tat ctg tac aga tcc tgg tct ggc aag       509
Gln Trp Ile Asp Gly Ala Met Tyr Leu Tyr Arg Ser Trp Ser Gly Lys
                110                 115                 120

tcc atg ggt ggg aac aag cac tgt gct gag atg agc tcc aat aac aac       557
Ser Met Gly Gly Asn Lys His Cys Ala Glu Met Ser Ser Asn Asn Asn
            125                 130                 135

ttt tta act tgg agc agc aac gaa tgc aac aag cgc caa cac ttc ctg       605
Phe Leu Thr Trp Ser Ser Asn Glu Cys Asn Lys Arg Gln His Phe Leu
        140                 145                 150

tgc aag tac cga cca tag agcaagaatc aagattctgc taactcctgc              653
Cys Lys Tyr Arg Pro
    155

acagccccgt cctcttcctt tctgctagcc tggctaaatc tgctcattat ttcagagggg     713

aaacctagca aactaagagt gataagggcc ctactacact ggctttttta ggcttagaga     773

cagaaacttt agcattggcc cagtagtggc ttctagctct aaatgtttgc cccgccatcc     833

ctttccacag tatccttctt ccctcctccc ctgtctctgg ctgtctcgag cagtctagaa     893

gagtgcatct ccagcctatg aaacagctgg gtctttggcc ataagaagta aagatttgaa     953

gacagaagga agaaactcag gagtaagctt ctagacccct tcagcttcta cacccttctg    1013

ccctctctcc attgcctgca ccccacccca gccactcaac tcctgcttgt ttttcctttg    1073

gccatgggaa ggtttaccag tagaatcctt gctaggttga tgtgggccat acattccttt    1133

aataaaccat tgtgtacata agaggttgct gtgttccagt tcagtaatgg tgaatgtgga    1193

aaagtgaaat aagaccaaga aatacaccca a                                   1224


<210> SEQ ID NO 50
<211> LENGTH: 158
<212> TYPE: PRT
<213> ORGANISM: Homo sapiens

<400> SEQUENCE: 50
```

```
Met Ala Ser Arg Ser Met Arg Leu Leu Leu Leu Leu Ser Cys Leu Ala
1               5                   10                  15

Lys Thr Gly Val Leu Gly Asp Ile Ile Met Arg Pro Ser Cys Ala Pro
            20                  25                  30

Gly Trp Phe Tyr His Lys Ser Asn Cys Tyr Gly Tyr Phe Arg Lys Leu
        35                  40                  45

Arg Asn Trp Ser Asp Ala Glu Leu Glu Cys Gln Ser Tyr Gly Asn Gly
    50                  55                  60

Ala His Leu Ala Ser Ile Leu Ser Leu Lys Glu Ala Ser Thr Ile Ala
65                  70                  75                  80

Glu Tyr Ile Ser Gly Tyr Gln Arg Ser Gln Pro Ile Trp Ile Gly Leu
                85                  90                  95

His Asp Pro Gln Lys Arg Gln Gln Trp Gln Trp Ile Asp Gly Ala Met
            100                 105                 110

Tyr Leu Tyr Arg Ser Trp Ser Gly Lys Ser Met Gly Gly Asn Lys His
        115                 120                 125

Cys Ala Glu Met Ser Ser Asn Asn Asn Phe Leu Thr Trp Ser Ser Asn
    130                 135                 140

Glu Cys Asn Lys Arg Gln His Phe Leu Cys Lys Tyr Arg Pro
145                 150                 155


<210> SEQ ID NO 51
<211> LENGTH: 977
<212> TYPE: DNA
<213> ORGANISM: Homo sapiens
<220> FEATURE:
<221> NAME/KEY: CDS
<222> LOCATION: (350)..(646)

<400> SEQUENCE: 51

agagcagggg ttgcctcccc tcaccccggt ccaggatgcc cagtccccac gacacctccc     60

acttcccact gtggcctggg tgggctcagg ggctgccctt gacctggcct agagccctcc    120

cccagctggt ggtggagctg gcactctctg ggagggaggg ggctgggagg gaatgagtgg    180

gaatggcaag aggccagggt ttggtgggat caggttgagg caggtttggt ttccttaaaa    240

tgccaagttg ggggccagtg gggcccacat ataaatcctc accctgggag cctggctgcc    300

ttgctctcct tcctgggtct gtctctgcca cctggtctgc cacagatcc atg atg tgc    358
                                                      Met Met Cys
                                                      1

agt tct ctg gag cag gcg ctg gct gtg ctg gtc act acc ttc cac aag      406
Ser Ser Leu Glu Gln Ala Leu Ala Val Leu Val Thr Thr Phe His Lys
    5                   10                  15

tac tcc tgc caa gag ggc gac aag ttc aag ctg agt aag ggg gaa atg      454
Tyr Ser Cys Gln Glu Gly Asp Lys Phe Lys Leu Ser Lys Gly Glu Met
20                  25                  30                  35

aag gaa ctt ctg cac aag gag ctg ccc agc ttt gtg ggg gag aaa gtg      502
Lys Glu Leu Leu His Lys Glu Leu Pro Ser Phe Val Gly Glu Lys Val
                40                  45                  50

gat gag gag ggg ctg aag aag ctg atg ggc agc ctg gat gag aac agt      550
Asp Glu Glu Gly Leu Lys Lys Leu Met Gly Ser Leu Asp Glu Asn Ser
            55                  60                  65

gac cag cag gtg gac ttc cag gag tat gct gtt ttc ctg gca ctc atc      598
Asp Gln Gln Val Asp Phe Gln Glu Tyr Ala Val Phe Leu Ala Leu Ile
        70                  75                  80

act gtc atg tgc aat gac ttc ttc cag ggc tgc cca gac cga ccc tga      646
Thr Val Met Cys Asn Asp Phe Phe Gln Gly Cys Pro Asp Arg Pro
    85                  90                  95
```

agcagaactc ttgacttcct gccatggatc tcttgggccc aggactgttg atgcctttga 706 gttttgtatt caataaactt tttttgtctg ttgataatat tttaattgct cagtgatgtt 766 ccataacccg gctggctcag ctggagtgct gggagatgag ggcctcctgg atcctgctcc 826 cttctgggct ctgactctcc tggaaatctc tccaaggcca gagctatgct ttaggtctca 886 attttggaat ttcaaacacc agcaaaaaat tggaaatcga gataggttgc tgacttttat 946 tttgtcaaat aaagatatta aaaaaggcaa a 977

<210> SEQ ID NO 52
<211> LENGTH: 98
<212> TYPE: PRT
<213> ORGANISM: Homo sapiens

<400> SEQUENCE: 52

```
Met Met Cys Ser Ser Leu Glu Gln Ala Leu Ala Val Leu Val Thr Thr
1               5                   10                  15

Phe His Lys Tyr Ser Cys Gln Glu Gly Asp Lys Phe Lys Leu Ser Lys
            20                  25                  30

Gly Glu Met Lys Glu Leu Leu His Lys Glu Leu Pro Ser Phe Val Gly
        35                  40                  45

Glu Lys Val Asp Glu Glu Gly Leu Lys Lys Leu Met Gly Ser Leu Asp
    50                  55                  60

Glu Asn Ser Asp Gln Gln Val Asp Phe Gln Glu Tyr Ala Val Phe Leu
65                  70                  75                  80

Ala Leu Ile Thr Val Met Cys Asn Asp Phe Phe Gln Gly Cys Pro Asp
                85                  90                  95

Arg Pro
```

<210> SEQ ID NO 53
<211> LENGTH: 3330
<212> TYPE: DNA
<213> ORGANISM: Homo sapiens
<220> FEATURE:
<221> NAME/KEY: CDS
<222> LOCATION: (327)..(2042)

<400> SEQUENCE: 53

```
ggcggcggcg gcggcggaga gagctggctc agggcgtccg ctaggctcgg acgacctgct      60

gagcctccca aaccgcttcc ataaggcttt gcctttccaa cttcagctac agtgttagct     120

aagtttggaa agaaggaaaa aagaaaatcc ctgggcccct tttcttttgt tctttgccaa     180

agtcgtcgtt gtagtctttt tgcccaaggc tgttgtgttt ttagaggtgc tatctccagt     240

tccttgcact cctgttaaca agcacctcag cgagagcagc agcagcgata gcagccgcag     300

aagagccagc ggggtcgcct agtgtc atg acc agg gcg gga gat cac aac cgc     353
                             Met Thr Arg Ala Gly Asp His Asn Arg
                             1               5

cag aga gga tgc tgt gga tcc ttg gcc gac tac ctg acc tct gca aaa      401
Gln Arg Gly Cys Cys Gly Ser Leu Ala Asp Tyr Leu Thr Ser Ala Lys
10                  15                  20                  25

ttc ctt ctc tac ctt ggt cat tct ctc tct act tgg gga gat cgg atg      449
Phe Leu Leu Tyr Leu Gly His Ser Leu Ser Thr Trp Gly Asp Arg Met
                30                  35                  40

tgg cac ttt gcg gtg tct gtg ttt ctg gta gag ctc tat gga aac agc      497
Trp His Phe Ala Val Ser Val Phe Leu Val Glu Leu Tyr Gly Asn Ser
            45                  50                  55

ctc ctt ttg aca gca gtc tac ggg ctg gtg gtg gca ggg tct gtt ctg      545
```

```
Leu Leu Leu Thr Ala Val Tyr Gly Leu Val Val Ala Gly Ser Val Leu
        60                  65                  70

gtc ctg gga gcc atc atc ggt gac tgg gtg gac aag aat gct aga ctt      593
Val Leu Gly Ala Ile Ile Gly Asp Trp Val Asp Lys Asn Ala Arg Leu
    75                  80                  85

aaa gtg gcc cag acc tcg ctg gtg gta cag aat gtt tca gtc atc ctg      641
Lys Val Ala Gln Thr Ser Leu Val Val Gln Asn Val Ser Val Ile Leu
90                  95                  100                 105

tgt gga atc atc ctg atg atg gtt ttc tta cat aaa cat gag ctt ctg      689
Cys Gly Ile Ile Leu Met Met Val Phe Leu His Lys His Glu Leu Leu
                110                 115                 120

acc atg tac cat gga tgg gtt ctc act tcc tgc tat atc ctg atc atc      737
Thr Met Tyr His Gly Trp Val Leu Thr Ser Cys Tyr Ile Leu Ile Ile
            125                 130                 135

act att gca aat att gca aat ttg gcc agt act gct act gca atc aca      785
Thr Ile Ala Asn Ile Ala Asn Leu Ala Ser Thr Ala Thr Ala Ile Thr
        140                 145                 150

atc caa agg gat tgg att gtt gtt gtt gca gga gaa gac aga agc aaa      833
Ile Gln Arg Asp Trp Ile Val Val Val Ala Gly Glu Asp Arg Ser Lys
    155                 160                 165

cta gca aat atg aat gcc aca ata cga agg att gac cag tta acc aac      881
Leu Ala Asn Met Asn Ala Thr Ile Arg Arg Ile Asp Gln Leu Thr Asn
170                 175                 180                 185

atc tta gcc ccc atg gct gtt ggc cag att atg aca ttt ggc tcc cca      929
Ile Leu Ala Pro Met Ala Val Gly Gln Ile Met Thr Phe Gly Ser Pro
                190                 195                 200

gtc atc ggc tgt ggc ttt att tcg gga tgg aac ttg gta tcc atg tgc      977
Val Ile Gly Cys Gly Phe Ile Ser Gly Trp Asn Leu Val Ser Met Cys
            205                 210                 215

gtg gag tac gtt ctg ctc tgg aag gtt tac cag aaa acc cca gct cta     1025
Val Glu Tyr Val Leu Leu Trp Lys Val Tyr Gln Lys Thr Pro Ala Leu
        220                 225                 230

gct gtg aaa gct ggt ctt aaa gaa gag gaa act gaa ttg aaa cag ctg     1073
Ala Val Lys Ala Gly Leu Lys Glu Glu Glu Thr Glu Leu Lys Gln Leu
    235                 240                 245

aat tta cac aaa gat act gag cca aaa ccc ctg gag gga act cat cta     1121
Asn Leu His Lys Asp Thr Glu Pro Lys Pro Leu Glu Gly Thr His Leu
250                 255                 260                 265

atg ggt gtg aaa gac tct aac atc cat gag ctt gaa cat gag caa gag     1169
Met Gly Val Lys Asp Ser Asn Ile His Glu Leu Glu His Glu Gln Glu
                270                 275                 280

cct act tgt gcc tcc cag atg gct gag ccc ttc cgt acc ttc cga gat     1217
Pro Thr Cys Ala Ser Gln Met Ala Glu Pro Phe Arg Thr Phe Arg Asp
            285                 290                 295

gga tgg gtc tcc tac tac aac cag cct gtg ttt ctg gct ggc atg ggt     1265
Gly Trp Val Ser Tyr Tyr Asn Gln Pro Val Phe Leu Ala Gly Met Gly
        300                 305                 310

ctt gct ttc ctt tat atg act gtc ctg ggc ttt gac tgc atc acc aca     1313
Leu Ala Phe Leu Tyr Met Thr Val Leu Gly Phe Asp Cys Ile Thr Thr
    315                 320                 325

ggg tac gcc tac act cag gga ctg agt ggt tcc atc ctc agt att ttg     1361
Gly Tyr Ala Tyr Thr Gln Gly Leu Ser Gly Ser Ile Leu Ser Ile Leu
330                 335                 340                 345

atg gga gca tca gct ata act gga ata atg gga act gta gct ttt act     1409
Met Gly Ala Ser Ala Ile Thr Gly Ile Met Gly Thr Val Ala Phe Thr
                350                 355                 360

tgg cta cgt cga aaa tgt ggt ttg gtt cgg aca ggt ctg atc tca gga     1457
Trp Leu Arg Arg Lys Cys Gly Leu Val Arg Thr Gly Leu Ile Ser Gly
            365                 370                 375
```

```
ttg gca cag ctt tcc tgt ttg atc ttg tgt gtg atc tct gta ttc atg     1505
Leu Ala Gln Leu Ser Cys Leu Ile Leu Cys Val Ile Ser Val Phe Met
        380                 385                 390

cct gga agc ccc ctg gac ttg tcc gtt tct cct ttt gaa gat atc cga     1553
Pro Gly Ser Pro Leu Asp Leu Ser Val Ser Pro Phe Glu Asp Ile Arg
    395                 400                 405

tca agg ttc att caa gga gag tca att aca cct acc aag ata cct gaa     1601
Ser Arg Phe Ile Gln Gly Glu Ser Ile Thr Pro Thr Lys Ile Pro Glu
410                 415                 420                 425

att aca act gaa ata tac atg tct aat ggg tct aat tct gct aat att     1649
Ile Thr Thr Glu Ile Tyr Met Ser Asn Gly Ser Asn Ser Ala Asn Ile
                430                 435                 440

gtc ccg gag aca agt cct gaa tct gtg ccc ata atc tct gtc agt ctg     1697
Val Pro Glu Thr Ser Pro Glu Ser Val Pro Ile Ile Ser Val Ser Leu
            445                 450                 455

ctg ttt gca ggc gtc att gct gct aga atc ggt ctt tgg tcc ttt gat     1745
Leu Phe Ala Gly Val Ile Ala Ala Arg Ile Gly Leu Trp Ser Phe Asp
        460                 465                 470

tta act gtg aca cag ttg ctg caa gaa aat gta att gaa tct gaa aga     1793
Leu Thr Val Thr Gln Leu Leu Gln Glu Asn Val Ile Glu Ser Glu Arg
    475                 480                 485

ggc att ata aat ggt gta cag aac tcc atg aac tat ctt ctt gat ctt     1841
Gly Ile Ile Asn Gly Val Gln Asn Ser Met Asn Tyr Leu Leu Asp Leu
490                 495                 500                 505

ctg cat ttc atc atg gtc atc ctg gct cca aat cct gaa gct ttt ggc     1889
Leu His Phe Ile Met Val Ile Leu Ala Pro Asn Pro Glu Ala Phe Gly
                510                 515                 520

ttg ctc gta ttg att tca gtc tcc ttt gtg gca atg ggc cac att atg     1937
Leu Leu Val Leu Ile Ser Val Ser Phe Val Ala Met Gly His Ile Met
            525                 530                 535

tat ttc cga ttt gcc caa aat act ctg gga aac aag ctc ttt gct tgc     1985
Tyr Phe Arg Phe Ala Gln Asn Thr Leu Gly Asn Lys Leu Phe Ala Cys
        540                 545                 550

ggt cct gat gca aaa gaa gtt agg aag gaa aat caa gca aat aca tct     2033
Gly Pro Asp Ala Lys Glu Val Arg Lys Glu Asn Gln Ala Asn Thr Ser
    555                 560                 565

gtt gtt tga gacagtttaa ctgttgctat cctgttacta gattatatag             2082
Val Val
570

agcacatgtg cttattttgt actgcagaat tccaataaat ggctgggtgt tttgctctgt   2142

ttttaccaca gctgtgcctt gagaactaaa agctgtttag gaaacctaag tcagcagaaa   2202

ttaactgatt aatttccctt atgttgaggc atggaaaaaa aattggaaaa gaaaaactca   2262

gtttaaatac ggagactata atgataacac tgaattcccc tatttctcat gagtagatac   2322

aatcttacgt aaaagagtgg ttagtcacgt gaattcagtt atcatttgac agattcttat   2382

ctgtactaga attcagatat gtcagttttc tgcaaaactc actcttgttc aagactagct   2442

aatttatttt tttgcatctt agttattttt aaaaacaaat tcttcaagta tgaagactaa   2502

attttgataa ctaatattat ccttattgat cctattgatc ttaaggtatt tacatgtatg   2562

tggaaaaaca aaacacttaa ctagaattct ctaataaggt ttatggttta gcttaaagag   2622

cacctttgta tttttattat cagatggggc aacatattgt atgaagcata tgtagcactt   2682

cacagcatgg ttatcatgta agctgcaggt agaagcaaag ctgtaaagta gatttatcac   2742

acaatgactg catacagact tcaaatatgt caatagtttg gtcatagaac ctagaagcca   2802

aaagccacac agaagggcaa gaatcccaat ttaactcatg ttatcatcat tagtgatctg   2862

tgttgtagaa catgagggtg taagccttca gcctggcaag ttacatgtag aaagcccaca   2922
```

```
cttgtgaagg ttttgtttta caaatcactt gatttaacac actcaggtag aatattttta   2982

tttttactgt tttataccca gaagttattt ctacattgtt ctacagcaag aatattcata   3042

aaagtatccc tttcaaatgc ctttgagaag aatagaagaa aaaaagtttg tatatatttt   3102

aaaaaattgt tttaaaagtc agtttgcaac atgtctgtac caagatggta ctttgcctta   3162

accgtttata tgcactttca tggagactgc aatacgttgc tatgagcact ttctttatcc   3222

ttggagttta atcctttgct tcatctttct acagtatgac ataatgattt gctatgttgt   3282

aaaatctttg taaaaaattt ctatataaaa atattttgaa aatcttaa                3330
```

<210> SEQ ID NO 54
<211> LENGTH: 571
<212> TYPE: PRT
<213> ORGANISM: Homo sapiens

<400> SEQUENCE: 54

```
Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
            100                 105                 110

Val Phe Leu His Lys His Glu Leu Leu Thr Met Tyr His Gly Trp Val
        115                 120                 125

Leu Thr Ser Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
    210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270

Ile His Glu Leu Glu His Glu Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300
```

```
Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
            340                 345                 350

Gly Ile Met Gly Thr Val Ala Phe Thr Trp Leu Arg Arg Lys Cys Gly
        355                 360                 365

Leu Val Arg Thr Gly Leu Ile Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Thr Glu Ile Tyr Met
            420                 425                 430

Ser Asn Gly Ser Asn Ser Ala Asn Ile Val Pro Glu Thr Ser Pro Glu
        435                 440                 445

Ser Val Pro Ile Ile Ser Val Ser Leu Leu Phe Ala Gly Val Ile Ala
    450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
            500                 505                 510

Leu Ala Pro Asn Pro Glu Ala Phe Gly Leu Leu Val Leu Ile Ser Val
        515                 520                 525

Ser Phe Val Ala Met Gly His Ile Met Tyr Phe Arg Phe Ala Gln Asn
    530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570


<210> SEQ ID NO 55
<211> LENGTH: 492
<212> TYPE: DNA
<213> ORGANISM: Homo sapiens
<220> FEATURE:
<221> NAME/KEY: CDS
<222> LOCATION: (41)..(295)

<400> SEQUENCE: 55

atccctgact cggggtcgcc tttggagcag agaggaggca atg gcc acc atg gag       55
                                            Met Ala Thr Met Glu
                                            1               5

aac aag gtg atc tgc gcc ctg gtc ctg gtg tcc atg ctg gcc ctc ggc      103
Asn Lys Val Ile Cys Ala Leu Val Leu Val Ser Met Leu Ala Leu Gly
                10                  15                  20

acc ctg gcc gag gcc cag aca gag acg tgt aca gtg gcc ccc cgt gaa      151
Thr Leu Ala Glu Ala Gln Thr Glu Thr Cys Thr Val Ala Pro Arg Glu
            25                  30                  35

aga cag aat tgt ggt ttt cct ggt gtc acg ccc tcc cag tgt gca aat      199
Arg Gln Asn Cys Gly Phe Pro Gly Val Thr Pro Ser Gln Cys Ala Asn
        40                  45                  50
```

```
aag ggc tgc tgt ttc gac gac acc gtt cgt ggg gtc ccc tgg tgc ttc      247
Lys Gly Cys Cys Phe Asp Asp Thr Val Arg Gly Val Pro Trp Cys Phe
    55                  60                  65

tat cct aat acc atc gac gtc cct cca gaa gag gag tgt gaa ttt tag      295
Tyr Pro Asn Thr Ile Asp Val Pro Pro Glu Glu Glu Cys Glu Phe
70                  75                  80

acacttctgc agggatctgc ctgcatcctg acgcggtgcc gtccccagca cggtgattag    355

tcccagagct cggctgccac ctccaccgga cacctcagac acgcttctgc agctgtgcct    415

cggctcacaa cacagattga ctgctctgac tttgactact caaaattggc ctaaaaatta    475

aaagagatcg atattaa                                                   492


<210> SEQ ID NO 56
<211> LENGTH: 84
<212> TYPE: PRT
<213> ORGANISM: Homo sapiens

<400> SEQUENCE: 56

Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
        35                  40                  45

Ser Gln Cys Ala Asn Lys Gly Cys Cys Phe Asp Asp Thr Val Arg Gly
    50                  55                  60

Val Pro Trp Cys Phe Tyr Pro Asn Thr Ile Asp Val Pro Pro Glu Glu
65                  70                  75                  80

Glu Cys Glu Phe


<210> SEQ ID NO 57
<211> LENGTH: 1131
<212> TYPE: DNA
<213> ORGANISM: Homo sapiens
<220> FEATURE:
<221> NAME/KEY: CDS
<222> LOCATION: (180)..(893)

<400> SEQUENCE: 57

agtgccccag gagctatgac aagcaaagga acatacttgc ctggagatag cctttgcgat     60

atttaaatgt ccgtggatac agaaatctct gcaggcaagt tgctccagag catattgcag    120

gacaagcctg taacgaatag ttaaattcac ggcatctgga ttcctaatcc ttttccgaa     179

atg gca ggt gtg agt gcc tgt ata aaa tat tct atg ttt acc ttc aac      227
Met Ala Gly Val Ser Ala Cys Ile Lys Tyr Ser Met Phe Thr Phe Asn
1               5                   10                  15

ttc ttg ttc tgg cta tgt ggt atc ttg atc cta gca tta gca ata tgg      275
Phe Leu Phe Trp Leu Cys Gly Ile Leu Ile Leu Ala Leu Ala Ile Trp
            20                  25                  30

gta cga gta agc aat gac tct caa gca att ttt ggt tct gaa gat gta      323
Val Arg Val Ser Asn Asp Ser Gln Ala Ile Phe Gly Ser Glu Asp Val
        35                  40                  45

ggc tct agc tcc tac gtt gct gtg gac ata ttg att gct gta ggt gcc      371
Gly Ser Ser Ser Tyr Val Ala Val Asp Ile Leu Ile Ala Val Gly Ala
    50                  55                  60

atc atc atg att ctg ggc ttc ctg gga tgc tgc ggt gct ata aaa gaa      419
Ile Ile Met Ile Leu Gly Phe Leu Gly Cys Cys Gly Ala Ile Lys Glu
65                  70                  75                  80

agt cgc tgc atg ctt ctg ttg ttt ttc ata ggc ttg ctt ctg atc ctg      467
```

-continued

```
Ser Arg Cys Met Leu Leu Leu Phe Phe Ile Gly Leu Leu Leu Ile Leu
                85                  90                  95

ctc ctg cag gtg gcg aca ggt atc cta gga gct gtt ttc aaa tct aag      515
Leu Leu Gln Val Ala Thr Gly Ile Leu Gly Ala Val Phe Lys Ser Lys
            100                 105                 110

tct gat cgc att gtg aat gaa act ctc tat gaa aac aca aag ctt ttg      563
Ser Asp Arg Ile Val Asn Glu Thr Leu Tyr Glu Asn Thr Lys Leu Leu
        115                 120                 125

agc gcc aca ggg gaa agt gaa aaa caa ttc cag gaa gcc ata att gtg      611
Ser Ala Thr Gly Glu Ser Glu Lys Gln Phe Gln Glu Ala Ile Ile Val
    130                 135                 140

ttt caa gaa gag ttt aaa tgc tgc ggt ttg gtc aat gga gct gct gat      659
Phe Gln Glu Glu Phe Lys Cys Cys Gly Leu Val Asn Gly Ala Ala Asp
145                 150                 155                 160

tgg gga aat aat ttt caa cac tat cct gaa tta tgt gcc tgt cta gat      707
Trp Gly Asn Asn Phe Gln His Tyr Pro Glu Leu Cys Ala Cys Leu Asp
                165                 170                 175

aag cag aga cca tgc caa agc tat aat gga aaa caa gtt tac aaa gag      755
Lys Gln Arg Pro Cys Gln Ser Tyr Asn Gly Lys Gln Val Tyr Lys Glu
            180                 185                 190

acc tgt att tct ttc ata aaa gac ttc ttg gca aaa aat ttg att ata      803
Thr Cys Ile Ser Phe Ile Lys Asp Phe Leu Ala Lys Asn Leu Ile Ile
        195                 200                 205

gtt att gga ata tca ttt gga ctg gca gtt att gag ata ctg ggt ttg      851
Val Ile Gly Ile Ser Phe Gly Leu Ala Val Ile Glu Ile Leu Gly Leu
    210                 215                 220

gtg ttt tct atg gtc ctg tat tgc cag atc ggg aac aaa tga              893
Val Phe Ser Met Val Leu Tyr Cys Gln Ile Gly Asn Lys
225                 230                 235

atctgtggat gcatcaacct atcgtcagtc aaaccccttt aaaatgttgc tttggctttg    953

taaatttaaa tatgtaagtg ctatataagt caggagcagc tgtcttttta aaatgtctcg   1013

gctagctaga ccacagatat cttctagaca tattgaacac atttaagatt tgagggatat   1073

aagggaaaat gatatgaatg tgtattttta ctcaaaataa aagtaactgt ttacgttg     1131


<210> SEQ ID NO 58
<211> LENGTH: 237
<212> TYPE: PRT
<213> ORGANISM: Homo sapiens

<400> SEQUENCE: 58

Met Ala Gly Val Ser Ala Cys Ile Lys Tyr Ser Met Phe Thr Phe Asn
1               5                   10                  15

Phe Leu Phe Trp Leu Cys Gly Ile Leu Ile Leu Ala Leu Ala Ile Trp
            20                  25                  30

Val Arg Val Ser Asn Asp Ser Gln Ala Ile Phe Gly Ser Glu Asp Val
        35                  40                  45

Gly Ser Ser Ser Tyr Val Ala Val Asp Ile Leu Ile Ala Val Gly Ala
    50                  55                  60

Ile Ile Met Ile Leu Gly Phe Leu Gly Cys Cys Gly Ala Ile Lys Glu
65                  70                  75                  80

Ser Arg Cys Met Leu Leu Leu Phe Phe Ile Gly Leu Leu Leu Ile Leu
                85                  90                  95

Leu Leu Gln Val Ala Thr Gly Ile Leu Gly Ala Val Phe Lys Ser Lys
            100                 105                 110

Ser Asp Arg Ile Val Asn Glu Thr Leu Tyr Glu Asn Thr Lys Leu Leu
        115                 120                 125
```

```
Ser Ala Thr Gly Glu Ser Glu Lys Gln Phe Gln Glu Ala Ile Ile Val
    130                 135                 140

Phe Gln Glu Glu Phe Lys Cys Cys Gly Leu Val Asn Gly Ala Ala Asp
145                 150                 155                 160

Trp Gly Asn Asn Phe Gln His Tyr Pro Glu Leu Cys Ala Cys Leu Asp
                165                 170                 175

Lys Gln Arg Pro Cys Gln Ser Tyr Asn Gly Lys Gln Val Tyr Lys Glu
            180                 185                 190

Thr Cys Ile Ser Phe Ile Lys Asp Phe Leu Ala Lys Asn Leu Ile Ile
        195                 200                 205

Val Ile Gly Ile Ser Phe Gly Leu Ala Val Ile Glu Ile Leu Gly Leu
    210                 215                 220

Val Phe Ser Met Val Leu Tyr Cys Gln Ile Gly Asn Lys
225                 230                 235
```

<210> SEQ ID NO 59
<211> LENGTH: 100
<212> TYPE: DNA
<213> ORGANISM: Homo sapiens

<400> SEQUENCE: 59

```
ttgtggagac tatgtgcaag gaaccatctt cccagctccc aatttcaatc ccataatgga     60

tgcccaaatg ctaggaggag cactccaagg atttgactgt                         100
```

<210> SEQ ID NO 60
<211> LENGTH: 100
<212> TYPE: DNA
<213> ORGANISM: Homo sapiens

<400> SEQUENCE: 60

```
ctcagagaga cgtggcagga ccagcgagga atccagcctg tccacttcca gaacagtgtt     60

tcccaggccc cgctgagtgg accggacctc tgacacctcc                         100
```

<210> SEQ ID NO 61
<211> LENGTH: 100
<212> TYPE: DNA
<213> ORGANISM: Homo sapiens

<400> SEQUENCE: 61

```
gacttttgaa ctaactgggg agacagacaa catatttgtg atagaacggg agggacttct     60

gtattacaac agagccttgg acagggaaac aagatctact                         100
```

<210> SEQ ID NO 62
<211> LENGTH: 100
<212> TYPE: DNA
<213> ORGANISM: Homo sapiens

<400> SEQUENCE: 62

```
tttcaggact gcgtgatcgt gcactttgtg tggtaagagg tttgagtagt cctatatgtc     60

acctagggaa cagacattat agcttactag caaatgaata                         100
```

<210> SEQ ID NO 63
<211> LENGTH: 100
<212> TYPE: DNA
<213> ORGANISM: Homo sapiens

<400> SEQUENCE: 63

```
gttgccaccc tggggaccac aacatgctgc tcctttgaca atctcttaga agtcggtcct     60
```

atctgcaaca aggaagacat atggctgcac gttgatgcag 100

<210> SEQ ID NO 64
<211> LENGTH: 100
<212> TYPE: DNA
<213> ORGANISM: Homo sapiens

<400> SEQUENCE: 64
accaaataac gagctgcacg gccaagagag tcacaattca ggcaacagga gcgacgggcc 60
aggaaagaac accacccttc acaatgaatt tgacacaatt 100

<210> SEQ ID NO 65
<211> LENGTH: 100
<212> TYPE: DNA
<213> ORGANISM: Homo sapiens

<400> SEQUENCE: 65
ctgctgcccc gagcctgatt cctagtcctg cttctcttcc ctctctcctc cagcctctca 60
cactctcctc agctctctca tctcctggaa ccatggccag 100

<210> SEQ ID NO 66
<211> LENGTH: 100
<212> TYPE: DNA
<213> ORGANISM: Homo sapiens

<400> SEQUENCE: 66
tggtagcagc agcaatttcc acatcaatgt agaagagtca gtggatggac aggtggtttc 60
ttcccacaag agagaaatct aagtgtctat tgcaggagaa 100

<210> SEQ ID NO 67
<211> LENGTH: 100
<212> TYPE: DNA
<213> ORGANISM: Homo sapiens

<400> SEQUENCE: 67
agccagtact acaggacaat tgaggagctg cagaacaaga tcctcacagc caccgtggac 60
aatgccaaca tcctgctaca gattgacaat gcccgtctgg 100

<210> SEQ ID NO 68
<211> LENGTH: 100
<212> TYPE: DNA
<213> ORGANISM: Homo sapiens

<400> SEQUENCE: 68
agaagatcac ccacaaccca tttggtcccg gacagttctt tgatctgtcc attcgctgtg 60
gcttggatcg cttcaaggtt tacgccaatg gccagcacct 100

<210> SEQ ID NO 69
<211> LENGTH: 100
<212> TYPE: DNA
<213> ORGANISM: Homo sapiens

<400> SEQUENCE: 69
cggcagagaa caaatgccaa gaactgttgt gcaagtgtga ccaggagatt gctaactgct 60
tagcccaaac tgagtacaac ttaaagtacc tcttctaccc 100

<210> SEQ ID NO 70
<211> LENGTH: 100
<212> TYPE: DNA
<213> ORGANISM: Homo sapiens

<400> SEQUENCE: 70
tcctgggctt cgtctactcc tttctgggtc ctaacccttt tgtcgcctgg atgcacttcc 60
tggtcttcct cgtgggccgt gtggcacaca ccgtggccta 100

<210> SEQ ID NO 71
<211> LENGTH: 100
<212> TYPE: DNA
<213> ORGANISM: Homo sapiens

<400> SEQUENCE: 71
aacccaggag tttcaaagaa gcgctagtaa ggtctctgag atccttgcac tagctacatc 60
ctcagggtag gaggaagatg gcttccagaa gcatgcggct 100

<210> SEQ ID NO 72
<211> LENGTH: 100
<212> TYPE: DNA
<213> ORGANISM: Homo sapiens

<400> SEQUENCE: 72
ttttcctggc actcatcact gtcatgtgca atgacttctt ccagggctgc ccagaccgac 60
cctgaagcag aactcttgac ttcctgccat ggatctcttg 100

<210> SEQ ID NO 73
<211> LENGTH: 100
<212> TYPE: DNA
<213> ORGANISM: Homo sapiens

<400> SEQUENCE: 73
cggtgccgtc cccagcacgg tgattagtcc cagagctcgg ctgccacctc caccggacac 60
ctcagacacg cttctgcagc tgtgcctcgg ctcacaacac 100

<210> SEQ ID NO 74
<211> LENGTH: 100
<212> TYPE: DNA
<213> ORGANISM: Homo sapiens

<400> SEQUENCE: 74
ctggctatgt ggtatcttga tcctagcatt agcaatatgg gtacgagtaa gcaatgactc 60
tcaagcaatt tttggttctg aagatgtagg ctctagctcc 100

<210> SEQ ID NO 75
<211> LENGTH: 100
<212> TYPE: DNA
<213> ORGANISM: Homo sapiens

<400> SEQUENCE: 75
tttgtggcaa aaatacttcc taggtggtgc tgggtacttc ttgttgcatc ctgtcaggag 60
gcagataatg ctggtgcctc tctattggta atgttaagac 100

<210> SEQ ID NO 76
<211> LENGTH: 100
<212> TYPE: DNA
<213> ORGANISM: Homo sapiens

<400> SEQUENCE: 76
atgatggcaa aaccccagga gcagttaatg cctgtcattt atcctgcagt gctttgctgc 60
aagataacat cgctgatgct gtagcttgtg caaagagggt 100

<210> SEQ ID NO 77
<211> LENGTH: 100
<212> TYPE: DNA
<213> ORGANISM: Homo sapiens

<400> SEQUENCE: 77
cagttctgca atcagcaccc tttcaacaac tcctgttgac accagcacac ctgtgaccaa 60
ttctactgaa gcccgttcat ctcctacaac ttctgaaggt 100

<210> SEQ ID NO 78
<211> LENGTH: 100
<212> TYPE: DNA
<213> ORGANISM: Homo sapiens

<400> SEQUENCE: 78
catctcctct tggtttcggg gaaacatgca aaagaaatgc tatgggaaga taaaggcatc 60
cgtgttattg atccaggctt ttgtgagagg gtggaaggcc 100

<210> SEQ ID NO 79
<211> LENGTH: 100
<212> TYPE: DNA
<213> ORGANISM: Homo sapiens

<400> SEQUENCE: 79
gcaattcgcc attactctga agtcctacat tgaatgcaat cggccccagc ctgctcatag 60
gttcttgttc ctgaagatca tggctatgct caccgagctc 100

<210> SEQ ID NO 80
<211> LENGTH: 100
<212> TYPE: DNA
<213> ORGANISM: Homo sapiens

<400> SEQUENCE: 80
cttgctgaac tgtgaagaac tgcatgaact atatttaagc tgctttctgt accattgcca 60
atcacctttt tggagttgga agtgctattt tcctatggac 100

<210> SEQ ID NO 81
<211> LENGTH: 100
<212> TYPE: DNA
<213> ORGANISM: Homo sapiens

<400> SEQUENCE: 81
gcaaaggtgc acaagtcaat cagacagaga gatatgagaa attcaaccag attttaactg 60
ccctctcgcg taaattggaa cctcctcctg taaagcaggc 100

<210> SEQ ID NO 82
<211> LENGTH: 100
<212> TYPE: DNA
<213> ORGANISM: Homo sapiens

<400> SEQUENCE: 82
gacagtggcg actgcgctga cagaacgtga ttctcgtgcc tttattttga aagagatgtt 60
tttcccaaga ggcttgctga aagagtgaga gaagatggaa 100

<210> SEQ ID NO 83
<211> LENGTH: 100
<212> TYPE: DNA
<213> ORGANISM: Homo sapiens

<400> SEQUENCE: 83
aactctccga agagttgttc caaatgcttt acccggcaac caccagtaaa ggaacgaccc 60
acagttacgg atactcgttc tggctcatac tgctcgtcat 100

<210> SEQ ID NO 84
<211> LENGTH: 100
<212> TYPE: DNA
<213> ORGANISM: Homo sapiens

<400> SEQUENCE: 84
gaaagtcctc acatcaatag tacatatgaa agtgacctcc aaggggattg gtgaatactc 60
ataaggatct tcaggctgaa cagactatgt ctggggaaag 100

<210> SEQ ID NO 85
<211> LENGTH: 100
<212> TYPE: DNA
<213> ORGANISM: Homo sapiens

<400> SEQUENCE: 85
tccacagaga ggaggggacc aattctggac agacagatgt tgggaggata cagaggagat 60
gccacttctc actcaccact accagccagc ctcagaaggc 100

<210> SEQ ID NO 86
<211> LENGTH: 100
<212> TYPE: DNA
<213> ORGANISM: Homo sapiens

<400> SEQUENCE: 86
tgtggcaatg ggccacatta tgtatttccg atttgcccaa aatactctgg gaaacaagct 60
ctttgcttgc ggtcctgatg caaaagaagt taggaaggaa 100

<210> SEQ ID NO 87
<211> LENGTH: 100
<212> TYPE: DNA
<213> ORGANISM: Homo sapiens

<400> SEQUENCE: 87
ctggttctct tgctccacca ggaacaagcc accatgtctc gccagtcaag tgtgtccttc 60
cggagcgggg gcagtcgtag cttcagcacc gcctctgcca 100

<210> SEQ ID NO 88
<211> LENGTH: 100
<212> TYPE: DNA
<213> ORGANISM: Homo sapiens

<400> SEQUENCE: 88
ggaggagtcg gacgaggata tgggatttgg tctctttgac taatcaccaa aaagcaacca 60
acttagccag ttttatttgc aaaacaagga aataaaggct 100

<210> SEQ ID NO 89
<211> LENGTH: 100
<212> TYPE: DNA
<213> ORGANISM: Homo sapiens

<400> SEQUENCE: 89
tactgaagaa tggagagaga attgaaaaag tggagcattc agacttgtct ttcagcaagg 60
actggtcttt ctatctcttg tactacactg aattcacccc 100

<210> SEQ ID NO 90

<211> LENGTH: 100
<212> TYPE: DNA
<213> ORGANISM: Homo sapiens

<400> SEQUENCE: 90
ttaatagtca ttccaaatat gagatgcgtt gttacaggaa gtcccttgcc atcctaaaag 60
ccaccccact tctctctaag gagaatggcc cagtcctctc 100

<210> SEQ ID NO 91
<211> LENGTH: 100
<212> TYPE: DNA
<213> ORGANISM: Homo sapiens

<400> SEQUENCE: 91
atgcccgaat gccagagaag gtcacatgga tgaggagaat gaggattttg cgccggctgc 60
tcagaagata ccgtgaatct aagaagatcg atcgccacat 100

<210> SEQ ID NO 92
<211> LENGTH: 100
<212> TYPE: DNA
<213> ORGANISM: Homo sapiens

<400> SEQUENCE: 92
actgaatctc ccctcctcac agttgccatg tagacccctt gaagagggga ggggcctagg 60
gagccgcacc ttgtcatgta ccatcaataa agtaccctgt 100

<210> SEQ ID NO 93
<211> LENGTH: 100
<212> TYPE: DNA
<213> ORGANISM: Homo sapiens

<400> SEQUENCE: 93
gtccttgggg aacatggaga ttccagtgtg cctgtatgga gtggaatgaa tgttgctggt 60
gtctctctga agactctgca cccagattta gggactgata 100

<210> SEQ ID NO 94
<211> LENGTH: 100
<212> TYPE: DNA
<213> ORGANISM: Homo sapiens

<400> SEQUENCE: 94
agattcagct agtggccaag agatgcagtg ccaggaaccc ttaaacagtt gcacagcatc 60
tcagctcatc ttcactgcac cctggatttg catacattct 100

<210> SEQ ID NO 95
<211> LENGTH: 100
<212> TYPE: DNA
<213> ORGANISM: Homo sapiens

<400> SEQUENCE: 95
ttctaagtat gtccatttcc catctcagct tcaagggagg tgtcagcagt attatctcca 60
ctttcaatct ccctccaagc tctactctgg aggagtctgt 100

<210> SEQ ID NO 96
<211> LENGTH: 100
<212> TYPE: DNA
<213> ORGANISM: Homo sapiens

<400> SEQUENCE: 96
tcggtacatg gtgccaaccg cctcggggca aactcgctct tggacctggt tgtctttggt 60
cgggcatgtg ccctgagcat cgaagagtca tgcaggcctg 100

<210> SEQ ID NO 97
<211> LENGTH: 100
<212> TYPE: DNA
<213> ORGANISM: Homo sapiens

<400> SEQUENCE: 97
gcgaaagtga tgagtctaaa aaagtagtcc ctccggttcc tctgtttccc cccatgtggc 60
gtcaggaagc gaggcaccgg gcgcactgcg ccccgaattc 100

<210> SEQ ID NO 98
<211> LENGTH: 100
<212> TYPE: DNA
<213> ORGANISM: Homo sapiens

<400> SEQUENCE: 98
gagcctatag actatcagtt ccctttgggc ggattgttgt ttaacttgta aatgaaaaaa 60
ttctcttaaa ccacagcact attgagtgaa acattgaact 100

<210> SEQ ID NO 99
<211> LENGTH: 100
<212> TYPE: DNA
<213> ORGANISM: Homo sapiens

<400> SEQUENCE: 99
gtggagtgtg accttgatgt gaccgggatc ccactctgat tgcatccatt tctctgaaag 60
acttgtttgt tctgcttctc ttcatataac tgagctggcc 100

<210> SEQ ID NO 100
<211> LENGTH: 100
<212> TYPE: DNA
<213> ORGANISM: Homo sapiens

<400> SEQUENCE: 100
ccgatttcat gactgaacag tcaccgacga gagtgctggg gaataaaaag gggatcttca 60
ctcggcagag acaaccaaaa agtgcagcgt tccttttgcg 100

<210> SEQ ID NO 101
<211> LENGTH: 100
<212> TYPE: DNA
<213> ORGANISM: Homo sapiens

<400> SEQUENCE: 101
gcaggcaaca cagggaacct caggccaggc accacagctc ttccactcac agactctcac 60
aactgcaccc ttgccgggca ccactccact gtatccctcc 100

<210> SEQ ID NO 102
<211> LENGTH: 100
<212> TYPE: DNA
<213> ORGANISM: Homo sapiens

<400> SEQUENCE: 102
acaagggcaa cgagcgtttc gtttggactt ctcgacttga gtgcccgcct ccttcgccgc 60
cgcctctgca gtcctcagcg cagttatgcc cagttcttcc 100